(12) United States Patent
Frankard et al.

(10) Patent No.: US 7,619,146 B2
(45) Date of Patent: *Nov. 17, 2009

(54) METHOD FOR MODIFYING PLANT MORPHOLOGY, BIOCHEMISTRY AND PHYSIOLOGY

(76) Inventors: Valérie Frankard, Rue de Percke 78, B-1180 Brussels (BE); Thomas Schmülling, Preussenallee 30, D-14052 Berlin (DE); Tomàs Werner, Berlinerstr 118/119, D10713, Berlin (DE)

( * ) Notice: Subject to any disclaimer, the term of this patent is extended or adjusted under 35 U.S.C. 154(b) by 422 days.

This patent is subject to a terminal disclaimer.

(21) Appl. No.: 11/057,473

(22) Filed: Feb. 14, 2005

(65) Prior Publication Data
US 2005/0223429 A1 Oct. 6, 2005

Related U.S. Application Data

(63) Continuation-in-part of application No. 10/871,304, filed on Jun. 18, 2004, which is a continuation-in-part of application No. 10/014,101, filed on Dec. 10, 2001, now Pat. No. 7,259,296, which is a continuation-in-part of application No. PCT/EP01/06833, filed on Jun. 18, 2001.

(60) Provisional application No. 60/544,393, filed on Feb. 13, 2004.

(51) Int. Cl.
C12N 15/82 (2006.01)
C12N 5/04 (2006.01)
A01H 5/00 (2006.01)
A01H 5/10 (2006.01)

(52) U.S. Cl. ............... 800/320.1; 800/278; 800/298; 800/287; 800/320; 800/284; 800/290; 435/419

(58) Field of Classification Search ............ 800/278, 800/290, 298, 287; 435/419, 468
See application file for complete search history.

(56) References Cited

U.S. PATENT DOCUMENTS 6,992,237 B1 * 1/2006 Habben et al. ............. 800/298
7,259,296 B2 * 8/2007 Schmulling et al. ........ 800/298

FOREIGN PATENT DOCUMENTS

| EP | 1 580 270 A1 | 9/2005 |
|---|---|---|
| WO | WO 99/06571 | 2/1999 |
| WO | WO 99/06579 | 2/1999 |
| WO | 00/63401 | * 10/2000 |
| WO | WO 00/63401 | * 10/2000 |
| WO | WO 01/96580 A2 | 12/2001 |
| WO | WO 03/050287 A2 | 6/2003 |
| WO | WO 2004/044200 A1 | 5/2004 |

OTHER PUBLICATIONS

Bilyeu et al (2003. Plant Growth Regulation 39:195-203).*
Hare et al (1994, Physiologia Plantarum 91:128-136).*
Kaminek et al (1990, Plant Physiol. 93:1530-1538).*
Bowie et al, Science 247:1306-1310, 1990.*
McConnell et al, Nature 411 (6838):709-713, 2001.*
Li et al (1994, Cereal Chem. 71(1):87-90).*
Bilyeu et al (2003, Plant Growth Regulation 39:195-203).*
Bilyeu et al., (2001) "Molecular and biochemical characterization of a cytokinin oxidase from maize" *Plant Physiology* 125: 378-386.
Bilyeu et al., (2003) "Dynamics of expression and distribution of cytokinin oxidase/dehydrogenase in developing maize kernels", *Plant Growth Regulation* 39: 195-203.
Bowie et al., (1990) "Deciphering the message in protein sequences: tolerance to amino acid substitutions", *Science* 247: 1306-1310.
Burch et al., (1989) "The purification of cytokinin oxidase from *Zea mays* kernels", *Phytochemistry* 28(5): 1313-1319.
Dietrich et al., (1995) "Changes in cytokinins and cytokinin oxidase activity in developing maize kernels and the effects of exogenous cytokinin on kernel development". *Plant Physiology and Biochenistry* 33(3): 327-336.
Doerner, et al., (1996) "Control of root growth and development by cyclin expression", *Nature* 380: 520-523.
Faiss et al., (1997) "Conditional transgenic expression of the *IPT* gene indicates a function for cytokinins in paracrine signaling in whole tobacco plants", *Plant Journal* 12(2): 401-415.
Fourgoux-Nicol et al., (1999) "Isolation of Rapeseed Genes Expressed Early and Specifically During Development of the Male Gametophyte", *Plant Molecular Biology* 40: 857-872.

(Continued)

*Primary Examiner*—Stuart F. Baum
(74) *Attorney, Agent, or Firm*—Ann R. Pokalsky; Dilworth & Barrese, LLP

(57) ABSTRACT

The present invention relates to methods for stimulating root growth and/or enhancing the formation of lateral or adventitious roots and/or altering root geotropism comprising expression of a cytokinin oxidase or comprising expression of another protein that reduces the level of active cytokinins in plants or plant parts. Also provided by the present invention are methods for increasing seed size and/or weight, embryo size and/or weight, and cotyledon size and/or weight. The methods comprise expression of a cytokinin oxidase or expression of another protein that reduces the level of active cytokinins in plants or plant parts. Methods and compositions for increasing seed yield are also provided. The invention also relates to isolated plant cytokinin oxidase proteins, nucleic acid sequences encoding cytokinin oxidase proteins as well as to vectors, host cells, transgenic cells and plants comprising such sequences. The use of these sequences for improving root-related characteristics including increasing yield and/or enhancing early vigor and/or modifying root/shoot ratio and/or improving resistance to lodging and/or increasing drought tolerance and/or promoting in vitro propagation of explants and/or modifying cell fate and/or plant development and/or plant morphology and/or plant biochemistry and/or plant physiology, is also provided. The invention also relates to methods for identifying and obtaining proteins and compounds interacting with cytokinin oxidase proteins as well as the use of such proteins and/or compounds as plant growth regulators or herbicides.

25 Claims, 22 Drawing Sheets

OTHER PUBLICATIONS

Frank et al., (1999) "*TSD* Genes Negatively Regulate Meristematic Activity in Araidopsis", *Bio. Plant* 42: S47.

Hare et al. (1994), "Inhibitory Effect of Thidiazuron on the Activity of Cytokinin Oxidase Isolated from Soybean Callus", *Plant Cell Physiology* 35(8): 1121-1125.

Hare et al., (1994) "Cytokinin Oxidase: Biochemical Features and Physiological Significance", *Physiologia Plantarum* 91: 128-136.

Houba-Herin et al., (1999) "Cytokinin oxidase From *Zea mays*: Purification, cDNA cloning and expression in moss protoplasts", *The Plant Journal* 17(6): 615-626.

Kaminek et al., (1990) "Genotypic variation in cytokinin oxidase from phaseolus callus cultures", *Plant Physiology* 93: 1530-1538.

Klee et al. (1995), "Transgenic plants in hormone biology" *Plant Hormones: Physiology, Biochemistry and Molecular Biology*, 340-353.

Koda et al., (1989) "Cytokinin production by tomato root identification of a major cytokinin produced by the root and environmental factors affecting the production", *Journal of the Faculty of Agriculture Hokkaido University* 64.

Li et al., (1994) "Transgenic tobacco plants that overproduce cytokinins show increased tolerance to exogenous auxin and auxin transport inhibitors", *Plant Science* 100: 9-14.

Lin et al., (1999) "Putative cytokinin oxidase", *Swall* Q9ZUP1.

McConnell et al., (2001) "Role of Phabulosa and Phavoluta in determining radial patterning in shoots", *Nature* 411: 709-713.

Meilan et al., (1994) "Cloning the cytokinin oxidase gene", *Plant Physiology* 105: 68.

Mok, (1994) "Cytokinins and plant development—An Overview", *Cytokines: Chemistry, Activity and Function* 155-166.

Morris, (1999) "Isolation of a gene encoding a glycosylated cytokinin oxidase from maize", *Biochem. Biophys. Res. Commun.* 255: 328-333.

Motyka et al., (1996) "Changes in cytokinin content and cytokinin oxidase activity in response to derepression of *ipt* gene transgenic tobacco calli and plants", *Plant Physiology* 112: 1035-1043.

Qu et al., (2004) "Evaluation of tissue specificity and expression strength of rice seed component gene promoters in transgenic rice", *Genbank* AY427563.

Qu et al., (2004) "Evaluation of tissue specificity and expression strength of rice seed component gene promoters in transgenic rice", *Plant Biotechnology Journal* 2: 113-125.

Rinaldi et al., (1999) "Cytokinin oxidase strikes again", *Trends in Plant Science* 4(8): 300.

Rounsley et al., (1998) T32G6.3. *Swall* 022213.

Schmulling (2002) "New insights into the functions of cytokinins in plant development", *Journal of Plant Growth Regulation* 21: 40-49.

Schmulling el al., (1999) "Recent advances in cytokinin research: receptor candidates, primary response genes, mutants and transgenic plants", *Advances in Regulation of Plant Growth and Development* 21:85-96.

Schmulling et al., (2003) "Structure and function of cytokinin oxidase/dehydrogenase genes of maize, rice, *Arabidopsis* and other species", *Journal of Plant Research* 116: 241-252.

Schmulling et al., (2003) "Cytokinin as a regulatory factor for yield and biomass distribution in crop plants", *Photohormones in Plant Biotechnology and Agriculture*: 97-108.

Sha et al., (1995) "Cloning and sequence of a rice gene encoding the 13kDa prolamin polypeptide", D63901.

Smigocki et al., (1991) "Cytokinin content and tissue distribution in plants transformed by a reconstructed isopentenyl transferase gene", *Plant Molecular Biology* 16: 105-115.

Ulloa et al., (1993) "Dephosporylation of distinct sites on microtubule-associated protein MAP1B by protein phosphatases 1, 2A and 2B," *FEBS Letters* 330(1): 85-89.

Werner et al., (2001) "Regulation of plant growth by cytokinin", *PNAS* 98(18): 10487-10492.

Werner et al., (2003) "Cytokinin-deficient transgenic *Arabidopsis* plants show multiple developmental; alterations indicating opposite functions of cytokinin oxidase in the regulation of shoot and root meristem activity", *Plant Cell* 15: 2532-2550.

Yang et al., (2003) "Functional characterisation of a cytokinin oxidase gene *DSCKX1* in *Dendrobium* orchid", *Plant Molecular Biology* 51: 237-248.

Zhang et al., (1999) "Initiation and elongation of lateral roots in *Lactuca sativa*", *International Journal of Plant Sciences* 160(3): 511-519.

\* cited by examiner

FIGURE 2

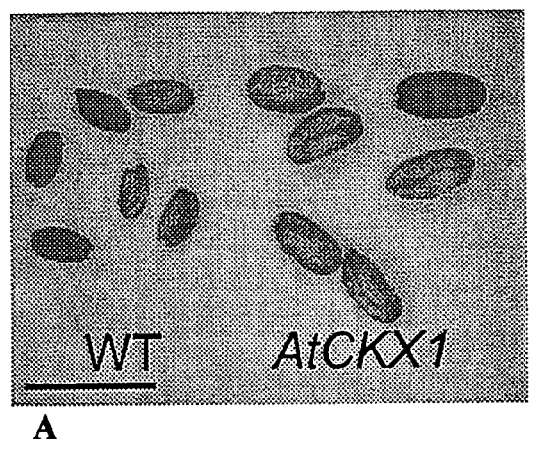 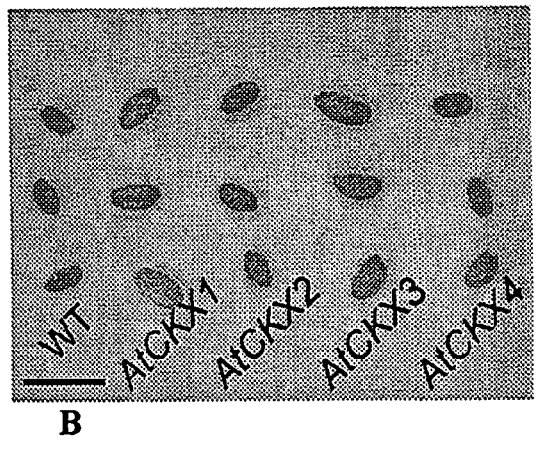
Figure 13A
Figure 13B

PRO0109::CKX2 transformants

A) A-plant

B) B-plant

C) C-plant beta-expansin EXPB9 promoter expression pattern

METHOD FOR MODIFYING PLANT MORPHOLOGY, BIOCHEMISTRY AND PHYSIOLOGY

This application claims the benefit of U.S. Provisional Application Ser. No. 60/544,393, filed Feb. 13, 2004, and is a continuation in part of U.S. Ser. No. 10/871,304, filed Jun. 18, 2004, which is a continuation-in-part application of U.S. Ser. No. 10/014,101, filed Dec. 10, 2001, now U.S. Pat. No. 7,259, 296, which is a continuation-in-part of PCT/EP01/06833, having an international filing date of Jun. 18, 2001.

FIELD OF THE INVENTION

The present invention generally relates to methods for modifying plant morphological, biochemical and physiological properties or characteristics, such as one or more developmental processes and/or environmental adaptive processes, including but not limited to the modification of initiation or stimulation or enhancement of root growth, and/or adventitious root formation, and/or lateral root formation, and/or root geotropism, and/or shoot growth, and/or apical dominance, and/or branching, and/or timing of senescence, and/or timing of flowering, and/or flower formation, and/or seed development, and/or seed yield. Methods for increasing seed size and/or weight, increasing embryo size and/or weight, and increasing cotyledon size and/or weight are also provided. The methods comprise expressing a cytokinin degradation control protein, in particular cytokinin oxidase, in the plant, operably under the control of a regulatable promoter sequence such as a cell-specific promoter, tissue-specific promoter, or organ-specific promoter sequence. Preferably, the characteristics modified by the present invention are cytokinin-mediated and/or auxin-mediated characteristics. The present invention extends to genetic constructs which are useful for performing the inventive method and to transgenic plants produced therewith having altered morphological and/or biochemical and/or physiological properties compared to their otherwise isogenic counterparts.

BACKGROUND OF THE INVENTION

Roots are an important organ of higher plants. Their main functions are anchoring of the plant in the soil and uptake of water and nutrients (N-nutrition, minerals, etc.). Thus, root growth has a direct or indirect influence on growth and yield of aerial organs, particularly under conditions of nutrient limitation. Roots are also relevant for the production of secondary plant products, such as defense compounds and plant hormones.

Seeds are the reproduction unit of higher plants. Plant seeds contain reserve compounds to ensure nutrition of the embryo after germination. These storage organs contribute significantly to human nutrition as well as cattle feeding. Seeds consist of three major parts, namely the embryo, the endosperm and the seed coat. Reserve compounds are deposited in the storage organ which is either the endosperm (resulting form double fertilisation; e.g. in all cereals), the so-called perisperm (derived from the nucellus tissue) or the cotyledons (e.g. bean varieties). Storage compounds are lipids (oil seed rape), proteins (e.g. in the aleuron of cereals) or carbohydrates (starch, oligosaccharides like raffinose).

Starch is the storage compound in the seeds of cereals. The most important species are maize (yearly production ca. 570 mio t; according to FAO 1995), rice (540 mio t p.a.) and wheat (530 mio t p.a.). Protein rich seeds are found in different kinds of beans (*Phaseolus* spec., *Vicia faba, Vigna* spec.; ca. 20 mio t p.a.), pea (*Pisum sativum;* 14 mio t p.a.) and soybean (*Glycine max*. 136 mio t p.a.). Soybean seeds are also an important source of lipids. Lipid rich seeds are as well those of different *Brassica* species (app. 30 mio t p.a.), cotton, oriental sesame, flax, poppy, castor bean, sunflower, peanut, coconut, oilpalm and some other plants of less economic importance.

After fertilization, the developing seed becomes a sink organ that attracts nutritional compounds from source organs of the plant and uses them to produce the reserve compounds in the storage organ. Increases in seed size and weight, are desirable for many different crop species. In addition to increased starch, protein and lipid reserves and hence enhanced nutrition upon ingestion, increases in seed size and/or weight and cotyledon size and/or weight are correlated with faster growth upon germination (early vigor) and enhanced stress tolerance. Cytokinins are an important factor in determining sink strength. The common concept predicts that cytokinins are a positive regulator of sink strength.

Numerous reports ascribe a stimulatory or inhibitory function to cytokinins in different developmental processes such as root growth and branching, control of apical dominance in the shoot, chloroplast development, and leaf senescence (Mok M. C. (1994) in *Cytokines: Chemistry, Activity and Function*, eds., Mok, D. W. S. & Mok, M. C. (CRC Boca Raton, Fla.), pp. 155-166). Conclusions about the biological functions of cytokinins have mainly been derived from studies on the consequences of exogenous cytokinin application or endogenously enhanced cytokinin levels (Klee, H. J. & Lanehon, M. B. (1995) in *Plant Hormones: Physiology, Biochemisry and Molecular Biology*, ed. Davies, P. J. (Kluwer, Dordrdrocht, the Netherlands), pp. 340-353, Smulling, T., Rupp, H. M. Frank, M& Schafer, S. (1999) in *Advances in Regulation of Plant Growth and Development*, eds. Surnad, M. Pac P. & Beck, E. (Peres, Prague), pp. 85-96). Up to now, it has not been possible to address the reverse question: what are the consequences for plant growth and development if the endogenous cytokinin concentration is decreased? Plants with a reduced cytokinin content are expected to yield more precise information about processes cytokinins limit and, therefore, might regulate. Unlike other plant hormones such as abscisic acid, gibberellins, and ethylene, no cytokinin biosynthetic mutants have been isolated (Hooykens, P. J. J., Hall, M. A. & Libbeuga, K. R., eds. (1999) *Biochemistry and Molecular Biology of Plant Hormones* (Elsevier, Amsterdam).

The catabolic enzyme cytokinin oxidase (CKX) plays a principal role in controlling cytokinin levels in plant tissues. CKX activity has been found in a great number of higher plants and in different plant tissues. The enzyme is a FAD-containing oxidoreductase that catalyzes the degradation of cytokinins bearing unsaturated isoprenoid side chains. The free bases iP and Z, and their respective ribosides are the preferred substrates. The reaction products of iP catabolism are adenine and the unsaturated aldehyde 3-methyl-2-butonal (Armstrong, D. J. (1994) in *Cytokinins: Chemistry, Activity and Functions*, eds. Mok. D. W. S & Mok, M. C. (CRC Boca Raton, Fla.), pp. 139-154). Recently, a cytokinin oxidase gene from *Zea mays* has been isolated (Morris, R. O., Bilyeu, K. D., Laskey, J. G. & Cherich, N. N. (1999) *Biochem. Biophys. Res. Commun.* 255, 328-333, Houba-Heria, N., Pethe, C. d'Alayer, J & Lelouc, M. (1999) *Plant J.* 17:615-626). The manipulation of CKX gene expression could partially overcome the lack of cytokinin biosynthetic mutants and can be used as a powerful tool to study the relevance of iP- and Z-type cytokinins during the whole life cycle of higher plants.

The present invention overcomes problems related to containment of auxin effects, maintenance of root outgrowth, and promotion of increased seed, embryo, and cotyledon size and/or weight through reduction of endogenous cytokinin concentration.

WO99/06571 discloses the first cloning of a cytokinin oxidase, and plants transformed with the maize cytokinin oxidase were presented. In the same document the idea is proposed to modulate cytokinin levels in plant cells by modifying cytokinin oxidase levels for altering pathogen resistance or plant growth properties (like increased grain production or desired secondary growth characteristics). A practically worked out example is found in US2003163847, showing a method for producing male sterile plants by increasing cytokinin oxidase expression under control of a pollen or anther specific promoter, such that pollen formation or male organ development was inhibited. Increasing cytokinin levels back to normal restored male fertility. Plants overexpressing CKX genes under control of a constitutive promoter had various desirable characteristics, including enhanced root growth and altered root geotropism, increased leaf thickness, parthenocarpy, improved standability of seedlings, increased branching, improved lodging resistance, whereas downregulating cytokinin oxidase expression resulted in plants having delayed leaf senescence, increased shoot meristems, increased vessel size (WO01/96580). An attempt to modify seed yield using cytokinin oxidase is presented in WO00/63401 by Habben et al. This disclosure aims at improving seed size, decreasing tip kernel abortion, increasing seed set during unfavourable environmental conditions and stability of yield by increasing cytokinin levels in the developing seed. The two approaches proposed are to either inhibit or abolish cytokinin oxidase activity with antagonists or through antisense molecules, or to increase the synthesis of cytokinin. The opposite strategy is used in WO03/050287 for increasing seed yield. Schmülling et al. demonstrated that increased seed size/weight, increased embryo size/weight or increased cotyledon size/weight is obtained in tobacco or *Arabidopsis* by overexpressing a CKX gene under control of a constitutive promoter. Also the use of seed specific, embryo specific or cotyledon specific promoters is contemplated for reaching this goal.

It has now surprisingly been found that heterologous expression of a nucleic acid molecule encoding a cytokinin oxidase (hereafter abbreviated as CKX) in the shoot of a plant gives rise to plants having modified growth characteristics, especially increased yield, in particular increased seed yield. The present invention therefore provides a method for increasing seed yield of a plant, comprising introducing and expressing in said plant an isolated nucleic acid molecule encoding a cytokinin oxidase/dehydrogenase, a homologue, a derivative or an active fragment thereof, characterised in that said expression is primarily obtained in the shoot of said plant.

SUMMARY OF THE INVENTION

The present invention provides plant cytokinin oxidase proteins, nucleic acid sequences encoding such proteins, and vectors, host cells and transgenic plant cells, plants, and plant parts comprising the proteins, nucleic acid sequences, and vectors. For example, the present invention relates to a genetic construct comprising a gene encoding a protein with cytokinin oxidase activity from *Arabidopsis thaliana*. This gene may be expressed under control of a regulated promoter. This promoter may be regulated by endogenous tissue-specific or environment-specific factors or, alternatively, it may be induced by application of specific chemicals. Preferably, the promoter is a shoot-preferred or shoot-specific promoter.

Additionally, the present invention relates to methods of increasing seed size and/or weight, embryo size and/or weight, and cotyledon size and/or weight. The methods involve expression of a cytokinin oxidase gene or expression of a nucleic acid encoding a protein that reduces the level of active cytokinins in plants or plant parts. Preferably, expression is under control of a promoter that directs expression preferentially in the shoot of a plant. Methods and compositions for increasing seed yield in a plant are also provided.

Shown are the structures of different cytokinin oxidase genes isolated from maize (ZmCKX1, accession number AF044603, Biochem. Biophys. Res. Com. 255:328-333, 1999) and *Arabidopsis* (AtCKX1 to AtCKX4). Exons are denominated with 'E' and represented by shaded boxes. Introns are represented by white boxes. Further indicated are the gene sizes (in kb, on top of each structure), the gene accession numbers (under the names) and a size bar representing 0.5 kb.

Figure 2:
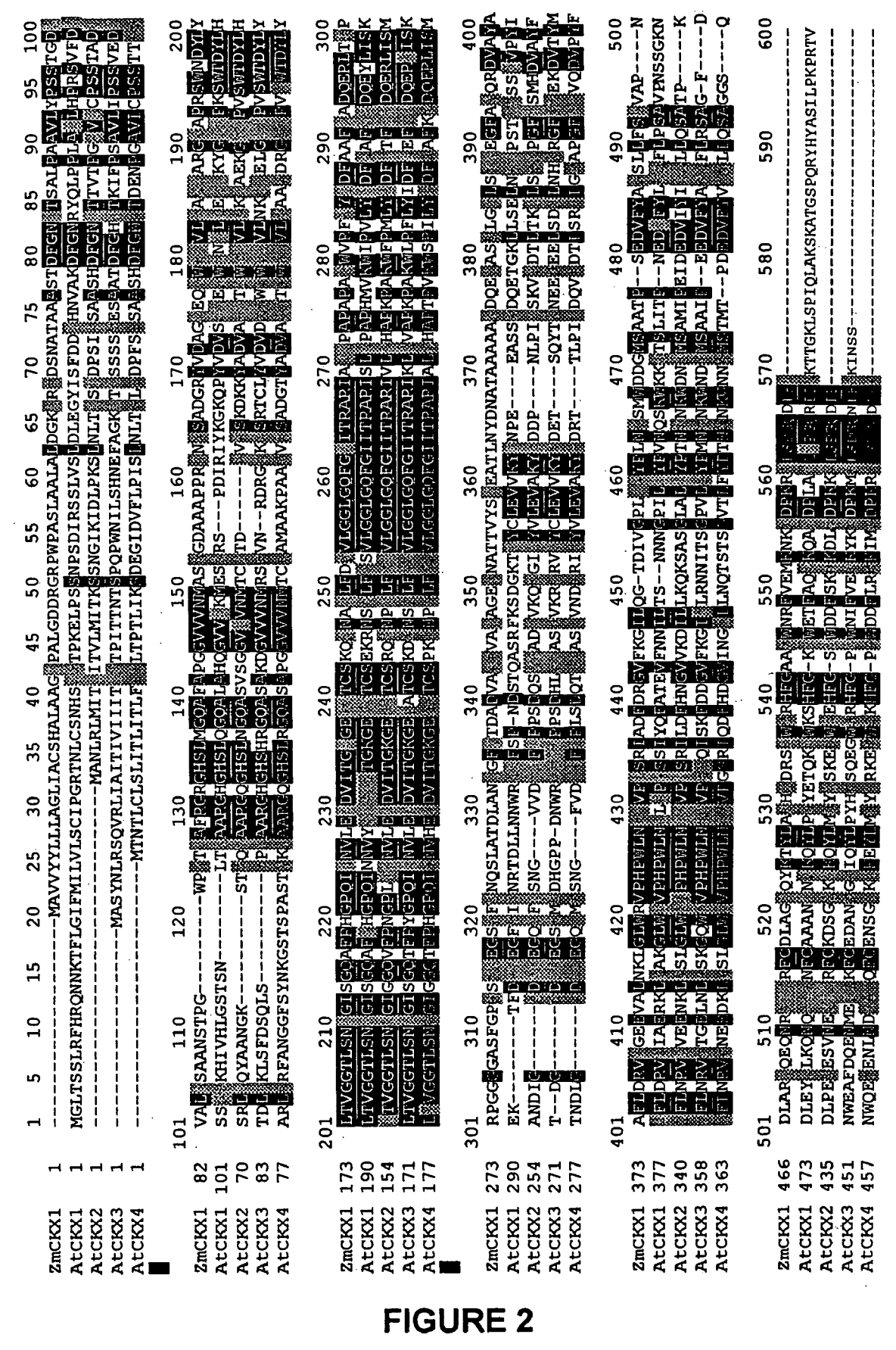

FIG. 2. Alignment of plant cytokinin oxidase amino acid sequences.

The amino acid sequences from cytokinin oxidases from maize (ZmCKX1) and Arabidopsis (AtCKX1 to AtCKX4) are aligned. Identical amino acid residues are marked by a black box, similar amino acid residues are in a grey box. Amino acid similarity groups: (M,I,L,V), (F,W,Y), (G,A), (S,T), (R,K,H), (E,D), (N,Q). ZmCKX1 is SEQ ID NO: 56: AtCKX1 is SEQ ID NO:2; AtCKX2 is SEQ ID NO:4; AtCKX3 is SEQ ID NO:6; and AtCKX4 is SEQ ID NO:8.

Figure 3:
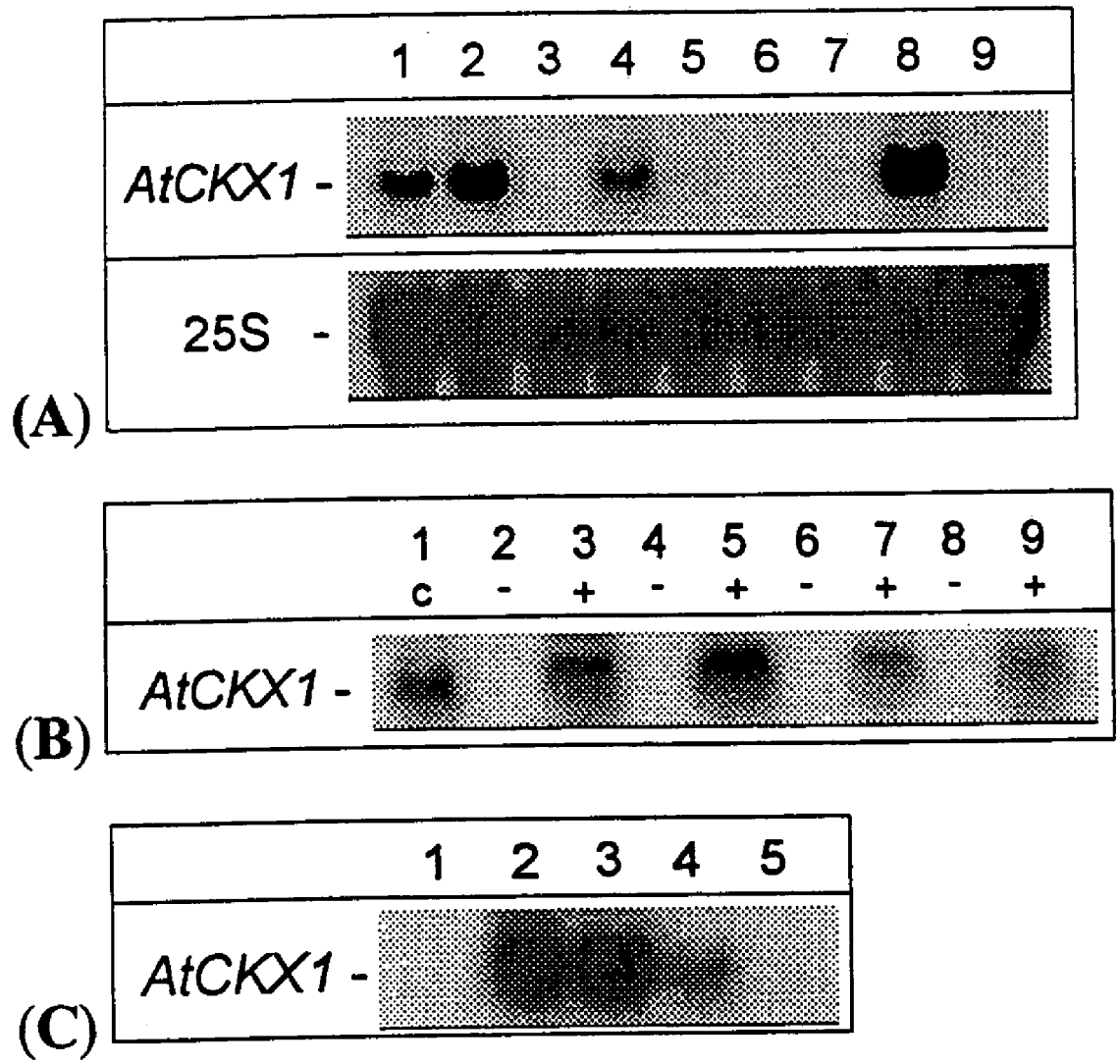

FIG. 3. Northern blot analysis of AtCKX1-expressing tobacco and *Arabidopsis* plants.

(A) Northern blot analysis of constitutively expressing tobacco plants (lanes 1-8) compared to wild type SNN tobacco (lane 9)

(B) Comparison of tetracycline-induced gene expression in leaves after 12 h of induction with a constitutively expressing clone. Lanes 2-9, leaves of four different AtCKX1-W38TetR clones (+, −, with or without tetracycline treatment), lane 1, constitutively expressing 35S::AtCKX1 clone.

(C) Northern blot analysis of *Arabidopsis* plants constitutively expressing AtCKX1 gene. Lanes 2-4, three different constitutively expressing 35S::AtCKX1 clones compared to wild type *Arabidopsis* plant (lane 1).

Figure 4:
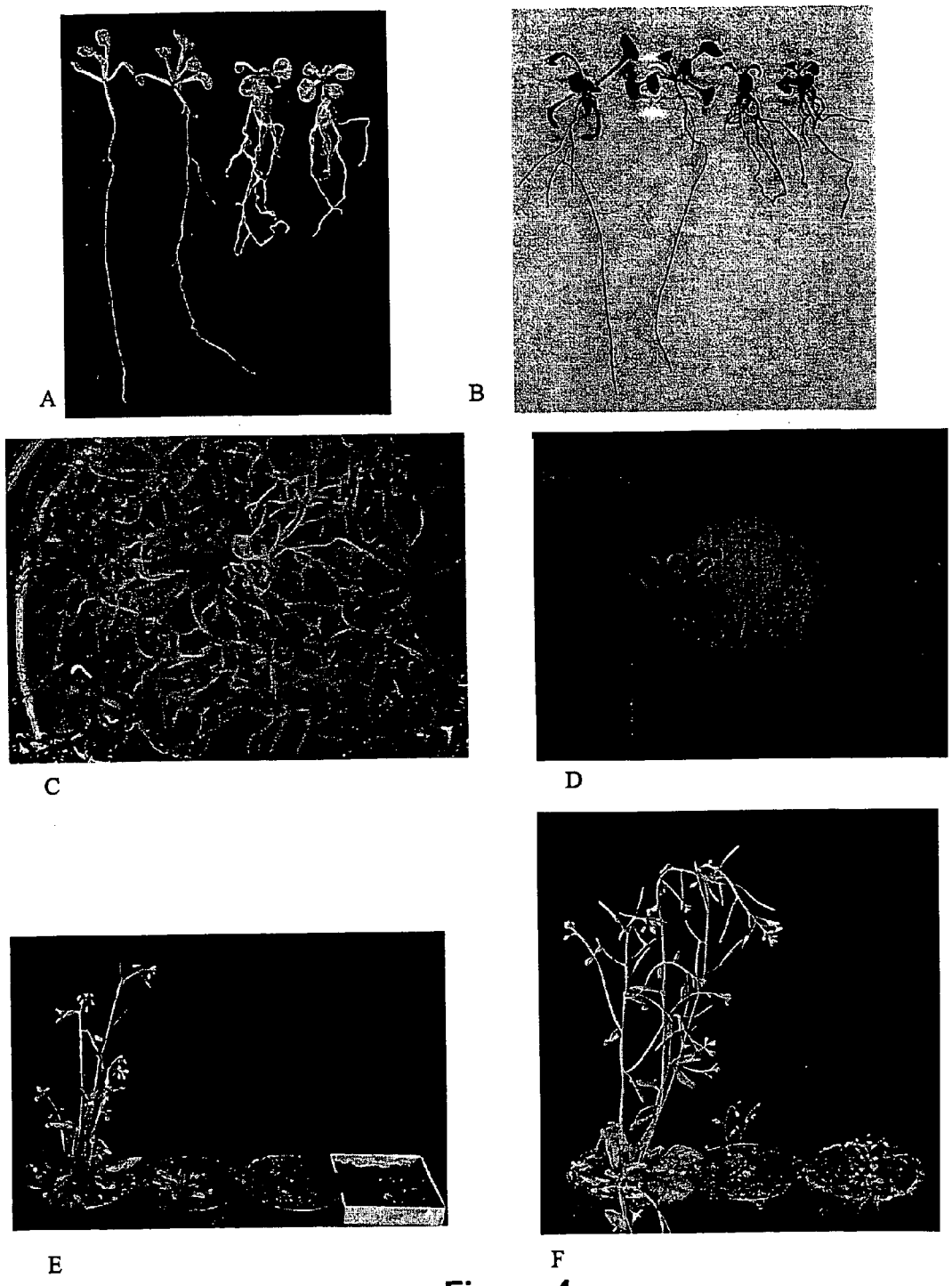

FIG. 4: Growth characteristics of 35S::AtCKX1 transgenic *Arabidopsis* plants.

(A) Two wild type seedlings (left) compared to two 35S::AtCKX1 expressing seedlings (right). Note the increased formation of adventitious roots and increased root branching in the transgenic seedlings. Pictures were taken 14 days after germination. Plants were grown in vitro on MS medium in petri dishes in a vertical position.

(B) Like A, but roots stained with toluidine blue.

(C) Top view of a petri dish with 35S::AtCKX1 transgenic seedlings three weeks after germination.

(D) A 35S::AtCKX1 transgenic plants grown in liquid culture. Roots of wild type seedlings grow poorly under these conditions (not shown).

(E) Transformants (T0) that express the 35S::AtCKX1 gene (three plants on the right), a wild type plant is shown on the left.

(F) Phenotype of T1 plants grown in soil. Wild type plant (left) compared to two 35S::AtCKX1 transgenic plants.

Figure 5:

FIG. 5: Phenotype of AtCKX2 overexpressing *Arabidopsis* plants.

T1 generation of 35S::AtCKX2 expressing *Arabidopsis* plants (two plants on the right) compared to wild type (plant on the left).

Figure 6:
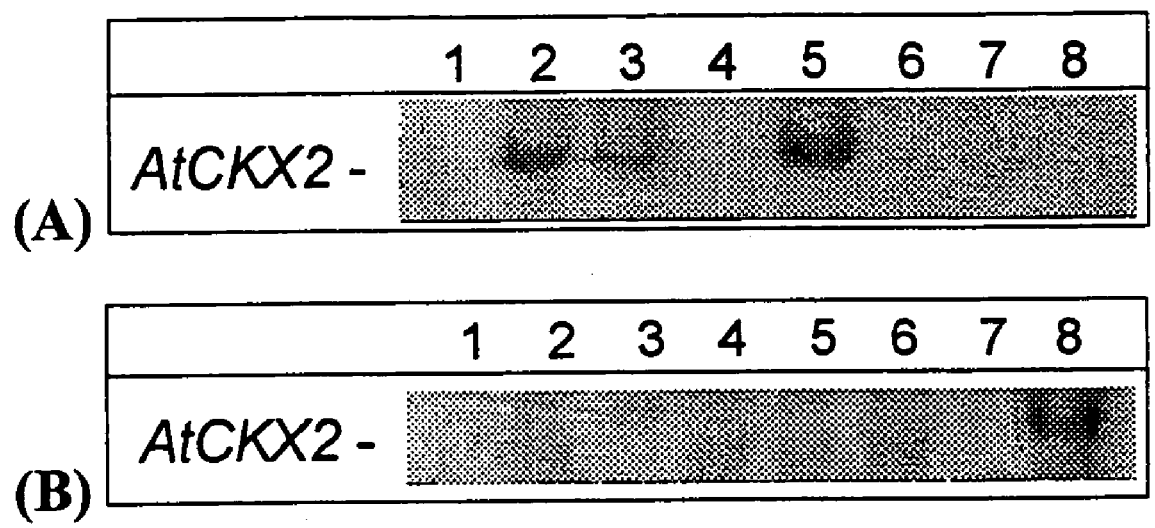

FIG. 6. Northern blot analysis of AtCKX2-expressing tobacco and *Arabidopsis* plants.

(A) Northern blot analysis of constitutively expressing tobacco plants (lanes 1-7) compared to wild type SNN tobacco (lane 8)

(B) Northern blot analysis of *Arabidopsis* plants constitutively expressing AtCKX2 gene. Lanes 2-8, seven different constitutively expressing 35S::AtCKX2 clones compared to wild type *Arabidopsis* plant (lane 1).

Figure 7:
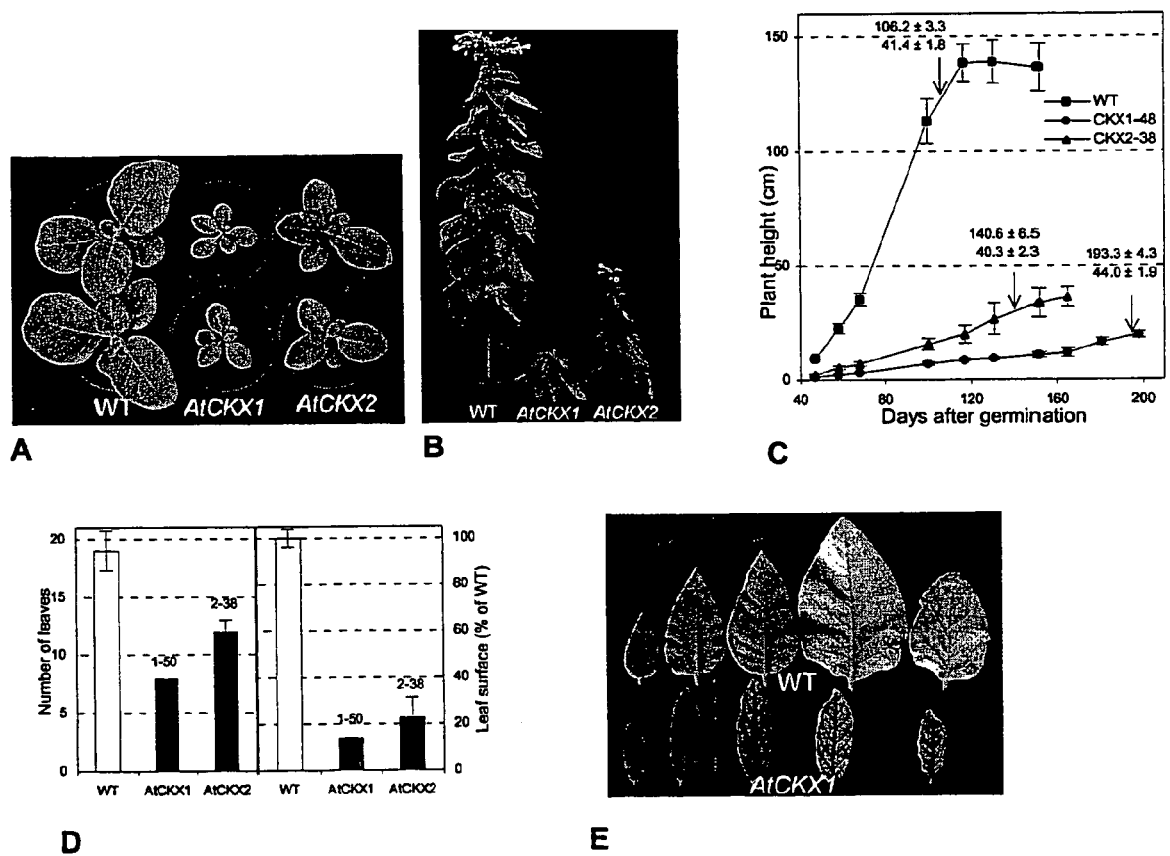

FIG. 7. Shoot phenotype of AtCKX1 and AtCKX2 expressing tobacco plants.

(A) Top view of six week old plants.

(B) Tobacco plants at the flowering stage.

(C) Kinetics of stem elongation. Arrows mark the onset of flowering. Age of plants (days after germination) and leaf number at that stage are indicated above the arrows. Bars indicate SD; n=12.

(D) Number of leaves (n=12) formed between day 68 and day 100 after germination and final surface area of these leaves (100% of wild type is 3646±144 $cm^2$; n=3).

(E) Comparison of leaf size and senescence. Leaves were from nodes number 4, 9, 12, 16 and 20 from the top (from left to right).

Figure 8:
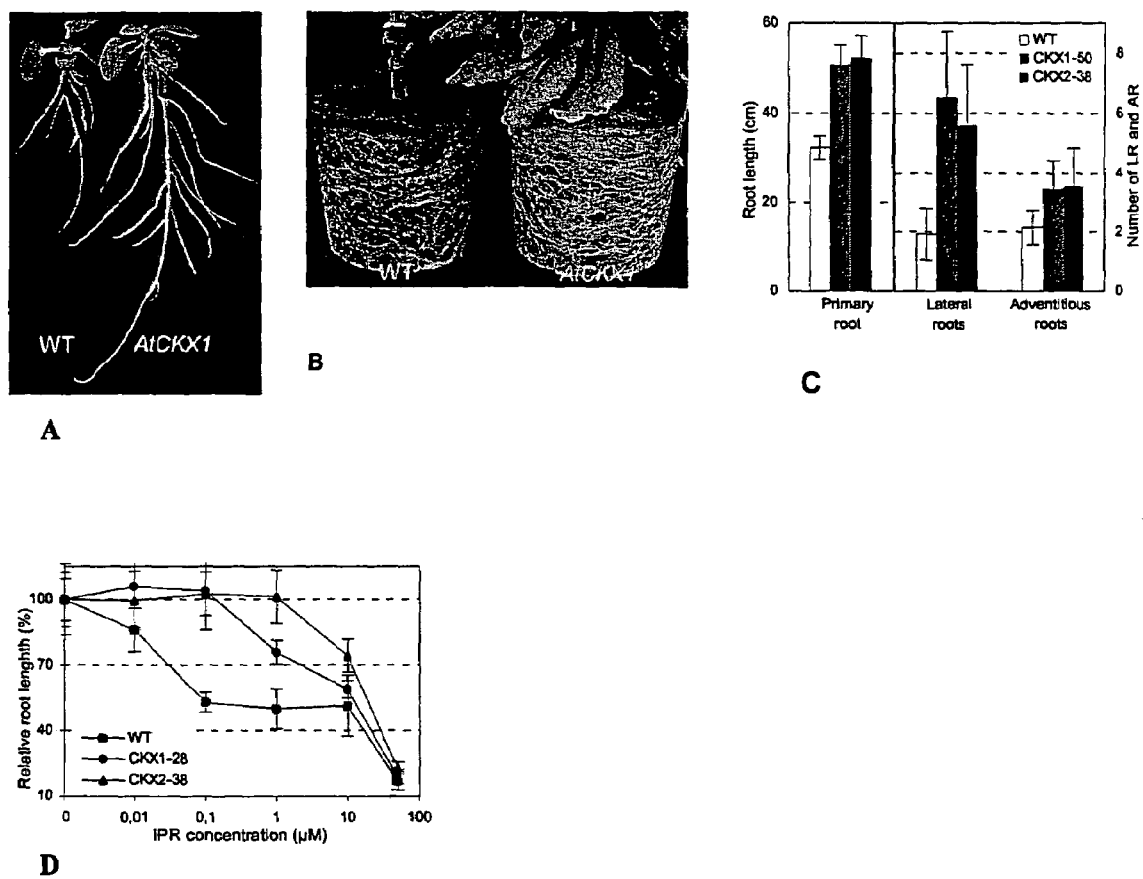

FIG. 8. Root phenotype of AtCKX expressing transgenic tobacco plants.

(A) Seedlings 17 days after germination.

(B) Root system of soil grown plants at the flowering stage.

(C) Root length, number of lateral roots (LR) and adventitious roots (AR) on day 10 after germination.

(D) Dose-response curve of root growth inhibition by exogenous cytokinin. Bars indicate ±SD; n=30.

Figure 9:

FIG. 9: Growth of axillary shoot meristems in 35S::AtCKX1 expressing tobacco plants.

Figure 10:
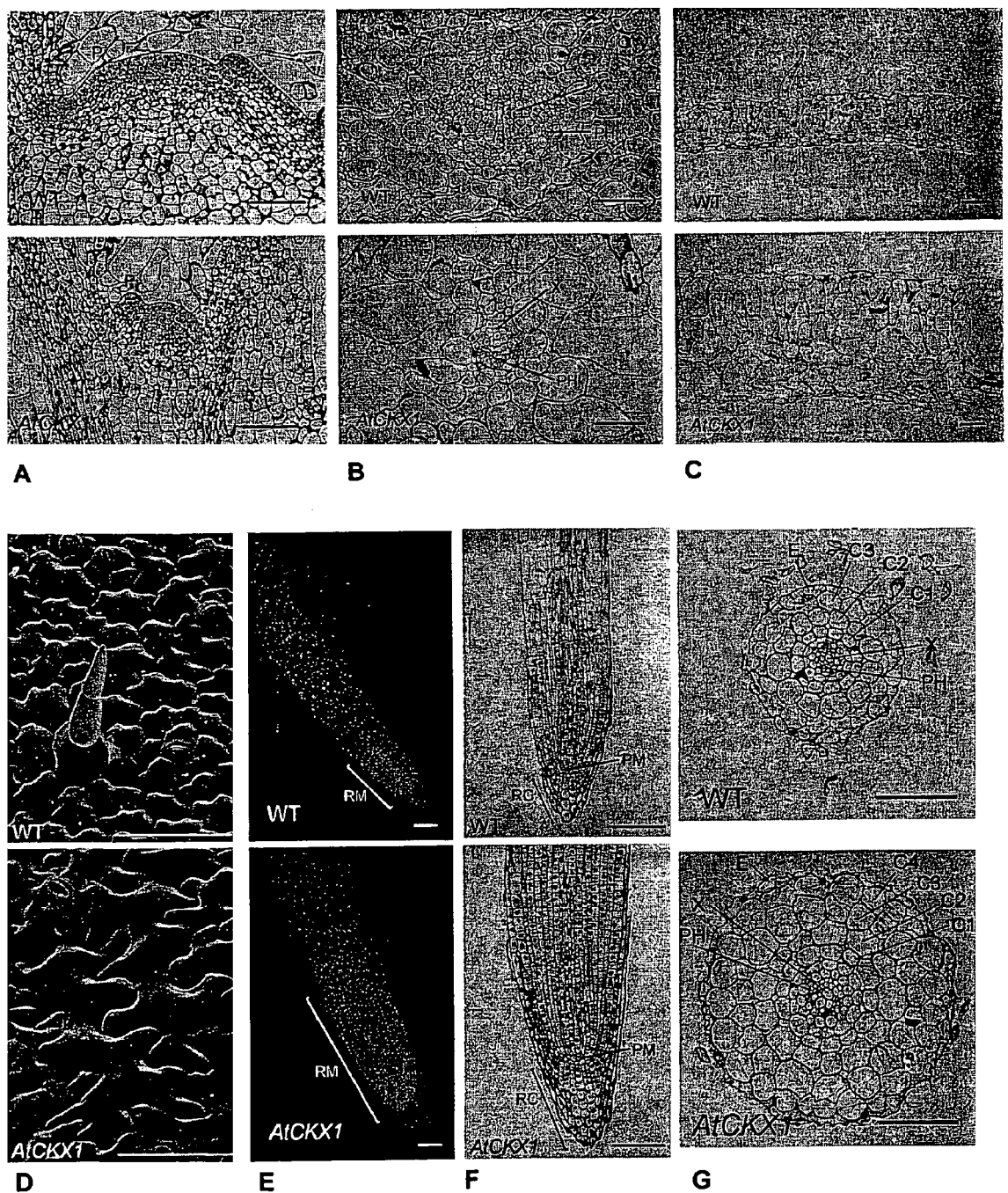

FIG. 10: Histology of shoot meristems, leaves and root meristems of AtCKX1 overexpressing tobacco plants versus wild type (WT) tobacco.

(A) Longitudinal median section through the vegetative shoot apical meristem. P, leaf primordia.

(B) Vascular tissue in second order veins of leaves. X, xylem, PH, a phloem bundle.

(C) Cross sections of fully developed leaves.

(D) Scanning electron microscopy of the upper leaf epidermis.

(E) Root apices stained with DAPI. RM, root meristem.

(F) Longitudinal median sections of root meristems ten days after germination. RC, root cap; PM, promeristem.

(G) Transverse root sections 10 mm from the apex. E, epidermis, C1-C4, cortical cell layer, X, xylem, PH, phloem. Bars are 100 µm.

Figure 11:
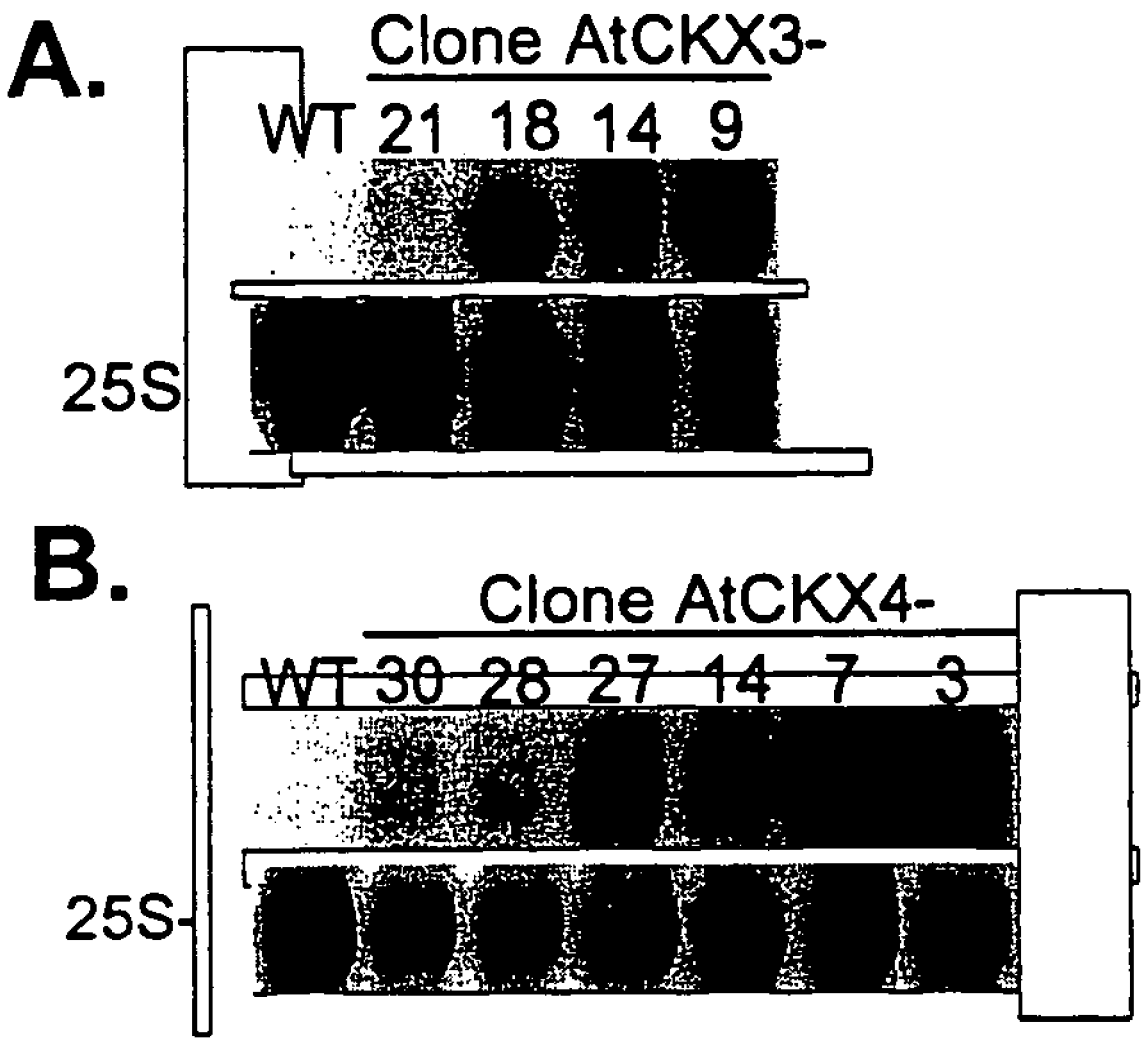

FIG. 11: Northern blot analysis of AtCKX3 and AtCKX4-expressing tobacco plants.

(A) Northern blot analysis of constitutively expressing AtCKX3 tobacco plants. Lane designations indicate individual transgenic plant numbers, WT is wild type SNN tobacco. The blot on top was probed with a AtCKX3 specific probe, the lower blot with a probe specific for the 25S rRNA and serves as a control for RNA loading.

(B) Northern blot analysis of constitutively expressing AtCKX4 tobacco plants. Lane designations indicate individual transgenic plant numbers, WT is wild type SNN tobacco. The blot on top was probed with an AtCKX4 specific probe, the lower blot with a probe specific for the 25S rRNA and serves as a control for RNA loading.

Figure 12:
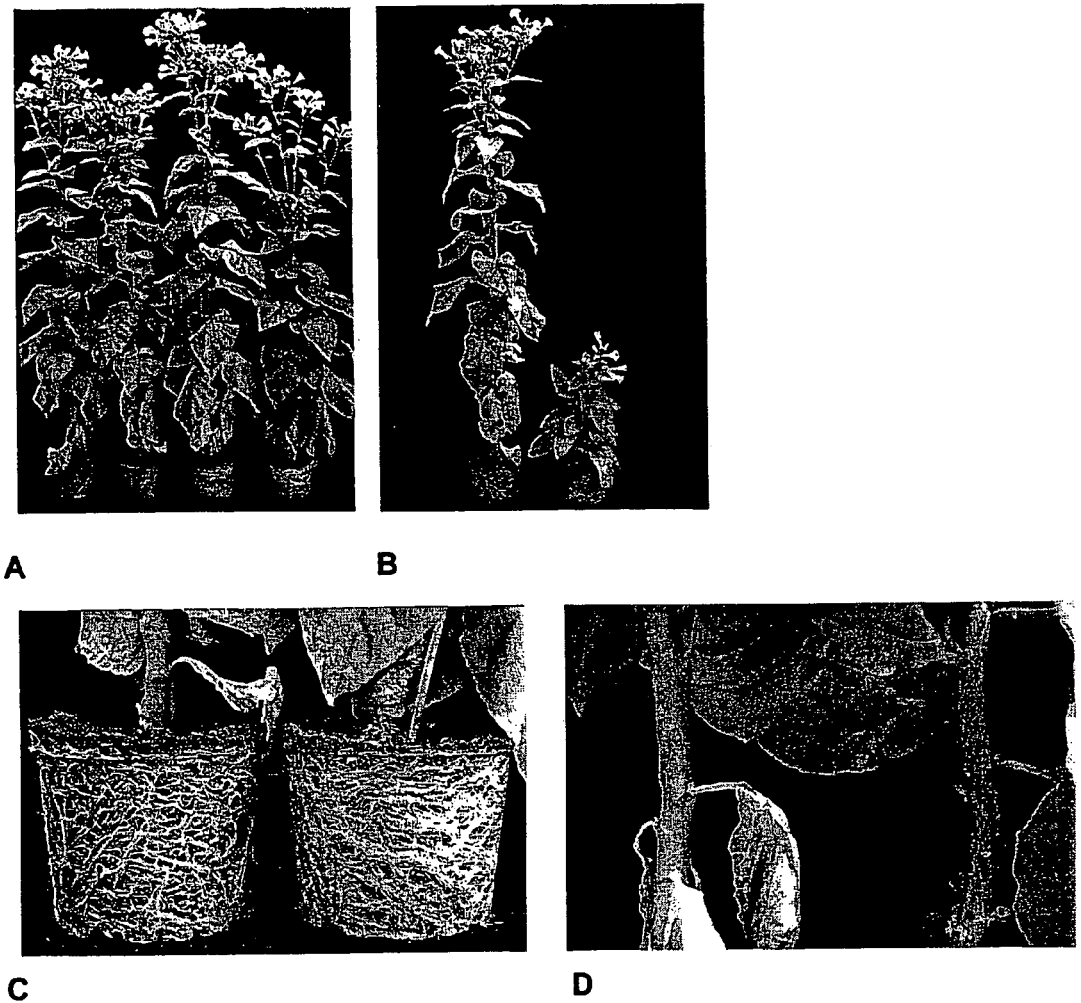

FIG. 12: Reciprocal grafts of AtCKX2 transgenic tobacco plants and wild type plants.

(A) Two plants on the left: Control (WT scion grafted on a WT rootstock).

Two plants on the right: WT scion grafted on a AtCKX2-38 transgenic rootstock.

(B) Left: Control (WT scion grafted on a WT rootstock).

Right: Scion of AtCKX2-38 plant grafted on WT rootstock.

(C) Magnification of root area.

Left: Control (WT scion grafted on a WT rootstock).

Right: WT scion grafted on an AtCKX2-38 transgenic rootstock.

(D) Formation of adventitious roots.

Left: Control (WT scion grafted on an WT rootstock).

Right: WT scion grafted on an AtCKX2-38 transgenic rootstock.

Figure 13C:
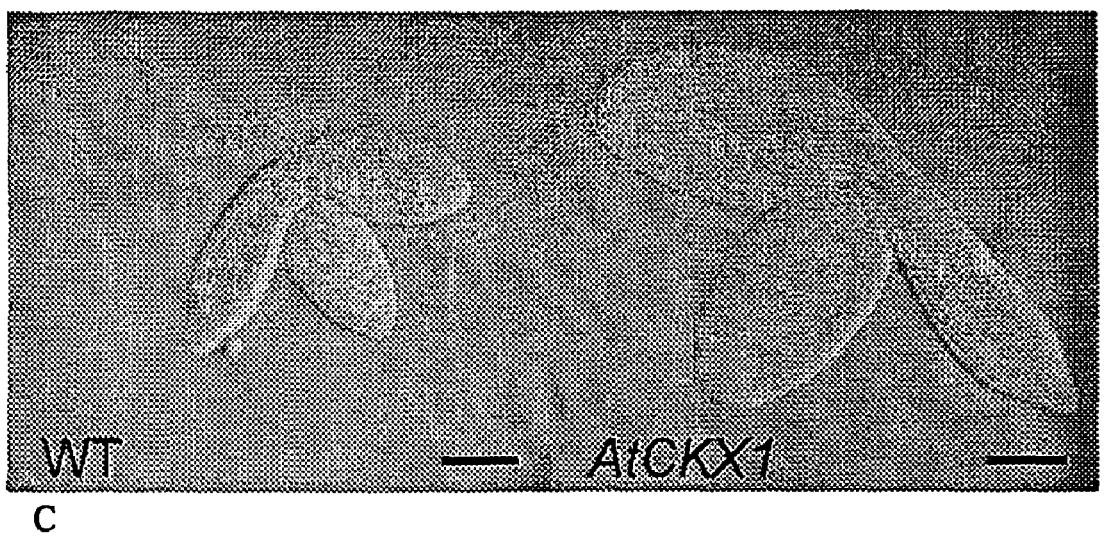
Figure 13D:
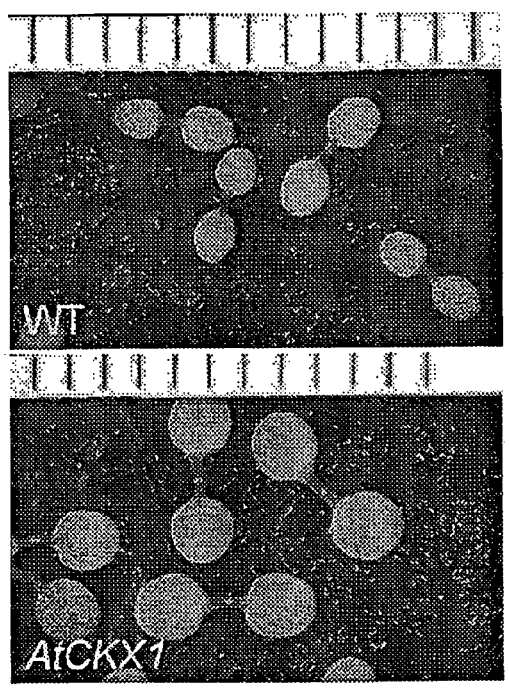
Figure 13E:
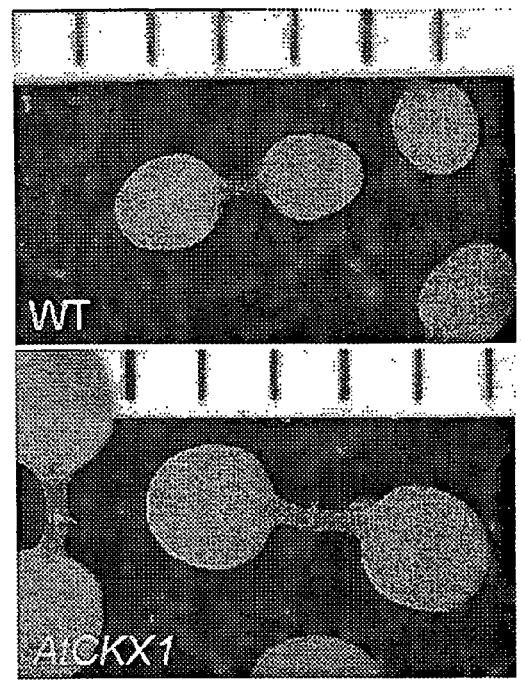

FIG. 13: Phenotype of *Arabidopsis* seeds, embryos and seedlings.

(A) Seeds of an AtCKX1 transgenic line and wild type seeds. Bar size 1 mm.

(B) Seeds of AtCKX1, AtCKX2, AtCKX3 and AtCKX4 transgenic lines and wild type seeds. Bar size 1 mm.

(C) Mature embryos of AtCKX1 transgenic *Arabidopsis* and of a wild type plant. Bar size 200 µm. Embryos were obtained from mature seeds that had been imbibed for 12 hours in 20% EtOH, squeezed out from the seed coat, cleared with chloralhydrate and photographed using Nomarski optics.

(D) Wild type (top) and AtCKX1 expressing *Arabidopsis* seedlings 4 days after germination.

(E) Close-up of D.

Figure 14:
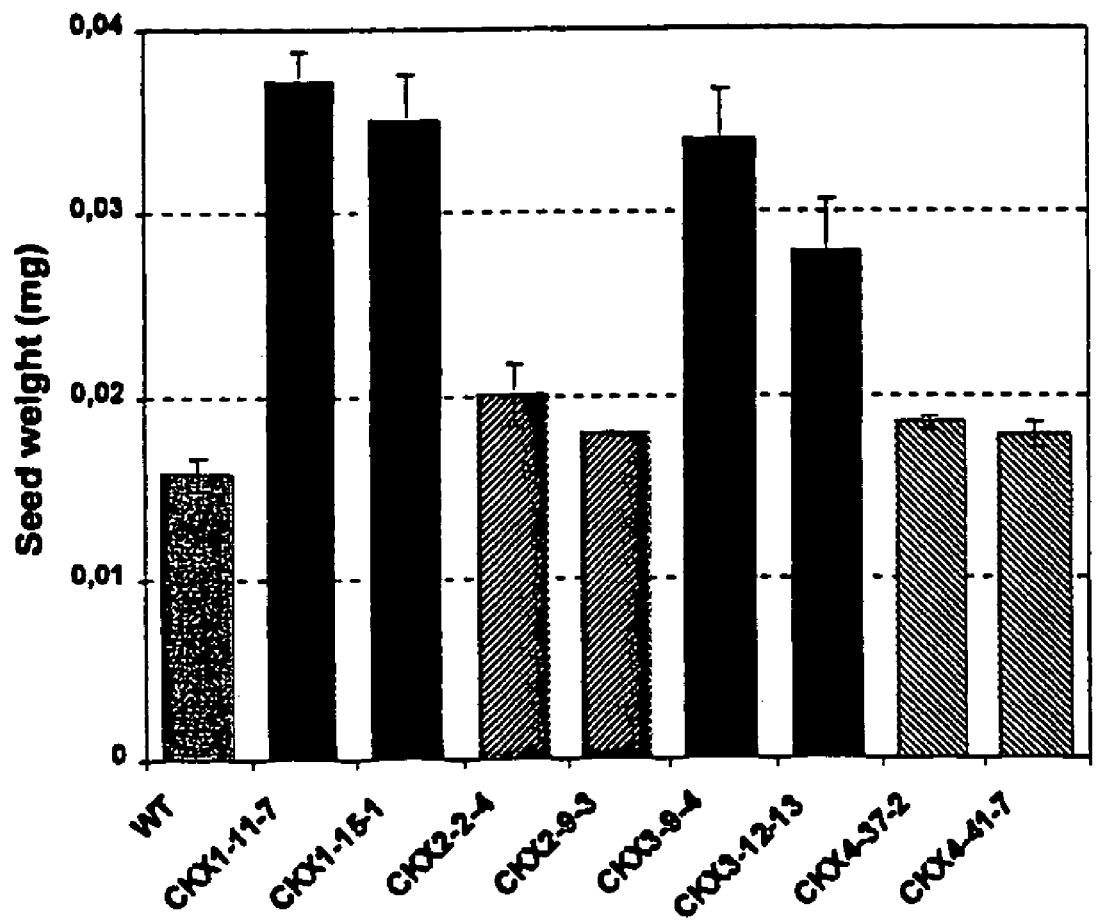

FIG. 14: Seed weight of wild type and two independent clones for each of the four investigated AtCKX genes. Average weight obtained by analysing five different batches of 200 seeds for each clone.

Figure 15:
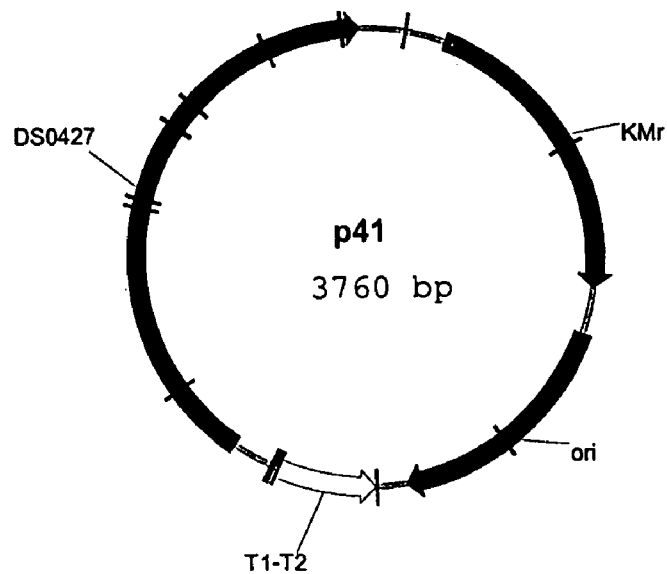

FIG. 15: Schematic presentation of the entry clone p41, containing CDS0427_2 within the AttL1 and AttL2 sites for Gateway® cloning in the pDONR201 backbone. CDS0427_2 is the internal code for the *Arabidopsis thaliana* CKX2 coding sequence (SEQ ID NO: 44). This vector contains also a bacterial kanamycine-resistance cassette and a bacterial origin of replication.

Figure 16:
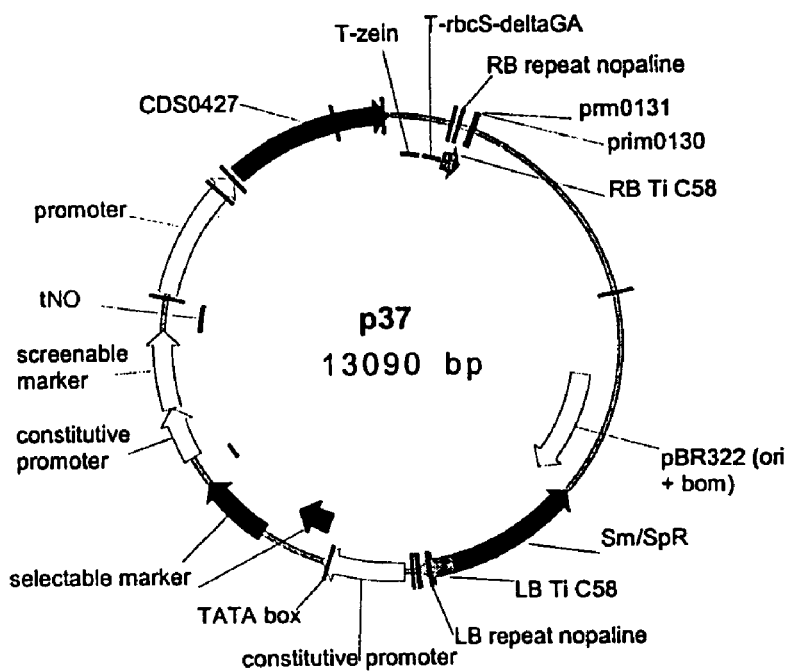

FIG. 16: Binary vector p37 for the expression in *Oryza sativa* of the *Arabidopsis thaliana* CKX2 gene under the control of the PRO0218 promoter. This vector contains a T-DNA derived from the Ti plasmid, limited by a left border (LB repeat, LB Ti C58) and a right border (RB repeat, RB Ti C58)). From the left border to the right border, this T-DNA contains: a selectable and a screenable marker for selection of transformed plants, each under control of a constitutive promoter; the PRO0218-CDS0427_2-zein and rbcS-deltaGA double terminator cassette for expression of the *Arabidopsis thaliana* CKX2 gene. This vector also contains an origin of replication from pBR322 for bacterial replication and a selectable marker (Spe/SmeR) for bacterial selection with spectinomycin and streptomycin.

Figure 17:
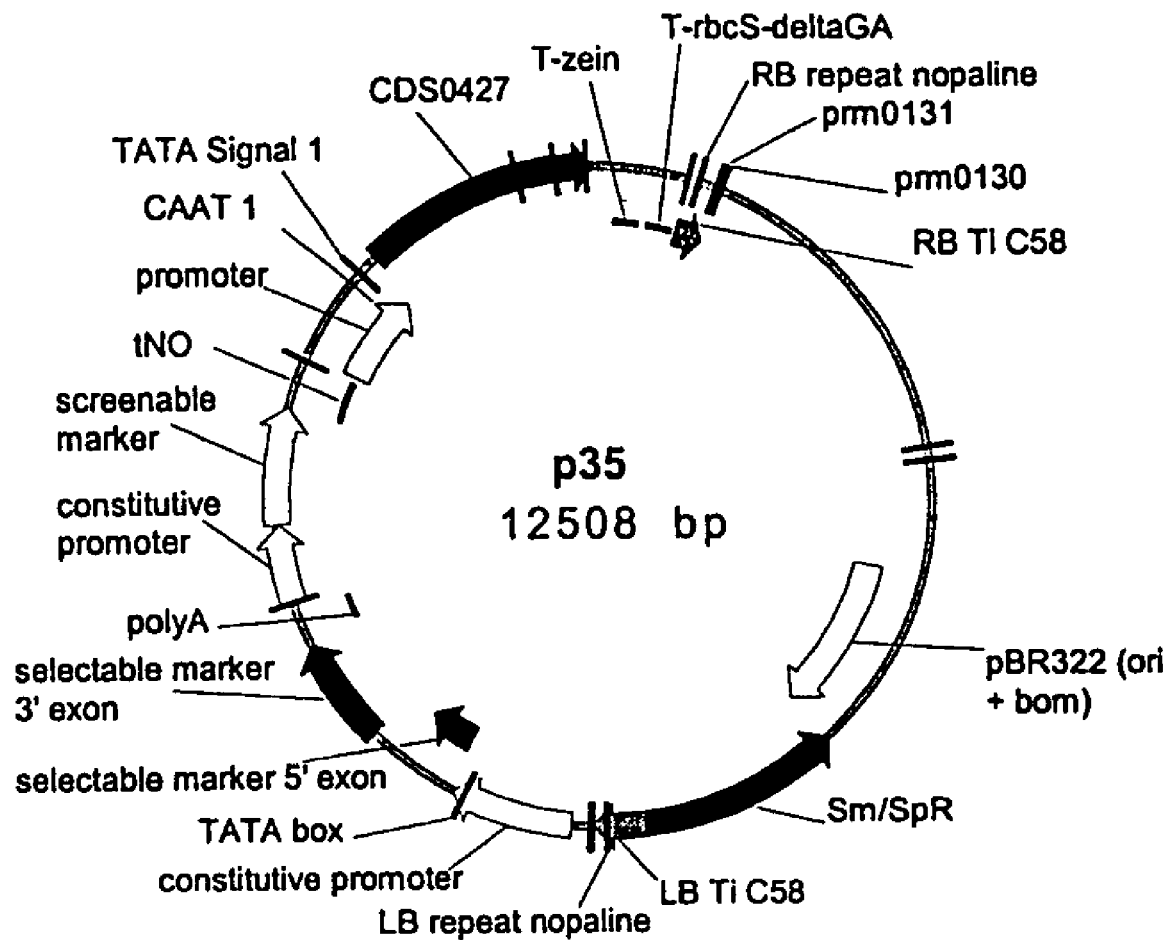

FIG. 17: Binary vector p35 for the expression in *Oryza sativa* of the *Arabidopsis thaliana* CKX2 gene under the control of the PRO0090 promoter. This vector contains a T-DNA derived from the Ti plasmid, limited by a left border (LB repeat, LB Ti C58) and a right border (RB repeat, RB Ti C58)). From the left border to the right border, this T-DNA contains: a selectable and a screenable marker for selection of transformed plants, each under control of a constitutive promoter; the PRO0090-CDS0427_2-zein and rbcS-deltaGA double terminator cassette for expression of the *Arabidopsis thaliana* CKX2 gene. This vector also contains an origin of replication from pBR322 for bacterial replication and a selectable marker (Spe/SmeR) for bacterial selection with spectinomycin and streptomycin.

Figure 18:
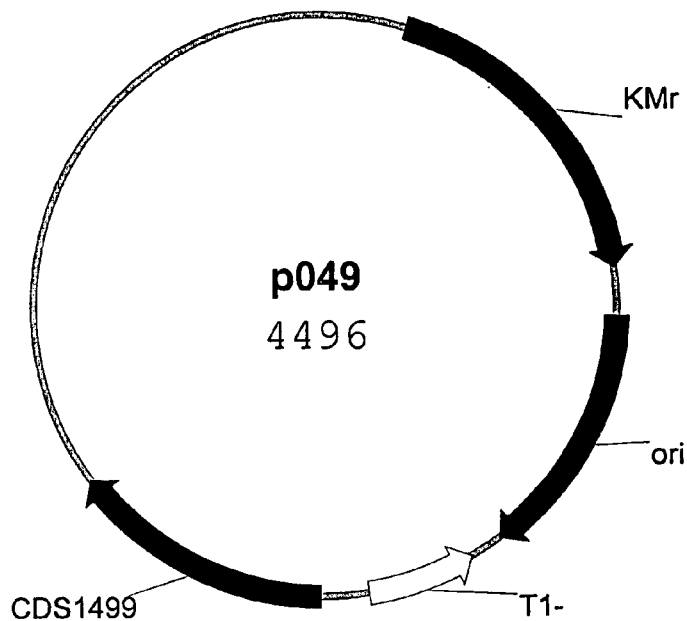

FIG. 18: Schematic presentation of the entry clone p049, containing CDS1499_2 within the AttL1 and AttL2 sites for Gateway® cloning in the pDONR201 backbone. CDS1499_2 is the internal code for the *Arabidopsis thaliana* CKX1 coding sequence (SEQ ID NO:48). This vector contains also a bacterial kanamycine-resistance cassette and a bacterial origin of replication.

Figure 19:
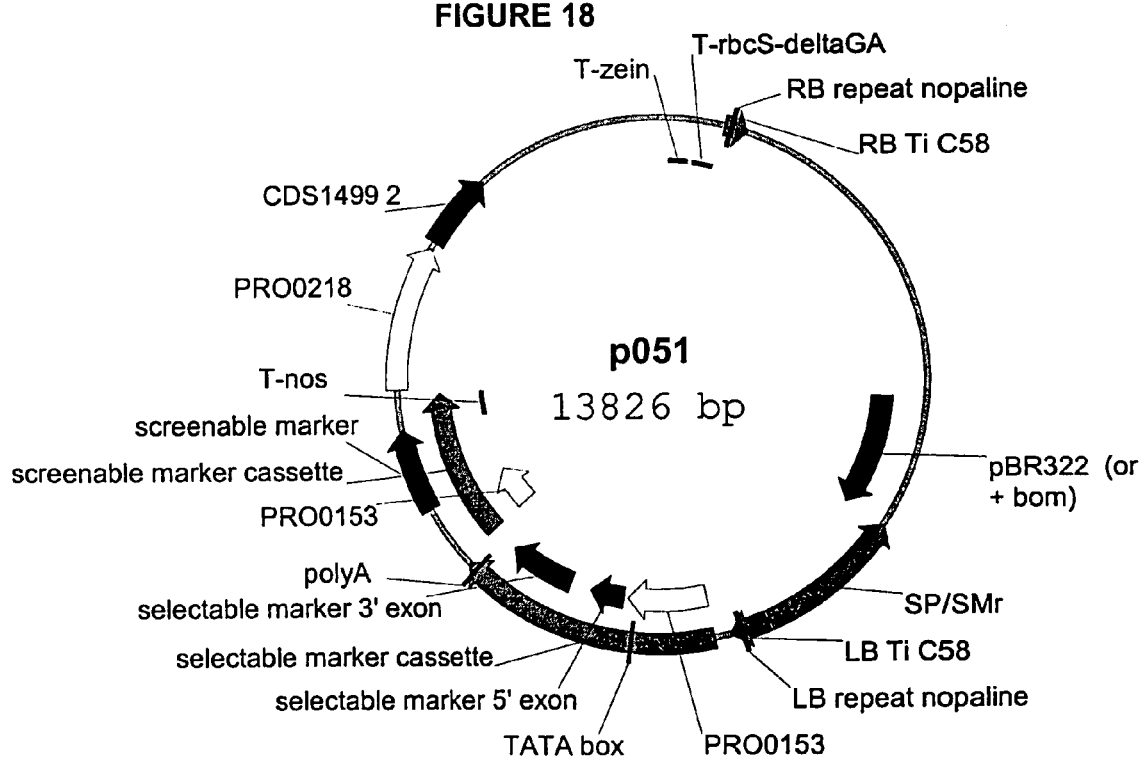

FIG. 19: Binary vector p051 for the expression in *Oryza sativa* of the *Arabidopsis thaliana* CKX1 gene under the control of the PRO0218 promoter. This vector contains a T-DNA derived from the Ti plasmid, limited by a left border (LB repeat, LB Ti C58) and a right border (RB repeat, RB Ti C58)). From the left border to the right border, this T-DNA contains: a selectable and a screenable marker for selection of transformed plants, each under control of a constitutive promoter; the PRO0218-CDS1499_2-zein and rbcS-deltaGA double terminator cassette for expression of the *Arabidopsis thaliana* CKX1 gene. This vector also contains an origin of replication from pBR322 for bacterial replication and a selectable marker (Spe/SmeR) for bacterial selection with spectinomycin and streptomycin.

Figure 20:
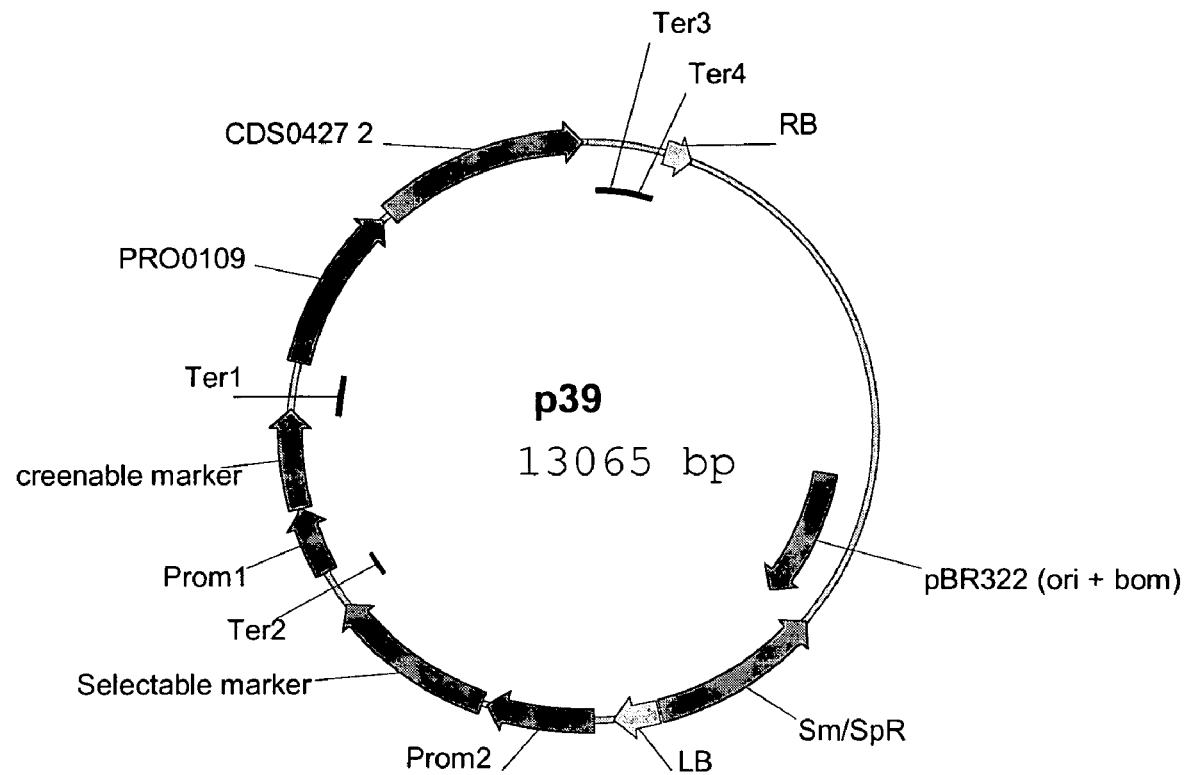

FIG. 20: Schematic presentation of the expression vector p39 for the expression in plants of *Arabidopsis* CKX under the control of the PRO0109 promoter (SEQ ID NO 56). CDS0427_2 is the internal code for CKX cDNA as presented in SEQ ID NO 50. To be expressible in the plant, the CKX expression cassette with the PRO0109 promoter and the double terminator sequence (Ter3 and Ter4), is located within the left border (LB repeat) and the right border (RB repeat) of the Ti plasmid. Within these T-borders, also a screenable marker and a selectable marker are cloned, each under a constitutive promoter (Prom1 and 2) and followed by a terminator sequence (Ter1 and 2). This vector furthermore contains an origin of replication (pBR322 (ori+bom)) for bacterial replication and a selectable marker (Sm/SpR) for bacterial selection.

Figure 21:
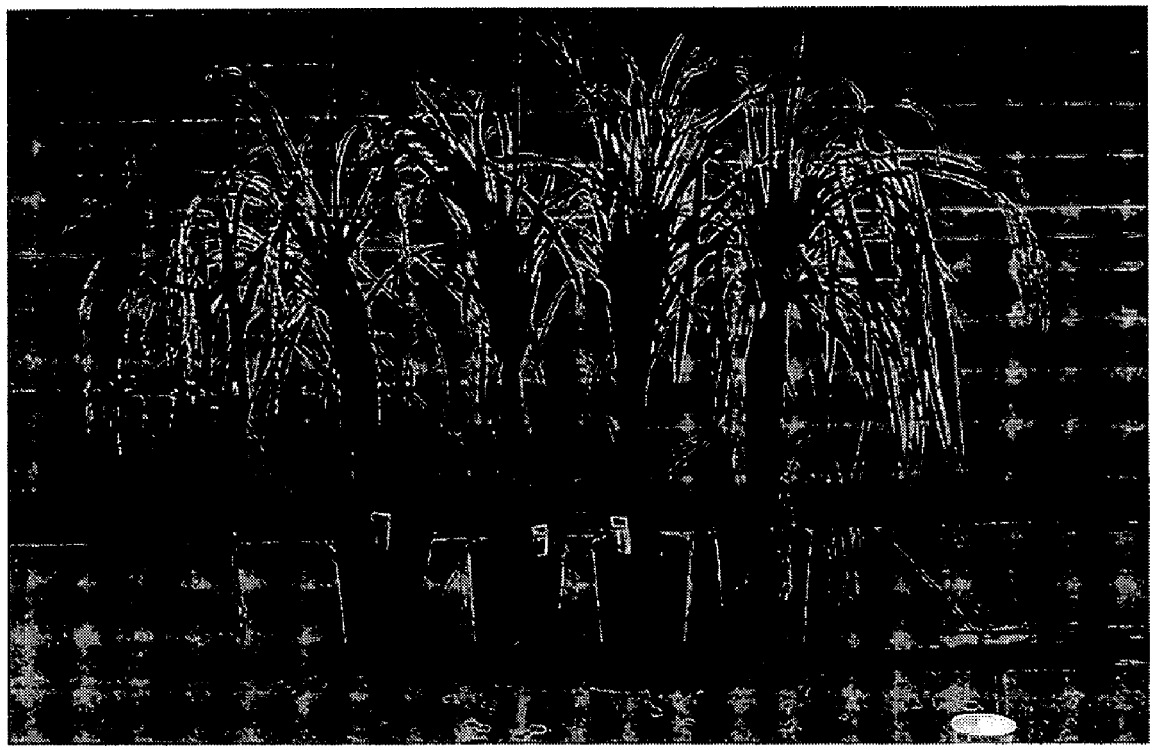

FIG. 21: Phenotype of rice plants transformed with SEQ ID NO 50 under control of the promoter as represented in SEQ ID NO 56. The plants on the left are nullizygous control plants.

Figure 22:
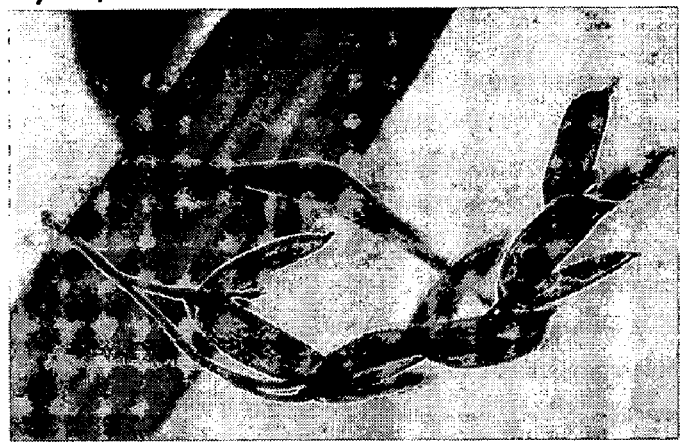
Figure 22:
Figure 22:

FIGS. 22A-C show the expression pattern of the beta expansine EXPB9 promoter (SEQ ID NO: 60). GUS staining is visible in young flowers of A plants (A) and in other young expanding tissues of B plants (B) and C plants (C).

DETAILED DESCRIPTION OF THE INVENTION

Novel genes encoding cytokinin oxidases (which are cytokinin metabolizing enzymes) were cloned from *Arabidopsis thaliana* (designated AtCKX) and were subsequently expressed under a strong constitutive promoter in transgenic tobacco and *Arabidopsis*. Transformants showing AtCKX mRNA expression and increased cytokinin oxidase activity also manifested enhanced formation and growth of roots. Negative effects on shoot growth were also observed. The latter is in accordance with the constitutive expression of the cytokinin oxidase gene in these plants, illustrating the importance of confined expression of the cytokinin oxidase gene for general plant growth properties. Containment of cytokinin oxidase activity can be achieved by using cell-, tissue- or organ-specific promoters, since cytokinin degradation is a process limited to the tissues or cells that express the CKX protein, this in contrast to approaches relying on hormone synthesis, as explained above.

The observed negative effects of cytokinin oxidase expression on shoot growth demonstrate that cytokinin oxidases are interesting targets for the design of or screening for growth-promoting chemicals. Such chemicals should inhibit cytokinin oxidase activity, should preferably not be transported to the root and should be rapidly degraded in soil, so that application of these chemicals will not inhibit root growth. Cytokinins also delay leaf senescence, which means that positive effects will include both growth and maintenance of photosynthetic tissues. In addition, the observation that cytokinins delay senescence, enhance greening (chlorophyll content) of leaves and reduce shoot apical dominance shows that strategies based on suppressing CKX activity (such as antisense, ribozyme, and cosuppression technology) in the aerial parts of the plant could result in delayed senescence, enhanced leaf greening and increased branching.

Similarly, the observed positive effects of cytokinin oxidase expression on root growth demonstrate that cytokinin oxidases are interesting targets for the design of or screening for herbicides. Such herbicides should inhibit cytokinin oxidase activity, should preferably not be transported to the shoot, and should be soluble and relatively stable in a solvent that can be administered to the root through the soil.

These effects of cytokinin oxidase overexpression on plant development and architecture were hitherto unknown and, as a consequence, the presented invention and its embodiments could not be envisaged.

The observed negative effects on shoot growth demonstrate that manipulation of cytokinin oxidases can also be used for obtaining dwarfing phenotypes. Dwarfing phenotypes are particularly useful in commercial crops such as cereals and fruit trees for example.

In accordance with the present invention, it has also been surprisingly discovered that transgenic plants overexpressing a cytokinin oxidase gene develop seeds (including embryos) and cotyledons of increased size and/or weight. These results are surprising as a reduced cytokinin content would have been expected to be associated with a reduced organ growth.

Preferable embodiments of the invention relate to the positive effect of cytokinin oxidase expression on plant growth and architecture, and in particular on root growth and architecture, harvest index, seed size and weight, embryo size and weight, and cotyledon size and weight. The cytokinin oxidase gene family contains at least six members in *Arabidopsis* (see examples below) and the present inventors have shown that there are quantitative differences in the effects achieved with some of these genes in transgenic plants. It is anticipated that functional homologs of the described *Arabidopsis* cytokinin oxidases can be isolated from other organisms, given the evidence for the presence of cytokinin oxidase activity in many green plants (Hare and van Staden, Physiol Plant 91:128-136, 1994; Jones and Schreiber, Plant Growth Reg 23:123-134, 1997), as well as in other organisms (Armstrong, in Cytokinins: Chemistry, Activity and Function. Eds Mok and Mok, CRC Press, pp 139-154, 1994). Therefore, the sequence of the cytokinin oxidase, functional in the invention, need not to be identical to those described herein. This invention is particularly useful for cereal crops and monocot crops in general and cytokinin oxidase genes from for example wheat or maize may be used as well (Morris et al., 1999; Rinaldi and Comandini, 1999). It is envisaged that other genes with cytokinin oxidase activity or with any other cytokinin metabolizing activity (see Zažímalová et al., Biochemistry and Molecular Biology of Plant Hormones, Hooykaas, Hall and Libbenga (Eds.), Elsevier Science, pp 141-160, 1997) can also be used for the purpose of this invention. Similarly, genes encoding proteins that would increase endogenous cytokinin metabolizing activity can also be used for the purpose of this invention. In principle, similar phenotypes could also be obtained by interfering with genes that function downstream of cytokinin such as receptors or proteins involved in signal transduction pathways of cytokinin.

For the purpose of this invention, it should be understood that the term 'root growth' encompasses all aspects of growth of the different parts that make up the root system at different stages of its development, both in monocotyledonous and dicotyledonous plants. It is to be understood that enhanced growth of the root can result from enhanced growth of one or more of its parts including the primary root, lateral roots, adventitious roots, etc. all of which fall within the scope of this invention.

For purposes of this invention, it should also be understood that increases in seed weight or seed size can include increases in the size of one or more of the embryo, the endosperm, aleurone, and seed coat. Moreover, increases in embryo size and/or weight can include increases in different organs associated therewith such as e.g., cotyledons, hypocotyl, and roots.

According to a first embodiment, the present invention relates to a method for stimulating root growth and/or enhancing the formation of lateral and/or adventitious roots and/or altering root geotropism comprising expression of a plant cytokinin oxidase or comprising expression of another protein that reduces the level of active cytokinins in plants or plant parts.

In another embodiment, the present invention relates to a method for increasing plant seed size and/or weight, by increasing the level or activity of a cytokinin oxidase in the plant or by expression of another protein that reduces the level of active cytokinins in a plant or plant part. Preferably, the increased level or activity of a cytokinin oxidase or expression of another protein that reduces the level of active cytokinins in a plant or plant part is localized in the seed including different tissues or cell types of the seed.

In another embodiment, the present invention relates to a method for increasing plant embryo size and/or weight, by increasing the level or activity of a cytokinin oxidase in the plant or by expression of another protein that reduces the level of active cytokinins in a plant or plant part. Preferably, the increased level or activity of a cytokinin oxidase or expression of another protein that reduces the level of active cytokinins in a plant or plant part is localized in the seed. Even more preferably, the increased level or activity of a cytokinin oxidase or expression of another protein that reduces the level of active cytokinins in a plant or plant part is localized in the embryo.

In yet another embodiment, the present invention relates to a method for increasing plant cotyledon size and/or weight, by increasing the level or activity of a cytokinin oxidase in the plant or by expression of another protein that reduces the level of active cytokinins in a plant or plant part. Preferably, the increased level or activity of a cytokinin oxidase or expression of another protein that reduces the level of active cytokinins in a plant or plant part is localized in the cotyledon.

In the context of the present invention it should be understood that the term "expression" and/or 'overexpression' are used interchangeably and both relate to an "enhanced and/or ectopic expression" of a plant cytokinin oxidase or any other protein that reduces the level of active cytokinins in plants. It should be clear that herewith an enhanced expression of the plant cytokinin oxidase as well as "de novo" expression of plant cytokinin oxidases or of said other proteins is meant. Alternatively, said other protein enhances the cytokinin metabolizing activity of a plant cytokinin oxidase.

It further should be understood that in the context of the present invention the expression "lateral and/or adventitious roots" can mean "lateral and adventitious roots" but also "lateral or adventitious roots". The enhancement can exist in the formation of lateral roots or in the formation of adventitious roots as well as in the formation of both types of non-primary roots, but not necessarily.

In addition, as used herein, "increasing seed size and/or weight," can mean increasing seed size and weight, but also size or weight. Thus, the enhancement can exist in an increase in the size of the seed or the weight of the seed or both. Similar interpretations should be applied to "increasing embryo size and/or weight" and "increasing cotyledon size and/or weight."

The terms "plant" and "plant part" are used interchangeably with the terms "plants" and "plant parts."

According to a further embodiment, the present invention relates to a method for stimulating root growth and/or enhancing the formation of lateral or adventitious roots and/or altering root geotropism and/or increasing yield and/or enhancing early vigor and/or modifying root/shoot ratio and/or improving resistance to lodging and/or increasing drought tolerance and/or promoting in vitro propagation of explants, comprising expression of a plant cytokinin oxidase or comprising expression of another protein that reduces the level of active cytokinins in plants or plant parts.

According to a preferred embodiment, the present invention relates to a method for stimulating root growth resulting in an increase of root mass by overexpression of a cytokinin oxidase, preferably a cytokinin oxidase according to the invention, or another protein that reduces the level of active cytokinins in plants or plant parts, preferably in roots.

Higher root biomass production due to overexpression of growth promoting sequences has a direct effect on the yield and an indirect effect of production of compounds produced by root cells or transgenic root cells or cell cultures of said transgenic root cells. One example of an interesting compound produced in root cultures is shikonin, the yield of which can be advantageously enhanced by said methods.

According to a more specific embodiment, the present invention relates to methods for stimulating root growth or for enhancing the formation of lateral and/or adventitious roots or for altering root geotropism or for increasing seed size and/or weight, or for increasing embryo size and/or weight, or for increasing cotyledon size and/or weight, or for increasing seed yield or harvest index. The methods comprise expression of a nucleic acid encoding a cytokinin oxidase selected from the group consisting of:

(a) nucleic acids comprising a DNA sequence as given in any of SEQ ID NOs: 48, 44, 38, 27, 1, 3, 5, 7, 9, 11, 25, 26, 28 to 31, 33, or 34, or the complement thereof, (b) nucleic acids comprising the RNA sequences corresponding to any of SEQ ID NOs: 48, 44, 38, 27, 1, 3, 5, 7, 9, 11, 25, 26, 28 to 31, 33, or 34, or the complement thereof, (c) nucleic acids specifically hybridizing to any of SEQ ID NOs: 48, 44, 38, 27, 1, 3, 5, 7, 9, 11, 25, 26, 28 to 31, 33, or 34 or to the complement thereof, (d) nucleic acids encoding a protein comprising the amino acid sequence as given in any of SEQ ID NOs: 2, 4, 6, 8, 10, 12, 32, 35, 37, or 39 or the complement thereof, (e) nucleic acids as defined in any of (a) to (d) characterized in that said nucleic acid is DNA, genomic DNA, cDNA, synthetic DNA or RNA wherein T is replaced by U, (f) nucleic acids which are degenerated compared to a nucleic acid as given in any of SEQ ID NOs: 48, 44, 38, 27, 1, 3, 5, 7, 9, 11, 25, 26, 28 to 31, 33, or 34 or which are degenerated compared to a nucleic acid as defined in any of (a) to (e) as a result of the genetic code, (g) nucleic acids which are diverging from a nucleic acid encoding a protein as given in any of SEQ ID NOs: 2, 4, 6, 8, 10, 12, 35, 37 or 39 or which are diverging from a nucleic acid as defined in any of (a) to (e), due to the differences in codon usage between the organisms, (h) nucleic acids encoding a protein as given in SEQ ID NOs: 2, 4, 6, 8, 10, 12, 35, 37 or 39, or nucleic acids as defined in (a) to (e) which are diverging due to the differences between alleles, (i) nucleic acids encoding a protein as given in any of SEQ ID NOs: 2, 4, 6, 8, 10, 12, 35, 37 or 39

(j) functional fragments of nucleic acids as defined in any of (a) to (i) having the biological activity of a cytokinin oxidase, and (k) nucleic acids encoding a cytokinin oxidase, or comprise expression, preferably in roots, or in seeds (including parts of seeds such as embryo, endosperm, seed coat or aleurone) or in cotyledons, of a nucleic acid encoding a protein that reduces the level of active cytokinins in plants or plant parts.

In the present invention, nucleic acids encoding novel *Arabidopsis thaliana* cytokinin oxidases have been isolated and for the first time, the present inventors have surprisingly shown that the expression of cytokinin oxidases in transgenic plants or in transgenic plant parts resulted in the above-mentioned root and seed-related features. In order that root-related features be effected, the expression of the cytokinin oxidase(s) should take place in roots, preferably under the control of a root-specific promoter. In order that seed-related features be effected (including the embryo), expression of the cytokinin oxidase(s) should take place in seeds, preferably under the control of a seed-specific promoter. One example of such a root-specific promoter is provided in SEQ ID NO: 36. Examples of seed-specific promoters include but are not limited to those listed in Table 4.

In order that cotyledon-related features be effected, the expression of the cytokinin oxidase(s) should take place in the cotyledons, preferably under the control of a promoter which preferentially expresses in cotyledon.

It should be clear that, although the invention is supported in the examples section by several new AtCKX genes and proteins, the inventive concept also relates to the use of other cytokinin oxidases isolated from and expressed in other plants, preferably in the roots and/or seeds and/or cotyledons of said other plants to obtain similar effects in plants as described in the examples section.

Therefore, the present invention more generally relates to the use of a nucleic acid encoding a plant cytokinin oxidase or encoding a protein that reduces the level of active cytokinins in plants or plant parts for stimulating root growth or for enhancing the formation of lateral or adventitious roots or for altering root geotropism. The present invention also relates to the use of a nucleic acid encoding a plant cytokinin oxidase or encoding a protein that reduces the level of active cytokinins in plants or plant parts for increasing seed size and/or weight, or for increasing embryo size and/or weight, or for increasing plant cotyledon size and/or weight or for increasing seed yield. Preferred cytokinin oxidases to be used are encoded by the nucleic acids encoding the cytokinin oxidases as defined below and are encoded by the novel nucleic acids of the invention as defined hereunder.

The invention relates to an isolated nucleic acid encoding a novel plant protein having cytokinin oxidase activity selected from the group consisting of:

(a) a nucleic acid comprising a DNA sequence as given in any of SEQ ID NOs: 48, 44, 38, 29, 3, 5, 9, 26, 27, 31, 33, or 34, or the complement thereof, (b) a nucleic acid comprising the RNA sequences corresponding to any of SEQ ID NOs: 48, 44, 38, 29, 3, 5, 9, 26, 27, 31, 33, 34, or the complement thereof, (c) a nucleic acid specifically hybridizing to a nucleic acid as given in any of SEQ ID NOs: 48, 44, 38, 29, 3, 5, 9, 26, 27, 31, 33, or 34 or the complement thereof, (d) a nucleic acid encoding a protein with an amino acid sequence comprising the polypeptide as given in SEQ ID NO: 32 and which is at least 70% similar, preferably at least 75%, 80% or 85%, more preferably at least 90% or 95%, most preferably at least 99% similar to the amino acid sequence as given in SEQ ID NO: 4, 37 or 39, (e) a nucleic acid encoding a protein with an amino acid sequence which is at least 35% similar, preferably 37%, 40%, 45%, 47% or 50%, similar, more preferably 55%, 60%, 65%, 70%, 75% or 80% similar, most preferably 85%, 90% or 95% similar to the amino acid sequence as given in SEQ ID NO: 6, (f) a nucleic acid encoding a protein with an amino acid sequence which is at least 35% similar, preferably 37%, 40%, 45%, 47% or 50%, similar, more preferably 55%, 60%, 65%, 70%, 75% or 80% similar, most preferably 85%, 90% or 95% similar to the amino acid sequence as given in SEQ ID NO: 10 or 35, (g) a nucleic acid encoding a protein comprising the amino acid sequence as given in any of SEQ ID NOs: 4, 6, 10, 32, 35, 37 or 39, (h) a nucleic acid which is degenerated compared to a nucleic acid as given in any of SEQ ID NOs: 48, 44, 38, 29, 3, 5, 9, 26, 27, 33, or 34, or which is degenerated compared to a nucleic acid as defined in any of (a) to (g) as a result of the genetic code, (i) a nucleic acid which is diverging from a nucleic acid encoding a protein as given in any of SEQ ID NOs: 4, 6, 10, 35, 37 or 39, or which is diverging from a nucleic acid as defined in any of (a) to (g) due to the differences in codon usage between the organisms, (j) a nucleic acid encoding a protein as given in SEQ ID NOs: 4, 6, 10, 35, 37 or 39, or a nucleic acid as defined in (a) to (g) which is diverging due to the differences between alleles, (k) a nucleic acid encoding an immunologically active fragment of a cytokinin oxidase encoded by a nucleic acid as given in any of SEQ ID NOs: 48, 44, 38, 29, 3, 5, 9, 26, 27, 31, 33, or 34, or an immunologically active fragment of a nucleic acid as defined in any of (a) to (j), (l) a nucleic acid encoding a functional fragment of a cytokinin oxidase encoded by a nucleic acid as given in any of SEQ ID NOs: 48, 44, 38, 29, 3, 5, 9, 26, 27, 31, 33, or 34, or a functional fragment of a nucleic acid as defined in any of (a) to (j), wherein said fragment has the biological activity of a cytokinin oxidase, and (m) a nucleic acid encoding a protein as defined in SEQ ID NOs: 4, 6, 10, 35, 37 or 39, provided that said nucleic acid is not the nucleic acid as deposited under any of the following Genbank accession numbers: AC005917, AB024035, and AC023754.

The invention also relates to an isolated nucleic acid of the invention which is DNA, cDNA, genomic DNA or synthetic DNA, or RNA wherein T is replaced by U.

The invention also relates to a nucleic acid molecule of at least 15 nucleotides in length hybridizing specifically with or specifically amplifying a nucleic acid of the invention.

Different cytokinin forms may have differing roles to play in the various developmental processes. Thus, differential effects of CKX1, CKX2, CKX 3 and CKX4 may relate to distinct effects on the pools of different cytokinins. For example, CKX1 and CKX3 mostly promote root elongation and branching, while CKX2 and CKX4 primarily stimulate the formation of adventitious roots. In addition, CKX1 and CKX3 increase seed size and weight to a greater degree than CKX2 and CKX4. Without being bound to a particular mode of action, this differential effect on cytokinin pools may result from some differences in substrate specificity or from differential compartmentation of cytokinin oxidases in the cell (predicted to be mitochondrial for CKX1 and CKX3, while extracellular for CKX 2, CKX4, CKX5, and CKX6).

According to another embodiment, the invention also relates to a vector comprising a nucleic acid of the invention. In a preferred embodiment, said vector is an expression vector wherein the nucleic acid is operably linked to one or more control sequences allowing the expression of said sequence in prokaryotic and/or eukaryotic host cells.

It should be understood that for expression of the cytokinin oxidase genes of the invention in monocots, a nucleic acid sequence corresponding to the cDNA sequence should be used to avoid mis-splicing of introns in monocots. Preferred cDNA sequences to be expressed in monocots have a nucleic acid sequence as represented in any of SEQ ID NOs: 25 to 30, 34, SEQ ID NO:38, or SEQ ID NO:44.

The invention also relates to a host cell containing any of the nucleic acid molecules or vectors of the invention. Said host cell is chosen from the group comprising bacterial, insect, fungal, plant or animal cells.

Another embodiment of the invention relates to an isolated polypeptide encodable by a nucleic acid of the invention, or a homologue or a derivative thereof, or an immunologically active or a functional fragment thereof. Preferred polypeptides of the invention comprise the amino acid sequences as represented in any of SEQ ID NOs: 2, 4, 6, 8, 10, 12, 32, 35 or 37, or a homologue or a derivative thereof, or an immunologically active and/or functional fragment thereof. In an even more preferred embodiment, the invention relates to a polypeptide which has an amino acid sequence as given in SEQ ID: NO 2, 4, 6, 8, 10, 12, 35 or 37, or a homologue or a derivative thereof, or an immunologically active and/or functional fragment thereof. Preferred functional fragments thereof are those fragments which are devoid of their signal peptide.

According to yet another embodiment, the invention relates to a method for producing a polypeptide of the invention comprising culturing a host cell of the invention under conditions allowing the expression of the polypeptide and recovering the produced polypeptide from the culture.

The invention also relates to an antibody specifically recognizing a polypeptide of the invention or a specific epitope thereof.

The invention further relates to a method for the production of transgenic plants, plant cells or plant tissues comprising the introduction of a nucleic acid molecule of the invention in an expressible format or a vector of the invention in said plant, plant cell or plant tissue.

The invention also relates to a method for the production of altered plants, plant cells or plant tissues comprising the introduction of a polypeptide of the invention directly into a cell, a tissue or an organ of said plant.

According to another embodiment, the invention relates to a method for effecting the expression of a polypeptide of the invention comprising the introduction of a nucleic acid molecule of the invention operably linked to one or more control sequences or a vector of the invention stably into the genome of a plant cell. The invention further relates to the method as described above further comprising regenerating a plant from said plant cell.

The invention also relates to a transgenic plant cell comprising a nucleic acid sequence of the invention which is operably linked to regulatory elements allowing transcription and/or expression of said nucleic acid in plant cells or obtainable by a method as explained above.

According to another preferred embodiment, the invention relates to a transgenic plant cell as described hereinabove wherein the nucleic acid of the invention is stably integrated into the genome of said plant cell.

The invention further relates to a transgenic plant or plant tissue comprising plant cells as herein described and also to a harvestable part of said transgenic plant, preferably selected from the group consisting of seeds, leaves, fruits, stem cultures, roots, tubers, rhizomes and bulbs. The present invention furthermore relates to products directly derived from a harvestable part of a transgenic plant, such as dry pellets or powders, oil, fat and fatty acids, starch, or proteins. The invention also relates to the progeny derived from any of said transgenic plants or plant parts.

According to another embodiment, the invention relates to a method for stimulating root growth comprising expression of a nucleic acid of the invention or comprising expression of another protein that reduces the level of active cytokinins in plants or plant parts.

In another aspect of the invention, there is provided a method of increasing seed size and/or weight. The method comprises increasing the level or activity of a cytokinin oxidase in a plant or increasing the level or activity of a protein that reduces the level of active cytokinins in a plant or plant part, preferably seeds.

Various parts (organs) of the seed may also be increased in size and/or weight such as e.g., embryo, endosperm, seed coat, or aleurone. For example, in accordance with the present invention, there is provided a method of increasing embryo size and/or weight. The method comprises increasing the level or activity of a cytokinin oxidase in a plant or increasing the level or activity of a protein that reduces the level of active cytokinins in a plant or plant part, preferably embryos.

In still another aspect of the invention, there is provided a method of increasing cotyledon size and/or weight. The method comprises increasing the level or activity of a cytokinin oxidase in a plant or increasing the level or activity of a protein that reduces the level of active cytokinins in a plant or plant part, preferably cotyledons.

In accordance with the methods of increasing seed size and/or weight, there is a resultant increase in the speed of growth of seedlings or an increase in early vigor. Increases in yield are also obtained. Similarly, in accordance with the methods of increasing embryo size and/or weight, or cotyledon size and/or weight, there is a resultant increase in speed of growth of seedlings or an increase in early vigor. In many cases, increases in yield are also obtained. Increases in growth of seedlings or early vigor is often associated with increased stress tolerance. For example, faster development of seedlings, including the root systems of seedlings upon germination is critical for survival particularly under adverse conditions such as drought.

Any nucleotide sequence encoding a polypeptide with cytokinin oxidase activity may be used in the methods of the invention. For example, any of the various sequences provided herein encoding a polypeptide with cytokinin oxidase activity may be used in the methods of increasing seed, embryo, or cotyledon size and/or weight, and/or seed yield.

Preferably, transgenic plants are produced which express a nucleic acid as set forth in any of SEQ ID NOs:1, 5, 25, 27, or 44 or an ortholog of said nucleic acid. Preferably, the ortholog is derived from a related species of the transgenic plant. Even more preferably, the ortholog is specific (native or endogenous) to the species of the transgenic plant.

As described above, promoters which control expression specifically, or preferentially may be used in the methods of the invention. Thus, where increases in seed size or weight are desired, a seed-specific promoter may be used. Where increases in embryo size or weight are desired, an embryo-specific promoter may be used. Where increases in cotyledon size or weight is desired, a promoter which controls expression in cotyledons is preferred. Such promoters are well known, widely available and listed herein in e.g., Table 6.

In another embodiment, the invention relates to a method for increasing seed size or seed weight, or both, said method comprising expression of a nucleic acid of the invention or comprising expression of another protein that reduces the level of active cytokinins in plants or plant parts.

In yet another embodiment, the invention relates to a method for increasing embryo size or weight, or both, said method comprising expression of a nucleic acid of the invention or comprising expression of another protein that reduces the level of active cytokinins in plants or plant parts.

In still another embodiment, the invention relates to a method for increasing cotyledon size comprising expression of a nucleic acid of the invention or comprising expression of another protein that reduces the level of active cytokinins in plants or plant parts. Localized expression of a subject cytokinin oxidase gene or part thereof, or of another protein that reduces the level of active cytokinins in plants or plant parts leads to enhanced growth of cotyledons. In species having cotyledons as storage organs, such enhanced growth of cotyledons leads to enhanced yields and/or to enhanced growth performance of seedlings. Further in this regard, carbohydrates, lipids and proteins are all stored within seeds and are metabolized during germination in order to provide energy and metabolites during early growth of the plant. Seed size is often associated with early vigor, since larger seeds contain more carbohydrates, lipids and proteins and thus confer faster growth. Thus, the methods of the present invention lead to faster growth of seedlings. Such early vigor is associated with enhanced stress tolerance. For example, faster development of a plant's root system is critical for survival, particularly under adverse conditions, such as drought. Early vigor is also related to enhanced yield and shortened time to flowering.

Also in accordance with the present invention, there are provided methods and compositions for increasing seed yield in a plant. Seed yield may be increased by increasing the level or activity of a cytokinin oxidase in the endosperm, embryo or aleurone of a plant seed. Thus for example, seed-preferred promoters may be utilized to drive expression of a cytokinin oxidase in these particular components of a seed. Preferably, a seed-preferred promoter is an embryo and/or aleurone preferred promoter, or an endosperm-preferred promoter. A seedling-preferred promoter may also be used.

Since it has now been surprisingly found that heterologous expression of a CKX in a plant shoot gives rise to plants having increased seed yield, the use of a shoot-specific or shoot-preferred promoter is especially preferred for producing plants with increased seed yield. Any of the nucleic acid molecules and corresponding amino acid sequences described herein and/or readily available will work in a method of increasing seed yield in a plant and in a method of producing transgenic plants having such increased seed yield.

In accordance with the present invention, a cytokinin oxidase gene may be placed in a genetic construct such as a vector, under control of an embryo/aleurone-preferred promoter or an endosperm-preferred promoter. For example, the AtCKX2 gene (SEQ ID NO:44) may be placed under control of a seed preferred promoter: (i) an embryo and aleurone preferred promoter which is also active in seedlings, as represented in GenBank under accession number AF019212 (sequence from nucleotide 1 to 1256, hereafter named PRO0218) and (ii) an endosperm preferred promoter as represented in GenBank under accession number X65064 (sequence from nucleotide 1 to 672, hereafter named PRO0090). Since the promoter PRO0090 is not only active in seed tissues but also in seedlings, in another embodiment of the invention, a seedling-preferred promoter may also be used to increase seed yield in a plant.

These constructs may then be used to transform plants, either dicots or monocots. In accordance with the present invention, transgenic plants have, when compared to nullizygous plants, an increased seed yield.

There are different well known parameters which may be used for measuring increased seed yield including but not limited to: total weight of seeds, total number of seeds, total number of filled seeds, harvest index, and Thousand Kernel Weight. As described in the examples, the total weight of seeds, may be measured by weighing all filled seeds harvested from a plant. The total number of seeds may be measured by counting the number of seeds harvested from a plant. The total number of filled seeds may be measured by counting the number of filled seeds harvested from a plant. The harvest index, may be defined as the ratio between the total seed weight and the above ground area ($mm^2$), multiplied by a factor $10^6$. Thousand Kernel Weight may be derived from the number of filled seeds counted and their total weight.

In addition to the cytokinin oxidase genes and corresponding proteins described above, a cytokinin oxidase 2 gene (CKX2) is particularly suited for use in increasing seed yield in a plant. For example, in addition to the *Arabidopsis thaliana* CKX2 protein set forth in SEQ ID NO:37, other CKX proteins from *Arabidopsis thaliana*, such as the ones represented in GenBank Accessions NP_181682, NP_200507, NP_849470, NP_194703, NP_850863 or AAG30909 may be used. CKX proteins from other species like *Zea mays* (for example GenBank Accessions CAE55202, CAE55200 or AAC27500), *Dendrobium* (GenBank CAC17752), *Hordeum vulgare* (GenBank AAN16383, AAO50082, AAM08400), or rice (GenBank NP_913145, NP_916348, NP_922039) are also available for use in the methods and compositions of the present invention. A prokaryotic homologue of SEQ ID NO:37 is represented by GenBank Accession P46377.

A plant cell or tissue culture is an artificially produced culture of plants cells or plant tissues that is grown in a special medium, either liquid or solid, which provides these plant cells or tissues with all requirements necessary for growth and/or production of certain compounds. Plant cell and/or tissue cultures can be used for the rapid propagation of plants and for the production of transgenic plant to name a few examples. Root formation can be difficult for some explants or under some conditions in said cultures and expression of a cytokinin oxidase gene in said cultured plant cells or tissue(s) can be used to enhance root formation. Plant cell and/or tissue culture can also be used for the industrial production of valuable compounds. Possible production compounds are pharmaceuticals, pesticides, pigments, cosmetics, perfumes, food additives, etc. An example of such a product is shikonin, which is produced by the roots of the plant *Lithospermum erythrorhizon*. An example of a plant tissue culture is a hairy root culture, which is an artificially produced mass of hairy roots. Roots of *L. erythrorhizon* are difficult to collect in large numbers and by preparing hairy root cultures, the end product shikonin could be industrially prepared at a faster rate than would normally occur. As disclosed herein, expression of cytokinin oxidases enhances root growth and development and can therefore be used advantageously in said plant cell and tissue culture procedures. Therefore, according to another embodiment of this invention, a method is provided for stimulating root growth and development comprising expression of a nucleic acid encoding a plant cytokinin oxidase, preferably a cytokinin oxidase of the invention, in a transgenic plant cell or tissue culture comprising said transgenic plant cells.

The invention further relates to a method for enhancing the formation of lateral or adventitious roots comprising expression of a nucleic acid of the invention or comprising expression of another protein that reduces the level of active cytokinins in plants or plant parts.

The invention also relates to method for altering root geotropism comprising altering the expression of a nucleic acid of the invention or comprising expression of another protein that that reduces the level of active cytokinins in plants or plant parts.

The invention also relates to methods for enhancing early vigor and/or for modifying root/shoot ratio and/or for improving resistance to lodging and/or for increasing drought tolerance and/or for promoting in vitro propagation of explants comprising expression of a nucleic acid of the invention comprising expression of another protein that reduces the level of active cytokinins in plants or plant parts.

The invention further relates to methods for increasing the root size or the size of the root meristem comprising expression of a nucleic acid of the invention or comprising expression of another protein that reduces the level of active cytokinins in plants or plant parts, preferably in roots.

According to yet another embodiment, the invention relates to a method for increasing the size of the shoot meristem comprising downregulation of expression of a nucleic acid of the invention, preferably in shoots.

According to a preferred embodiment the invention relates to a method for delaying leaf senescence comprising downregulation of expression of any of the cytokinin oxidases of the invention in leaves, preferably in senescing leaves. Also the invention relates to a method for altering leaf senescence comprising expression of one of the cytokinin oxidases in senescing leaves.

The invention also relates to methods for increasing leaf thickness comprising expression of a nucleic acid of the invention or comprising expression of another protein that reduces the level of active cytokinins in plants or plant parts, preferably in leaves.

The invention also relates to a method for reducing the vessel size comprising expression of a nucleic acid of the invention or comprising expression of another protein that reduces the level of active cytokinins in plants or plant parts, preferably in vessels.

The invention further relates to a method for increasing the vessel size comprising downregulation of expression of a nucleic acid of the invention in plants or plant parts.

According to another embodiment, the invention relates to a method for improving standability of seedlings comprising expression of a nucleic acid of the invention or comprising expression of another protein that reduces the level of active cytokinins in seedlings.

Furthermore, the invention relates to any of the above described methods, said method leading to an increase in yield.

The invention further relates to any of the methods of the invention wherein said expression of said nucleic acid occurs under the control of a strong constitutive promoter. With respect to those aspects of the invention having effects on plant roots such as e.g., methods for stimulating root growth, enhancing the formation of lateral or adventitious roots, or for altering root geotropism, preferably, expression of a subject nucleic acid preferably occurs under the control of a promoter that is preferentially expressed in roots. In Table 7 a non-exhaustive list of root specific promoters is included. A preferred promoter to be used in the methods of the invention is the root clavata homolog promoter, having a sequence as given in SEQ ID NO: 36.

With respect to those aspect of the invention having effects on plant seeds such as e.g., methods for increasing seed size or weight, embryo size or weight, or having effects on plant cotyledons such as methods for increasing cotyledon size of weight, expression of a subject nucleic acid occurs under the control of a promoter that is preferentially expressed in seeds. A seed specific promoter may be one which is expressed in all seed organs or one which shows a preference in expression to one or more organs or tissue such as the embryo, endosperm, or aleurone. Examples of such promoters are set forth herein at Table 6.

According to yet another embodiment, the invention relates to a method for modifying cell fate and/or modifying plant development and/or modifying plant morphology and/or modifying plant biochemistry and/or modifying plant physiology and/or modifying the cell cycle progression rate comprising the modification of expression in particular cells, tissues or organs of a plant, of a nucleic acid of the invention.

The invention also relates to a method for obtaining enhanced growth, and/or increased yield and/or altered senescence of a plant cell, tissue and/or organ and/or increased frequency of formation of lateral organs in a plant, comprising the ectopic expression of a nucleic acid of the invention.

The invention also relates to a method for promoting and extending cell division activity in cells in adverse growth conditions and/or in stress, comprising the ectopic expression of a nucleic acid sequence of the invention.

According to yet another embodiment, the invention relates to a method for identifying and obtaining proteins interacting with a polypeptide of the invention comprising a screening assay wherein a polypeptide of the invention is used.

In a more preferred embodiment, the invention relates to a method for identifying and obtaining proteins interacting with a polypeptide of the invention comprising a two-hybrid screening assay wherein a polypeptide of the invention as a bait and a cDNA library as prey are used.

The invention further relates to a method for modulating the interaction between a polypeptide of the invention and interacting protein partners obtainable by a method as described above.

In a further embodiment, the invention relates to a method for identifying and obtaining compounds interacting with a polypeptide of the invention comprising the steps of:
(a) providing a two-hybrid system wherein a polypeptide of the invention and an interacting protein partner obtainable by a method as described above, (b) interacting said compound with the complex formed by the expressed polypeptides as defined in a), and, (c) performing (real-time) measurement of interaction of said compound with said polypeptide or the complex formed by the expressed polypeptides as defined in a).

The invention further relates to a method for identifying compounds or mixtures of compounds which specifically bind to a polypeptide of the invention, comprising:

(a) combining a polypeptide of the invention with said compound or mixtures of compounds under conditions suitable to allow complex formation, and, (b) detecting complex formation, wherein the presence of a complex identifies a compound or mixture which specifically binds said polypeptide.

The invention also relates to a method as described above wherein said compound or mixture inhibits the activity of said polypeptide of the invention and can be used for the rational design of chemicals.

According to another embodiment, the invention relates to the use of a compound or mixture identified by means of a method as described above as a plant growth regulator or herbicide.

The invention also relates to a method for production of a plant growth regulator or herbicide composition comprising the steps of the compound screening methods described above and formulating the compounds obtained from said steps in a suitable form for the application in agriculture or plant cell or tissue culture.

The invention also relates to a method for increasing branching comprising expression of a nucleic acid of the invention in plants or plant parts, preferably in stems or axillary buds.

The invention also relates to a method for improving lodging resistance comprising expression of a nucleic acid of the invention in plants or plant parts, preferably in stems or axillary buds.

The invention also relates to a method for the design of or screening for growth-promoting chemicals or herbicides comprising the use of a nucleic acid of the invention or a vector of the invention.

According to another embodiment, the invention relates to the use of a nucleic acid molecule of the invention, a vector of the invention or a polypeptide of the invention for increasing yield.

The invention also relates to the use of a nucleic acid molecule of the invention, a vector of the invention or a polypeptide of the invention for stimulating root growth.

The invention also relates to the use of a nucleic acid molecule of the invention, a vector of the invention or a polypeptide of the invention for enhancing the formation of lateral or adventitious roots.

The invention also relates to the use of a nucleic acid molecule of the invention, a vector of the invention or a polypeptide of the invention for altering root geotropism.

The invention also relates to the use of a nucleic acid molecule of the invention, a vector of the invention or a polypeptide of the invention for increasing at least one of seed size, seed weight, embryo size, embryo weight, cotyledon size, and cotyledon weight.

The invention further relates to the use of a nucleic acid molecule of the invention, a vector of the invention or a polypeptide of the invention for enhancing early vigor and/or for modifying root/shoot ratio and/or for improving resistance to lodging and/or for increasing drought tolerance and/or for promoting in vitro propagation of explants.

The invention also relates to the use of a nucleic acid molecule of the invention, a recombinant vector of the invention or a polypeptide of the invention for modifying plant development and/or for modifying plant morphology and/or for modifying plant biochemistry and/or for modifying plant physiology.

According to yet another embodiment, the invention relates to a diagnostic composition comprising at least a nucleic acid molecule of the invention, a vector of the invention, a polypeptide of the invention or an antibody of the invention.

Another embodiment of the current invention relates to the use of a transgenic rootstock that has an enhanced root growth and development due to expression of a cytokinin oxidase in grafting procedures with a scion to produce a plant or tree with improved agricultural or horticultural characteristics. The scion may be transgenic or non-transgenic. Specific characteristics envisaged by this embodiment are those conferred by root systems and include improved anchoring of the plant/tree in the soil and/or improved uptake of water resulting for example in improved drought tolerance, and/or improved nutrient uptake from the soil and/or improved transport of organic substances throughout the plant and/or enhanced secretion of substances into the soil such as for example phytosiderophores, and/or improved respiration and/or improved disease resistance and/or enhanced yield. An advantage of using AtCKX transformed rootstocks for grafting, in addition to their enhanced root system, is the delayed senescence of leaves on the graft, as disclosed herein (see FIG. 12A). Preferred plants or trees for this particular embodiment include plants or trees that do not grow well on their own roots and are grafted in cultivated settings such as commercially profitable varieties of grapevines, citrus, apricot, almond, plum, peach, apple, pear, cherry, walnut, fig, hazel and loquat.

As mentioned supra, auxins and cytokinins act as antagonists in certain biological processes. For example, the cytokinin/auxin ratio regulates the production of roots and shoots with a high concentration of auxin resulting in organized roots and a high concentration of cytokinins resulting in shoot production. As disclosed in this invention, expression of cytokinin oxidases in tobacco and *Arabidopsis* results in enhanced root development consistent with enhanced auxin effects. Auxins are also involved in the development of fruit. Treatment of female flower parts with auxin results in the development of parthenocarpic fruit in some plant species. Parthenocarpic fruit development has been genetically engineered in several horticultural crop plants through increased biosynthesis of auxins in the female reproductive organs (WO0105985).

Therefore, according to another embodiment, this invention relates to a method for inducing the parthenocarpic trait in plants, said method consisting of downregulating the expression of one or more cytokinin oxidases or of another protein that reduces the level of active cytokinins in plants or plant parts, preferably in the female reproductive organs such as the placenta, ovules and tissues derived therefrom. The DefH9 promoter region from *Antirrhinum majus* or one of its homologues, which confer high expression specificity in placenta and ovules, can be used for this purpose.

Those skilled in the art will be aware that the invention described herein is subject to variations and modifications other than those specifically described. It is to be understood that the invention described herein includes all such variations and modifications. The invention also includes all such steps, features, compositions and compounds referred to or indicated in this specification, individually or collectively, and any and all combinations of any or more of said steps or features.

The present invention is applicable to any plant, in particular a monocotyledonous plants and dicotyledonous plants including a fodder or forage legume, ornamental plant, food crop, tree, or shrub selected from the list comprising *Acacia* spp., *Acer* spp., *Actinidia* spp., *Aesculus* spp., *Agathis australis, Albizia amara, Alsophila tricolor, Andropogon* spp., *Arachis* spp, *Areca catechu, Astelia fragrans, Astragalus cicer, Avena sativa, Baikiaea plurijuga, Betula* spp., *Brassica* spp., *Bruguiera gymmorrhiza, Burkea africana, Butea frondosa, Cadaba farinosa, Calliandra* spp, *Camellia sinensis, Canna indica, Capsicum* spp., *Cassia* spp., *Centroema pubescens, Chaenomeles* spp., *Cinnamomum cassia, Coffea arabica, Colophospermum mopane, Coronillia varia, Cotoneaster serotina, Crataegus* spp., *Cucumis* spp., *Cupressus* spp., *Cyathea dealbata, Cydonia oblonga, Cryptomeria japonica, Cymbopogon* spp., *Cynthea dealbata, Cydonia oblonga, Dalbergia monetaria, Davallia divaricata, Desmodium* spp., *Dicksonia squarosa, Diheteropogon amplectens, Dioclea* spp, *Dolichos* spp., *Dorycnium rectum, Echinochloa pyramidalis, Ehrartia* spp., *Eleusine coracana, Eragrestis* spp., *Erythrina* spp., *Eucalyptus* spp., *Euclea schimperi, Eulalia villosa, Fagopyrum* spp., *Feijoa sellowiana, Fragaria* spp., *Flemingia* spp, *Freycinetia banksii, Geranium thunbergii, Ginkgo biloba, Glycine javanica, Gliricidia* spp, *Gossypium hirsutum, Grevillea* spp., *Guibourtia coleosperma, Hedysarum* spp., *Hemarthia altissima, Heteropogon contortus, Hordeum vulgare, Hyparrhenia rufa, Hypericum erectum, Hyperthelia dissoluta, Indigo incarnata, Iris* spp., *Leptarrhena pyrolifolia, Lespediza* spp., *Lettuca* spp., *Leucaena leucocephala, Loudetia simplex, Lotonus bainesii, Lotus* spp., *Macrotyloma axillare, Malus* spp., *Manihot esculenta, Medicago sativa, Metasequoia glyptostroboides, Musa sapientum, Nicotianum* spp., *Onobrychis* spp., *Ornithopus* spp., *Oryza* spp., *Peltophorum africanum, Pennisetum* spp., *Persea gratissima, Petunia* spp., *Phaseolus* spp., *Phoenix canariensis, Phormium cookianum, Photinia* spp., *Picea glauca, Pinus* spp., *Pisum sativum, Podocarpus totara, Pogonarthria fleckii, Pogonarthria squarrosa, Populus* spp., *Prosopis cineraria, Pseudotsuga menziesii, Pterolobium stellatum, Pyrus communis, Quercus* spp., *Rhaphiolepsis umbellata, Rhopalostylis sapida, Rhusi natalensis, Ribes grossularia, Ribes* spp., *Robinia pseudoacacia, Rosa* spp., *Rubus* spp., *Salix* spp., *Schyzachyrium sanguineum, Sciadopitys verticillata, Sequoia sempervirens, Sequoiadendron giganteum, Sorghum bicolor, Spinacia* spp., *Sporobolus fimbriatus, Stiburus alopecuroides, Stylosanthos humilis, Tadehagi* spp, *Taxodium distichum, Themeda triandra, Trifolium* spp., *Triticum* spp., *Tsuga heterophylla, Vaccinium* spp., *Vicia* spp. *Vitis vinifera, Watsonia pyramidata, Zantedeschiai aethiopica, Zea mays,* amaranth, artichoke, asparagus, broccoli, brussel sprout, cabbage, canola, carrot, cauliflower, celery, collard greens, flax, kale, lentil, oilseed rape, okra, onion, potato, rice, soybean, straw, sugarbeet, sugar cane, sunflower, tomato, squash, and tea, amongst others, or the seeds of any plant specifically named above or a tissue, cell or organ culture of any of the above species.

Throughout this specification, unless the context requires otherwise the word "comprise", and variations such as "comprises" and "comprising", will be understood to imply the inclusion of a stated integer or step or group of integers or steps but not the exclusion of any other integer or step or group of integers or steps.

As used herein, the term "derived from" shall be taken to indicate that a particular integer or group of integers has originated from the species specified, but has not necessarily been obtained directly from the specified source.

The terms "protein(s)", "peptide(s)" or "oligopeptide(s)", when used herein refer to amino acids in a polymeric form of any length. Said terms also include known amino acid modifications such as disulphide bond formation, cysteinylation, oxidation, glutathionylation, methylation, acetylation, farnesylation, biotinylation, stearoylation, formylation, lipoic acid addition, phosphorylation, sulphation, ubiquitination, myristoylation, palmitoylation, geranylgeranylation, cyclization (e.g. pyroglutamic acid formation), oxidation, deamidation, dehydration, glycosylation (e.g. pentoses, hexosamines, N-acetylhexosamines, deoxyhexoses, hexoses, sialic acid etc.) and acylation as well as non-naturally occurring amino acid residues, L-amino acid residues and D-amino acid residues.

"Homologues" of a protein of the invention are those peptides, oligopeptides, polypeptides, proteins and enzymes which contain amino acid substitutions, deletions and/or additions relative to the said protein with respect to which they are a homologue, without altering one or more of its functional properties, in particular without reducing the activity of the resulting protein. For example, a homologue of said protein will consist of a bioactive amino acid sequence variant of said protein.

Two special forms of homology, orthologous and paralogous homology, are evolutionary concepts used to describe ancestral relationships of genes. The term "paralogous" relates to homologous genes that result from one or more gene duplications within the genome of a species. The term "orthologous" relates to homologous genes in different organisms due to ancestral relationship of these genes. The term "homologues" as used herein also encompasses paralogues and orthologues of the proteins useful in the methods according to the invention. Orthologous genes can be identified by querying one or more gene databases with a query gene of interest, using for example, the BLAST program. The highest-ranking subject genes that result from the search are then again subjected to a BLAST analysis, and only those subject genes that match again with the query gene are retained as true orthologous genes. For example, to find a rice orthologue of an *Arabidopsis thaliana* gene, one may perform a BLASTN or TBLASTX analysis on a rice database (such as (but not limited to) the *Oryza sativa* Nipponbare database available at the NCBI (ncbi.nlm.nih.gov) or the genomic sequences of rice (cultivars indica or japonica)). In a next step, the obtained rice sequences are used in a reverse BLAST analysis using an *Arabidopsis* database. The results may be further refined when the resulting sequences are analysed with ClustalW and visualised in a neighbour joining tree. The method can be used to identify orthologues from many different species.

To produce such homologues, amino acids present in the said protein can be replaced by other amino acids having similar properties, for example hydrophobicity, hydrophilicity, hydrophobic moment, antigenicity, propensity to form or break α-helical structures or β-sheet structures, and so on. An overview of physical and chemical properties of amino acids is given in Table 2.

The homologues useful in the methods according to the invention can alternatively be defined as having cytokinin oxidase/dehydrogenase activity and comprising at least 2 sequences of 17 and 19 consecutive amino acid residues respectively with a consensus sequence as shown below:

Consensus sequence 1 (17 amino acids): hTDYLhholG-GTLSssG (SEQ ID NO:54) Consensus sequence 2 (19 amino acids): cLF•ushGsLGQFGllstA (SEQ ID NO:55) wherein the capital letters are the standard single letter IUPAC codes for the various amino acids and the other letters or signs symbolise the nature of the amino acids, as shown in Table 1. The right column lists for each class the particular amino acids that are allowed in the consensus sequences. This classification is based on the amino acid grouping as defined in the SMART database (Schultz et al. (1998) Proc. Natl. Acad. Sci. USA 95, 5857-5864: Letunic et al. (2002) Nucleic Acids Res 30, 242-244).

TABLE 1

| Class | Key | Allowed amino acids |
|---|---|---|
| h | hydrophobic | G, H, L, R, T, W, Y |
| o | alcohol | S, T |
| l | aliphatic | V, I |
| s | Small | A, D, G, N, T, V |
| c | charged | D, E, R |
| • | Any | Y, R, N, F, D, H |
| u | Tiny | A, G, S |
| t | turnlike | R, N |

Substitutional variants of a protein of the invention are those in which at least one residue in said protein amino acid sequence has been removed and a different residue inserted in its place. Amino acid substitutions are typically of single residues, but may be clustered depending upon functional constraints placed upon the polypeptide; insertions will usually be of the order of about 1-10 amino acid residues and deletions will range from about 1-20 residues. Preferably, amino acid substitutions will comprise conservative amino acid substitutions, such as those described supra.

TABLE 2

Properties of naturally occurring amino acids.

| Charge properties/ hydrophobicity | Side group | Amino Acid |
|---|---|---|
| Nonpolar hydrophobic | Aliphatic | ala, ile, leu, val |
|  | aliphatic, S-containing | met |
|  | aromatic | phe, trp |
|  | imino | pro |
| polar uncharged | Aliphatic | gly |
|  | Amide | asn, gln |
|  | Aromatic | tyr |
|  | Hydroxyl | ser, thr |
|  | Sulfhydryl | cys |
| Positively charged | Basic | arg, his, lys |
| Negatively charged | Acidic | asp, glu |

Insertional amino acid sequence variants of a protein of the invention are those in which one or more amino acid residues are introduced into a predetermined site in said protein. Insertions can comprise amino-terminal and/or carboxy-terminal fusions as well as intra-sequence insertions of single or multiple amino acids. Generally, insertions within the amino acid sequence will be smaller than amino or carboxyl terminal fusions, of the order of about 1 to 10 residues. Examples of amino- or carboxy-terminal fusion proteins or peptides include the binding domain or activation domain of a transcriptional activator as used in a two-hybrid system, phage coat proteins, (histidine)$_6$-tag (SEQ ID NO:57), glutathione S-transferase, protein A, maltose-binding protein, dihydrofolate reductase, Tag•100 epitope (EETARFQPGYRS) (SEQ ID NO:58), c-myc epitope (EQKLISEEDL) (SEQ ID NO:59), FLAG®-epitope (DYKDDDK) (SEQ ID NO:60), lacZ, CMP (calmodulin-binding peptide), HA epitope (YPY-DVPDYA) (SEQ ID NO:61), protein C epitope (EDQVDPRLIDGK) (SEQ ID NO:62) and VSV epitope (YTDIEMNRLGK) (SEQ ID NO:63).

Deletional variants of a protein of the invention are characterized by the removal of one or more amino acids from the amino acid sequence of said protein.

Amino acid variants of a protein of the invention may readily be made using peptide synthetic techniques well known in the art, such as solid phase peptide synthesis and the like, or by recombinant DNA manipulations. The manipulation of DNA sequences to produce variant proteins which manifest as substitutional, insertional or deletional variants are well known in the art. For example, techniques for making substitution mutations at predetermined sites in DNA having known sequence are well known to those skilled in the art, such as by M13 mutagenesis, T7-Gen in vitro mutagenesis kit (USB, Cleveland, Ohio), QuickChange Site Directed mutagenesis kit (Stratagene, San Diego, Calif.), PCR-mediated site-directed mutagenesis or other site-directed mutagenesis protocols.

In the current invention "identity" and/or "similarity" percentages between DNA sequences and/or proteins are calculated using computer programs known in the art such as the DNAstar/MegAlign programs in combination with the Clustal method.

"Derivatives" of a protein of the invention are those peptides, oligopeptides, polypeptides, proteins and enzymes which comprise at least about five contiguous amino acid residues of said polypeptide but which retain the biological activity of said protein. A "derivative" may further comprise additional naturally-occurring, altered glycosylated, acylated or non-naturally occurring amino acid residues compared to the amino acid sequence of a naturally-occurring form of said polypeptide. Alternatively or in addition, a derivative may comprise one or more non-amino acid substituents compared to the amino acid sequence of a naturally-occurring form of said polypeptide, for example a reporter molecule or other ligand, covalently or non-covalently bound to the amino acid sequence such as, for example, a reporter molecule which is bound thereto to facilitate its detection.

With "immunologically active" is meant that a molecule or specific fragments thereof such as specific epitopes or haptens are recognized by, i.e. bind to antibodies. Specific epitopes may be determined using, for example, peptide scanning techniques as described in Geysen et al. (1996) (Geysen, H. M., Rodda, S. J. and Mason, T. J. (1986). A priori delineation of a peptide which mimics a discontinuous antigenic determinant. *Mol. Immunol.* 23, 709-715.).

The term "fragment of a sequence" or "part of a sequence" means a truncated sequence of the original sequence referred to. The truncated sequence (nucleic acid or protein sequence) can vary widely in length; the minimum size being a sequence of sufficient size to provide a sequence with at least a comparable function and/or activity or the original sequence referred to (e.g. "functional fragment"), while the maximum size is not critical. In some applications, the maximum size usually is not substantially greater than that required to provide the desired activity and/or function(s) of the original sequence. Typically, the truncated amino acid sequence will range from about 5 to about 60 amino acids in length. More typically, however, the sequence will be a maximum of about 50 amino acids in length, preferably a maximum of about 60 amino acids. It is usually desirable to select sequences of at least about 10, 12 or 15 amino acids, up to a maximum of about 20 or 25 amino acids.

Functional fragments can also include those comprising an epitope which is specific for the proteins according to the invention. Preferred functional fragments have a length of at least, for example, 5, 10, 25, 28, 100, 150 or 200 amino acids.

More preferably, functional fragments comprise at least 50 amino acids, include an FAD binding domain (as defined in Pfam (version 14.0, June 2004) accession number 1565, Bateman et al., Nucleic Acids Research Database Issue 32, D138-D141, 2004) and exhibit cytokinin oxidase/dehydrogenase activity. Methods for measuring cytokinin oxidase/dehydrogenase activity are well known in the art. Suitable methods are based on the conversion of [2-$^3$H]iP to adenine (Motyka et al., Plant Physiology 112, 1035-1043, 1996), on calorimetric assays (Libreros-Minotta and Tipton, Anal. Biochem. 231, 339-341, 1995) or on the measurement of reduced electron acceptors (Bilyeu et al., Plant Physiol. 125, 378-386, 2001).

It should thus be understood that functional fragments can also be immunologically active fragments or not.

In the context of the current invention are embodied homologues, derivatives and/or immunologically active and/or functional fragments of the cytokinin oxidases as defined supra. Particularly preferred homologues, derivatives and/or immunologically active and/or functional fragments of the cytokinin oxidase proteins which are contemplated for use in the current invention are derived from plants, more specifically from *Arabidopsis thaliana*, even more specifically said cytokinin oxidases are the *Arabidopsis thaliana* (At)CKX, or are capable of being expressed therein. The present invention clearly contemplates the use of functional homologues or derivatives and/or immunologically active fragments of the AtCKX proteins and is not to be limited in application to the use of a nucleotide sequence encoding one of said AtCKX proteins.

Any of said proteins, polypeptides, peptides and fragments thereof can be produced in a biological system, e.g. a cell culture. Alternatively any of said proteins, polypeptides, peptides and fragments thereof can be chemically manufactured e.g. by solid phase peptide synthesis. Said proteins or fragments thereof can be part of a fusion protein as is the case in e.g. a two-hybrid assay which enables e.g. the identification of proteins interacting with a cytokinin oxidase according to the invention.

The proteins or fragments thereof are furthermore useful e.g. to modulate the interaction between a cytokinin oxidase according to the invention and interacting protein partners obtained by a method of the invention. Chemically synthesized peptides are particularly useful e.g. as a source of antigens for the production of antisera and/or antibodies.

"Antibodies" include monoclonal, polyclonal, synthetic or heavy chain camel antibodies as well as fragments of antibodies such as Fab, Fv or scFv fragments. Monoclonal antibodies can be prepared by the techniques as described in e.g. Liddle and Cryer (1991) which comprise the fusion of mouse myeloma cells to spleen cells derived from immunized animals. Furthermore, antibodies or fragments thereof to a molecule or fragments thereof can be obtained by using methods as described in e.g. Harlow and Lane (1988). In the case of antibodies directed against small peptides such as fragments of a protein of the invention, said peptides are generally coupled to a carrier protein before immunization of animals. Such protein carriers include keyhole limpet hemocyanin (KLH), bovine serum albumin (BSA), ovalbumin and Tetanus toxoid. The carrier protein enhances the immune response of the animal and provides epitopes for T-cell receptor binding sites. The term "antibodies" furthermore includes derivatives thereof such as labeled antibodies. Antibody labels include alkaline phosphatase, PKH2, PKH26, PKH67, fluorescein (FITC), Hoechst 33258, R-phycoerythrin (PE), rhodamine (TRITC), Quantum Red, Texas Red, Cy3, biotin, agarose, peroxidase and gold spheres. Tools in molecular biology relying on antibodies against a protein include protein gel blot analysis, screening of expression libraries allowing gene identification, protein quantitative methods including ELISA and RIA, immunoaffinity purification of proteins, immunoprecipitation of proteins (see e.g. Example 6) and immunolocalization. Other uses of antibodies and especially of peptide antibodies include the study of proteolytic processing (Loffler et al. 1994, Woulfe et al. 1994), determination of protein active sites (Lerner 1982), the study of precursor and post-translational processing (Baron and Baltimore 1982, Lerner et al. 1981, Semier et al. 1982), identification of protein domains involved in protein-protein interactions (Murakami et al. 1992) and the study of exon usage in gene expression (Tamura et al. 1991).

Embodied in the current invention are antibodies specifically recognizing a cytokinin oxidase or homologue, derivative or fragment thereof as defined supra. Preferably said cytokinin oxidase is a plant cytokinin oxidase, more specifically one of the *Arabidopsis thaliana* cytokinin oxidases (AtCKX).

The terms "gene(s)", "polynucleotide(s)", "nucleic acid(s)", "nucleic acid sequence(s)", "nucleotide sequence(s)", or "nucleic acid molecule(s)", when used herein refer to nucleotides, either ribonucleotides or deoxyribonucleotides or a combination of both, in a polymeric form of any length. Said terms furthermore include double-stranded and single-stranded DNA and RNA. Said terms also include known nucleotide modifications such as methylation, cyclization and 'caps' and substitution of one or more of the naturally occurring nucleotides with an analog such as inosine. Modifications of nucleotides include the addition of acridine, amine, biotin, cascade blue, cholesterol, Cy3®, Cy5®, Cy5.5® Dabcyl, digoxigenin, dinitrophenyl, Edans, 6-FAM, fluorescein, 3'-glyceryl, HEX, IRD-700, IRD-800, JOE, phosphate psoralen, rhodamine, ROX, thiol (SH), spacers, TAMRA, TET, AMCA-S®, SE, BODIPY®, Marina Blue®, Pacific Blue®, Oregon Green®, Rhodamine Green®, Rhodamine Red®, Rhodol Green® and Texas Red®. Polynucleotide backbone modifications include methylphosphonate, 2'-OMe-methylphosphonate RNA, phosphorothioate, RNA, 2'-OMeRNA. Base modifications include 2-amino-dA, 2-aminopurine, 3'-(ddA), 3'dA(cordycepin), 7-deaza-dA, 8-Br-dA, 8-oxo-dA, N$^6$—Me-dA, abasic site (dSpacer), biotin dT, 2'-OMe-5Me-C, 2'-OMe-propynyl-C, 3'-(5-MedC), 3'-(ddC), 5-Br-dC, 5-I-dC, 5-Me-dC, 5-F-dC, carboxy-dT, convertible dA, convertible dC, convertible dG, convertible dT, convertible dU, 7-deaza-dG, 8-Br-dG, 8-oxo-dG, O$^6$—Me-dG, S6-DNP-dG, 4-methyl-indole, 5-nitroindole, 2'-OMe-inosine, 2'-dI, 0$^6$-phenyl-dI, 4-methyl-indole, 2'-deoxynebularine, 5-nitroindole, 2-aminopurine, dP (purine analogue), dK (pyrimidine analogue), 3-nitropyrrole, 2-thio-dT, 4-thio-dT, biotin-dT, carboxy-dT, O$^4$—Me-dT, O$^4$-triazol dT, 2'-OMe-propynyl-U, 5-Br-dU, 2'-dU, 5-F-dU, 5-I-dU, O$^4$-triazol dU. Said terms also encompass peptide nucleic acids (PNAs), a DNA analogue in which the backbone is a pseudopeptide consisting of N-(2-aminoethyl)-glycine units rather than a sugar. PNAs mimic the behavior of DNA and bind complementary nucleic acid strands. The neutral backbone of PNA results in stronger binding and greater specificity than normally achieved. In addition, the unique chemical, physical and biological properties of PNA have been exploited to produce powerful biomolecular tools, antisense and antigene agents, molecular probes and biosensors.

The present invention also advantageously provides nucleic acid sequences of at least approximately 15 contiguous nucleotides of a nucleic acid according to the invention and preferably from 15 to 50 nucleotides. These sequences may, advantageously be used as probes to specifically hybridize to sequences of the invention as defined above or primers to initiate specific amplification or replication of sequences of the invention as defined above, or the like. Such nucleic acid sequences may be produced according to techniques well known in the art, such as by recombinant or synthetic means. They may also be used in diagnostic kits or the like for detecting the presence of a nucleic acid according to the invention. These tests generally comprise contacting the probe with the sample under hybridising conditions and detecting the presence of any duplex or triplex formation between the probe and any nucleic acid in the sample.

Advantageously, the nucleic acid sequences, according to the invention may be produced using such recombinant or synthetic means, such as for example using PCR cloning mechanisms which generally involve making a pair of primers, which may be from approximately 15 to 50 nucleotides to a region of the gene which is desired to be cloned, bringing the primers into contact with mRNA, cDNA or genomic DNA from a cell, performing a polymerase chain reaction under conditions which bring about amplification of the desired region, isolating the amplified region or fragment and recovering the amplified DNA. Generally, such techniques as defined herein are well known in the art, such as described in Sambrook et al. (Molecular Cloning: a Laboratory Manual, 1989).

A "coding sequence" or "open reading frame" or "ORF" is defined as a nucleotide sequence that can be transcribed into mRNA and/or translated into a polypeptide when placed under the control of appropriate control sequences or regulatory sequences, i.e. when said coding sequence or ORF is present in an expressible format. Said coding sequence of ORF is bounded by a 5' translation start codon and a 3' translation stop codon. A coding sequence or ORF can include, but is not limited to RNA, mRNA, cDNA, recombinant nucleotide sequences, synthetically manufactured nucleotide sequences or genomic DNA. Said coding sequence or ORF can be interrupted by intervening nucleic acid sequences.

Genes and coding sequences essentially encoding the same protein but isolated from different sources can consist of substantially divergent nucleic acid sequences. Reciprocally, substantially divergent nucleic acid sequences can be designed to effect expression of essentially the same protein. Said nucleic acid sequences are the result of e.g. the existence of different alleles of a given gene, of the degeneracy of the genetic code or of differences in codon usage. Thus, as indicated in Table 2, amino acids such as methionine and tryptophan are encoded by a single codon whereas other amino acids such as arginine, leucine and serine can each be translated from up to six different codons. Differences in preferred codon usage are illustrated in Table 4 for *Agrobacterium tumefaciens* (a bacterium), *A. thaliana*, *M. sativa* (two dicotyledonous plants) and *Oryza sativa* (a monocotyledonous plant). To extract one example, the codon GGC (for glycine) is the most frequently used codon in *A. tumefaciens* (36.2%), is the second most frequently used codon in *O. sativa* but is used at much lower frequencies in *A. thaliana* and *M. sativa* (9% and 8.4%, respectively). Of the four possible codons encoding glycine (see Table 3), said GGC codon is most preferably used in *A. tumefaciens* and *O. sativa*. However, in *A. thaliana* this is the GGA (and GGU) codon whereas in *M. sativa* this is the GGU (and GGA) codon.

DNA sequences as defined in the current invention can be interrupted by intervening sequences. With "intervening sequences" is meant any nucleic acid sequence which disrupts a coding sequence comprising said inventive DNA sequence or which disrupts the expressible format of a DNA sequence comprising said inventive DNA sequence. Removal of the intervening sequence restores said coding sequence or said expressible format. Examples of intervening sequences include introns and mobilizable DNA sequences such as transposons. With "mobilizable DNA sequence" is meant any DNA sequence that can be mobilized as the result of a recombination event.

The methods according to the present invention may also be practised using an alternative splice variant of a nucleic acid molecule encoding a CKX protein. The term "alternative splice variant" as used herein encompasses variants of a nucleic acid molecule in which selected introns and/or exons have been excised, replaced or added. Such variants will be ones in which the biological activity of the protein remains unaffected, which can be achieved by selectively retaining functional segments of the protein. Such splice variants may be found in nature or can be manmade. Methods for making such splice variants are well known in the art. Therefore according to another aspect of the present invention, there is provided a method for modifying the growth characteristics of plants, in particular seed yield, comprising modulating expression in a plant of an alternative splice variant of a nucleic acid molecule encoding a CKX and/or by modulating activity and/or levels of a CKX encoded by the alternative splice variant. Preferably, the splice variant is a splice variant of a sequence represented by SEQ ID NO: 1, 3, 5, 7, 9, 11, 33, or 48. A preferred splice variant is as represented by SEQ ID NO 38/39.

TABLE 3

Degeneracy of the genetic code.

| Amino Acid | Three-letter code | One-letter code | Possible codons |
|---|---|---|---|
| Alanine | Ala | A | GCA GCC GCG GCU |
| Arginine | Arg | R | AGA AGG CGA CGC CGG CGU |
| Asparagine | Asn | N | AAC AAU |
| Aspartic Acid | Asp | D | GAC GAU |
| Cysteine | Cys | C | UGC UGU |
| Glutamic Acid | Glu | E | GAA GAG |
| Glutamine | Gln | Q | CAA CAG |
| Glycine | Gly | G | GGA GGC GGG GGU |
| Histidine | His | H | CAC CAU |
| Isoleucine | Ile | I | AUA AUC AUU |
| Leucine | Leu | L | UUA UUG CUA CUC CUG CUU |
| Lysine | Lys | K | AAA AAG |
| Methionine | Met | M | AUG |
| Phenylalanine | Phe | F | UUC UUU |
| Proline | Pro | P | CCA CCC CCG CCU |
| Serine | Ser | S | AGC AGU UCA UCC UCG UCU |
| Threonine | Thr | T | ACA ACC ACG ACU |

TABLE 3-continued

Degeneracy of the genetic code.

| Amino Acid | Three-letter code | One-letter code | Possible codons |
|---|---|---|---|
| Tryptophan | Trp | W | UGG |
| Tyrosine | Tyr | Y | UAC UAU |
| Valine | Val | V | GUA GUC GUG GUU |
| | | | Possible "STOP" codons |
| | | | UAA UAG UGA |

TABLE 4

Usage of the indicated codons in the different organisms given as frequency per thousand codons (kazusa.or.jp/codon).

| Codon | Agrobacterium tumefaciens | Arabidopsis thaliana | Medicago sativa | Oryza sativa |
|---|---|---|---|---|
| UUU | 13.9 | 22.5 | 24.1 | 11.3 |
| UUC | 24.3 | 20.7 | 16.9 | 26.3 |
| UUA | 3.5 | 12.9 | 10.4 | 4.7 |
| UUG | 13.2 | 21.0 | 22.4 | 11.8 |
| UCU | 7.0 | 24.6 | 19.8 | 10.1 |
| UCC | 14.8 | 10.8 | 7.7 | 16.9 |
| UCA | 7.4 | 17.8 | 17.2 | 9.7 |
| UCG | 18.2 | 8.9 | 3.2 | 10.8 |
| UAU | 12.3 | 15.2 | 16.6 | 9.2 |
| UAC | 10.3 | 13.7 | 14.0 | 20.6 |
| UAA | 0.9 | 0.9 | 1.2 | 0.9 |
| UAG | 0.6 | 0.5 | 0.8 | 0.8 |
| UGU | 3.0 | 10.8 | 10.6 | 5.0 |
| UGC | 7.4 | 7.2 | 5.8 | 14.3 |
| UGA | 1.8 | 1.0 | 0.8 | 1.3 |
| UGG | 12.2 | 12.7 | 10.0 | 12.8 |
| CUU | 19.1 | 24.3 | 28.3 | 14.6 |
| CUC | 25.7 | 15.9 | 12.0 | 28.0 |
| CUA | 5.2 | 10.0 | 8.8 | 5.7 |
| CUG | 31.6 | 9.9 | 8.5 | 22.1 |
| CCU | 7.7 | 18.3 | 23.2 | 11.8 |
| CCC | 10.6 | 5.3 | 5.3 | 12.5 |
| CCA | 8.9 | 16.1 | 22.6 | 12.2 |
| CCG | 20.7 | 8.3 | 3.6 | 16.7 |
| CAU | 10.6 | 14.0 | 14.6 | 9.2 |
| CAC | 9.1 | 8.7 | 9.1 | 14.6 |
| CAA | 11.2 | 19.7 | 23.2 | 11.9 |
| CAG | 24.9 | 15.2 | 12.3 | 24.6 |
| CGU | 12.2 | 8.9 | 10.1 | 6.8 |
| CGC | 25.5 | 3.7 | 4.2 | 15.9 |
| CGA | 8.2 | 6.2 | 4.2 | 4.2 |
| CGG | 13.2 | 4.8 | 1.8 | 9.7 |
| AUU | 15.4 | 22.0 | 29.4 | 13.8 |
| AUC | 36.9 | 18.5 | 14.7 | 25.5 |
| AUA | 6.2 | 12.9 | 11.7 | 7.2 |
| AUG | 24.7 | 24.5 | 21.7 | 24.4 |
| ACU | 6.4 | 17.8 | 20.8 | 10.3 |
| ACC | 20.9 | 10.3 | 11.7 | 18.6 |
| ACA | 9.1 | 15.9 | 18.9 | 10.0 |
| ACG | 18.8 | 7.6 | 2.8 | 10.8 |
| AAU | 13.5 | 22.7 | 25.0 | 12.9 |
| AAC | 18.7 | 20.9 | 18.7 | 25.1 |
| AAA | 13.6 | 31.0 | 32.2 | 12.0 |
| AAG | 24.4 | 32.6 | 35.1 | 39.4 |
| AGU | 5.7 | 14.0 | 12.6 | 7.3 |
| AGC | 15.8 | 11.1 | 8.8 | 16.9 |
| AGA | 5.3 | 18.7 | 13.6 | 7.7 |
| AGG | 6.5 | 10.9 | 11.7 | 14.9 |
| GUU | 16.6 | 27.3 | 34.7 | 15.0 |
| GUC | 29.3 | 12.7 | 9.9 | 22.8 |
| GUA | 6.1 | 10.1 | 10.0 | 5.7 |
| GUG | 19.7 | 17.5 | 16.5 | 25.0 |

TABLE 4-continued

Usage of the indicated codons in the different organisms given as frequency per thousand codons (kazusa.or.jp/codon).

| Codon | Agrobacterium tumefaciens | Arabidopsis thaliana | Medicago sativa | Oryza sativa |
|---|---|---|---|---|
| GCU | 17.4 | 28.0 | 34.6 | 19.8 |
| GCC | 35.8 | 10.3 | 11.4 | 33.2 |
| GCA | 19.5 | 17.6 | 25.9 | 15.6 |
| GCG | 31.7 | 8.8 | 3.4 | 25.3 |
| GAU | 25.8 | 36.8 | 40.0 | 21.5 |
| GAC | 28.0 | 17.3 | 15.5 | 31.6 |
| GAA | 29.9 | 34.4 | 35.9 | 17.1 |
| GAG | 26.3 | 32.2 | 27.4 | 41.1 |
| GGU | 16.5 | 22.2 | 28.7 | 16.3 |
| GGC | 36.2 | 9.0 | 8.4 | 34.7 |
| GGA | 12.5 | 23.9 | 27.3 | 15.0 |
| GGG | 11.3 | 10.2 | 7.4 | 16.6 |

"Hybridization" is the process wherein substantially homologous complementary nucleotide sequences anneal to each other. The hybridization process can occur entirely in solution, i.e. both complementary nucleic acids are in solution. Tools in molecular biology relying on such a process include PCR, subtractive hybridization and DNA sequence determination. The hybridization process can also occur with one of the complementary nucleic acids immobilized to a matrix such as magnetic beads, Sepharose beads or any other resin. Tools in molecular biology relying on such a process include the isolation of poly (A+) mRNA. The hybridization process can furthermore occur with one of the complementary nucleic acids immobilized to a solid support such as a nitrocellulose or nylon membrane or immobilized by e.g. photolithography to e.g. a silicious glass support (the latter known as nucleic acid arrays or microarrays or as nucleic acid chips). Tools in molecular biology relying on such a process include RNA and DNA gel blot analysis, colony hybridization, plaque hybridization and microarray hybridization. In order to allow hybridization to occur, the nucleic acid molecules are generally thermally or chemically (e.g. by NaOH) denatured to melt a double strand into two single strands and/or to remove hairpins or other secondary structures from single stranded nucleic acids. The stringency of hybridization is influenced by conditions such as temperature, salt concentration and hybridization buffer composition. High stringency conditions for hybridization include high temperature and/or low salt concentration (salts include NaCl and Na3-citrate) and/or the inclusion of formamide in the hybridization buffer and/or lowering the concentration of compounds such as SDS (detergent) in the hybridization buffer and/or exclusion of compounds such as dextran sulfate or polyethylene glycol (promoting molecular crowding) from the hybridization buffer. Conventional hybridization conditions are described in e.g. Sambrook et al. (1989) but the skilled craftsman will appreciate that numerous different hybridization conditions can be designed in function of the known or the expected homology and/or length of the nucleic acid sequence. Sufficiently low stringency hybridization conditions are particularly preferred to isolate nucleic acids heterologous to the DNA sequences of the invention defined supra. Elements contributing to said heterology include allelism, degeneration of the genetic code and differences in preferred codon usage as discussed supra.

The term "specifically hybridizing" or "hybridizing specifically" refers to the binding, duplexing, or hybridizing of a molecule to a particular nucleotide sequence under medium to stringent conditions when that sequence is presented in a complex mixture e.g., total cellular DNA or RNA.

"Stringent hybridization conditions" and "stringent hybridization wash conditions" in the context of nucleic acid hybridization experiments such as Southern and Northern hybridizations are sequence dependent and are different under different environmental parameters. For example, longer sequences hybridize specifically at higher temperatures. The $T_m$ is the temperature under defined ionic strength and pH, at which 50% of the target sequence hybridizes to a perfectly matched probe. Specificity is typically the function of post-hybridization washes. Critical factors of such washes include the ionic strength and temperature of the final wash solution.

Generally, stringent conditions are selected to be about 50° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. The $T_m$ is dependent upon the solution conditions and the base composition of the probe, and may be calculated using the following equation:

$$T_m = 79.8° \text{ C.} + (18.5 \times \text{Log[Na+]}) + (58.4° \text{ C.} \times \%[G+C]) - (820/\text{\# } bp \text{ in duplex}) - (0.5 \times \% \text{ formamide})$$

More preferred stringent conditions are when the temperature is 20° C. below $T_m$, and the most preferred stringent conditions are when the temperature is 10° C. below $T_m$. Nonspecific binding may also be controlled using any one of a number of known techniques such as, for example, blocking the membrane with protein-containing solutions, addition of heterologous RNA, DNA, and SDS to the hybridization buffer, and treatment with RNase.

Wash conditions are typically performed at or below stringency. Generally, suitable stringent conditions for nucleic acid hybridization assays or gene amplification detection procedures are as set forth above. More or less stringent conditions may also be selected.

For the purposes of defining the level of stringency, reference can conveniently be made to Sambrook, J., E. F. Fritsch, et al. 1989 "Molecular Cloning: a Laboratory Manual, 2$^{nd}$ Edition, Cold Spring Harbor, N.Y., Cold Spring Harbor Laboratory Press, at 11.45. An example of low stringency conditions is 4-6×SSC/0.1-0.5% w/v SDS at 37°-45° C. for 2-3 hours. Depending on the source and concentration of the nucleic acid involved in the hybridization, alternative conditions of stringency may be employed such as medium stringent conditions. Examples of medium stringent conditions include 1-4×SSC/0.25% w/v SDS at ≧45° C. for 2-3 hours. An example of high stringency conditions includes 0.1-1× SSC/0.1% w/v SDS at 60 C for 1-3 hours. The skilled artisan is aware of various parameters which may be altered during hybridization and washing and which will either maintain or change the stringency conditions. For example, another stringent hybridization condition is hybridization at 4×SSC at 65° C., followed by a washing in 0.1×SSC at 65° C. for about one hour. Alternatively, an exemplary stringent hybridization condition is in 50% formamide, 4×SSC, at 42° C. Still another example of stringent conditions include hybridization at 62° C. in 6×SSC, 0.05×BLOTTO, and washing at 2×SSC, 0.1% SDS at 62° C.

The $T_m$ is the temperature under defined ionic strength and pH, at which 50% of the target sequence hybridises to a perfectly matched probe. The $T_m$ is dependent upon the solution conditions and the base composition and length of the probe. For example, longer sequences hybridise specifically at higher temperatures. The maximum rate of hybridisation is obtained from about 16° C. up to 32° C. below $T_m$. The presence of monovalent cations in the hybridisation solution reduce the electrostatic repulsion between the two nucleic acid strands thereby promoting hybrid formation; this effect is visible for sodium concentrations of up to 0.4M. Formamide reduces the melting temperature of DNA-DNA and DNA-RNA duplexes with 0.6 to 0.7° C. for each percent formamide, and addition of 50% formamide allows hybridisation to be performed at 30 to 45° C., though the rate of hybridisation will be lowered. Base pair mismatches reduce the hybridisation rate and the thermal stability of the duplexes. On average and for large probes, the $T_m$ decreases about 1° C. per % base mismatch.

The $T_m$ may alternatively be calculated using the following equations, depending on the types of hybrids:

1. DNA-DNA hybrids (Meinkoth and Wahl, Anal. Biochem., 138: 267-284, 1984):

$$T_m = 81.5° \text{ C.} + 16.6 \times \log [Na^+]^a + 0.41 \times \%[G/C^b] - 500 \times [L^c]^{-1} - 0.61 \times \% \text{ formamide}$$

DNA-RNA or RNA-RNA hybrids:

$$T_m = 79.8 + 18.5(\log_{10}[Na^+]^a) + 0.58(\%G/C^b) + 11.8(\% G/C^b)^2 - 820/L^c$$

oligo-DNA or oligo-RNA$^d$ hybrids:

For <20 nucleotides: $T_m = 2(l_n)$

For 20-35 nucleotides: $T_m = 22 + 1.46(l_n)$ $^a$ or for other monovalent cation, but only accurate in the 0.01-0.4 M range.

$^b$ only accurate for % GC in the 30% to 75% range.

$^c$ L=length of duplex in base pairs.

$^d$ Oligo, oligonucleotide; $l_n$, effective length of primer=2×(no. of G/C)+(no. of A/T).

Note: for each 1% formamide, the $T_m$ is reduced by about 0.6 to 0.7° C., while the presence of 6M urea reduces the $T_m$ by about 30° C.

Specificity of hybridisation is typically the function of post-hybridisation washes. To remove background resulting from non-specific hybridisation, samples are washed with dilute salt solutions. Critical factors of such washes include the ionic strength and temperature of the final wash solution: the lower the salt concentration and the higher the wash temperature, the higher the stringency of the wash. Wash conditions are typically performed at or below hybridisation stringency. Generally, suitable stringent conditions for nucleic acid hybridisation assays or gene amplification detection procedures are as set forth above. More or less stringent conditions may also be selected. Generally, low stringency conditions are selected to be about 50° C. lower than the thermal melting point ($T_m$) for the specific sequence at a defined ionic strength and pH. Medium stringency conditions are when the temperature is 20° C. below T., and high stringency conditions are when the temperature is 10° C. below $T_m$. For example, stringent conditions are those that are at least as stringent as, for example, conditions A-L; and reduced stringency conditions are at least as stringent as, for example, conditions M-R. Non-specific binding may be controlled using any one of a number of known techniques such as, for example, blocking the membrane with protein containing solutions, additions of heterologous RNA, DNA, and SDS to the hybridisation buffer, and treatment with Rnase.

Examples of hybridisation and wash conditions are listed in table 5:

TABLE 5

| Stringency Condition | Polynucleotide Hybrid± | Hybrid Length (bp)‡ | Hybridization Temperature and Buffer† | Wash Temperature and Buffer† |
|---|---|---|---|---|
| A | DNA:DNA | > or equal to 50 | 65° C. 1 × SSC; or 42° C., 1 × SSC and 50% formamide | 65° C.; 0.3 × SSC |
| B | DNA:DNA | <50 | Tb*; 1 × SSC | Tb*; 1 × SSC |
| C | DNA:RNA | > or equal to 50 | 67° C. 1 × SSC; or 45° C., 1 × SSC and 50% formamide | 67° C.; 0.3 × SSC |
| D | DNA:RNA | <50 | Td*; 1 × SSC | Td*; 1 × SSC |
| E | RNA:RNA | > or equal to 50 | 70° C. 1 × SSC; or 50° C., 1 × SSC and 50% formamide | 70° C.; 0.3 × SSC |
| F | RNA:RNA | <50 | Tf*; 1 × SSC | Tf*; 1 × SSC |
| G | DNA:DNA | > or equal to 50 | 65° C. 4 × SSC; or 45° C., 4 × SSC and 50% formamide | 65° C.; 1 × SSC |
| H | DNA:DNA | <50 | Th*; 4 × SSC | Th*; 4 × SSC |
| I | DNA:RNA | > or equal to 50 | 67° C. 4 × SSC; or 45° C., 4 × SSC and 50% formamide | 67° C.; 1 × SSC |
| J | DNA:RNA | <50 | Tj*; 4 × SSC | Tj*; 4 × SSC |
| K | RNA:RNA | > or equal to 50 | 70° C. 4 × SSC; or 40° C., 6 × SSC and 50% formamide | 67° C.; 1 × SSC |
| L | RNA:RNA | <50 | Tl*; 2 × SSC | Tl*; 2 × SSC |
| M | DNA:DNA | > or equal to 50 | 50° C. 4 × SSC; or 40° C., 6 × SSC and 50% formamide | 50° C.; 2 × SSC |
| N | DNA:DNA | <50 | Tn*; 6 × SSC | Tn*; 6 × SSC |
| O | DNA:RNA | >or equal to 50 | 55° C. 4 × SSC; or 42° C., 6 × SSC and 50% formamide | 55° C.; 2 × SSC |
| P | DNA:RNA | <50 | Tp*; 6 × SSC | Tp*; 6 × SSC |
| Q | RNA:RNA | > or equal to 50 | 60° C. 4 × SSC; or 45° C., 6 × SSC and 50% formamide | 60° C.; 2 × SSC |
| R | RNA:RNA | <50 | Tr*; 4 × SSC | Tr*; 4 × SSC |

‡The "hybrid length" is the anticipated length for the hybridising nucleic acid. When nucleic acids of known sequence are hybridised, the hybrid length may be determined by aligning the sequences and identifying the conserved regions described herein.
†SSPE (1 × SSPE is 0.15 M NaCl, 10 mM $NaH_2PO_4$, and 1.25 mM EDTA, pH7.4) may be substituted for SSC (1 × SSC is 0.15 M NaCl and 15 mM sodium citrate) in the hybridisation and wash buffers; washes are performed for 15 minutes after hybridisation is complete. The hybridisations and washes may additionally include 5 × Denhardt's reagent, 0.5-1.0% SDS, 100 μg/ml denatured, fragmented salmon sperm DNA, 0.5% sodium pyrophosphate, and up to 50% formamide.
*Tb-Tr: The hybridisation temperature for hybrids anticipated to be less than 50 base pairs in length should be 5-10° C. less than the melting temperature $T_m$ of the hybrids; the $T_m$ is determined according to the above-mentioned equations.
±The present invention also encompasses the substitution of any one, or more DNA or RNA hybrid partners with either a PNA, or a modified nucleic acid.

For the purposes of defining the level of stringency, reference can conveniently be made to Sambrook et al. (2001) Molecular Cloning: a laboratory manual, 3$^{rd}$ Edition Cold Spring Harbor Laboratory Press, CSH, New York or to Current Protocols in Molecular Biology, John Wiley & Sons, N.Y. (1989).

After hybridisation and washing, the duplexes may be detected by autoradiography (when radiolabeled probes were used) or by chemiluminescence, immunodetection, by fluorescent or chromogenic detection, depending on the type of probe labelling. Alternatively, a ribonuclease protection assay can be performed for detection of RNA: RNA hybrids Clearly, the current invention embodies the use of the inventive DNA sequences encoding a cytokinin oxidase, homologue, derivative or immunologically active and/or functional fragment thereof as defined higher in any method of hybridization. The current invention furthermore also relates to DNA sequences hybridizing to said inventive DNA sequences. Preferably said cytokinin oxidase is a plant cytokinin oxidase, more specifically the *Arabidopsis thaliana* (At)CKX.

To effect expression of a protein in a cell, tissue or organ, preferably of plant origin, either the protein may be introduced directly to said cell, such as by microinjection or ballistic means or alternatively, an isolated nucleic acid molecule encoding said protein may be introduced into said cell, tissue or organ in an expressible format.

Preferably, the DNA sequence of the invention comprises a coding sequence or open reading frame (ORF) encoding a cytokinin oxidase protein or a homologue or derivative thereof or an immunologically active and/or functional fragment thereof as defined supra. The preferred protein of the invention comprises the amino acid sequence of said cytokinin oxidase. Preferably said cytokinin oxidase is a plant cytokinin oxidase and more specifically a *Arabidopsis thaliana* (At)CKX.

With "vector" or "vector sequence" is meant a DNA sequence which can be introduced in an organism by transformation and can be stably maintained in said organism. Vector maintenance is possible in e.g. cultures of *Escherichia coli, A. tumefaciens, Saccharomyces cerevisiae* or *Schizosaccharomyces pombe*. Other vectors such as phagemids and cosmid vectors can be maintained and multiplied in bacteria and/or viruses. Vector sequences generally comprise a set of unique sites recognized by restriction enzymes, the multiple cloning site (MCS), wherein one or more non-vector sequence(s) can be inserted.

With "non-vector sequence" is accordingly meant a DNA sequence which is integrated in one or more of the sites of the MCS comprised within a vector.

"Expression vectors" form a subset of vectors which, by virtue of comprising the appropriate regulatory or control sequences enable the creation of an expressible format for the inserted non-vector sequence(s), thus allowing expression of the protein encoded by said non-vector sequence(s). Expression vectors are known in the art enabling protein expression in organisms including bacteria (e.g. *E. coli*), fungi (e.g. *S. cerevisiae, S. pombe, Pichia pastoris*), insect cells (e.g. baculoviral expression vectors), animal cells (e.g. COS or CHO cells) and plant cells (e.g. potato virus X-based expression vectors).

The current invention clearly includes any cytokinin oxidase, homologue, derivative and/or immunologically active and/or functional fragment thereof as defined supra. Preferably said cytokinin oxidase is a plant cytokinin oxidase, more specifically a *Arabidopsis thaliana* (At)CKX.

As an alternative to expression vector-mediated protein production in biological systems, chemical protein synthesis can be applied. Synthetic peptides can be manufactured in solution phase or in solid phase. Solid phase peptide synthesis (Merrifield 1963) is, however, the most common way and involves the sequential addition of amino acids to create a linear peptide chain. Solid phase peptide synthesis includes cycles consisting of three steps: (i) immobilization of the carboxy-terminal amino acid of the growing peptide chain to a solid support or resin; (ii) chain assembly, a process consisting of activation, coupling and deprotection of the amino acid to be added to the growing peptide chain; and (iii) cleavage involving removal of the completed peptide chain from the resin and removal of the protecting groups from the amino acid side chains. Common approaches in solid phase peptide synthesis include Fmoc/tBu (9-fluorenylmethyloxycarbonyl/t-butyl) and Boc (t-butyloxycarbonyl) as the amino-terminal protecting groups of amino acids. Amino acid side chain protecting groups include methyl (Me), formyl (CHO), ethyl (Et), acetyl (Ac), t-butyl (t-Bu), anisyl, benzyl (Bzl), trifluoroacetyl (Tfa), N-hydroxysuccinimide (ONSu, OSu), benzoyl (Bz), 4-methylbenzyl (Meb), thioanizyl, thiocresyl, benzyloxymethyl (Bom), 4-nitrophenyl (ONp), benzyloxycarbonyl (Z), 2-nitrobenzoyl (NBz), 2-nitrophenylsulphenyl (Nps), 4-toluenesulphonyl (Tosyl, Tos), pentafluorophenyl (Pfp), diphenylmethyl (Dpm), 2-chlorobenzyloxycarbonyl (Cl-Z), 2,4,5-trichlorophenyl, 2-bromobenzyloxycarbonyl (Br-Z), tripheylmethyl (Trityl, Trt), and 2,5,7,8-pentamethyl-chroman-6-sulphonyl (Pmc). During chain assembly, Fmoc or Boc are removed resulting in an activated amino-terminus of the amino acid residue bound to the growing chain. The carboxy-terminus of the incoming amino acid is activated by conversion into a highly reactive ester, e.g. by HBTU. With current technologies (e.g. PerSeptive Biosystems 9050 synthesizer, Applied Biosystems Model 431A Peptide Synthesizer), linear peptides of up to 50 residues can be manufactured. A number of guidelines is available to produce peptides that are suitable for use in biological systems including (i) limiting the use of difficult amino acids such as cys, met, trp (easily oxidized and/or degraded during peptide synthesis) or arg; (ii) minimize hydrophobic amino acids (can impair peptide solubility); and (iii) prevent an amino-terminal glutamic acid (can cyclize to pyroglutamate).

By "expressible format" is meant that the isolated nucleic acid molecule is in a form suitable for being transcribed into mRNA and/or translated to produce a protein, either constitutively or following induction by an intracellular or extracellular signal, such as an environmental stimulus or stress (mitogens, anoxia, hypoxia, temperature, salt, light, dehydration, etc) or a chemical compound such as IPTG (isopropyl-β-D-thiogalactopyranoside) or such as an antibiotic (tetracycline, ampicillin, rifampicin, kanamycin), hormone (e.g. gibberellin, auxin, cytokinin, glucocorticoid, brassinosteroid, ethylene, abscisic acid etc), hormone analogue (indoleacetic acid (IAA), 2,4-D, etc), metal (zinc, copper, iron, etc), or dexamethasone, amongst others. As will be known to those skilled in the art, expression of a functional protein may also require one or more post-translational modifications, such as glycosylation, phosphorylation, dephosphorylation, or one or more protein-protein interactions, amongst others. All such processes are included within the scope of the term "expressible format".

Preferably, expression of a protein in a specific cell, tissue, or organ, preferably of plant origin, is effected by introducing and expressing an isolated nucleic acid molecule encoding said protein, such as a cDNA molecule, genomic gene, synthetic oligonucleotide molecule, mRNA molecule or open reading frame, to said cell, tissue or organ, wherein said nucleic acid molecule is placed operably in connection with suitable regulatory or control sequences including a promoter, preferably a plant-expressible promoter, and a terminator sequence.

Reference herein to a "promoter" is to be taken in its broadest context and includes the transcriptional regulatory sequences derived from a classical eukaryotic genomic gene, including the TATA box which is required for accurate transcription initiation, with or without a CCAAT box sequence and additional regulatory or control elements (i.e. upstream activating sequences, enhancers and silencers) which alter gene expression in response to developmental and/or external stimuli, or in a tissue-specific manner.

The term "promoter" also includes the transcriptional regulatory sequences of a classical prokaryotic gene, in which case it may include a −35 box sequence and/or a −10 box transcriptional regulatory sequences.

The term "promoter" is also used to describe a synthetic or fusion molecule, or derivative which confers, activates or enhances expression of a nucleic acid molecule in a cell, tissue or organ.

Promoters may contain additional copies of one or more specific regulatory elements, to further enhance expression and/or to alter the spatial expression and/or temporal expression of a nucleic acid molecule to which it is operably connected. Such regulatory elements may be placed adjacent to a heterologous promoter sequence to drive expression of a nucleic acid molecule in response to e.g. copper, glucocorticoids, dexamethasone, tetracycline, gibberellin, cAMP, abscisic acid, auxin, wounding, ethylene, jasmonate or salicylic acid or to confer expression of a nucleic acid molecule to specific cells, tissues or organs such as meristems, leaves, roots, embryo, flowers, seeds or fruits.

In the context of the present invention, the promoter preferably is a plant-expressible promoter sequence. Promoters that also function or solely function in non-plant cells such as bacteria, yeast cells, insect cells and animal cells are not excluded from the invention. By "plant-expressible" is meant that the promoter sequence, including any additional regulatory elements added thereto or contained therein, is at least capable of inducing, conferring, activating or enhancing expression in a plant cell, tissue or organ, preferably a monocotyledonous or dicotyledonous plant cell, tissue, or organ.

The terms "plant-operable" and "operable in a plant" when used herein, in respect of a promoter sequence, shall be taken to be equivalent to a plant-expressible promoter sequence.

Regulatable promoters as part of a binary viral plant expression system are also known to the skilled artisan (Yadav 1999—WO9922003; Yadav 2000—WO0017365).

In the present context, a "regulatable promoter sequence" is a promoter that is capable of conferring expression on a structural gene in a particular cell, tissue, or organ or group of cells, tissues or organs of a plant, optionally under specific conditions, however does generally not confer expression throughout the plant under all conditions. Accordingly, a regulatable promoter sequence may be a promoter sequence that confers expression on a gene to which it is operably connected in a particular location within the plant or alternatively, throughout the plant under a specific set of conditions, such as following induction of gene expression by a chemical compound or other elicitor.

Preferably, the regulatable promoter used in the performance of the present invention confers expression in a specific location within the plant, either constitutively or following induction, however not in the whole plant under any circumstances. Included within the scope of such promoters are cell-specific promoter sequences, tissue-specific promoter sequences, organ-specific promoter sequences, cell cycle specific gene promoter sequences, inducible promoter sequences and constitutive promoter sequences that have been modified to confer expression in a particular part of the plant at any one time, such as by integration of said constitutive promoter within a transposable genetic element (Ac, Ds, Spm, En, or other transposon).

Similarly, the term "tissue-specific" shall be taken to indicate that expression is predominantly in a particular tissue or tissue-type, preferably of plant origin, albeit not necessarily exclusively in said tissue or tissue-type.

Similarly, the term "organ-specific" shall be taken to indicate that expression is predominantly in a particular organ, preferably of plant origin, albeit not necessarily exclusively in said organ.

Similarly, the term "cell cycle specific" shall be taken to indicate that expression is predominantly cyclic and occurring in one or more, not necessarily consecutive phases of the cell cycle albeit not necessarily exclusively in cycling cells, preferably of plant origin.

Those skilled in the art will be aware that an "inducible promoter" is a promoter the transcriptional activity of which is increased or induced in response to a developmental, chemical, environmental, or physical stimulus. Similarly, the skilled craftsman will understand that a "constitutive promoter" is a promoter that is transcriptionally active throughout most, but not necessarily all parts of an organism, preferably a plant, during most, but not necessarily all phases of its growth and development.

Those skilled in the art will readily be capable of selecting appropriate promoter sequences for use in regulating appropriate expression of the cytokinin oxidase protein from publicly-available or readily-available sources, without undue experimentation.

Placing a nucleic acid molecule under the regulatory control of a promoter sequence, or in operable connection with a promoter sequence, means positioning said nucleic acid molecule such that expression is controlled by the promoter sequence. A promoter is usually, but not necessarily, positioned upstream, or at the 5'-end, and within 2 kb of the start site of transcription, of the nucleic acid molecule which it regulates. In the construction of heterologous promoter/structural gene combinations it is generally preferred to position the promoter at a distance from the gene transcription start site that is approximately the same as the distance between that promoter and the gene it controls in its natural setting (i.e., the gene from which the promoter is derived). As is known in the art, some variation in this distance can be accommodated without loss of promoter function. Similarly, the preferred positioning of a regulatory sequence element with respect to a heterologous gene to be placed under its control is defined by the positioning of the element in its natural setting (i.e., the gene from which it is derived). Again, as is known in the art, some variation in this distance can also occur.

Examples of promoters suitable for use in gene constructs of the present invention include those listed in Table 6, amongst others. The promoters listed in Table 6 are provided for the purposes of exemplification only and the present invention is not to be limited by the list provided therein. Those skilled in the art will readily be in a position to provide additional promoters that are useful in performing the present invention.

Further examples of promoters suitable for use in the present invention especially with respect to increasing seed yield in a plant may be found in Table 19.

In the case of constitutive promoters or promoters that induce expression throughout the entire plant, it is preferred that such sequences are modified by the addition of nucleotide sequences derived from one or more of the tissue-specific promoters listed in Table 6, or alternatively, nucleotide sequences derived from one or more of the above-mentioned tissue-specific inducible promoters, to confer tissue-specificity thereon. For example, the CaMV 35S promoter may be modified by the addition of maize Adh1 promoter sequence, to confer anaerobically-regulated root-specific expression thereon, as described previously (Ellis et al., 1987). Another example describes conferring root specific or root abundant gene expression by fusing the CaMV35S promoter to elements of the maize glycine-rich protein GRP3 gene (Feix and Wulff 2000—WO0015662). Such modifications can be achieved by routine experimentation by those skilled in the art.

The term "terminator" refers to a DNA sequence at the end of a transcriptional unit which signals termination of transcription. Terminators are 3'-non-translated DNA sequences containing a polyadenylation signal, which facilitates the addition of polyadenylate sequences to the 3'-end of a primary transcript. Terminators active in cells derived from viruses, yeasts, molds, bacteria, insects, birds, mammals and plants are known and described in the literature. They may be isolated from bacteria, fungi, viruses, animals and/or plants.

TABLE 6

Examples of plant-expressible promoters for use
in the performance of the present invention

| GENE SOURCE | EXPRESSION PATTERN | REFERENCE |
|---|---|---|
| I: CELL-SPECIFIC, TISSUE-SPECIFIC, AND ORGAN-SPECIFIC PROMOTERS | | |
| α-amylase (Amy32b) | aleurone | Lanahan, M. B., et al., Plant Cell 4: 203-211, 1992; Skriver, K., et al. Proc. Natl. Acad. Sci. (USA) 88: 7266-7270, 1991 |
| cathepsin β-like gene | aleurone | Cejudo, F. J., et al. Plant Molecular Biology 20: 849-856, 1992. |
| *Agrobacterium rhizogenes* rolB | cambium | Nilsson et al., Physiol. Plant. 100: 456-462, 1997 |
| AtPRP4 | flowers | http://salus.medium.edu/mmg/tierney/html |
| chalcone synthase (chsA) | flowers | Van der Meer, et al., Plant Mol. Biol. 15, 95-109, 1990. |
| LAT52 | anther | Twell et al Mol. Gen Genet. 217: 240-245 (1989) |
| *apetala*-3 | flowers | |
| Chitinase | fruit (berries, grapes, etc) | Thomas et al. CSIRO Plant Industry, Urrbrae, South Australia, Australia; http://winetitles.com.au/gwrdc/csh95-1.html |
| rbcs-3A | green tissue (eg leaf) | Lam, E. et al., The Plant Cell 2: 857-866, 1990.; Tucker et al., Plant Physiol. 113: 1303-1308, 1992. |
| leaf-specific genes | leaf | Baszczynski, et al., Nucl. Acid Res. 16: 4732, 1988. |
| AtPRP4 | leaf | http://salus.medium.edu/mmg/tierney/html |
| chlorella virus adenine methyltransferase gene promoter | leaf | Mitra and Higgins, 1994, Plant Molecular Biology 26: 85-93 |
| aldP gene promoter from rice | leaf | Kagaya et al., 1995, Molecular and General Genetics 248: 668-674 |
| rbcs promoter from rice or tomato | leaf | Kyozuka et al., 1993, Plant Physiology 102: 991-1000 |
| Pinus cab-6 | leaf | Yamamoto et al., Plant Cell Physiol. 35: 773-778, 1994. |
| rubisco promoter | leaf | |
| cab (chlorophyll a/b/binding protein | leaf | |
| SAM22 | senescent leaf | Crowell, et al., Plant Mol. Biol. 18: 459-466, 1992. |
| ltp gene (lipid transfer gene) | | Fleming, et al., Plant J. 2, 855-862. |
| *R. japonicum* nif gene | Nodule | U.S. Pat. No. 4,803,165 |
| *B. japonicum* nifH gene | Nodule | U.S. Pat. No. 5,008,194 |
| GmENOD40 | Nodule | Yang, et al., The Plant J. 3: 573-585. |
| PEP carboxylase (PEPC) | Nodule | Pathirana, et al., Plant Mol. Biol. 20: 437-450, 1992. |
| Leghaemoglobin (Lb) | Nodule | Gordon, et al., J. Exp. Bot. 44: 1453-1465, 1993. |
| *Tungro bacilliform* virus gene | phloem | Bhattacharyya-Pakrasi, et al., The Plant J. 4: 71-79, 1992. |
| pollen-specific genes | pollen; microspore | Albani, et al., Plant Mol. Biol. 15: 605, 1990; Albani, et al., Plant Mol. Biol. 16: 501, 1991) |
| Zm13 | pollen | Guerrero et al Mol. Gen. Genet. 224: 161-168 (1993) |
| apg gene | microspore | Twell et al Sex. Plant Reprod. 6: 217-224 (1993) |
| maize pollen-specific gene | pollen | Hamilton, et al., Plant Mol. Biol. 18: 211-218, 1992. |
| sunflower pollen-expressed gene | pollen | Baltz, et al., The Plant J. 2: 713-721, 1992. |
| *B. napus* pollen-specific gene | pollen; anther; tapetum | Arnoldo, et al., J. Cell. Biochem., Abstract No. Y101, 204, 1992. |
| root-expressible genes | roots | Tingey, et al., EMBO J. 6: 1, 1987. |
| tobacco auxin-inducible gene | root tip | Van der Zaal, et al., Plant Mol. Biol. 16,983, 1991. |
| β-tubulin | root | Oppenheimer, et al., Gene 63: 87, 1988. |
| tobacco root-specific genes | root | Conkling, et al., Plant Physiol. 93: 1203, 1990. |

TABLE 6-continued

Examples of plant-expressible promoters for use in the performance of the present invention

| Promoter | Expression | Reference |
|---|---|---|
| *B. napus* G1-3b gene | root | U.S. Pat. No. 5,401,836 |
| SbPRP1 | roots | Suzuki et al., Plant Mol. Biol. 21: 109-119, 1993. |
| AtPRP1; AtPRP3 | roots; root hairs | http://salus.medium.edu/mmg/tiemey/html |
| RD2 gene | root cortex | http://www2.cnsu.edu/ncsu/research |
| TobRB7 gene | root vasculature | http://www2.cnsu.edu/ncsu/research |
| AtPRP4 | leaves; flowers; lateral root primordia | http://salus.medium.edu/mmg/tierney/html |
| seed-specific genes | seed | Simon, et al., Plant Mol. Biol. 5: 191, 1985; Scofield, et al., J. Biol. Chem. 262: 12202, 1987.; Baszczynski, et al., Plant Mol. Biol. 14: 633, 1990. |
| Brazil Nut albumin | seed | Pearson, et al., Plant Mol. Biol. 18: 235-245, 1992. |
| Legumin | seed | Ellis, et al., Plant Mol. Biol. 10: 203-214, 1988. |
| glutelin (rice) | seed | Takaiwa, et al., Mol. Gen. Genet. 208: 15-22, 1986; Takaiwa, et al., FEBS Letts. 221: 43-47, 1987. |
| Zein | seed | Matzke et al Plant Mol Biol, 14(3): 323-32 1990 |
| NapA | seed | Stalberg, et al, Planta 199: 515-519, 1996. |
| wheat LMW and HMW glutenin-1 | endosperm | Mol Gen Genet 216: 81-90, 1989; NAR 17: 461-2, 1989 |
| wheat SPA | seed | Albani et al, Plant Cell, 9: 171-184, 1997 |
| wheat α, β, γ-gliadins | endosperm | EMBO 3: 1409-15, 1984 |
| barley ltr1 promoter | endosperm | |
| barley B1, C, D, hordein | endosperm | Theor Appl Gen 98: 1253-62, 1999; Plant J 4: 343-55, 1993; Mol Gen Genet 250: 750-60, 1996 |
| barley DOF | endosperm | Mena et al, The Plant Journal, 116(1): 53-62, 1998 |
| blz2 | endosperm | EP99106056.7 |
| synthetic promoter | endosperm | Vicente-Carbajosa et al., Plant J. 13: 629-640, 1998. |
| rice prolamin NRP33 | endosperm | Wu et al, Plant Cell Physiology 39(8) 885-889, 1998 |
| rice α-globulin Glb-1 | endosperm | Wu et al, Plant Cell Physiology 39(8) 885-889, 1998 |
| rice OSH1 | embryo | Sato et al, Proc. Natl. Acad. Sci. USA, 93: 8117-8122, 1996 |
| rice α-globulin REB/OHP-1 | endosperm | Nakase et al. Plant Mol. Biol. 33: 513-522, 1997 |
| rice ADP-glucose PP | endosperm | Trans Res 6: 157-68, 1997 |
| maize ESR gene family | endosperm | Plant J 12: 235-46, 1997 |
| sorgum γ-kafirin | endosperm | PMB 32: 1029-35, 1996 |
| KNOX | embryo | Postma-Haarsma et al, Plant Mol. Biol. 39: 257-71, 1999 |
| rice oleosin | embryo and aleuron | Wu et at, J. Biochem., 123: 386, 1998 |
| sunflower oleosin | seed (embryo and dry seed) | Cummins, et al., Plant Mol. Biol. 19: 873-876, 1992 |
| LEAFY | shoot meristem | Weigel et al., Cell 69: 843-859, 1992. |
| *Arabidopsis thaliana* knat1 | shoot meristem | Accession number AJ131822 |
| *Malus domestica* kn 1 | shoot meristem | Accession number Z71981 |
| CLAVATA1 | shoot meristem | Accession number AF049870 |
| stigma-specific genes | stigma | Nasrallah, et al., Proc. Natl. Acad. Sci. USA 85: 5551, 1988; Trick, et al., Plant Mol. Biol. 15: 203, 1990. |
| class I patatin gene | tuber | Liu et al., Plant Mol. Biol. 153: 386-395, 1991. |
| PCNA rice | meristem | Kosugi et al, Nucleic Acids Research 19: 1571-1576, 1991; Kosugi S. and Ohashi Y, Plant Cell 9: 1607-1619, 1997. |
| Pea TubA1 tubulin | Dividing cells | Stotz and Long, Plant Mol. Biol. 41, 601-614. 1999 |
| *Arabidopsis* cdc2a | cycling cells | Chung and Parish, FEBS Lett, 3; 362(2): 215-9, 1995 |
| *Arabidopsis* Rop1A | Anthers; mature pollen + pollen tubes | Li et al. 1998 Plant Physiol 118, 407-417. |

TABLE 6-continued

Examples of plant-expressible promoters for use
in the performance of the present invention

| | | |
|---|---|---|
| *Arabidopsis* AtDMC1 | Meiosis-associated | Klimyuk and Jones 1997 Plant J. 11, 1-14. |
| Pea PS-IAA4/5 and PS-IAA6 | Auxin-inducible | Wong et al., 1996 Plant J. 9, 587-599. |
| Pea farnesyltransferase | Meristematic tissues; phloem near growing tissues; light- and sugar-repressed | Zhou et al. 1997 Plant J. 12, 921-930 |
| Tobacco (*N. sylvestris*) cyclin B1;1 | Dividing cells/ meristematic tissue | Trehin et al. 1997 Plant Mol. Biol. 35, 667-672. |
| Mitotic cyclins CYS (A-type) and CYM (B-type) | Dividing cells/ meristematic tissue | Ito et al. 1997 Plant J. 11, 983-992 |
| *Arabidopsis* cyc1At (= cyc B1; 1)and cyc3aAt (A-type) | Dividing cells/ meristematic tissue | Shaul et al. 1996 Proc. Natl. Acad. Sci. U.S.A 93, 4868-4872. |
| *Arabidopsis* tef1 promoter box | Dividing cells/ meristematic tissue | Regad et al. 1995 Mol. Gen. Genet. 248, 703-711. |
| *Catharanthus roseus* cyc07 | Dividing cells/ meristematic tissue | Ito et al. 1994 Plant Mol. Biol. 24, 863-878. |

II: EXAMPLES OF CONSTITUTIVE PROMOTERS

| | | |
|---|---|---|
| Actin | constitutive | McElroy et al., Plant Cell, 2: 163-171, 1990 |
| CAMV 35S | constitutive | Odell et al, Nature, 313: 810-812, 1985 |
| CaMV 19S | constitutive | Nilsson et al., Physiol. Plant. 100: 456-462, 1997 |
| GOS2 | constitutive | de Pater et al, Plant J. 2: 837-844, 1992 |
| Ubiquitin | constitutive | Christensen et al, Plant Mol. Biol. 18: 675-689, 1992 |
| rice cyclophilins | constitutive | Buchholz et al, Plant Mol Biol 25: 837-843, 1994 |
| maize histone H3 | constitutive | Lepetit et al., Mol. Gen. Genet. 231: 276-285, 1992 |
| alfalfa histone H3 | constitutive | Wu et al., Nucleic Acids Res. 17: 3057-3063, 1989; Wu et al., Plant Mol. Biol. 11: 641-649, 1988 |
| actin 2 | constitutive | An et al, Plant J. 10(1); 107-121, 1996 |

III: EXAMPLES OF STRESS-INDUCIBLE PROMOTERS

| NAME | STRESS | REFERENCE |
|---|---|---|
| P5CS (delta(1)-pyrroline-5-carboxylate syntase) | salt, water | Zhang et al. Plant Science. 129: 81-89, 1997 |
| cor15a | cold | Hajela et al., Plant Physiol. 93: 1246-1252, 1990 |
| cor15b | cold | Wlihelm et al., Plant Mol Biol. 23: 1073-1077, 1993 |
| cor15a (−305 to +78 nt) | cold, drought | Baker et al., Plant Mol Biol. 24: 701-713, 1994 |
| rd29 | salt, drought, cold | Kasuga et al., Nature Biotechnology 18: 287-291, 1999 |
| heat shock proteins, including artificial promoters containing the heat shock element (HSE) | heat | Barros et al., Plant Mol Biol 19: 665-75, 1992. Marrs et al., Dev Genet. 14: 27-41, 1993. Schoffl et al., Mol Gen Gent, 217: 246-53, 1989. |
| smHSP (small heat shock proteins) | heat | Waters et al, J Experimental Botany 47: 325-338, 1996 |
| wcs120 | cold | Ouellet et al., FEBS Lett. 423: 324-328, 1998 |
| ci7 | cold | Kirch et al., Plant Mol Biol 33: 897-909, 1997 |
| Adh | cold, drought, hypoxia | Dolferus et al., Plant Physiol 105: 1075-87, 1994 |
| pwsi18 | water: salt and drought | Joshee et al., Plant Cell Physiol 39: 64-72, 1998 |
| ci21A | cold | Schneider et al., Plant Physiol 113: 335-45, 1997 |

TABLE 6-continued

Examples of plant-expressible promoters for use
in the performance of the present invention

| | | |
|---|---|---|
| Trg-31 | drought | Chaudhary et al., Plant Mol Biol 30: 1247-57, 1996 |
| Osmotin | osmotic | Raghothama et al., Plant Mol Biol 23: 1117-28, 1993 |
| Rab17 | osmotic, ABA | Vilardell et al., Plant Mol Biol 17: 985-93, 1991 |
| LapA | wounding, enviromental | WO99/03977 University of California/INRA |

IV: EXAMPLES OF PATHOGEN-INDUCIBLE PROMOTERS

| NAME | PATHOGEN | REFERENCE |
|---|---|---|
| RB7 | Root-knot nematodes (Meloidogyne spp.) | US5760386 - North Carolina State University; Opperman et al (1994) Science 263: 221-23. |
| PR-1, 2, 3, 4, 5, 8, 11 | fungal, viral, bacterial | Ward et al (1991) Plant Cell 3: 1085-1094; Reiss et al 1996; Lebel et al (1998), Plant J, 16(2): 223-33; Melchers et al (1994), Plant J, 5(4): 469-80; Lawton et al (1992), Plant Mol Biol, 19(5): 735-43. |
| HMG2 | nematodes | WO9503690 - Virginia Tech Intellectual Properties Inc. |
| Abi3 | Cyst nematodes (Heterodera spp.) | Unpublished |
| ARM1 | nematodes | Barthels et al., (1997) The Plant Cell 9, 2119-2134. WO 98/31822 - Plant Genetic Systems |
| Att0728 | nematodes | Barthels et al., (1997) The Plant Cell 9, 2119-2134. PCT/EP98/07761 |
| Att1712 | nematodes | Barthels et al., (1997) The Plant Cell 9, 2119-2134. PCT/EP98/07761 |
| Gst1 | Different types of pathogens | Strittmatter et al (1996) Mol. Plant-Microbe Interact. 9, 68-73. |
| LEMMI | nematodes | WO 92/21757- Plant Genetic Systems |
| CLE | geminivirus | PCT/EP99/03445 - CINESTAV |
| PDF1.2 | Fungal including *Alternaria brassicicola* and *Botrytis cinerea* | Manners et al (1998), Plant Mol Biol, 38(6): 1071-80. |
| Thi2.1 | Fungal - *Fusarium oxysporum* f sp. *matthiolae* | Vignutelli et al (1998) Plant J; 14(3): 285-95 |
| DB#226 | nematodes | Bird and Wilson (1994) Mol. Plant-Microbe Interact., 7, 419-42 WO 95.322888 |
| DB#280 | nematodes | Bird and Wilson (1994) Mol. Plant-Microbe Interact., 7, 419-42 WO 95.322888 |
| Cat2 | nematodes | Niebel et al (1995) Mol Plant Microbe Interact 1995 May-Jun; 8(3): 371-8 |
| ☐Tub | nematodes | Aristizabal et al (1996), 8<sup>th</sup> International Congress on Plant-Microbe Interaction, Knoxville US B-29 |
| SHSP | nematodes | Fenoll et al (1997) In: Cellular and molecular aspects of plant-nematode interactions. Kluwer Academic, C. Fenoll, F. M. W. Grundler and S. A. Ohl (Eds.), |
| Tsw12 | nematodes | Fenoll et al (1997) In: Cellular and molecular aspects of plant-nematode interactions. Kluwer Academic, C. Fenoll, F. M. W. Grundler and S. A. Ohl (Eds.) |
| Hs1(pro 1) | nematodes | WO 98/122335 - Jung |
| NsLTP | viral, fungal, bacterial | Molina & Garc'ia-Olmedo (1993) FEBS Lett, 316(2): 119-22 |

TABLE 6-continued

Examples of plant-expressible promoters for use in the performance of the present invention

| | | |
|---|---|---|
| RIP | viral, fungal | Turner et al (1997) Proc Natl Acad Sci USA, 94(8): 3866-71 |

Examples of terminators particularly suitable for use in the gene constructs of the present invention include the *Agrobacterium tumefaciens* nopaline synthase (NOS) gene terminator, the *Agrobacterium tumefaciens* octopine synthase (OCS) gene terminator sequence, the Cauliflower mosaic virus (CaMV) 35S gene terminator sequence, the *Oryza sativa* ADP-glucose pyrophosphorylase terminator sequence (t3'Bt2), the *Zea mays* zein gene terminator sequence, the rbcs-1A gene terminator, and the rbcs-3A gene terminator sequences, amongst others.

Preferred promoter sequences of the invention include root specific promoters and seed-specific promoters such as but not limited to the ones listed in Table 7, Table 6, and as outlined in the Examples.

TABLE 7

Examples of root specific promoters for use in the performance of the present invention

| NAME | ORIGIN | REFERENCE |
|---|---|---|
| SbPRP1 | Soybean | Suzuki et al., Plant Mol Biol, 21: 109-119, 1993 |
| 636 bp fragment of TobRB7 | Tobacco | Yamamoto et al., Plant Cell 3: 371-382, 1991 |
| GGPS3 | Arabidopsis | Okada et al., Plant Physiol 122: 1045-1056, 2000 |
| 580 bp fragment of prxEa | Arabidopsis | Wanapu and Shinmyo, Ann N Y Acad Sci 782: 107-114, 1996 |
| Ids2 promoter | Barley | Okumura et al., Plant Mol Biol 25: 705-719, 1994 |
| AtPRP3 | Arabidopsis | Fowler et al., Plant Physiol 121: 1081-1092, 1999 |

Those skilled in the art will be aware of additional promoter sequences and terminator sequences which may be suitable for use in performing the invention. Such sequences may readily be used without any undue experimentation.

In the context of the current invention, "ectopic expression" or "ectopic overexpression" of a gene or a protein are conferring to expression patterns and/or expression levels of said gene or protein normally not occurring under natural conditions, more specifically is meant increased expression and/or increased expression levels. Ectopic expression can be achieved in a number of ways including operably linking of a coding sequence encoding said protein to an isolated homologous or heterologous promoter in order to create a chimeric gene and/or operably linking said coding sequence to its own isolated promoter (i.e. the unisolated promoter naturally driving expression of said protein) in order to create a recombinant gene duplication or gene multiplication effect. With "ectopic co-expression" is meant the ectopic expression or ectopic overexpression of two or more genes or proteins. The same or, more preferably, different promoters are used to confer ectopic expression of said genes or proteins.

Preferably, the promoter sequence used in the context of the present invention is operably linked to a coding sequence or open reading frame (ORF) encoding a cytokinin oxidase protein or a homologue, derivative or an immunologically active and/or functional fragment thereof as defined supra.

"Downregulation of expression" as used herein means lowering levels of gene expression and/or levels of active gene product and/or levels of gene product activity. Decreases in expression may be accomplished by e.g. the addition of coding sequences or parts thereof in a sense orientation (if resulting in co-suppression) or in an antisense orientation relative to a promoter sequence and furthermore by e.g. insertion mutagenesis (e.g. T-DNA insertion or transposon insertion) or by gene silencing strategies as described by e.g. Angell and Baulcombe (1998—WO9836083), Lowe et al. (1989—WO9853083), Lederer et al. (1999—WO9915682) or Wang et al. (1999—WO9953050). Genetic constructs aimed at silencing gene expression may have the nucleotide sequence of said gene (or one or more parts thereof) contained therein in a sense and/or antisense orientation relative to the promoter sequence. Another method to downregulate gene expression comprises the use of ribozymes.

Modulating, including lowering, the level of active gene products or of gene product activity can be achieved by administering or exposing cells, tissues, organs or organisms to said gene product, a homologue, derivative and/or immunologically active fragment thereof. Immunomodulation is another example of a technique capable of downregulation levels of active gene product and/or of gene product activity and comprises administration of or exposing to or expressing antibodies to said gene product to or in cells, tissues, organs or organisms wherein levels of said gene product and/or gene product activity are to be modulated. Such antibodies comprise "plantibodies", single chain antibodies, IgG antibodies and heavy chain camel antibodies as well as fragments thereof.

Modulating, including lowering, the level of active gene products or of gene product activity can furthermore be achieved by administering or exposing cells, tissues, organs or organisms to an agonist of said gene product or the activity thereof. Such agonists include proteins (comprising e.g.

kinases and proteinases) and chemical compounds identified according to the current invention as described supra.

In the context of the current invention is envisaged the downregulation of the expression of a cytokinin oxidase gene as defined earlier. Preferably said cytokinin oxidase gene is a plant cytokinin oxidase gene, more specifically an AtCKX. The invention further comprises downregulation of levels of a cytokinin oxidase protein or of a cytokinin oxidase activity whereby said cytokinin oxidase protein has been defined supra. Preferably said cytokinin oxidase protein is a plant cytokinin oxidase, more specifically an AtCKX.

By "modifying cell fate and/or plant development and/or plant morphology and/or biochemistry and/or physiology" is meant that one or more developmental and/or morphological and/or biochemical and/or physiological characteristics of a plant is altered by the performance of one or more steps pertaining to the invention described herein.

"Cell fate" refers to the cell-type or cellular characteristics of a particular cell that are produced during plant development or a cellular process therefor, in particular during the cell cycle or as a consequence of a cell cycle process.

"Plant development" or the term "plant developmental characteristic" or similar term shall, when used herein, be taken to mean any cellular process of a plant that is involved in determining the developmental fate of a plant cell, in particular the specific tissue or organ type into which a progenitor cell will develop. Cellular processes relevant to plant development will be known to those skilled in the art. Such processes include, for example, morphogenesis, photomorphogenesis, shoot development, root development, vegetative development, reproductive development, stem elongation, flowering, and regulatory mechanisms involved in determining cell fate, in particular a process or regulatory process involving the cell cycle.

"Plant morphology" or the term "plant morphological characteristic" or similar term will, when used herein, be understood by those skilled in the art to refer to the external appearance of a plant, including any one or more structural features or combination of structural features thereof. Such structural features include the shape, size, number, position, color, texture, arrangement, and patternation of any cell, tissue or organ or groups of cells, tissues or organs of a plant, including the root, stem, leaf, shoot, petiole, trichome, flower, petal, stigma, style, stamen, pollen, ovule, seed, embryo, endosperm, seed coat, aleurone, fiber, fruit, cambium, wood, heartwood, parenchyma, aerenchyma, sieve element, phloem or vascular tissue, amongst others.

"Plant biochemistry" or the term "plant biochemical characteristic" or similar term will, when used herein, be understood by those skilled in the art to refer to the metabolic and catalytic processes of a plant, including primary and secondary metabolism and the products thereof, including any small molecules, macromolecules or chemical compounds, such as but not limited to starches, sugars, proteins, peptides, enzymes, hormones, growth factors, nucleic acid molecules, celluloses, hemicelluloses, calloses, lectins, fibers, pigments such as anthocyanins, vitamins, minerals, micronutrients, or macronutrients, that are produced by plants.

"Plant physiology" or the term "plant physiological characteristic" or similar term will, when used herein, be understood to refer to the functional processes of a plant, including developmental processes such as growth, expansion and differentiation, sexual development, sexual reproduction, seed set, seed development, grain filling, asexual reproduction, cell division, dormancy, germination, light adaptation, photosynthesis, leaf expansion, fiber production, secondary growth or wood production, amongst others; responses of a plant to externally-applied factors such as metals, chemicals, hormones, growth factors, environment and environmental stress factors (e.g. anoxia, hypoxia, high temperature, low temperature, dehydration, light, daylength, flooding, salt, heavy metals, amongst others), including adaptive responses of plants to said externally-applied factors.

Advantageously, performance of the methods according to the present invention results in plants having a variety of modified growth characteristics, such modified growth characteristics including modified yield or biomass, relative to corresponding wild type plants. Preferably, the modified growth characteristics are improved growth characteristics and include increased yield or biomass, relative to corresponding wild type plants.

By "yield" is meant the amount of harvested material per area of production. The term "increased yield" encompasses an increase in biomass in one or more parts of a plant relative to the biomass of corresponding wild-type plants. Depending on the crop, the harvested part of the plant can be a different part or tissue of the plant, such as seed (e.g. rice, sorghum or corn when grown for seed); total above-ground biomass (e.g. corn, when used as silage, sugarcane), root (e.g. sugar beet), fruit (e.g. tomato), cotton fibres, or any other part of the plant which is of economic value. For example, the methods of the present invention are used to increase seed yield of rice and of corn, or also to increase yield of silage corn in terms of overall above ground biomass and energy content. The increase in yield encompasses an increase in seed yield, which includes an increase in the total biomass of the seed (total seed weight), total number of seeds and/or an increase in the number of (filled) seeds. The increase in yield is also reflected in an increase of the Harvest Index, which is expressed as a ratio of the yield of harvestable parts, such as seeds, over the total biomass and is also reflected in an increased Thousand Kernel Weight (derived from the number of filled seeds counted and their total weight).

Therefore, there is provided a method for increasing seed yield of a plant, comprising introducing and overexpressing primarily in the seed of this plant a nucleic acid sequence encoding a cytokinin oxidase/dehydrogenase, a homologue, a derivative or an active fragment thereof compared to corresponding wild type plants, and wherein the increase of seed yield comprises at least one of increased total weight of seeds, increased total number of seeds, increased number of filled seeds, increased harvest index or increased thousand kernel weight, each relative to corresponding wild type plants.

Yield is by its nature a complex parameter whereby total yield depends on a number of yield components. The parameters for increased yield of a crop are well known by a person skilled in the art. By way of example, key yield components for corn include number of plants per hectare or acre, number of ears per plant, number of rows (of seeds) per ear, number of kernels per row, and Thousand Kernel Weight. The improvement in yield as obtained in accordance to the method of the invention, can be obtained as a result of one or more of these yield components. By way of example, key yield components for rice include number of plants per hectare or acre, number of panicles per plant, number of spikelets per panicle, seed filling rate and thousand kernel weight. The improvement in yield as obtained in accordance to the method of the invention can be obtained as a result in one or more of these yield components, preferentially the improvement in yield is obtained primarily on the basis of an increased number of flowers per panicle and an increased seed filling rate.

According to a preferred feature of the present invention, performance of the methods according to the present invention result in plants having modified seed yield. Preferably, the modified yield includes at least an increase in any one or more of total weight of seeds, total seed number, number of filled seeds, thousand kernel weight and harvest index, each relative to control plants. Therefore, according to the present invention, there is provided a method for increasing total seed number, total weight of seeds, number of filled seeds and/or harvest index of plants, which method comprises modulating expression of a nucleic acid molecule encoding a CKX protein and/or modulating activity of the CKX itself in a plant in a seed/seedling preferred way, preferably wherein the CKX protein is encoded by a nucleic acid sequence represented by SEQ ID NO:44 or SEQ ID NO:48, or a portion thereof or by sequences capable of hybridising therewith or wherein the CKX is represented by SEQ ID NO:37 or SEQ ID NO:2, or a homologue, derivative or active fragment thereof. Alternatively, the CKX may be encoded by a nucleic acid sequence represented by SEQ ID NO:38, or by a portion thereof or by sequences capable of hybridising therewith, or wherein the CKX is represented by SEQ ID NO: 39, or a homologue, derivative or active fragment of any thereof.

Means for introducing recombinant DNA into plant tissue or cells include, but are not limited to, transformation using $CaCl_2$ and variations thereof, in particular the method described by Hanahan (1983), direct DNA uptake into protoplasts (Krens et al, 1982; Paszkowski et al, 1984), PEG-mediated uptake to protoplasts (Armstrong et al, 1990) microparticle bombardment, electroporation (Fromm et al., 1985), microinjection of DNA (Crossway et al., 1986), microparticle bombardment of tissue explants or cells (Christou et al, 1988; Sanford, 1988), vacuum-infiltration of tissue with nucleic acid, or in the case of plants, T-DNA-mediated transfer from *Agrobacterium* to the plant tissue as described essentially by An et al. (1985), Dodds et al., (1985), Herrera-Estrella et al. (1983a, 1983b, 1985). Methods for transformation of monocotyledonous plants are well known in the art and include *Agrobacterium*-mediated transformation (Cheng et al., 1997—WO9748814; Hansen 1998—WO9854961; Hiei et al., 1994—WO9400977; Hiei et al., 1998—WO9817813; Rikiushi et al., 1999—WO9904618; Saito et al., 1995—WO9506722), microprojectile bombardment (Adams et al., 1999—U.S. Pat. No. 5,969,213; Bowen et al., 1998—U.S. Pat. No. 5,736,369; Chang et al., 1994—WO9413822; Lundquist et al., 1999—U.S. Pat. No. 5,874,265/U.S. Pat. No. 5,990,390; Vasil and Vasil, 1995—U.S. Pat. No. 5,405,765. Walker et al., 1999—U.S. Pat. No. 5,955,362), DNA uptake (Eyal et al., 1993—WO9318168), microinjection of *Agrobacterium* cells (von Holt, 1994—DE4309203) and sonication (Finer et al., 1997—U.S. Pat. No. 5,693,512).

For microparticle bombardment of cells, a microparticle is propelled into a cell to produce a transformed cell. Any suitable ballistic cell transformation methodology and apparatus can be used in performing the present invention. Exemplary apparatus and procedures are disclosed by Stomp et al. (U.S. Pat. No. 5,122,466) and Sanford and Wolf (U.S. Pat. No. 4,945,050). When using ballistic transformation procedures, the gene construct may incorporate a plasmid capable of replicating in the cell to be transformed. Examples of microparticles suitable for use in such systems include 1 to 5 μm gold spheres. The DNA construct may be deposited on the microparticle by any suitable technique, such as by precipitation.

A whole plant may be regenerated from the transformed or transfected cell, in accordance with procedures well known in the art. Plant tissue capable of subsequent clonal propagation, whether by organogenesis or embryogenesis, may be transformed with a gene construct of the present invention and a whole plant regenerated therefrom. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem).

The term "organogenesis", as used herein, means a process by which shoots and roots are developed sequentially from meristematic centers.

The term "embryogenesis", as used herein, means a process by which shoots and roots develop together in a concerted fashion (not sequentially), whether from somatic cells or gametes.

Preferably, the plant is produced according to the inventive method is transfected or transformed with a genetic sequence, or amenable to the introduction of a protein, by any art-recognized means, such as microprojectile bombardment, microinjection, *Agrobacterium*-mediated transformation (including in planta transformation), protoplast fusion, or electroporation, amongst others. Most preferably said plant is produced by *Agrobacterium*-mediated transformation.

*Agrobacterium*-mediated transformation or agrolistic transformation of plants, yeast, molds or filamentous fungi is based on the transfer of part of the transformation vector sequences, called the T-DNA, to the nucleus and on integration of said T-DNA in the genome of said eukaryote.

With "*Agrobacterium*" is meant a member of the Agrobacteriaceae, more preferably *Agrobacterium* or *Rhizobacterium* and most preferably *Agrobacterium tumefaciens*.

With "T-DNA", or transferred DNA, is meant that part of the transformation vector flanked by T-DNA borders which is, after activation of the *Agrobacterium* vir genes, nicked at the T-DNA borders and is transferred as a single stranded DNA to the nucleus of an eukaryotic cell.

When used herein, with "T-DNA borders", "T-DNA border region", or "border region" are meant either right T-DNA border (RB) or left T-DNA border (LB). Such a border comprises a core sequence flanked by a border inner region as part of the T-DNA flanking the border and/or a border outer region as part of the vector backbone flanking the border. The core sequences comprise 22 bp in case of octopine-type vectors and 25 bp in case of nopaline-type vectors. The core sequences in the right border region and left border region form imperfect repeats. Border core sequences are indispensable for recognition and processing by the *Agrobacterium* nicking complex consisting of at least VirD1 and VirD2. Core sequences flanking a T-DNA are sufficient to promote transfer of said T-DNA. However, efficiency of transformation using transformation vectors carrying said T-DNA solely flanked by said core sequences is low. Border inner and outer regions are known to modulate efficiency of T-DNA transfer (Wang et al. 1987). One element enhancing T-DNA transfer has been characterized and resides in the right border outer region and is called overdrive (Peralta et al. 1986, van Haaren et al. 1987).

With "T-DNA transformation vector" or "T-DNA vector" is meant any vector encompassing a T-DNA sequence flanked by a right and left T-DNA border consisting of at least the right and left border core sequences, respectively, and used for transformation of any eukaryotic cell.

With "T-DNA vector backbone sequence" or "T-DNA vector backbone sequences" is meant all DNA of a T-DNA containing vector that lies outside of the T-DNA borders and, more specifically, outside the nicking sites of the border core imperfect repeats.

The current invention includes optimized T-DNA vectors such that vector backbone integration in the genome of a eukaryotic cell is minimized or absent. With "optimized T-DNA vector" is meant a T-DNA vector designed either to decrease or abolish transfer of vector backbone sequences to the genome of a eukaryotic cell. Such T-DNA vectors are known to the one familiar with the art and include those described by Hanson et al. (1999) and by Stuiver et al. (1999—WO9901563).

The current invention clearly considers the inclusion of a DNA sequence encoding a cytokinin oxidase, homologue, derivative or immunologically active and/or functional fragment thereof as defined supra, in any T-DNA vector comprising binary transformation vectors, super-binary transformation vectors, co-integrate transformation vectors, Ri-derived transformation vectors as well as in T-DNA carrying vectors used in agrolistic transformation. Preferably, said cytokinin oxidase is a plant cytokinin oxidase, more specifically an *Arabidopsis thaliana* (At)CKX.

With "binary transformation vector" is meant a T-DNA transformation vector comprising:

(a) a T-DNA region comprising at least one gene of interest and/or at least one selectable marker active in the eukaryotic cell to be transformed; and (b) a vector backbone region comprising at least origins of replication active in *E. coli* and *Agrobacterium* and markers for selection in *E. coli* and *Agrobacterium*.

The T-DNA borders of a binary transformation vector can be derived from octopine-type or nopaline-type Ti plasmids or from both. The T-DNA of a binary vector is only transferred to a eukaryotic cell in conjunction with a helper plasmid.

With "helper plasmid" is meant a plasmid that is stably maintained in *Agrobacterium* and is at least carrying the set of vir genes necessary for enabling transfer of the T-DNA. Said set of vir genes can be derived from either octopine-type or nopaline-type Ti plasmids or from both.

With "super-binary transformation vector" is meant a binary transformation vector additionally carrying in the vector backbone region a vir region of the Ti plasmid pTiBo542 of the super-virulent *A. tumefaciens* strain A281 (EP0604662, EP0687730). Super-binary transformation vectors are used in conjunction with a helper plasmid.

With "co-integrate transformation vector" is meant a T-DNA vector at least comprising:

(a) a T-DNA region comprising at least one gene of interest and/or at least one selectable marker active in plants; and (b) a vector backbone region comprising at least origins of replication active in *Escherichia coli* and *Agrobacterium*, and markers for selection in *E. coli* and *Agrobacterium*, and a set of vir genes necessary for enabling transfer of the T-DNA.

The T-DNA borders and said set of vir genes of a said T-DNA vector can be derived from either octopine-type or nopaline-type Ti plasmids or from both.

With "Ri-derived plant transformation vector" is meant a binary transformation vector in which the T-DNA borders are derived from a Ti plasmid and said binary transformation vector being used in conjunction with a 'helper' Ri-plasmid carrying the necessary set of vir genes.

As used herein, the term "selectable marker gene" or "selectable marker" or "marker for selection" includes any gene which confers a phenotype on a cell in which it is expressed to facilitate the identification and/or selection of cells which are transfected or transformed with a gene construct of the invention or a derivative thereof. Suitable selectable marker genes contemplated herein include the ampicillin resistance (Amp$^r$), tetracycline resistance gene (Tc$^r$), bacterial kanamycin resistance gene (Kan$^r$), phosphinothricin resistance gene, neomycin phosphotransferase gene (nptII), hygromycin resistance gene, β-glucuronidase (GUS) gene, chloramphenicol acetyltransferase (CAT) gene, green fluorescent protein (gfp) gene (Haseloff et al, 1997), and luciferase gene, amongst others.

With "agrolistics", "agrolistic transformation" or "agrolistic transfer" is meant here a transformation method combining features of *Agrobacterium*-mediated transformation and of biolistic DNA delivery. As such, a T-DNA containing target plasmid is co-delivered with DNA/RNA enabling in planta production of VirD1 and VirD2 with or without VirE2 (Hansen and Chilton 1996; Hansen et al. 1997; Hansen and Chilton 1997—WO9712046).

With "foreign DNA" is meant any DNA sequence that is introduced in the host's genome by recombinant techniques. Said foreign DNA includes e.g. a T-DNA sequence or a part thereof such as the T-DNA sequence comprising the selectable marker in an expressible format. Foreign DNA furthermore include intervening DNA sequences as defined supra.

With "recombination event" is meant either a site-specific recombination event or a recombination event effected by transposon 'jumping'.

With "recombinase" is meant either a site-specific recombinase or a transposase.

With "recombination site" is meant either site-specific recombination sites or transposon border sequences.

With "site specific recombination event" is meant an event catalyzed by a system generally consisting of three elements: a pair of DNA sequences (the site-specific recombination sequences or sites) and a specific enzyme (the site-specific recombinase). The site-specific recombinase catalyzes a recombination reaction only between two site-specific recombination sequences depending on the orientation of the site-specific recombination sequences. Sequences intervening between two site-specific recombination sites will be inverted in the presence of the site-specific recombinase when the site-specific recombination sequences are oriented in opposite directions relative to one another (i.e. inverted repeats). If the site-specific recombination sequences are oriented in the same direction relative to one another (i.e. direct repeats), then any intervening sequences will be deleted upon interaction with the site-specific recombinase. Thus, if the site-specific recombination sequences are present as direct repeats at both ends of a foreign DNA sequence integrated into a eukaryotic genome, such integration of said sequences can subsequently be reversed by interaction of the site-specific recombination sequences with the corresponding site specific recombinase.

A number of different site specific recombinase systems can be used including but not limited to the Cre/lox system of bacteriophage P1, the FLP/FRT system of yeast, the Gin recombinase of phage Mu, the Pin recombinase of *E. coli*, the PinB, PinD and PinF from *Shigella*, and the R/RS system of the pSR1 plasmid. Recombinases generally are integrases, resolvases or flippases. Also dual-specific recombinases can be used in conjunction with direct or indirect repeats of two different site-specific recombination sites corresponding to the dual-specific recombinase (WO99/25840). The two preferred site-specific recombinase systems are the bacteriophage P1 Cre/lox and the yeast FLP/FRT systems. In these systems a recombinase (Cre or FLP) interact specifically with its respective site-specific recombination sequence (lox or FRT respectively) to invert or excise the intervening sequences. The site-specific recombination sequences for each of these two systems are relatively short (34 bp for lox and 47 bp for FRT). Some of these systems have already been used with high efficiency in plants such as tobacco (Dale et al. 1990) and *Arabidopsis* (Osborne et al. 1995). Site-specific recombination systems have many applications in plant molecular biology including methods for control of homologous recombination (e.g. U.S. Pat. No. 5,527,695), for targeted insertion, gene stacking, etc. (WO99/25821) and for resolution of complex T-DNA integration patterns or for excision of a selectable marker (WO99/23202).

Although the site-specific recombination sequences must be linked to the ends of the DNA to be excised or to be inverted, the gene encoding the site specific recombinase may be located elsewhere. For example, the recombinase gene could already be present in the eukaryote's DNA or could be supplied by a later introduced DNA fragment either introduced directly into cells, through crossing or through cross-pollination. Alternatively, a substantially purified recombinase protein could be introduced directly into the eukaryotic cell, e.g. by micro-injection or particle bombardment. Typically, the site-specific recombinase coding region will be operably linked to regulatory sequences enabling expression of the site-specific recombinase in the eukaryotic cell.

With "recombination event effected by transposon jumping" or "transposase-mediated recombination" is meant a recombination event catalyzed by a system consisting of three elements: a pair of DNA sequences (the transposon border sequences) and a specific enzyme (the transposase). The transposase catalyzes a recombination reaction only between two transposon border sequences which are arranged as inverted repeats.

A number of different transposon/transposase systems can be used including but not limited to the Ds/Ac system, the Spm system and the Mu system. These systems originate from corn but it has been shown that at least the Ds/Ac and the Spm system also function in other plants (Fedoroff et al. 1993, Schlappi et al. 1993, Van Sluys et al. 1987). Preferred are the Ds- and the Spm-type transposons which are delineated by 11 bp- and 13 bp-border sequences, respectively.

Although the transposon border sequences must be linked to the ends of the DNA to be excised, the gene encoding the transposase may be located elsewhere. For example, the recombinase gene could already be present in the eukaryote's DNA or could be supplied by a later introduced DNA fragment either introduced directly into cells, through crossing or through cross-pollination. Alternatively, a substantially purified transposase protein could be introduced directly into cells, e.g. by microinjection or by particle bombardment.

As part of the current invention, transposon border sequences are included in a foreign DNA sequence such that they lie outside said DNA sequence and transform said DNA into a transposon-like entity that can move by the action of a transposase.

As transposons often reintegrate at another locus of the host's genome, segregation of the progeny of the hosts in which the transposase was allowed to act might be necessary to separate transformed hosts containing e.g. only the transposon footprint and transformed hosts still containing the foreign DNA.

In performing the present invention, the genetic element is preferably induced to mobilize, such as, for example, by the expression of a recombinase protein in the cell which contacts the integration site of the genetic element and facilitates a recombination event therein, excising the genetic element completely, or alternatively, leaving a "footprint", generally of about 20 nucleotides in length or greater, at the original integration site. Those hosts and host parts that have been produced according to the inventive method can be identified by standard nucleic acid hybridization and/or amplification techniques to detect the presence of the mobilizable genetic element or a gene construct comprising the same. Alternatively, in the case of transformed host cells, tissues, and hosts wherein the mobilizable genetic element has been excised, it is possible to detect a footprint in the genome of the host which has been left following the excision event, using such techniques. As used herein, the term "footprint" shall be taken to refer to any derivative of a mobilizable genetic element or gene construct comprising the same as described herein which is produced by excision, deletion or other removal of the mobilizable genetic element from the genome of a cell transformed previously with said gene construct. A footprint generally comprises at least a single copy of the recombination loci or transposon used to promote excision. However, a footprint may comprise additional sequences derived from the gene construct, for example nucleotide sequences derived from the left border sequence, right border sequence, origin of replication, recombinase-encoding or transposase-encoding sequence if used, or other vector-derived nucleotide sequences. Accordingly, a footprint is identifiable according to the nucleotide sequence of the recombination locus or transposon of the gene construct used, such as, for example, a sequence of nucleotides corresponding or complementary to a lox site or frt site.

The term "cell cycle" means the cyclic biochemical and structural events associated with growth and with division of cells, and in particular with the regulation of the replication of DNA and mitosis. Cell cycle includes phases called: G0, Gap1 (G1), DNA synthesis (S), Gap2 (G2), and mitosis (M). Normally these four phases occur sequentially, however, the cell cycle also includes modified cycles wherein one or more phases are absent resulting in modified cell cycle such as endomitosis, acytokinesis, polyploidy, polyteny, and endoreduplication.

The term "cell cycle progression" refers to the process of passing through the different cell cycle phases. The term "cell cycle progression rate" accordingly refers to the speed at which said cell cycle phases are run through or the time spans required to complete said cell cycle phases.

With "two-hybrid assay" is meant an assay that is based on the observation that many eukaryotic transcription factors comprise two domains, a DNA-binding domain (DB) and an activation domain (AD) which, when physically separated (i.e. disruption of the covalent linkage) do not effectuate target gene expression. Two proteins able to interact physically with one of said proteins fused to DB and the other of said proteins fused to AD will re-unite the DB and AD domains of the transcription factor resulting in target gene expression. The target gene in the yeast two-hybrid assay is usually a reporter gene such as the β-galactosidase gene. Interaction between protein partners in the yeast two-hybrid assay can thus be quantified by measuring the activity of the reporter gene product (Bartel and Fields 1997). Alternatively, a mammalian two-hybrid system can be used which includes e.g. a chimeric green fluorescent protein encoding reporter gene (Shioda et al., 2000).

Furthermore, folding simulations and computer redesign of structural motifs of the protein of the invention can be performed using appropriate computer programs (Olszewski, Proteins 25 (1996), 286-299; Hoffman, Comput. Appl. Biosci. 1 (1995), 675-679). Computer modeling of protein folding can be used for the conformational and energetic analysis of detailed peptide and protein models (Monge, J. Mol. Biol. 247 (1995), 995-1012; Renouf, Adv. Exp. Med. Biol. 376

(1995), 37-45). In particular, the appropriate programs can be used for the identification of interactive sites of the cytokinin oxidases, its ligands or other interacting proteins by computer assistant searches for complementary peptide sequences (Fassina, Immunomethods 5 (1994), 114-120). Further appropriate computer systems for the design of protein and peptides are described in the prior art, for example in Berry, Biochem. Soc. Trans. 22 (1994), 1033-1036; Wodak, Ann, N.Y. Acac. Sci. 501 (1987), 1-13; Pabo, Biochemistry 25 (1986), 5987-5991. The results obtained form the above-described computer analysis can be used for, e.g. the preparation of peptidomimetics of the protein of the invention or fragments thereof. Such pseudopeptide analogues of the natural amino acid sequence of the protein may very efficiently mimic the parent protein (Benkirane, J. Biol. Chem. 271 (1996), 33218-33224). For example, incorporation of easily available achiral Ω-amino acid residues into a protein of the invention or a fragment thereof results in the substitution of amino bonds by polymethylene units of an aliphatic chain, thereby providing a convenient strategy for constructing a peptidomimetic (Banerjee, Biopolymers 39 (1996), 769-777). Superactive peptidomimetic analogues of small peptide hormones in other systems are described in the prior art (Zhang, Biochem. Biophys. Res. Commun. 224 (1996), 327-331). Appropriate peptidomimetics of the protein of the present invention can also be identified by the synthesis of peptidomimetic combinatorial libraries through successive amine alkylation and testing the resulting compounds, e.g., for their binding, kinase inhibitory and/or immunological properties. Methods for the generation and use of peptidomimetic combinatorial libraries are described in the prior art, for example in Ostresh, Methods in Enzymology 267 (1996), 220-234 and Dorner, Bioorg. Med. Chem. 4 (1996), 709-715.

Furthermore, a three-dimensional and/or crystallographic structure of the protein of the invention can be used for the design of peptidomimetic inhibitors of the biological activity of the protein of the invention (Rose, Biochemistry 35 (1996), 12933-12944; Ruterber, Bioorg. Med. Chem. 4 (1996), 1545-1558).

The compounds to be obtained or identified in the methods of the invention can be compounds that are able to bind to any of the nucleic acids, peptides or proteins of the invention. Other interesting compounds to be identified are compounds that modulate the expression of the genes or the proteins of the invention in such a way that either the expression of said gene or protein is enhanced or decreased by the action of said compound. Alternatively the compound can exert his action by enhancing or decreasing the activity of any of the proteins of the invention. Herein, preferred proteins are novel cytokinin oxidases.

Said compound or plurality of compounds may be comprised in, for example, samples, e.g., cell extracts from, e.g., plants, animals or microorganisms. Furthermore, said compound(s) may be known in the art but hitherto not known to be capable of suppressing or activating cytokinin oxidase interacting proteins. The reaction mixture may be a cell free extract of may comprise a cell or tissue culture. Suitable set ups for the method of the invention are known to the person skilled in the art and are, for example, generally described in Alberts et al., Molecular Biology of the Cell, third edition (1994), in particular Chapter 17. The plurality of compounds may be, e.g., added to the reaction mixture, culture medium or injected into the cell.

If a sample containing a compound or a plurality of compounds is identified in the method of the invention, then it is either possible to isolate the compound form the original sample identified as containing the compound capable of acting as an agonist, or one can further subdivide the original sample, for example, if it consists of a plurality of different compounds, so as to reduce the number of different substances per sample and repeat the method with the subdivisions of the original sample. Depending on the complexity of the samples, the steps described above can be performed several times, preferably until the sample identified according to the method of the invention only comprises a limited number of or only one substance(s). Preferably said sample comprises substances or similar chemical and/or physical properties, and most preferably said substances are identical. Preferably, the compound identified according to the above-described method or its derivative is further formulated in a form suitable for the application in plant breeding or plant cell and tissue culture.

The term "early vigor" refers to the ability of a plant to grow rapidly during early development, and relates to the successful establishment, after germination, of a well-developed root system and a well-developed photosynthetic apparatus.

The term "resistance to lodging" or "standability" refers to the ability of a plant to fix itself to the soil. For plants with an erect or semi-erect growth habit this term also refers to the ability to maintain an upright position under adverse (environmental) conditions. This trait relates to the size, depth and morphology of the root system.

The term 'grafting' as used herein, refers to the joining together of the parts of two different plants so that they bind together and the sap can flow, thus forming a single new plant that can grow and develop. A graft therefore consists of two parts: (i) the lower part is the rootstock as referred to herein and essentially consists of the root system and a portion of the stem, and (ii) the upper part, the scion or graft, which gives rise to the aerial parts of the plant.

As used herein, tblastn refers to an alignment tool that is part of the BLAST (Basic Local Alignment Search Tool) family of programs (ncbi.nlm.nih.gov/BLAST/). BLAST aims to identify regions of optimal local alignment, i.e. the alignment of some portion of two nucleic acid or protein sequences, to detect relationships among sequences which share only isolated regions of similarity (Altschul et al., 1990). In the present invention, tblastn of the BLAST 2.0 suite of programs was used to compare the maize cytokinin oxidase protein sequence against a nucleotide sequence database dynamically translated in all reading frames (Altschul et al., Nucleic Acids Res. 25: 3389-3402 (1997)).

It has now surprisingly been found that heterologous expression in the shoot of a plant of a nucleic acid encoding a cytokinin oxidase (hereafter abbreviated as CKX) gives rise to plants having modified growth characteristics, especially increased yield, in particular increased seed yield. Therefore according to a first embodiment of the present invention there is provided a method for increasing seed yield of a plant, comprising introducing and expressing in said plant an isolated nucleic acid sequence, encoding a cytokinin oxidase/dehydrogenase, a homologue, a derivative or an active fragment thereof, characterised in that said overexpression is primarily obtained in the shoot of said plant.

Additionally, by "yield" is meant the amount of harvested material per area of production. The term "increased yield" encompasses an increase in biomass in one or more parts of a plant relative to the biomass of corresponding wild-type plants. Depending on the crop, the harvested part of the plant can be a different part or tissue of the plant, such as seed (e.g. rice, sorghum or corn when grown for seed); total aboveground biomass (e.g. corn, when used as silage, sugarcane), root (e.g. sugar beet), fruit (e.g. tomato), cotton fibres, or any other part of the plant which is of economic value. For example, the methods of the present invention are used to increase seed yield of rice and of corn, or also to increase yield of silage corn in terms of overall above ground biomass and energy content. The increase in yield encompasses an increase in seed yield, which includes an increase in the total biomass of the seed (total seed weight) and/or an increase in the number of (filled) seeds. The increase in yield is also reflected in an increase of the harvest index, which is expressed as a ratio of the yield of harvestable parts, such as seeds, over the total biomass.

Yield is by its nature a complex parameter whereby total yield depends on a number of yield components. The parameters for increased yield of a crop are well known by a person skilled in the art. By way of example, key yield components for corn include number of plants per hectare or acre, number of ears per plant, number of rows (of seeds) per ear, number of kernels per row, and Thousand Kernel Weight. The improvement in yield as obtained in accordance to the method of the invention, can be obtained as a result in one or more of these yield components. By way of example, key yield components for rice include number of plants per hectare or acre, number of panicles per plant, number of spikelets per panicle, seed filling rate and thousand kernel weight. The improvement in yield as obtained in accordance to the method of the invention can be obtained as a result in one or more of these yield components, preferentially the improvement in yield is obtained primarily on the basis of an increased number of flowers per panicle and an increased seed filling rate.

According to a preferred feature of the present invention, performance of the methods according to the present invention result in plants having modified yield. Preferably, the modified yield includes at least an increase in any one or more of number of panicles, number of spikelets per panicle, total seed number, number of filled seeds, seed size, seed volume, Thousand Kernel Weight and harvest index, each relative to control plants. Therefore, according to the present invention, there is provided a method for increasing seed yield of a plant, in particular total weight of seeds, number of filled seeds and/or harvest index of plants, each relative to corresponding wild type plants, and which method comprises modulating expression of a nucleic acid molecule encoding a CKX protein and/or modulating activity of the CKX itself in a plant in a shoot preferred way, preferably wherein the CKX protein is encoded by a nucleic acid sequence represented by SEQ ID NO:44 or a portion thereof or by sequences capable of hybridising therewith or wherein the CKX is represented by SEQ ID NO:37 or a homologue, derivative or active fragment thereof. Alternatively, the CKX may be encoded by a nucleic acid sequence represented by SEQ ID NO:38, or by a portion thereof or by sequences capable of hybridising therewith, or wherein the CKX is represented by SEQ ID NO:39, or a homologue, derivative or active fragment of any thereof.

Since the transgenic plants according to the present invention have increased yield, it is likely that these plants exhibit an increased growth rate (during at least part of their life cycle), relative to the growth rate of corresponding wild type plants at a corresponding stage in their life cycle. The increased growth rate may be specific to one or more parts of a plant (including seeds), or may be throughout substantially the whole plant. A plant having an increased growth rate may even exhibit early flowering. The increase in growth rate may take place at one or more stages in the life cycle of a plant or during substantially the whole plant life cycle. Increased growth rate during the early stages in the life cycle of a plant may reflect enhanced vigour. The increase in growth rate may alter the harvest cycle of a plant allowing plants to be sown later and/or harvested sooner than would otherwise be possible. If the growth rate is sufficiently increased, it may allow for the sowing of further seeds of the same plant species (for example sowing and harvesting of rice plants followed by sowing and harvesting of further rice plants all within one conventional growing period). Similarly, if the growth rate is sufficiently increased, it may allow for the sowing of further seeds of different plants species (for example the sowing and harvesting of rice plants followed by, for example, the sowing and optional harvesting of soy bean, potato or any other suitable plant). Harvesting additional times from the same rootstock in the case of some plants may also be possible. Altering the harvest cycle of a plant may lead to an increase in annual biomass production per acre (due to an increase in the number of times (say in a year) that any particular plant may be grown and harvested). An increase in growth rate may also allow for the cultivation of transgenic plants in a wider geographical area than their wild-type counterparts, since the territorial limitations for growing a crop are often determined by adverse environmental conditions either at the time of planting (early season) or at the time of harvesting (late season). Such adverse conditions may be avoided if the harvest cycle is shortened. The growth rate may be determined by deriving various parameters from growth curves, such parameters may be: T-Mid (the time taken for plants to reach 50% of their maximal size) and T-90 (time taken for plants to reach 90% of their maximal size), amongst others.

Performance of the methods of the invention gives plants having an increased growth rate. Therefore, according to the present invention, there is provided a method for increasing the growth rate of a plant, which method comprises increasing activity of a CKX polypeptide or a homologue thereof in the plant shoot.

An increase in yield and/or growth rate occurs whether the plant is under non-stress conditions or whether the plant is exposed to various stresses compared to control plants. Plants typically respond to exposure to stress by growing more slowly. In conditions of severe stress, the plant may even stop growing altogether. Mild stress on the other hand is defined herein as being any stress to which a plant is exposed which does not result in the plant ceasing to grow altogether without the capacity to resume growth. Due to advances in agricultural practices (irrigation, fertilization, pesticide treatments) severe stresses are not often encountered in cultivated crop plants. As a consequence, the compromised growth induced by mild stress is often an undesirable feature for agriculture. Mild stresses are the typical stresses to which a plant may be exposed. These stresses may be the everyday biotic and/or abiotic (environmental) stresses to which a plant is exposed. Typical abiotic or environmental stresses include temperature stresses caused by atypical hot or cold/freezing temperatures; salt stress; water stress (drought or excess water). Abiotic stresses may also be caused by chemicals. Biotic stresses are typically those stresses caused by pathogens, such as bacteria, viruses, fungi and insects.

The above mentioned growth characteristics may advantageously be modified in any plant.

The term "plant" as used herein encompasses whole plants, ancestors and progeny of the plants and plant parts, including seeds, fruits, flowers, shoots, leaves, stems, roots (including tubers), and plant cells, tissues and organs, wherein each of the aforementioned comprise the gene/nucleic acid of interest. The term "plant" also encompasses suspension cultures, embryos, meristematic regions, callus tissue, gametophytes, sporophytes, pollen, and microspores.

With respect to increase in seed yield, plants that are particularly useful in the methods of the invention include algae, ferns, and all plants which belong to the superfamily Viridiplantae, in particular monocotyledonous and dicotyledonous plants, including fodder or forage legumes, ornamental plants, food crops, trees, or shrubs selected from the list comprising *Abelmoschus* spp., *Acer* spp., *Actinidia* spp., *Agropyron* spp., *Allium* spp., *Amaranthus* spp., *Ananas comosus*, *Annona* spp., *Apium graveolens*, *Arabidopsis thaliana*, *Arachis* spp, *Artocarpus* spp., *Asparagus officinalis*, *Avena sativa*, *Averrhoa carambola*, *Benincasa hispida*, *Bertholletia excelsea*, *Beta vulgaris*, *Brassica* spp., *Cadaba farinosa*, *Camellia sinensis*, *Canna indica*, *Capsicum* spp., *Carica papaya*, *Carissa macrocarpa*, *Carthamus tinctorius*, *Carya* spp., *Castanea* spp., *Cichorium endivia*, *Cinnamomum* spp., *Citrullus lanatus*, *Citrus* spp., *Cocos* spp., *Coffea* spp., *Cola* spp., *Colocasia esculenta*, *Corylus* spp., *Crataegus* spp., *Cucumis* spp., *Cucurbita* spp., *Cynara* spp., *Daucus carota*, *Desmodium* spp., *Dimocarpus longan*, *Dioscorea* spp., *Diospyros* spp., *Echinochloa* spp., *Eleusine coracana*, *Eriobotrya japonica*, *Eugenia uniflora*, *Fagopyrum* spp., *Fagus* spp., *Ficus carica*, *Fortunella* spp., *Fragaria* spp., *Ginkgo biloba*, *Glycine* spp., *Gossypium hirsutum*, *Helianthus* spp., *Hibiscus* spp., *Hordeum* spp., *Ipomoea batatas*, *Juglans* spp., *Lactuca sativa*, *Lathyrus* spp., *Lenina* spp., *Lens culinaris*, *Linum usitatissimum*, *Litchi chinensis*, *Lotus* spp., *Luffa acutangula*, *Lupinus* spp., *Macrotyloma* spp., *Malpighia emarginata*, *Malus* spp., *Mammea americana*, *Mangifera indica*, *Manihot* spp., *Manilkara zapota*, *Medicago sativa*, *Melilotus* spp., *Mentha* spp., *Momordica* spp., *Morus nigra*, *Musa* spp., *Nicotiana* spp., *Olea* spp., *Opuntia* spp., *Ornithopus* spp., *Oryza* spp., *Panicum miliaceum*, *Passiflora edulis*, *Pastinaca sativa*, *Persea* spp., *Petroselinum crispum*, *Phaseolus* spp., *Phoenix* spp., *Physalis* spp., *Pinus* spp., *Pistacia vera*, *Pisum* spp., *Poa* spp., and other members of the Poaceae family, *Populus* spp., *Prosopis* spp., *Prunus* spp., *Psidium* spp., *Punica granatum*, *Pyrus communis*, *Quercus* spp., *Raphanus sativus*, *Rheum rhabarbarum*, *Ribes* spp., *Rubus* spp., *Saccharum* spp., *Sambucus* spp., *Secale cereale*, *Sesamum* spp., *Solanum* spp., *Sorghum bicolor*, *Spinacia* spp., *Syzygium* spp., *Tamarindus indica*, *Theobroma cacao*, *Trifolium* spp., *Triticosecale rimpaui*, *Triticum* spp., *Vaccinium* spp., *Vicia* spp., *Vigna* spp., *Vitis* spp., *Zea mays*, *Zizania palustris*, *Ziziphus* spp., amongst others.

The methods of the present invention are favourable to apply to crop plants because the methods of the present invention are used to increase the seed yield, in particular total weight of seeds, number of filled seeds and harvest index of a plant. Therefore, the methods of the present invention are particularly useful for crop plants cultivated for their seeds, such as cereals, sunflower, soybean, cotton, pea, flax, lupines, canola etcs) . . . According to a preferred feature of the present invention, the plant is a crop plant comprising soybean, sunflower, canola, alfalfa, rapeseed or cotton. Further preferably, the plant according to the present invention is a monocotyledonous plant, including members of the Poaceae, such as sugarcane, most preferably a cereal, such as rice, maize, wheat, millet, barley, oats, rye and sorghum. Accordingly, a particular embodiment of the present invention relates to a method to increase seed yield, in particular total weight of seeds, number of filled seeds and/or harvest index of a cereal.

The activity of a CKX protein may be increased by increasing levels of the polypeptide (in the shoot). Alternatively, activity may also be increased when there is no change in levels of CKX, or even when there is a reduction in levels of a CKX protein. This may occur when the intrinsic properties of the polypeptide are altered, for example, by making mutant versions that are more active than the wild type polypeptide.

The activity may be increased in the shoot using techniques well known in the art, such as by specifically expressing CKX in the shoot.

Preferably the expression of CKX is primarily effected in the shoot of a plant. The term "shoot" as used in this invention encompasses all aerial parts of the plants, including stems and branches, the leaves, buds, reproductive organs (but not seeds), and also including shoot-derived structures like stolons, corms, rhizomes or tubers.

The term "CKX" or "CKX protein", as defined herein, refers to any cytokinin oxidase or cytokinin dehydrogenase. Preferably the CKX is from *Arabidopsis thaliana*, more preferably the CKX protein is a protein as represented by SEQ ID NO:37, or is a homologue, derivative or active fragment thereof, which homologues, derivatives or active fragments have similar biological activity to that of SEQ ID NO:37. Methods for measuring cytokinin oxidase/dehydrogenase activity are well known in the art. Suitable methods are based on the conversion of $[2-^3H]$iP to adenine (Motyka et al., Plant Physiology 112, 1035-1043, 1996), on calorimetric assays (Libreros-Minotta and Tipton, Anal. Biochem. 231, 339-341, 1995) or on the measurement of reduced electron acceptors (Bilyeu et al., Plant Physiol. 125, 378-386, 2001).

Methods for the search and identification of CKX homologues would be well within the realm of persons skilled in the art. Such methods comprise comparison of the sequences represented by SEQ ID Nos: 37 or 44 in a computer readable format with sequences that are available in public databases such as MIPS (http://mips.gsf.de/), GenBank (http://www.ncbi.nlm.nih.gov/Genbank/index.html) or EMBL Nucleotide Sequence Database (http://www.ebi.ac.uk/embl/index.html), using algorithms well known in the art for alignment or comparison of sequences, such as GAP (Needleman and Wunsch, J. Mol. Biol. 48, 443-453 (1970)), BESTFIT (using the local homology algorithm of Smith and Waterman (Advances in Applied Mathematics 2, 482-489 (1981))), BLAST (Altschul, S. F., Gish, W., Miller, W., Myers, E. W. & Lipman, D. J., J. Mol. Biol. 215, 403-410 (1990)), FASTA and TFASTA (W. R. Pearson and D. J. Lipman, Proc. Natl. Acad. Sci. USA 85, 2444-2448 (1988)). The software for performing BLAST analysis is publicly available at the National Centre for Biotechnology Information.

When using an alignment program such as GAP, with a gap penalty of 10, an extend penalty of 0.5 and the BLOSUM 62 matrix, the homologues useful in the methods according to the invention have at least 50% sequence similarity to an unmodified protein, alternatively at least 60% sequence similarity to an unmodified protein, alternatively at least 70% sequence similarity to an unmodified protein. Typically, the homologues have at least 80% sequence identity or similarity to an unmodified protein, preferably at least 85% sequence identity or similarity, further preferably at least 90% sequence identity or similarity to an unmodified protein, most preferably at least 95%, 96%, 97%, 98% or 99% sequence identity or similarity to an unmodified protein. The percentage of identity can also be calculated using alignment programs such as GAP.

Homologues of SEQ ID NO:37 may be found in various prokaryotic and eukaryotic organisms. A prokaryotic homologue of SEQ ID NO:37 is represented by GenBank Accession P46377. The closest homologues however are generally found in the plant kingdom. Suitable homologues of SEQ ID NO:37 are listed in Table 8.

TABLE 8

Examples of useful CKX homologues, relatedness is expressed towards SEQ ID NO: 37.

| Accession number | % identity | % similarity |
|---|---|---|
| NP_181682 | 36.0 | 54.1 |
| NP_200507 | 47.8 | 67.9 |
| NP_849470 | 53.8 | 63.4 |
| NP_194703 | 65.8 | 78.9 |
| NP_850863 | 39.2 | 55.6 |
| AAG30909 | 44.1 | 61.0 |
| NP_191903 | 40.7 | 59.4 |
| CAE55202 | 38.7 | 57.8 |
| CAE55200 | 38.6 | 58.9 |
| AAC27500 | 43.8 | 59.7 |
| CAC17752 | 46.5 | 61.7 |
| AAN16383 | 40.5 | 59.3 |
| AAO50082 | 40.8 | 60.4 |
| AAM08400 | 40.3 | 59.1 |
| NP_913145 | 41.7 | 59.0 |
| NP_916348 | 42.8 | 60.0 |
| NP_922039 | 39.4 | 58.0 |

As more genomes are being sequenced, it is expected that many more CKX homologues shall be identifiable.

These above-mentioned analyses for sequence homology can be done with a full-length query sequence or with certain regions of such a sequence, for example with conserved domains such as sequences corresponding to the consensus sequences mentioned above. Also the identification of family members of the CKX (as defined below) or the determination of the percentage of sequence identity between the CKX and a homologue (as defined below) can be performed by using these conserved sequences. The identification of such domains in a protein sequence would also be well within the realm of the person skilled in the art and involve a computer readable format of the nucleic acids used in the present invention, the use of alignment software programs and the use of publicly available information on protein domains, conserved motifs and boxes. An integrated search can be done using the INTERPRO database (Mulder et al., (2003) Nucl. Acids Res. 31, 315-318, http://www.ebi.ac.uk/interpro/scan.html) which combines several databases on protein families, domains and functional sites, such as the PRODOM (Servant et al., (2002) Briefings in Bioinformatics 3, 246-251, http://prodes.toulouse.inra.fr/prodom/2002.1/html/home.php), PIR (Huang et al. (2003) Nucl. Acids Res. 31, 390-392, http://pir.georgetown.edu/) or Pfam (Bateman et al. (2002) Nucl. Acids Res. 30, 276-280, http://pfam.wustl.edu/) databases. Sequence analysis programs designed for motif searching can be used for identification of conserved fragments, regions and domains as mentioned above. Suitable computer programs to this end include for example MEME (Bailey and Elkan (1994) Proceedings of the Second International Conference on Intelligent Systems for Molecular Biology, pp. 28-36, AAAI Press, Menlo Park, Calif., http://meme.sdsc.edu/meme/website/intro.html).

Homologous proteins can be grouped in "protein families". A protein family can be defined by functional and sequence similarity analysis, using programs such as, for example, Clustal W. A neighbour-joining tree of proteins homologous to SEQ ID NO 51, generated by the Clustal W program gives a good overview of their structural and ancestral relationships. In the *Arabidopsis* genome several family members of the CKX protein as presented in SEQ ID NO 2 are known (GenBank Accessions NP_181682, NP_200507, NP-849470, NP-194703, NP_850863, NP_191903 or AAG30909). Also in other plants such as rice, maize and other monocotyledonous plants, family members of CKX were identified. Advantageously also these family members are useful in the methods of the present invention.

The term "derivatives" refers to peptides, oligopeptides, polypeptides, proteins and enzymes which may comprise substitutions, deletions or additions of naturally and non-naturally occurring amino acid residues compared to the amino acid sequence of a naturally-occurring form of the protein, for example, as presented in SEQ ID NO: 37. "Derivatives" of a protein encompass peptides, oligopeptides, polypeptides, proteins and enzymes which may comprise naturally occurring altered, glycosylated, acylated or non-naturally occurring amino acid residues compared to the amino acid sequence of a naturally-occurring form of the polypeptide. A derivative may also comprise one or more non-amino acid substituents compared to the amino acid sequence from which it is derived, for example a reporter molecule or other ligand, covalently or non-covalently bound to the amino acid sequence to facilitate its detection, and non-naturally occurring amino acid residues relative to the amino acid sequence of a naturally-occurring protein. "Active fragments" of a CKX protein encompass at least 28 contiguous amino acid residues of a CKX protein, which residues retain similar biological and/or functional activity to the naturally occurring protein.

The term CKX encoding nucleic acid/gene, as defined herein, refers to any nucleic acid encoding a cytokinin oxidase or cytokinin dehydrogenase as defined above, or the complement thereof. The nucleic acid may be derived (either directly or indirectly (if subsequently modified)) from any source provided that the nucleic acid, when expressed in a plant, leads to modulated expression of a CKX nucleic acid/gene. The nucleic acid may be isolated from a microbial source, such as bacteria, yeast or fungi, or from a plant, algal or animal source. This nucleic acid may be substantially modified from its native form in composition and/or genomic environment through deliberate human manipulation. The nucleic acid molecule is preferably a homologous nucleic acid molecule, i.e. a structurally and/or functionally related nucleic acid molecule, preferably obtained from a plant, whether from the same plant species or different. The nucleic acid molecule may be isolated from a dicotyledonous (monocotyledonous) species, preferably from the family Brassicaceae, further preferably from *Arabidopsis thaliana*. More preferably, the nucleic acid is as represented by SEQ ID NO:44 or a portion thereof or is a nucleic acid molecule capable of hybridising therewith, which hybridising molecules encode proteins having cytokinin oxidase or cytokinin dehydrogenase activity, i.e. similar biological activity to that of SEQ ID NO:37; or the nucleic acid encodes an amino acid represented by SEQ ID NO:37 or encodes a homologue, derivative or active fragment thereof. The term CKX encoding nucleic acid/gene also encompasses variants of the nucleic acid encoding a CKX due to the degeneracy of the genetic code; allelic variants of the nucleic acid encoding a CKX; different splice variants of the nucleic acid encoding a CKX and variants that are interrupted by one or more intervening sequences.

Advantageously, the methods according to the present invention may also be practised using portions of a DNA or nucleic acid molecule, which portions retain cytokinin oxidase activity, i.e. a similar biological function to that of SEQ ID NO:37. Portions of a DNA molecule refer to a piece of DNA derived or prepared from an original (larger) DNA molecule, which DNA portion, when expressed in a plant, gives rise to plants having modified growth characteristics.

The portion may comprise many genes, with or without additional control elements, or may contain just spacer sequences.

The methods of the present invention also encompass use of nucleic acid molecules capable of hybridising with a nucleic acid molecule encoding a CKX protein.

The methods according to the present invention may also be practised using an alternative splice variant of a nucleic acid molecule encoding a CKX protein. The term "alternative splice variant" as used herein encompasses variants of a nucleic acid molecule in which selected introns and/or exons have been excised, replaced or added. Such variants will be ones in which the biological activity of the protein remains unaffected, which can be achieved by selectively retaining functional segments of the protein. Such splice variants may be found in nature or can be manmade. Methods for making such splice variants are well known in the art. Therefore according to another aspect of the present invention, there is provided a method for modifying the growth characteristics of plants, in particular seed yield, comprising modulating expression in a plant of an alternative splice variant of a nucleic acid molecule encoding a CKX and/or by modulating activity and/or levels of a CKX encoded by the alternative splice variant. Preferably, the splice variant is a splice variant of the sequence represented by SEQ ID NO:38.

Advantageously, the methods according to the present invention may also be practised using allelic variants of a nucleic acid molecule encoding a CKX, preferably an allelic variant of a sequence represented by SEQ ID NO:44. Allelic variants exist in nature and encompassed within the methods of the present invention is the use of these natural alleles. Allelic variants are further defined as to comprise single nucleotide polymorphisms (SNPs) as well as small insertion/deletion polymorphisms (INDELs; the size of INDELs is usually less than 100 bp). SNPs and INDELs form the largest set of sequence variants in naturally occurring polymorphic strains of most organisms. They are helpful in mapping genes and discovery of genes and gene functions. They are furthermore helpful in identification of genetic loci, e.g. plant genes, involved in determining processes such as growth rate, plant size and plant yield, plant vigour, disease resistance, stress tolerance etc.

The activity of a CKX protein or a homologue thereof may also be modulated (increased or decreased) by introducing a genetic modification (preferably in the locus of a CKX gene). The locus of a gene as defined herein is taken to mean a genomic region, which includes the gene of interest and 10 KB up- or downstream of the coding region.

The genetic modification may be introduced, for example, by any one (or more) of the following methods: TDNA activation, TILLING, site-directed mutagenesis, homologous recombination or by introducing and expressing in a plant cell a nucleic acid encoding a CKX protein or a homologue thereof. Following introduction of the genetic modification, there follows a step of selecting for increased activity of a CKX protein, which increase in activity gives plants having improved growth characteristics.

T-DNA activation tagging (Hayashi et al. Science (1992) 1350-1353) involves insertion of T-DNA usually containing a promoter (may also be a translation enhancer or an intron), in the genomic region of the gene of interest or 10 KB up- or down stream of the coding region of a gene in a configuration such that the promoter directs expression of the targeted gene. Typically, regulation of expression of the targeted gene by its natural promoter is disrupted and the gene falls under the control of the newly introduced promoter. The promoter is typically embedded in a T-DNA. This T-DNA is randomly inserted into the plant genome, for example, through *Agrobacterium* infection and leads to overexpression of genes near to the inserted T-DNA. The resulting transgenic plants show dominant phenotypes due to overexpression of genes close to the introduced promoter. The promoter to be introduced may be any promoter capable of directing expression of a gene in the desired organism, in this case a plant. For example, constitutive, tissue-preferred, cell type-preferred and inducible promoters are all suitable for use in T-DNA activation.

A genetic modification may also be introduced in the locus of a CKX gene using the technique of TILLING (Targeted Induced Local Lesions IN Genomes). This is a mutagenesis technology useful to generate and/or identify, and to eventually isolate mutagenised variants of a CKX nucleic acid capable of exhibiting CKX activity. TILLING also allows selection of plants carrying such mutant variants. These mutant variants may even exhibit higher CKX activity than that exhibited by the gene in its natural form. TILLNG combines high-density mutagenesis with high-throughput screening methods. The steps typically followed in TILLING are: (a) EMS mutagenesis (Redei and Koncz, 1992; Feldmann et al., 1994; Lightner and Caspar, 1998); (b) DNA preparation and pooling of individuals; (c) PCR amplification of a region of interest; (d) denaturation and annealing to allow formation of heteroduplexes; (e) DHPLC, where the presence of a heteroduplex in a pool is detected as an extra peak in the chromatogram; (f) identification of the mutant individual; and (g) sequencing of the mutant PCR product. Methods for TILLING are well known in the art (McCallum Nat Biotechnol. 2000 April; 18 (4):455-7, reviewed by Stemple 2004 (TILLING-a high-throughput harvest for functional genomics. Nat Rev Genet. 2004 February; 5 (2):145-50.)).

Site directed mutagenesis may be used to generate variants of CKX nucleic acids or portions thereof. Several methods are available to achieve site directed mutagenesis, the most common being PCR based methods (current protocols in molecular biology. Wiley Eds. http://www.4ulr.com/products/currentprotocols/index.html).

TDNA activation, TILLING and site-directed mutagenesis are examples of technologies that enable the generation of novel alleles and CKX variants.

Homologous recombination allows introduction in a genome of a selected nucleic acid at a defined selected position. Homologous recombination is a standard technology used routinely in biological sciences for lower organisms such as yeast or the moss *Physcomitrella*. Methods for performing homologous recombination in plants have been described not only for model plants (Offringa et al. Extrachromosomal homologous recombination and gene targeting in plant cells after *Agrobacterium*-mediated transformation. 1990 EMBO J. 1990 October; 9 (10):3077-84) but also for crop plants, for example rice (Terada R, Urawa H, Inagaki Y, Tsugane K, Iida S. Efficient gene targeting by homologous recombination in rice. Nat Biotechnol. 2002. Iida and Terada: A tale of two integrations, transgene and T-DNA: gene targeting by homologous recombination in rice. Curr Opin Biotechnol. 2004 April; 15 (2): 132-8). The nucleic acid to be targeted (which may be a CKX nucleic acid or variant thereof as hereinbefore defined) need not be targeted to the locus of a CKX gene, but may be introduced in, for example, regions of high expression. The nucleic acid to be targeted may be an improved allele used to replace the endogenous gene or may be introduced in addition to the endogenous gene.

According to a preferred aspect of the present invention, an increase of expression of a nucleic acid is envisaged. Increasing or decreasing expression (or modulating expression) of a nucleic acid encoding a CKX protein encompasses altered expression of this gene in the whole organism or in specific cells or tissues. Modulating expression of a CKX gene may be effected directly and may result from altered expression levels of an endogenous CKX gene and/or may result from altered expression of a CKX encoding nucleic acid that was previously introduced into a plant. The altered expression is to be understood as altered when compared to expression of a corresponding CKX in corresponding wild type plants.

According to a preferred embodiment of the present invention, modulation of expression of a nucleic acid encoding a CKX and/or modulation of activity and/or levels of the CKX protein itself may be effected by recombinant means. Such recombinant means may comprise a direct and/or indirect approach for modulation of expression of a nucleic acid.

For example, an indirect recombinant approach may comprise introduction into a plant of a nucleic acid capable of modulating activity and/or levels of the protein in question (a cytokinin oxidase) and/or capable of modulating expression of the gene in question (a gene encoding a cytokinin oxidase). Examples of such nucleic acids to be introduced into a plant are nucleic acids encoding transcription factors, activators, inhibitors or other ligands that bind to the promoter of the CKX gene or that interact with the CKX protein. Methods to test these kinds of interaction and to isolate the nucleic acids encoding these interactors are for example yeast one-hybrid or yeast two-hybrid screening. The CKX gene or the CKX protein may be the native or endogenous nucleic acid or polypeptide. Alternatively, it may be a nucleic acid derived from the same or another species, which gene is introduced as a transgene, for example by transformation. This transgene may be substantially modified from its native form in composition and/or genomic environment through deliberate human manipulation. Also encompassed by an indirect approach for modulating expression of a CKX gene is the inhibition or stimulation of regulatory sequences, or the provision of new regulatory sequences, that drive expression of the native gene encoding a CKX or the transgene encoding a CKX. Such regulatory sequences may be introduced into a plant. For example, the regulatory sequence introduced into the plant is a promoter, capable of driving the expression of an endogenous CKX gene.

A direct and preferred approach for modulating expression of a CKX gene comprises introduction into a plant of a nucleic acid molecule encoding a CKX protein or a homologue, derivative or active fragment thereof. The nucleic acid may be introduced into a plant by, for example, transformation.

A more preferred way comprises the introduction into a plant of a CKX gene as presented in SEQ ID NO:44. A most preferred way comprises the introduction into a plant of a CKX encoding gene coupled in sense direction to a weak shoot-preferred promoter.

Methods for obtaining enhanced or increased expression of genes or gene products are well documented in the art and include overexpression driven by a suitable promoter and the use of transcription enhancers or translation enhancers. The term overexpression as used herein means any form of expression (including weak expression) that is additional to the original wild-type expression level. Preferably the nucleic acid to be introduced into the plant and/or to be overexpressed, is in a sense direction with respect to the promoter to which it is operably linked. The nucleic acid to be overexpressed preferably encodes a CKX protein, further preferably a CKX protein of plant origin. More preferably, the nucleic acid molecule encoding the CKX protein is isolated from a dicotyledonous plant, preferably of the family Brassicaceae, further preferably the sequence is isolated from *Arabidopsis thaliana*. Most preferably the nucleic acid sequence is as represented by SEQ ID NO:44 or a portion thereof, or encodes an amino acid sequence as represented by SEQ ID NO:37 or encodes a homologue, derivative or active fragment thereof. However, it should be noted that the applicability of the invention does not rest upon the use of the nucleic acid represented by SEQ ID NO:44, nor upon the nucleic acid molecule encoding the amino acid sequence of SEQ ID NO:37, but that other nucleic acid molecules encoding homologues, derivatives or active fragments of SEQ ID NO:37, or portions of SEQ ID NO:44, or sequences hybridising with SEQ ID NO:44 may be used in the methods of the present invention.

According to a further embodiment of the present invention, genetic constructs and vectors to facilitate introduction and/or expression of the nucleotide sequences useful in the methods according to the invention are provided. Therefore, according to the second embodiment of the present invention, there is provided a gene construct comprising:
 (i) an isolated nucleic acid molecule encoding a cytokinin oxidase/dehydrogenase;
 (ii) one or more control sequences capable of driving shoot preferred expression of the nucleic acid molecule of (i); and optionally
 (iii) a transcription termination sequence.

Constructs useful in the methods according to the present invention may be created using recombinant DNA technology well known to persons skilled in the art. The gene constructs may be inserted into vectors, which may be commercially available, suitable for transforming into plants and suitable for expression of the gene of interest in the transformed cells. The genetic construct can be an expression vector wherein the nucleic acid molecule is operably linked to one or more control sequences allowing expression in prokaryotic and/or eukaryotic host cells.

According to a preferred embodiment of the invention, the genetic construct is an expression vector designed to overexpress the nucleic acid molecule, in particular low overexpression confined to the shoot of the plant is aimed at. The nucleic acid molecule capable of modulating expression of a nucleic acid encoding a CKX protein may be a nucleic acid molecule encoding a CKX or a homologue, derivative or active fragment thereof, such as any of the nucleic acid molecules described hereinbefore. A preferred nucleic acid molecule is the sequence represented by SEQ ID NO:44 or a portion thereof or sequences capable of hybridising therewith or a nucleic acid molecule encoding a sequence represented by SEQ ID NO:37 or encoding a homologue, derivative or active fragment thereof. Preferably, this nucleic acid is cloned in sense orientation relative to the control sequence to which it is operably linked.

Plants are transformed with a vector comprising the sequence of interest (i.e., the nucleic acid molecule capable of modulating expression of a nucleic acid encoding a CKX protein), which sequence is operably linked to one or more control sequences (at least a promoter). The terms "regulatory element", "regulatory sequence", "control sequence" and "promoter" are all used herein interchangeably and are to be taken in a broad context to refer to regulatory nucleic acid sequences capable of effecting expression of the sequences to which they are ligated. Encompassed by the aforementioned terms are transcriptional regulatory sequences derived from a classical eukaryotic genomic gene (including the TATA box which is required for accurate transcription initiation, with or without a CCAAT box sequence) and additional regulatory elements (i.e. upstream activating sequences, enhancers and silencers) which alter gene expression in response to developmental and/or external stimuli, or in a tissue-specific manner. Also included within the term is a transcriptional regulatory sequence of a classical prokaryotic gene, in which case it may include a −35 box sequence and/or −10 box transcriptional regulatory sequences. The term "regulatory element" also encompasses a synthetic fusion molecule or derivative which confers, activates or enhances expression of a nucleic acid molecule in a cell, tissue or organ. The term "operably linked" as used herein refers to a functional linkage between the promoter sequence and the gene of interest, such that the promoter sequence is able to initiate transcription of the gene of interest.

0000 transcripts per cell. Conversely, a "strong promoter" drives expression of a coding sequence at high level, or at about 1/10 transcripts to about 1/100 transcripts to about 1/1,000 transcripts per cell. Examples of other shoot preferred promoters are presented in table 10, these promoters or derivatives thereof may also be useful in the methods of the present invention. By way of example, an overview of the expression pattern of the weak shoot-specific promoter beta-expansion EXPB9 (SEQ ID NO: 53) is given in Example 24 and FIG. 22.

TABLE 9

Promoters that are active exclusively or predominantly in shoots:

| | | |
|---|---|---|
| PRO0080 | metallothionein like ML2 | Shoot, embryo/scutellum, calli |
| PRO0081 | putative caffeoyl-CoA 3-O-methyltransferase | shoot |
| PRO0111 | uclacyanin 3-like protein | weak discrimination center/shoot meristem |
| PRO0117 | putative 40S ribosomal protein | Shoot, endosperm |
| PRO0122 | chlorophyll a/b-binding protein presursor (Cab27) | very weak in shoot |
| PRO0123 | putative protochlorophyllid reductase | shoot |
| PRO0126 | metallothionein RiCMT | strong discrimination center/shoot meristem |
| PRO0141 | cyclophyllin 2 | shoot and seed |
| PRO0173 | cytosolic MDH | shoot |
| PRO208 | putative chlorophylase | shoot |
| PRO0 61 | Beta expansin EXPB9 | weak in young green tissue |

In order to obtain desired modified growth characteristics, it is important that the gene of interest is expressed at a suitable level and in a spatially and developmentally suitable pattern. Preferably, the nucleic acid molecule encoding a CKX protein is operably linked to a weak shoot-preferred promoter. The term "shoot preferred" promoter as defined herein refers to a promoter that is expressed predominantly in one or more shoot tissue(s). Preferably the shoot-preferred promoter is a promoter as presented in SEQ ID NO:49 (effecting a low expression level primarily confined to the shoot), or a promoter of similar strength and/or a similar expression pattern. Therefore, the invention also provides a method for modifying the growth characteristics of a plant, in particular seed yield, comprising increasing expression in a plant of a nucleic acid encoding a CKX protein, wherein the increased expression is primarily obtained in the shoot. Preferably, this expression is effected under control of a shoot preferred promoter, more preferably the shoot preferred promoter is a weak shoot preferred promoter, most preferably the shoot preferred promoter is a weak shoot preferred promoter as represented in SEQ ID NO:49. Promoter strength and/or expression pattern can be analysed for example by coupling the promoter to a reporter gene and assay the expression of the reporter gene in various tissues of the plant. One suitable reporter gene well known to a person skilled in the art is beta-glucuronidase. The promoter strength and/or expression pattern can then be compared to that of a well-characterised shoot preferred reference promoter, such as the Cab27 promoter (weak expression, GenBank AP004700) or the putative protochlorophyllid reductase promoter (strong expression, GenBank AL606456). Generally by "weak promoter" is intended a promoter that drives expression of a coding sequence at a low level. By "low level" is intended at levels of about 1/10,000 transcripts to about 1/100,000 transcripts, to about 1/500, Optionally, one or more terminator sequences may also be used in the construct introduced into a plant. The term "terminator" encompasses a control sequence which is a DNA sequence at the end of a transcriptional unit which signals 3' processing and polyadenylation of a primary transcript and termination of transcription. Additional regulatory elements may include transcriptional as well as translational enhancers. Those skilled in the art will be aware of terminator and enhancer sequences which may be suitable for use in performing the invention. Such sequences would be known or may readily be obtained by a person skilled in the art.

The genetic constructs of the invention may further include an origin of replication sequence which is required for maintenance and/or replication in a specific cell type. One example is when a genetic construct is required to be maintained in a bacterial cell as an episomal genetic element (e.g. plasmid or cosmid molecule). Preferred origins of replication include, but are not limited to, the fl-ori and colE1.

The genetic construct may optionally comprise a selectable marker gene. As used herein, the term "selectable marker gene" includes any gene which confers a phenotype on a cell in which it is expressed to facilitate the identification and/or selection of cells which are transfected or transformed with a nucleic acid construct of the invention. Suitable markers may be selected from markers that confer antibiotic or herbicide resistance, that introduce a new metabolic trait or that allow visual selection. Examples of selectable marker proteins include proteins conferring resistance to antibiotics (such as nptII that phosphorylates neomycin and kanamycin, or hpt, phosphorylating hygromycin), to herbicides (for example bar which provides resistance to Basta; aroA or gox providing resistance against glyphosate), or genes that provide a metabolic trait (such as manA that allows plants to use mannose as sole carbon source). Visual marker genes result in the formation of colour (for example β-glucuronidase, GUS), luminescence (such as luciferase) or fluorescence (Green Fluorescent Protein, GFP, and derivatives thereof).

In a preferred embodiment, the genetic construct as mentioned above, comprises a CKX in sense orientation coupled to a promoter that is preferably a weak shoot-preferred promoter, such as for example the promoter as presented in SEQ ID NO:49. Therefore, another aspect of the present invention is a vector construct comprising an expression cassette essentially similar to SEQ ID NO:50, comprising the promoter presented in SEQ ID NO:49, the *Arabidopsis* CKX2 gene and the T-zein+T-rubisco transcription terminator sequence. A sequence essentially similar to SEQ ID NO:50 encompasses a first nucleic acid sequence encoding a protein homologous to SEQ ID NO:37 or hybridising to SEQ ID NO:44, which first nucleic acid is operably linked to a promoter as presented in SEQ ID NO:49, or a promoter with a similar expression pattern and which first nucleic acid is optionally linked to a transcription termination sequence.

The present invention also encompasses plants obtainable by the methods according to the present invention. The present invention therefore provides plants obtainable by the methods according to the present invention, which plants have increased seed yield, particularly, increased total weight of seeds, increased number of filled seeds, and/or increased harvest index, and which plants have introduced therein a nucleic acid encoding a CKX protein.

The invention also provides a method for the production of transgenic plants having improved growth characteristics, comprising introduction and expression in a plant cell of a CKX nucleic acid or a variant thereof.

More specifically, the present invention provides a method for the production of transgenic plants having improved growth characteristics, which method comprises:
  (i) introducing into a plant or into a plant cell a nucleic acid molecule encoding a cytokinin oxidase/dehydrogenase or a homologue, derivative or active fragment thereof, which nucleic acid is under control of a shoot preferred promoter;
  (ii) cultivating the plant cell under conditions promoting regeneration and mature plant growth.

Thus, there is provided a method for increasing seed yield of a plant, or for obtaining a plant with increased seed yield, which method comprises:
  1. introducing and expressing in the plant an isolated nucleic acid sequence in an expressible format encoding a cytokinin oxidase/dehydrogenase, or a homologue, derivative or active fragment thereof, wherein the expression is primarily obtained in the shoot of the plant;
  2. growing the plant and self or cross-fertilizing or allowing self or cross-fertilization of the plant;
  3. obtaining seed from the selfed or cross-fertilized plant;
  4. selecting a plant which produces an increased seed yield compared to the seed yield of a corresponding selfed or crossed-fertilized wild type plant.

The nucleic acid may be introduced directly into a plant cell or into the plant itself (including introduction into a tissue, organ or any other part of the plant). According to a preferred feature of the present invention, the nucleic acid is preferably introduced into a plant by transformation. The nucleic acid is preferably as represented by SEQ ID NO:44 or a portion thereof or sequences capable of hybridising therewith, or is a nucleic acid encoding an amino acid sequence represented by SEQ ID NO:37 or a homologue, derivative or active fragment thereof. Alternatively, the nucleic acid sequence is as represented by SEQ ID NO:38 or a portion thereof or sequences capable of hybridising with any of the aforementioned sequences. The amino acid sequence may alternatively be a sequence as represented by SEQ ID NO:39 or by homologues, derivatives or active fragments thereof. The nucleic acid sequence is preferably under control of a weak shoot-preferred promoter, further preferably a promoter as represented by SEQ ID NO:49 or SEQ ID NO:53.

The term "transformation" as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated therefrom. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell can then be used to regenerate a transformed plant in a manner known to persons skilled in the art.

Transformation of a plant species is now a fairly routine technique. Advantageously, any of several transformation methods may be used to introduce the gene of interest into a suitable ancestor cell. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A. et al., 1882, Nature 296, 72-74; Negrutiu I. et al., June 1987, Plant Mol. Biol. 8, 363-373); electroporation of protoplasts (Shillito R. D. et al., 1985 Bio/Technol 3, 1099-1102); microinjection into plant material (Crossway A. et al., 1986, Mol. Gen Genet 202, 179-185); DNA or RNA-coated particle bombardment (Klein T. M. et al., 1987, Nature 327, 70) infection with (non-integrative) viruses and the like. A preferred method for rice transformation is the protocol of Hiei et al. (Plant J. 6, 271-282, 1994), the protocol in the published European patent application EP 1198985 A1, in Aldemita and Hodges (Planta 199, 612-617, 1996) or in Chan et al. (Plant Mol. Biol. 22, 491-506, 1993), which disclosures are incorporated by reference herein as if fully set forth. Preferred methods to transform corn with high efficiency are the protocols described in Ishida et al. (1996, Nat Biotechnol. 14, 745-50), and in Frame et al. (2002, Plant Physiol. 129, 13-22), which disclosures are incorporated by reference herein as if fully set forth.

Generally after transformation, plant cells or cell groupings are selected for the presence of one or more markers which are encoded by plant-expressible genes co-transferred with the gene of interest, following which the transformed material is regenerated into a whole plant.

Following DNA transfer and regeneration, putatively transformed plants may be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed to give homozygous second generation (or T2) transformants, and the T2 plants further propagated through classical breeding techniques.

The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The present invention clearly extends to any plant cell or plant produced by any of the methods described herein, and to all plant parts and propagules thereof. The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced in the parent by the methods according to the invention. The invention also includes host cells containing an isolated nucleic acid molecule encoding a CKX protein. Preferred host cells according to the invention are plant cells. The invention also extends to harvestable parts of a plant according to the invention, such as, but not limited to, seeds, leaves, fruits, flowers, stems or stem cultures, rhizomes, roots, tubers and bulbs. The invention further relates to products derived directly from a harvestable part of such a plant, such products including dry pellets or powders, oil, fat and fatty acids, starch or proteins.

The present invention also encompasses the use of CKX nucleic acids, portions or variants thereof and to the use of CKX polypeptides, homologues or derivatives thereof.

One such use relates to improving the growth characteristics of plants, in particular in improving yield, especially seed yield. The seed yield may include one or more of the following: increased number of (filled) seeds, increased total seed weight, increased harvest index, increased thousand kernel weight, seed filling rate, among others.

CKX nucleic acids or variants thereof or CKX polypeptides or homologues thereof may find use in breeding programmes in which a DNA marker is identified which may be genetically linked to a CKX gene or variant thereof. The CKX or variants thereof or CKX or homologues thereof may be used to define a molecular marker. This DNA or protein marker may then be used in breeding programmes to select plants having altered growth characteristics. The CKX gene or variant thereof may, for example, be a nucleic acid as represented by SEQ ID NO:44, or a nucleic acid encoding any of the above mentioned homologues.

Allelic variants of a CKX may also find use in marker-assisted breeding programmes. Such breeding programmes sometimes require introduction of allelic variation by mutagenic treatment of the plants, using for example EMS mutagenesis; alternatively, the programme may start with a collection of allelic variants of so called "natural" origin caused unintentionally. Identification of allelic variants then takes place by, for example, PCR. This is followed by a selection step for selection of superior allelic variants of the sequence in question and which give rise to improved growth characteristics in a plant, such as increased CKX activity. Selection is typically carried out by monitoring growth performance of plants containing different allelic variants of the sequence in question, for example, different allelic variants of SEQ ID NO:44, or of nucleic acids encoding any of the above mentioned plant homologues. Growth performance may be monitored in a greenhouse or in the field. Further optional steps include crossing plants, in which the superior allelic variant resulting in increased CKX activity was identified, with another plant. This could be used, for example, to make a combination of interesting phenotypic features.

A CKX nucleic acid or variant thereof may also be used as probes for genetically and physically mapping the genes that they are a part of, and as markers for traits linked to those genes. Such information may be useful in plant breeding in order to develop lines with desired phenotypes. Such use of CKX nucleic acids or variants thereof requires only a nucleic acid sequence of at least 10 nucleotides in length. The CKX nucleic acids or variants thereof may be used as restriction fragment length polymorphism (RFLP) markers. Southern blots of restriction-digested plant genomic DNA may be probed with the CKX nucleic acids or variants thereof. The resulting banding patterns may then be subjected to genetic analyses using computer programs such as MapMaker (Lander et al. (1987) Genomics 1, 174-181) in order to construct a genetic map. In addition, the nucleic acids may be used to probe Southern blots containing restriction endonuclease-treated genomic DNAs of a set of individuals representing parent and progeny of a defined genetic cross. Segregation of the DNA polymorphisms is noted and used to calculate the position of the CKX nucleic acid or variant thereof in the genetic map previously obtained using this population (Botstein et al. (1980) Am. J. Hum. Genet. 32, 314-331).

The production and use of plant gene-derived probes for use in genetic mapping is described in Bematzky and Tanksley (Plant Mol. Biol. Reporter 4, 37-41, 1986). Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

The nucleic acid probes may also be used for physical mapping (i.e., placement of sequences on physical maps; see Hoheisel et al. In: Nonmammalian Genomic Analysis: A Practical Guide, Academic press 1996, pp. 319-346, and references cited therein).

In another embodiment, the nucleic acid probes may be used in direct fluorescence in situ hybridization (FISH) mapping (Trask (1991) Trends Genet. 7, 149-154). Although current methods of FISH mapping favour use of large clones (several to several hundred kb; see Laan et al. (1995) Genome Res. 5, 13-20), improvements in sensitivity may allow performance of FISH mapping using shorter probes.

A variety of nucleic acid amplification-based methods of genetic and physical mapping may be carried out using the nucleic acids. Examples include allele-specific amplification (Kazazian (1989) J. Lab. Clin. Med. 11, 95-96), polymorphism of PCR-amplified fragments (CAPS; Sheffield et al. (1993) Genomics 16, 325-332), allele-specific ligation (Landegren et al. (1988) Science 241, 1077-1080), nucleotide extension reactions (Sokolov (1990) Nucleic Acid Res. 18, 3671), Radiation Hybrid Mapping (Walter et al. (1997) Nat. Genet. 7, 22-28) and Happy Mapping (Dear and Cook (1989) Nucleic Acid Res. 17, 6795-6807). For these methods, the sequence of a nucleic acid is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

In this way, generation, identification and/or isolation of modified plants with altered CKX activity displaying improved growth characteristics can be performed.

CKX nucleic acids or variants thereof or CKX polypeptides or homologues thereof may also find use as growth regulators. Since these molecules have been shown to be useful in improving the growth characteristics of plants, they would also be useful growth regulators, such as herbicides or growth stimulators. The present invention therefore provides a composition comprising a CKX or variant thereof or a CKX polypeptide or homologue thereof, together with a suitable carrier, diluent or excipient, for use as a growth regulator, preferably as a growth promoter.

The methods according to the present invention result in plants having improved growth characteristics, as described hereinbefore. These advantageous growth characteristics may also be combined with other economically advantageous traits, such as further yield-enhancing traits, tolerance to various stresses, traits modifying various architectural features and/or biochemical and/or physiological features. Accordingly, the methods of the present invention can also be used in so-called "gene stacking" procedures.

The following examples are given by means of illustration of the present invention and are in no way limiting. The contents of all references included in this application are incorporated by reference herein as if fully set forth.

EXAMPLES

Example 1

Brief Description of the Sequences of the Invention

| SEQ ID NO: | DESCRIPTION |
|---|---|
| 1 | AtCKX1 genomic |
| 2 | AtCKX1 protein |
| 3 | AtCKX2 genomic |
| 4 | AtCKX2 protein |
| 5 | AtCKX3 genomic |
| 6 | AtCKX3 protein |
| 7 | AtCKX4 genomic |
| 8 | AtCKX4 protein |
| 9 | AtCKX5 genomic (short version) |
| 10 | AtCKX5 protein (short version) |
| 11 | AtCKX6 genomic |
| 12 | AtCKX6 protein |
| 13 | 5' primer AtCKX1 |
| 14 | 3' primer AtCKX1 |
| 15 | 5' primer AtCKX2 |
| 16 | 3' primer AtCKX2 |
| 17 | 5' primer AtCKX3 |
| 18 | 3' primer AtCKX3 |
| 19 | 5' primer AtCKX4 |
| 20 | 3' primer AtCKX4 |
| 21 | 5' primer AtCKX5 |
| 22 | 3' primer AtCKX5 |
| 23 | 5' primer AtCKX6 |
| 24 | 3' primer AtCKX6 |
| 25 | AtCKX1 cDNA |
| 26 | AtCKX2 cDNA |
| 27 | AtCKX3 cDNA |
| 28 | AtCKX4 cDNA |
| 29 | AtCKX5 cDNA (short version) |
| 30 | AtCKX6 cDNA |
| 31 | AtCKX2 cDNA fragment |
| 32 | AtCKX2 peptide fragment |

-continued

| SEQ ID NO: | DESCRIPTION |
|---|---|
| 33 | AtCKX5 genomic (long version) |
| 34 | AtCKX5 cDNA (long version) |
| 35 | AtCKX5 protein (long version) |
| 36 | root clavata homolog promoter |
| 37 | AtCKX2, CDS0427_2 deduced protein sequence |
| 38 | AtCKX2 splice variant, DNA sequence |
| 39 | AtCKX2 splice variant, deduced protein sequence |
| 40 | PRM3769 (sense, start codon at positions 35 to 37) |
| 41 | PRM1526 (reverse, complementary stop codon at positions 30-32) |
| 42 | Expression cassette with PRO0218 - CDS0427_2 - zein and rbcS-deltaGA double terminator |
| 43 | Expression cassette with PRO0090 - CDS0427_2 - zein and rbcS-deltaGA double terminator |
| 44 | AtCKX2, CDS0427_2 cDNA |
| 45 | PRM02958 (sense, start codon at positions 37 to 37) |
| 46 | PRM02959 (reverse complementary stop codon at positions 30 to 32) |
| 47 | Expression cassette with PRO0218 - CKX1 - zein and rbcS-deltaGA double terminator |
| 48 | AtCKX1 genomic sequence used in example 18 |
| 49 | Rice promoter PR00109 sequence |
| 50 | Expression cassette: Rice promoter PR00109 and CKX |
| 51 | Primer 2426 |
| 52 | Primer 2427 |
| 53 | Beta-expansion EXPB9 promoter sequence |

Example 2

Identification of Candidate Cytokinin Oxidase Encoding Genes from *Arabidopsis thaliana*

Six different genes were identified from *Arabidopsis thaliana* that bear sequence similarity to a cytokinin oxidase gene from maize (Morris et al., Biochem Biophys Res Comm 255:328-333, 1999; Houda-Herin et al. Plant J 17:615-626; WO 99/06571). These genes were found by screening 6-frame translations of nucleotide sequences from public genomic databases with the maize protein sequence, employing tblastn program. These sequences were designated as *Arabidopsis thaliana* cytokinin oxidase-like genes or AtCKX. They were arbitrarily numbered as AtCKX1 to AtCKX6. The below list summarizes the information on these genes. The predicted ORF borders and protein sequences are indicative, in order to illustrate by approximation the protein sequence divergence between the *Arabidopsis* and maize cytokinin oxidases, as well as amongst the different *Arabidopsis* cytokinin oxidases. The ORF borders and protein sequences shown should not be taken as conclusive evidence for the mode of action of these AtCKX genes. For DNA and protein sequence comparisons the program MegAlign from DNAstar was used. This program uses the Clustal method for alignments. For multiple alignments of protein and cDNA sequences the gap penalty and gap length penalty was set at 10 each. For pairwise alignments of proteins the parameters were as follows: Ktuple at 1; Gap penalty at 3; window at 5; diagonals saved at 5. For pairwise alignments of cDNA's the parameters were as follows: Ktuple at 2; Gap penalty at 5; window at 4; diagonals saved at 4. The similarity groups for protein alignments was: (M,I,L,V), (F,W,Y), (G,A), (S,T), (R,K,H), (E,D), (N,Q). The values that are indicated amongst the *Arabidopsis* cDNA and protein sequences represent the lowest and highest values found with all combinations.

A. Gene Name: AtCKX1 (*Arabidopsis thaliana* Cytokinin Oxidase-Like Protein 1, SEQ ID NO: 1)

Location in database (accession number, location on bac): AC002510, *Arabidopsis thaliana* chromosome II section 225 of 255 of the complete sequence. Sequence from clones T32G6.

ORF Predicted in the Database:

15517 . . . 16183, 16415 . . . 16542, 16631 . . . 16891, 16995 . . . 17257, 17344 . . . 17752

The AtCKX1 cDNA sequence is listed as SEQ ID NO: 25

Predicted Protein Sequence: SEQ ID NO: 2:

Homologies

% identity with *Z. mays* cDNA:
  31.5% (Dnastar/MegAlign—Clustal method)

% similarity with *Z. mays* protein:
  32.2% (Dnastar/MegAlign—Clustal method)

% identity with other *Arabidopsis* cDNA's (range):
  38.2% (AtCKX2)-54.1% (AtCKX6) (Dnastar/MegAlign—Clustal method)

% similarity with other *Arabidopsis* proteins (range):
  37.1% (AtCKX2)-58.1% (AtCKX6) (Dnastar/MegAlign—Clustal method)

B. Gene Name: AtCKX2 (*Arabidopsis thaliana* Cytokinin Oxidase-Like Protein 2, SEQ ID NO: 3)

Location in database (accession number, location on bac): AC005917, *Arabidopsis thaliana* chromosome II section 113 of 255 of the complete sequence. Sequence from clones F27F23, F3P11.

ORF Predicted in the Database:

complement, 40721 . . . 41012, 41054 . . . 41364, 41513 . . . 41770, 42535 . . . 42662, 43153 . . . 43711

Please note: The cDNA sequence identified by the inventor using the gene prediction program NetPlantGene (cbs.dtu.dk/services/NetGene2/) was different than the one annotated in the database. Based on the new cDNA sequence the ORF predicted in the database was revised:

complement, 40721 . . . 41012, 41095 . . . 41364, 41513 . . . 41770, 42535 . . . 42662, 43153 . . . 43711

The protein sequence encoded by this cDNA is listed as SEQ ID NO: 4. The cDNA of AtCKX2 was cloned by RT-PCR from total RNA of AtCKX2 transgenic plant tissue with the one-step RT-PCR kit (Qiagen, Hilden, Germany) and sequenced using an ABI PRISM Big Dye Terminator cycle sequencing reaction kit (Perkin Elmer Applied Biosystems Division). This confirmed that the cDNA sequence identified and predicted by the inventor was correct. The new AtCKX2 cDNA sequence is listed as SEQ ID NO: 26. An 84-bp fragment corresponding to nucleotides 1171 through 1254 of the AtCKX2 cDNA is listed as SEQ ID NO: 31. The corresponding peptide sequence of this 84-bp cDNA sequence is listed as SEQ ID NO: 32.

Homologies

% identity with *Z. mays* cDNA:
  38.4% (Dnastar/MegAlign—Clustal method)

% similarity with *Z. mays* protein:
  37.5% (Dnastar/MegAlign—Clustal method)

% identity with other *Arabidopsis* cDNA's (range):
  34.9% (AtCKX6)-64.5% (AtCKX4) (Dnastar/MegAlign—Clustal method)

% similarity with other *Arabidopsis* proteins (range):
  36.5% (AtCKX6)-66.1% (AtCKX4) (Dnastar/MegAlign—Clustal method)

C. Gene Name: AtCKX3 (*Arabidopsis thaliana* Cytokinin Oxidase-Like Protein 3, SEQ ID NO: 5)

Location in database (accession number, location on bac): AB024035, *Arabidopsis thaliana* genomic DNA, chromosome 5, P1 clone: MHM17, complete sequence.

No Prediction of the ORF in the Database.

The gene was identified by the inventor using several gene prediction programs including GRAIL (arthur.epm.ornl.gov/pub/xgrail), Genscan (http://CCR-081.mit.edu/GENSCAN html) and NetPlantGene (cbs.dtu.dk/services/NetGene2/):

complement, 29415 . . . 29718, 29813 . . . 30081, 30183 . . . 30443, 30529 . . . 30656, 32107 . . . 32716 The new AtCKX3 cDNA sequence identified by the inventor is listed as SEQ ID NO: 27.

Predicted Protein Sequence, Based on Own ORF Prediction: SEQ ID NO: 6

Homologies

% identity with *Z. mays* cDNA:
  38.7% (Dnastar/MegAlign—Clustal method)

% similarity with *Z. mays* protein:
  39.2% (Dnastar/MegAlign—Clustal method)

% identity with other *Arabidopsis* cDNA's (range):
  38.8% (AtCKX6)-51.0% (AtCKX2) (Dnastar/MegAlign—Clustal method)

% similarity with other *Arabidopsis* proteins (range):
  39.9% (AtCKX6)-46.7% (AtCKX2) (Dnastar/MegAlign—Clustal method)

D. Gene Name: AtCKX4 (*Arabidopsis thaliana* Cytokinin Oxidase-Like Protein 4, SEQ ID NO: 7)

Location in database (accession number, location on bac):

1) AL079344, *Arabidopsis thaliana* DNA chromosome 4, BAC clone T16L4 (ESSA project)

2) AL161575, *Arabidopsis thaliana* DNA chromosome 4, contig fragment No. 71.

ORF Predicted in the Database:

1) 76187 . . . 76814, 77189 . . . 77316, 77823 . . . 78080, 78318 . . . 78586, 78677 . . . 78968

2) 101002 . . . 101629, 102004 . . . 102131, 102638 . . . 102895, 103133 . . . 103401, 103492 . . . 103783

The AtCKX4 cDNA sequence is listed as SEQ ID NO: 28

Predicted Protein Sequence: SEQ ID NO: 8

Homologies

% identity with *Z. mays* cDNA:
  41.0% (Dnastar/MegAlign—Clustal method)

% similarity with *Z. mays* protein:
  41.0% (Dnastar/MegAlign—Clustal method)

% identity with other *Arabidopsis* cDNA's (range):

35.2% (AtCKX6)-64.5% (AtCKX2) (Dnastar/MegAlign—Clustal method)

% similarity with other *Arabidopsis* proteins (range):
35.1% (AtCKX6)-66.1% (AtCKX2) (Dnastar/MegAlign—Clustal method)

E. Gene Name: AtCKX5 (*Arabidopsis thaliana* Cytokinin Oxidase-Like Protein 5, SEQ ID NO: 9)

Location in database (accession number, location on bac): AC023754, F1B16, complete sequence, chromosome 1

No Prediction of the ORF in the Database.

The gene was identified by the inventors using several gene prediction programs including GRAIL (epm.ornl.gov/pub/xgrail), Genscan (CCR-081.mit.edu/GEN SCAN.html) and NetPlantGene (cbs.dtu.dk/services/NetGene2/).

43756 . . . 44347, 44435 . . . 44562, 44700 . . . 44966, 45493 . . . 45755, 46200 . . . 46560

The new AtCKX5 cDNA sequence identified and predicted by the inventor is listed as SEQ ID NO: 29. The predicted protein sequence for this cDNA is listed as SEQ ID NO: 10. A second potential ATG start codon is present 9 nucleotides more upstream in the genomic sequence. It is unclear which of these 2 start codons encodes the first amino acid of the protein. Therefore, a second potential AtCKX5 cDNA starting at this upstream start codon is also listed in this invention as SEQ ID NO: 34. The corresponding genomic sequence is listed as SEQ ID NO: 33 and the encoded protein as SEQ ID NO: 35.

Homologies

% identity with *Z. mays* cDNA:
39.1% (Dnastar/MegAlign—Clustal method)

% similarity with *Z. mays* protein:
36.6% (Dnastar/MegAlign—Clustal method)

% identity with other *Arabidopsis* cDNA's (range):
40.1% (AtCKX2)-44.0% (AtCKX3) (Dnastar/MegAlign—Clustal method)

% similarity with other *Arabidopsis* proteins (range):
41.6% (AtCKX4)-46.4% (AtCKX6) (Dnastar/MegAlign—Clustal method)

F. Gene Name: AtCKX6 (*Arabidopsis thaliana* Cytokinin Oxidase-Like Protein 6, SEQ ID NO: 11)

Location in database (accession number, location on bac): AL163818, *Arabidopsis thaliana* DNA chromosome 3, P1 clone MAA21 (ESSA project).

ORF Predicted in the Database:

46630 . . . 47215, 47343 . . . 47470, 47591 . . . 47806, 47899 . . . 48161, 48244 . . . 48565

The AtCKX6 cDNA sequence is listed as SEQ ID NO: 30

Predicted Protein Sequence: SEQ ID NO: 12

Homologies

% identity with *Z. mays* cDNA:
37.3% (Dnastar/MegAlign—Clustal method)

% similarity with *Z. mays* protein:
36.1% (Dnastar/MegAlign—Clustal method)

% identity with other *Arabidopsis* cDNA's (range):
34.9% (AtCKX2)-54.1% (AtCKX1) (Dnastar/MegAlign—Clustal method)

% similarity with other *Arabidopsis* proteins (range):
35.1% (AtCKX4)-58.1% (AtCKX1) (Dnastar/MegAlign—Clustal method)

Genes AtCKX3 and AtCKX5 were not annotated as putative cytokinin oxidases in the database and ORFs for these genes were not given. Furthermore, the ORF (and consequently the protein structures) predicted for AtCKX2 was different from our own prediction and our prediction was confirmed by sequencing the AtCKX2 cDNA.

Figure 1:
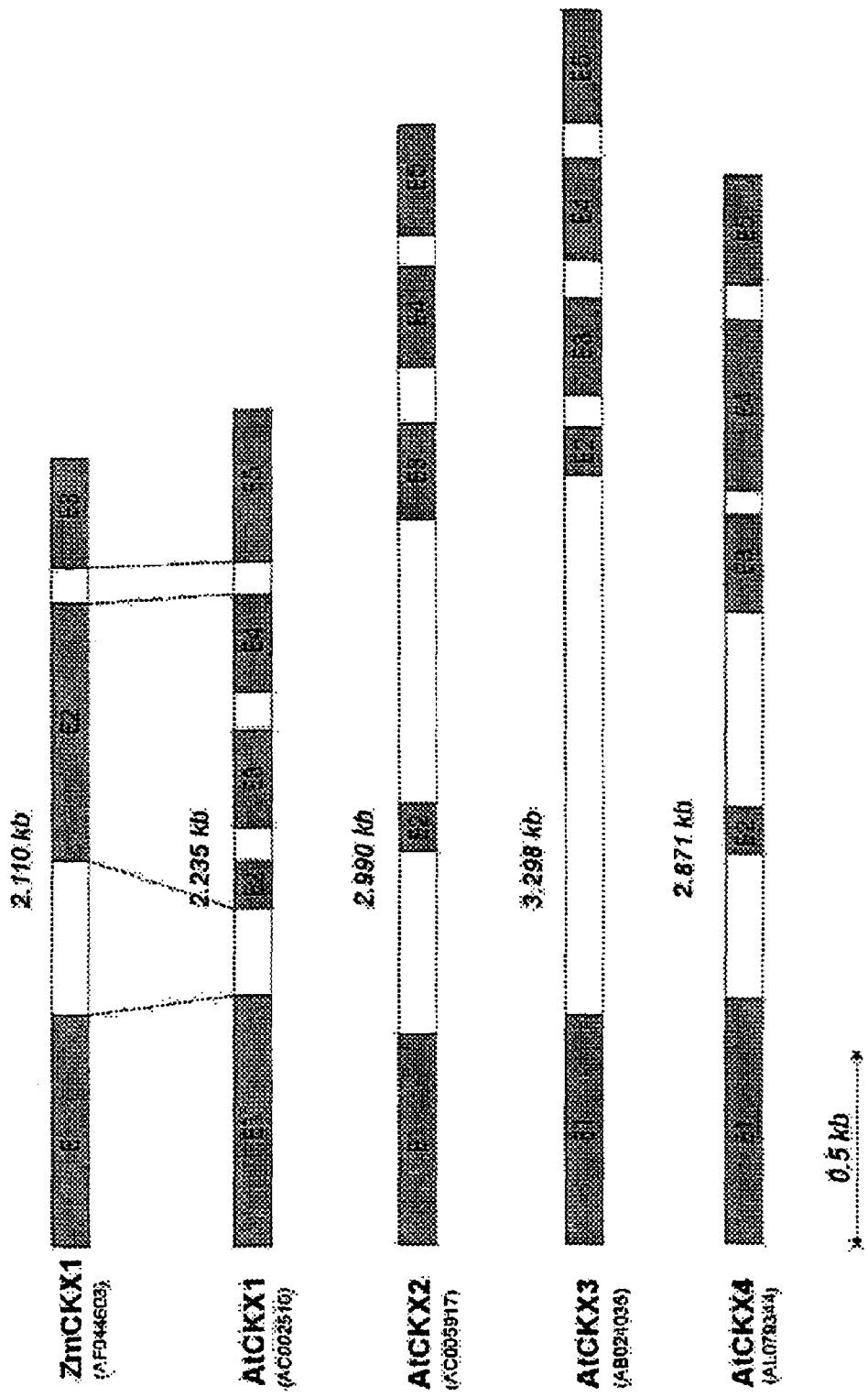
FIG. 1. Schematic representation of plant cytokinin oxidase genes.

A comparison of the gene structure of the *Arabidopsis* AtCKX genes 1 to 4 and the maize CKX gene is shown in FIG. 1.

The predicted proteins encoded by the *Arabidopsis* AtCKX genes show between 32% and 41% sequence similarity with the maize protein, while they show between 35% and 66% sequence similarity to each other. Because of this reduced sequence conservation, it is not clear a priori whether the *Arabidopsis* AtCKX genes encode proteins with cytokinin oxidase activity. An alignment of the *Arabidopsis* AtCKX predicted proteins 1 to 4 and the maize CKX gene is shown in FIG. 2.

Example 3

Transgenic Plants Overexpressing AtCKX1 Showed Increased Cytokinin Oxidase Activity and Altered Plant Morphology 1. Description of the Cloning Process The following primers were used to PCR amplify the AtCKX1 gene from *Arabidopsis thaliana*, accession Columbia (non-homologous sequences used for cloning are in lower case):

```
Sequence of 5' primer:
cggtcgacATGGGATTGACCTCATCCTTACG        (SEQ ID NO:13)

Sequence of 3' primer:
gcgtcgacTTATACAGTTCTAGGTTTCGGCAGTAT    (SEQ ID NO:14)
```

A 2235-bp PCR fragment, amplified by these primers, was inserted in the Sal I site of pUC19. The insert was sequenced and confirmed that the PCR amplification product did not contain any mutations. The SalI/SalI fragment of this vector was subcloned in the SalI site downstream of a modified CaMV 35S promoter (carrying three tetracycline operator sequences) in the binary vector pBinHyg-Tx (Gatz et al., 1992). The resulting construct was introduced into tobacco and *Arabidopsis thaliana* through *Agrobacterium*-mediated transformation, using standard transformation protocols.

2. Molecular Analysis of the Transgenic Lines

Several transgenic lines were identified that synthesize the AtCKX1 transcript at high levels (FIG. 3). Transgenic lines expressing AtCKX1 transcript also showed increased cytokinin oxidase activity as determined by a standard assay for cytokinin oxidase activity based on conversion of [2-$^3$H]iP to adenine as described (Motyka et al., 1996). This is exemplified for 2 tobacco and 2 *Arabidopsis* lines in Table 10. This result proves that the AtCKX1 gene encodes a protein with cytokinin oxidase activity.

TABLE 10

Cytokinin oxidase activity in AtCKX1 transgenic plant tissues

| Leaf sample | | Cytokinin oxidase activity |
|---|---|---|
| Plant species | Plant line | (nmol Ade/mg protein.h) |
| Arabidopsis | Col-0 wild-type | 0.009 |
| | CKX1-11 | 0.024 |
| | CKX1-22 | 0.026 |
| | CKX1-22 | 0.027 |
| Tobacco | SNN wild-type | 0.004 |
| | CKX1-SNN-8 | 0.016 |
| | CKX1-SNN-28 | 0.021 |

3. Phenotypic Description of the Transgenic Lines 3.1 In Tobacco:

The plants had a dwarfed phenotype with reduced apical dominance (FIGS. 7A, B and C) and increased root production (FIG. 8).

Five Categories of Phenotype:
1) strong—2 clones
2) intermediate—3 clones
3) weak—4 clones
4) tall plants (as WT) with large inflorescence—5 clones
5) similar to WT, 9 clones Height (see FIGS. 7B and C)
WT: between 100-150 cm
weak: approximately 75 cm
intermediate: appr. 40-45 cm (main stem app. 25 cm but overgrown by side branches.
strong: appr. 10 cm The transgenics AtCKX1-48 and AtCKX1-50 displayed a strong phenotype. Below are measurements for stem elongation as compared to WT plants:

| Line Days after germination | Wild-type Height (cm) | AtCKX1-48 Height (cm) | AtCKX1-50 Height (cm) |
|---|---|---|---|
| 47 | 9.5 ± 0.5 | 1.3 ± 0.3 | 1.2 ± 0.2 |
| 58 | 22.4 ± 2.3 | 2.2 ± 0.3 | 2.3 ± 0.3 |
| 68 | 35.3 ± 2.6 | 3.1 ± 0.5 | 2.6 ± 0.5 |
| 100 | 113.3 ± 9.8 | 7.1 ± 0.8 | 4.8 ± 0.9 |
| 117 | 138.6 ± 8.1 | 8.7 ± 0.7 | 6.6 ± 0.9 |
| 131 | 139.0 ± 9.3 | 9.3 ± 0.7 | 8.6 ± 1.0 |
| 152 | 136.6 ± 10.4 | 10.9 ± 1.1 | 10.0 ± 1.0 |
| 165 | | 11.8 ± 1.9 | 11.4 ± 1.4 |
| 181 | | 16.5 ± 1.7 | 14.9 ± 1.2 |
| 198 | | 19.5 ± 1.5 | 18.1 ± 1.3 |

Experimental:

Plants were grown in soil in a greenhouse. Data were collected from at least ten plants per line.

Leaves (see FIGS. 7D and E)

The shape of leaves of AtCKX1 transgenic expressors was lanceolate (longer and narrow): the width-to-length ratio of mature leaves was reduced from 1:2 in wild type plants to 1:3 in AtCKX1 transgenics (FIG. 7E). The number of leaves and leaf surface was reduced compared to WT (see FIG. 7D). A prominent difference was also noted for progression of leaf senescence. In WT tobacco, leaf senescence starts in the most basal leaves and leads to a uniform reduction of leaf pigment (FIG. 7E). By contrast, ageing leaves of strongly expressing AtCKX1 plants stayed green along the leaf veins and turned yellow in the intercostal regions, indicating altered leaf senescence. The texture of older leaves was more rigid.

Roots

In vitro grown plants highly expressing the gene were easily distinguishable from the WT by their ability to form more roots which are thicker (stronger) (FIG. 8 A), as well as by forming aerial roots along the stem.

The primary root was longer and the number of lateral and adventitious roots was higher as illustrated in FIG. 8C for AtCKX1-50 overexpressing seedlings (see also Example 9).

The dose-response curve of root growth inhibition by exogenous cytokinin showed that roots of transgenic seedlings are more cytokinin resistant than WT roots (FIG. 8D). The resistance of AtCKX1 transgenics to iPR was less marked than for AtCKX2, which is consistent with the smaller changes in iP-type cytokinins in the latter (see Table 10).

A large increase in root biomass was observed for adult plants grown in soil (see FIG. 8B for a plant grown in soil for 4 to 5 months) despite the fact that growth of the aerial plant parts was highly reduced.

Internode Distance intermediate phenotype: the $5^{th}$ internode below inflorescence is about 2.5 cm long and $9^{th}$ internode was about 0.5 cm long compared to 5 cm and 2 cm for the length of the $5^{th}$ and $9^{th}$ internode respectively, in WT plants.

strong phenotype: plant AtCKX1-50 The length of the $20^{th}$ internode from the bottom measured at day 131 after germination was 1.3±0.4 mm compared to 39.2±3.8 mm for WT Apical Dominance and Branching More side branches were formed indicating reduced apical dominance compared to WT plants during vegetative growth (see FIG. 9). The side branches overgrew the main stem, reaching a height of 40-45 cm for intermediate AtCKX1 expressors. Even secondary branches appeared. However, the buds were not completely released from apical dominance, i.e. lateral shoots did not really continue to develop. The reduced apical dominance might be due to reduced auxin production by the smaller shoot apical meristem (see Example 10).

Reproductive Development

The onset of flowering in AtCKX1 transgenics was delayed, the number of flowers and the seed yield per capsule was reduced. The size of flowers was not altered in transgenic plants and the weight of the individual seeds was comparable to the weight of seeds from wild type plants. Data for two representative AtCKX1 transgenics is summarized below:

A. Onset of Flowering

| Line | Wild-type | AtCKX1-48 | AtCKX1-50 |
|---|---|---|---|
| Flowering time (DAG) | 106.2 ± 3.3 | 193.3 ± 4.3 | 191.8 ± 3.8 |

Experimental:

Data collected for at least ten plants per line. The full elongation of the first flower was defined as onset of flowering. DAG=days after germination.

B. Number of Seed Capsules per Plant

| Line | Wild-type | AtCKX1-48 | AtCKX1-50 |
|---|---|---|---|
| Number of capsules | 83.33 ± 5.13 | 2.00 ± 1.00 | 2.60 ± 1.67 |

Experimental:

Number of seed capsules was determined at least from 5 different plants. Please note that these plants were grown under greenhouse conditions during winter time. This affects negatively the number of flowers that are formed, in particular in the transgenic clones. However, the general picture that they form a reduced number of flowers is correct. n.d., not determined C. Seed Yield/Capsule (mg)

| Line | Wild-type | AtCKX1-48 | AtCKX1-50 |
|---|---|---|---|
| Seed/capsule (mg) | 87.41 ± 28.75 | 23.83 ± 13.36 | 61.8 ± 40.66 |

Experimental:

Seed yield was determined for at least 12 seed capsules. The size of seed capsules was very variable, hence the large standard deviations. n.d., not determined D. Weight of 100 Seeds (mg)

| Line | Wild-type | AtCKX1-48 | AtCKX1-50 |
|---|---|---|---|
| Seeds weight (mg) | 9.73 ± 0.44 | 10.70 ± 1.60 | 9.54 ± 0.94 |

Experimental:

The seed biomass was determined as the weight of 100 seed from at least 5 different seed capsules. n.d., not determined 3.2 In *Arabidopsis*
- onset of germination was same as for WT
- the total root system was enlarged and the number of side roots and adventitious roots was enhanced (see FIG. 4A through D)
- the growth of aerial organs was reduced resulting in a dwarfed phenotype (see FIGS. 4E and F) and the leaf biomass was reduced. Leaf and flower formation is delayed.
- the life cycle was longer compared to WT and the seed yield was lower compared to WT The following morphometric data illustrate these phenotypes:

Root Development
A. Total Length of the Root System

| Line | Wild-type | AtCKX1-11 | AtCKX1-15 |
|---|---|---|---|
| Length (mm) | 32.5 | 76.5 | 68.4 |

B. Primary Root Length

| Line | Wild-type | AtCKX1-11 | AtCKX1-15 |
|---|---|---|---|
| Length (mm) | 32.3 ± 3.8 | 52.3 ± 4.8 | 39.9 ± 4.2 |

C. Lateral Roots (LR) Length

| Line | Wild-type | AtCKX1-11 | AtCKX1-15 |
|---|---|---|---|
| Length (mm) | 0.2 ± 0.4 | 15.6 ± 11.0 | 10.4 ± 7.6 |

D. Adventitious Roots Length

| Line | Wild-type | AtCKX1-11 | AtCKX1-15 |
|---|---|---|---|
| Length (mm) | 0.03 ± 0.18 | 8.6 ± 8.5 | 19.1 ± 11.0 |

E. Number of Lateral Roots (LR)

| Line | Wild-type | AtCKX1-11 | AtCKX1-15 |
|---|---|---|---|
| Number of LR | 0.3 ± 0.5 | 10.4 ± 5.4 | 2.6 ± 1.1 |

F. Number of Adventitious Roots (AR)

| Line | Wild-type | AtCKX1-11 | AtCKX1-15 |
|---|---|---|---|
| Number of AR | 0.03 ± 0.18 | 1.6 ± 1.1 | 2.6 ± 1.1 |

Experimental:

Measurements were carried out on plants 8 days after germination in vitro on MS medium. At least 17 plants per line were scored.

Shoot Development
A. Leaf Surface

| Line | Wild-type | AtCKX1-11-7 T3 homozygous plants | AtCKX1-11-12 T3 homozygous plants | AtCKX1-15-1 T3 homozygous plants |
|---|---|---|---|---|
| Leaf surface (cm$^2$) | 21.16 ± 1.73 | 2.28 ± 0.58 | 2.62 ± 0.28 | 1.66 ± 0.22 |

Experimental:

Leaf surface area of main rosette leaves formed after 30 days after germination was measured. 3 plants per clone were analyzed.

Reproductive Development

Onset of Flowering

| Line | Wild-type | AtCKX1-11 T3 heterozygous plants | AtCKX2-2 T2 heterozygous plants | AtCKX2-5 T2 heterozygous plants |
|---|---|---|---|---|
| Flowering time (DAG) | 43.6 ± 5.8 | 69.7 ± 9.4 | 51.2 ± 4.1 | 45.1 ± 6.9 |

Experimental:

Plants were grown under greenhouse condition. At least 13 plants per clone were analyzed. DAG=days after germination.

Conclusion:

The analysis of AtCKX1 transgenic *Arabidopsis* plants confirmed largely the results obtained from tobacco and indicates the general nature of the consequences of a reduced cytokinin content. The total root system was enlarged (the total root length was increased app. 110-140% in AtCKX1 transgenics), the shoot developed more slowly (retarded flowering) and the leaf biomass was reduced. The seed yield was lower in the transgenics as well.

Example 4

Transgenic Plants Overexpressing AtCKX2 Showed Increased Cytokinin Oxidase Activity and Altered Plant Morphology 1. Description of the Cloning Process The following primers were used to PCR amplify the AtCKX2 gene from *Arabidopsis thaliana*, accession Columbia (non-homologous sequences used for cloning are in lower case):

```
Sequence of 5' primer:
gcggtaccAGAGAGAGAAACATAAACAAATGGC   (SEQ ID NO:15)

Sequence of 3' primer:
gcggtaccCAATTTTACTTCCACCAAAATGC     (SEQ ID NO:16)
```

A 3104-bp PCR fragment, amplified by these primers, was inserted in the KpnI site of pUC19. The insert was sequenced to check that no differences to the published sequence were introduced by the PCR procedure. The KpnI/KpnI fragment of this vector was subcloned in the KpnI site downstream of a modified CaMV 35S promoter (carrying three tetracycline operator sequences) in the binary vector pBinHyg-Tx (Gatz et al., 1992). The resulting construct was introduced into tobacco and *Arabidopsis thaliana* through *Agrobacterium*-mediated transformation, using standard transformation protocols.

2. Molecular Analysis of the Transgenic Lines

Several transgenic lines were identified that synthesize the AtCKX2 transcript at high levels (FIG. 6). Transgenic lines expressing AtCKX2 transcript also showed increased cytokinin oxidase activity. This is exemplified for 2 tobacco and 3 *Arabidopsis* lines in Table 11. This result proves that the AtCKX2 gene encodes a protein with cytokinin oxidase activity.

TABLE 11

Cytokinin oxidase activity in AtCKX2 transgenic plant tissues

| Sample | | |
|---|---|---|
| Plant species and tissue | Plant line | Cytokinin oxidase activity (nmol Ade/mg protein.h) |
| *Arabidopsis* callus | Col-0 wild-type | 0.037 |
| | CKX2-15 | 0.351 |
| | CKX2-17 | 0.380 |
| | CKX2-55 | 0.265 |
| Tobacco leaves | SNN wild-type | 0.009 |
| | CKX2-SNN-18 | 0.091 |
| | CKX2-SNN-19 | 0.091 |

3. Phenotypic Description of the Transgenic Lines 3.1 In Tobacco (see FIG. 7 to 10):

Three Categories of Phenotype:

1) strong—15 clones (similar to intermediate phenotype of AtCKX1)

2) weak—6 clones 3) others—similar to WT plants, 7 clones

Aerial Plant Parts

The observations concerning plant height, internode distance, branching, leaf form and yellowing were similar as for AtCKX1 transgenics with some generally minor quantitative differences in that the dwarfing characteristics were more severe in AtCKX1 transgenics than in AtCKX2 transgenics (compare AtCKX1 plants with AtCKX2 plants in FIGS. 7A and B). This is illustrated below for stem elongation and internode distance measurements of clones with a strong phenotype AtCKX2-38 and AtCKX2-40:

Stem Elongation

| Line Days after germination | Wild-type Height (cm) | AtCKX2-38 Height (cm) | AtCKX2-40 Height (cm) |
|---|---|---|---|
| 47 | 9.5 ± 0.5 | 2.4 ± 0.1 | 2.6 ± 0.2 |
| 58 | 22.4 ± 2.3 | 5.5 ± 0.7 | 5.3 ± 0.5 |
| 68 | 35.3 ± 2.6 | 7.1 ± 0.8 | 7.0 ± 0.7 |
| 100 | 113.3 ± 9.8 | 15.5 ± 2.5 | 20.3 ± 6.4 |
| 117 | 138.6 ± 8.1 | 19.8 ± 3.8 | 29.5 ± 6.0 |
| 131 | 139.0 ± 9.3 | 26.5 ± 7.0 | 33.4 ± 5.8 |
| 152 | 136.6 ± 10.4 | 33.7 ± 6.3 | 33.9 ± 6.4 |
| 165 | | 36.2 ± 4.3 | |

Experimental:

Plants were grown in soil in a green house. Data were collected from at least ten plants per line.

Internode Distance

| Line | Wild-type | AtCKX2-38 |
|---|---|---|
| Internode distance (mm) | 39.2 ± 3.8 | 7.2 ± 1.6 |

Experimental:

The length of the 20$^{th}$ internode from the bottom was measured at day 131 after germination.

Roots

In vitro grown plants highly expressing the gene were easily distinguishable from WT plants by their ability to form more roots which are thicker (stronger) as well as by forming aerial roots along the stem.

The primary root was longer and the number of lateral and adventitious roots was higher as illustrated in FIG. 8C for AtCKX2-38 overexpressing seedlings (see also Example 9).

The dose-response curve of root growth inhibition by exogenous cytokinin showed that roots of transgenic seedlings were more cytokinin resistant than WT roots (FIG. 8D). The resistance of AtCKX1-28 transgenics to iPR was less marked than for AtCKX2-38, which is consistent with the smaller changes in iP-type cytokinins in the latter (see Table 10).

An increase in fresh and dry weight of the root biomass of T0 lines of AtCKX2 transgenic plants compared to WT was observed for plant grown in soil, as illustrated in the following table:

| Line | Wild-type | AtCKX2 (T0) |
|---|---|---|
| Fresh weight (g) | 45.2 ± 15.4 | 77.1 ± 21.3 |
| Dry weight (g) | 6.3 ± 1.9 | 8.6 ± 2.2 |

Experimental:

Six WT plants and six independent T0 lines of 35S::AtCKX2 clone were grown on soil. After flowering the root system was washed with water, the soil was removed as far as possible and the fresh weight and dry weight was measured.

| Line | Wild-type | AtCKX2-38 | AtCKX2-40 |
|---|---|---|---|
| Fresh weight ROOT (g) | 19.76 ± 6.79 | 33.38 ± 7.76 | 50.04 ± 15.59 |
| Dry weight ROOT (g) | 2.36 ± 0.43 | 2.61 ± 0.39 | 3.52 ± 1.06 |
| Fresh weight SHOOT (g) | 159.8 ± 44.53 | 33.66 ± 2.67 | 48.84 ± 11.83 |
| Fresh weight SHOOT/ROOT ratio | 8.24 ± 0.63 | 1.04 ± 0.18 | 1.08 ± 0.51 |

Experimental:

Soil grown plants were transferred 60 days after germination to a hydroponic system (Hoagland's solution) and grown for additional 60 days. The hydroponic solution was aerated continuously and replaced by fresh solution every third day. In summary, transgenic plants grown in hydroponic solution formed approximately 65-150% more root biomass (fresh weight) than wild type plants. The increase in dry weight was 10-50%. This difference is possibly in part due to the larger cell volume of the transgenics. This reduces the relative portion of cell walls, which forms the bulk of dry matter material. The shoot biomass was reduced to 20%-70% of wild type shoots. The difference in fresh weight leads to a shift in the shoot/root ratio, which was approximately 8 in wild type but approximately 1 in the transgenic clones.

Conclusion:

An increase in root growth and biomass was observed for AtCKX2 transgenic seedlings and adult plants grown under different conditions compared to WT controls despite the fact that growth of the aerial plant parts is reduced. Quantitative differences were observed between different transgenic plants: higher increases in root biomass were observed for the strongest expressing clones.

Reproductive Development

The onset of flowering in AtCKX2 transgenics was delayed, the number of flowers and the seed yield per capsule was reduced. These effects were very similar to those observed in the AtCKX1 transgenic plants but they were less prominent in the AtCKX2 transgenics, as indicated in the tables below. The size of flowers was not altered in transgenic plants and the weight of the individual seeds was comparable to the weight of seeds from wild type plants.

A. Onset of Flowering

| Line | Wild-type | AtCKX1-48 | AtCKX1-50 | AtCKX2-38 | AtCKX2-40 |
|---|---|---|---|---|---|
| Flowering time (DAG) | 106.2 ± 3.3 | 193.3 ± 4.3 | 191.8 ± 3.8 | 140.6 ± 6.5 | 121.9 ± 9.8 |

An increase in fresh and dry weight of the root biomass was also observed for F1 progeny of AtCKX2 transgenics grown in hydroponics as compared to WT, as illustrated in the following table:

Experimental:

Data collected for at least ten plants per line. The full elongation of the first flower was defined as onset of flowering. DAG=days after germination.

B. Number of Seed Capsules per Plant

| Line | Wild-type | AtCKX1-48 | AtCKX1-50 | AtCKX2-38 | AtCKX2-40 |
|---|---|---|---|---|---|
| Number of capsules | 83.33 ± 5.13 | 2.00 ± 1.00 | 2.60 ± 1.67 | 4.30 ± 2.58 | n.d. |

Experimental:

Number of seed capsules was determined at least from 5 different plants. Please note that these plants were grown under green house conditions during winter time. This affects negatively the number of flowers that are formed, in particular in the transgenic clones. However, the general picture that they form a reduced number of flowers is correct. n.d., not determined C. Seed Yield/Capsule (mg)

| Line | Wild-type | AtCKX1-48 | AtCKX1-50 | AtCKX2-38 | AtCKX2-40 |
|---|---|---|---|---|---|
| Seed/capsule (mg) | 87.41 ± 28.75 | 23.83 ± 13.36 | 61.8 ± 40.66 | 46.98 ± 29.30 | n.d. |

Experimental:

Seed yield was determined for at least 12 seed capsules. The size of seed capsules was very variable, hence the large standard deviations. n.d., not determined.

D. Weight of 100 Seeds (mg)

| Line | Wild-type | AtCKX1-48 | AtCKX1-50 | AtCKX2-38 | AtCKX2-40 |
|---|---|---|---|---|---|
| Seeds weight (mg) | 9.73 ± 0.44 | 10.70 ± 1.60 | 9.54 ± 0.94 | 10.16 ± 0.47 | n.d. |

Experimental:

The seed biomass was determined as the weight of 100 seed from at least 5 different seed capsules. nd., not determined 3.2 In *Arabidopsis:*

The following morphometric data were obtained for AtCKX2 transgenics:

Root Development

A. Total Length of the Root System

| Line | Wild-type | AtCKX2-2 | AtCKX2-5 |
|---|---|---|---|
| Length (mm) | 32.5 | 50.6 | 48.5 |

B. Primary Root Length

| Line | Wild-type | AtCKX2-2 | AtCKX2-5 |
|---|---|---|---|
| Length (mm) | 32.3 ± 3.8 | 30.7 ± 4.8 | 31.6 ± 6.8 |

C. Lateral Roots Length

| Line | Wild-type | AtCKX2-2 | AtCKX2-5 |
|---|---|---|---|
| Length (mm) | 0.2 ± 0.4 | 5.5 ± 9.0 | 1.9 ± 2.5 |

D. Adventitious Roots Length

| Line | Wild-type | AtCKX2-2 | AtCKX2-5 |
|---|---|---|---|
| Length (mm) | 0.03 ± 0.18 | 14.4 ± 10.2 | 14.9 ± 9.1 |

E. Number of Lateral Roots (LR)

| Line | Wild-type | AtCKX2-2 | AtCKX2-5 |
|---|---|---|---|
| Number of LR | 0.3 ± 0.5 | 2.9 ± 2.3 | 1.9 ± 1.0 |

F. Number of Adventitious Roots (AR)

| Line | Wild-type | AtCKX2-2 | AtCKX2-5 |
|---|---|---|---|
| Number of AR | 0.03 ± 0.18 | 1.8 ± 0.9 | 1.8 ± 1.0 |

Experimental:

Measurements were carried out on plants 8 d.a.g. in vitro on MS medium. At least 17 plants per line were scored.

Shoot Development
  Leaf Surface

| Line | Wild-type | AtCKX2-2 T2 heterozygous plants | AtCKX2-5 T2 heterozygous plants | AtCKX2-9 T2 heterozygous plants |
|---|---|---|---|---|
| Leaf surface (cm²) | 21.16 ± 1.73 | 8.20 ± 2.35 | 8.22 ± 0.55 | 7.72 ± 0.85 |

Experimental:
Leaf surface area of main rosette leaves formed after 30 days after germination was measured. 3 plants per clone were analyzed.

Reproductive Development
  Onset of Flowering

| Line | Wild-type | AtCKX1-11 T3 heterozygous plants | AtCKX2-2 T2 heterozygous plants | AtCKX2-5 T2 heterozygous plants |
|---|---|---|---|---|
| Flowering time (DAG) | 43.6 ± 5.8 | 69.7 ± 9.4 | 51.2 ± 4.1 | 45.1 ± 6.9 |

Experimental:
Plants were grown under greenhouse condition. At least 13 plants per clone were analyzed. DAG=days after germination.

Conclusion:
Arabidopsis AtCKX2 transgenics had reduced leaf biomass and a dwarfing phenotype similar to AtCKX1 transgenics (compare FIG. 5 with FIG. 4F). The total root system was also enlarged in AtCKX2 transgenic Arabidopsis. The total root length is increased approximately 50% in AtCKX2 transgenics. The AtCKX1 transgenics have longer primary roots, more side roots and form more adventitious roots. AtCKX2 transgenics lack the enhanced growth of the primary root but form more side roots and lateral roots than WT.

Summary:
The phenotypes observed for AtCKX2 transgenics were very similar but not identical to the AtCKX1 transgenics, which in turn were very similar but not identical to the results obtained for the tobacco transgenics. This confirms the general nature of the consequences of a reduced cytokinin content in these two plant species and therefore, similar phenotypes can be expected in other plant species as well. The main difference between tobacco and Arabidopsis is the lack of enhanced primary root growth in AtCKX2 overexpressing plants.

Example 5

Transgenic Plants Overexpressing AtCKX3 Showed Increased Cytokinin Oxidase Activity and Altered Plant Morphology 1. Description of the Cloning Process
The following primers were used to PCR amplify the AtCKX3 gene from Arabidopsis thaliana, accession Columbia (non-homologous sequences used for cloning are in lower case):

Sequence of 5' primer:
gcggtaccTTCATTGATAAGAATCAAGCTATTCA (SEQ ID NO:17)

Sequence of 3' primer:
gcggtaccCAAAGTGGTGAGAACGACTAACA (SEQ ID NO:18)

A 3397-bp PCR fragment, produced by this PCR amplification, was inserted in the KpnI site of pBluescript. The insert was sequenced to confirm that the PCR product has no sequence changes as compared to the gene. The KpnI/KpnI fragment of this vector was subcloned in the KpnI site downstream of a modified CaMV 35S promoter (carrying three tetracycline operator sequences) in the binary vector pBin-Hyg-Tx (Gatz et al., 1992). The resulting construct was introduced into tobacco and Arabidopsis thaliana through Agrobacterium-mediated transformation, using standard transformation protocols.

2. Molecular Analysis of the Transgenic Lines
Several transgenic tobacco lines were identified that synthesize the AtCKX3 transcript at high levels (FIG. 11A.). Transgenic tobacco lines expressing AtCKX3 transcript also showed increased cytokinin oxidase activity. This is exemplified for three plants in Table 12. This proves that the AtCKX3 gene encodes a protein with cytokinin oxidase activity.

TABLE 12

Cytokinin oxidase activity in AtCKX4 transgenic plant tissues

| Sample | | |
|---|---|---|
| Plant species and tissue | Plant line | Cytokinin oxidase activity (nmol Ade/mg protein.h) |
| tobacco leaves | SNN wild-type | 0.011 |
| | CKX3-SNN-3 | 0.049 |
| | CKX3-SNN-6 | 0.053 |
| | CKX3-SNN-21 | 0.05 |

3. Plant Phenotypic Analysis
The phenotypes generated by overexpression of the AtCKX3 gene in tobacco and Arabidopsis were basically similar as those of AtCKX1 and AtCKX2 expressing plants, i.e. enhanced rooting and dwarfing. However, overexpression of the AtCKX3 gene in tobacco resulted in a stronger phenotype compared to AtCKX2. In this sense AtCKX3 overexpression was more similar to AtCKX1 overexpression.

Example 6

Transgenic Plants Overexpressing AtCKX4 Showed Increased Cytokinin Oxidase Activity and Altered Plant Morphology 1. Description of the Cloning Process The following primers were used to PCR amplify the AtCKX4 gene from *Arabidopsis thaliana*, accession Columbia (non-homologous sequences used for cloning are in lower case):

```
Sequence of 5' primer:
gcggtaccCCCATTAACCTACCCGTTTG        (SEQ ID NO:19)

Sequence of 3' primer:
gcggtaccAGACGATGAACGTACTTGTCTGTA    (SEQ ID NO:20)
```

A 2890-bp PCR fragment, produced by this PCR amplification, was inserted in the KpnI site of pBluescript. The insert was sequenced to confirm that the PCR product has no sequence changes as compared to the gene. The KpnI/KpnI fragment of this vector was subcloned in the KpnI site downstream of a modified CaMV 35S promoter (carrying three tetracycline operator sequences) in the binary vector pBin-Hyg-Tx (Gatz et al., 1992). The resulting construct was introduced into tobacco and *Arabidopsis thaliana* through *Agrobacterium*-mediated transformation, using standard transformation protocols.

2. Molecular Analysis of the Transgenic Lines

Several transgenic tobacco lines synthesized the AtCKX4 transcript at high levels (FIG. 11B.). Transgenic lines expressing AtCKX4 transcript also showed increased cytokinin oxidase activity. This is exemplified for 3 *Arabidopsis* and 3 tobacco lines in Table 13. This result proves that the AtCKX4 gene encodes a protein with cytokinin oxidase activity.

TABLE 13

Cytokinin oxidase activity in AtCKX4 transgenic plant tissues

| Sample | | |
|---|---|---|
| Plant species and tissue | Plant line | Cytokinin oxidase activity (nmol Ade/mg protein.h) |
| *Arabidopsis* callus | Col-0 wild-type | 0.037 |
|  | CKX4-37 | 0.244 |
|  | CKX4-40 | 0.258 |
|  | CKX4-41 | 0.320 |
| tobacco leaves | SNN wild-type | 0.011 |
|  | CKX4-SNN-3 | 0.089 |
|  | CKX4-SNN-18 | 0.085 |
|  | CKX4-SNN-27 | 0.096 |

Overall, the data showed that the apparent $K_m$ values for the four cytokinin oxidases were in the range of 0.2 to 9.5 µM with iP as substrate, which further demonstrates that the proteins encoded by AtCKX1 through 4 are indeed cytokinin oxidase enzymes as disclosed herein.

3. Plant Phenotypic Analysis

The phenotypes generated by overexpression of the AtCKX4 gene in tobacco and *Arabidopsis* were basically similar as those of AtCKX1 and AtCKX2 expressing plants, i.e. enhanced rooting, reduced apical dominance, dwarfing and yellowing of intercostal regions in older leaves of tobacco. An additional phenotype in tobacco was lanceolate leaves (altered length-to-width ratio).

General Observations of AtCKX Overexpressing Tobacco Plants

Overall, the phenotypic analysis demonstrated that AtCKX gene overexpression caused drastic developmental alterations in the plant shoot and root system in tobacco, including enhanced development of the root system and dwarfing of the aerial plant part. Other effects such as altered leaf senescence, formation of adventitious root on stems, and others were also observed as disclosed herein. The alterations were very similar, but not identical, for the different genes. In tobacco, AtCKX1 and AtCKX3 overexpressors were alike as were AtCKX2 and AtCKX4. Generally, the two former showed higher expression of the traits, particularly in the shoot. Therefore, a particular cytokinin oxidase gene may be preferred for achieving the phenotypes that are described in the embodiments of this invention.

Example 7

Cloning of the AtCKX5 Gene

The following primers were used to PCR amplify the AtCKX5 gene from *Arabidopsis thaliana*, accession Columbia (non-homologous sequences used for cloning are in lower case):

```
Sequence of 5' primer:
ggggtaccTTGATGAATCGTGAAATGAC         (SEQ ID NO:21)

Sequence of 3' primer:
ggggtaccCTTTCCTCTTGGTTTTGTCCTGT      (SEQ ID NO:22)
```

The sequence of the 5' primer includes the two potential start codons of the AtCKX5 protein, the most 5' start codon is underlined and a second ATG is indicated in italics.

A 2843-bp PCR fragment, produced by this PCR amplification, was inserted as a blunt-end product in pCR-Blunt II-TOPO cloning vector (Invitrogen).

Example 8

Cloning of the AtCKX6 Gene

The following primers were used to PCR amplify the AtCKX6 gene from *Arabidopsis thaliana*, accession Columbia (non-homologous sequences used for cloning are in lower case):

```
Sequence of 5' primer:
gctctagaTCAGGAAAAGAACCATGCTTATAG     (SEQ ID NO:23)

Sequence of 3' primer:
gctctagaTCATGAGTATGAGACTGCCTTTTG     (SEQ ID NO:24)
```

A 1949-bp PCR fragment, produced by this PCR amplification, was inserted as a blunt-end product in pCR-Blunt II-TOPO cloning vector (Invitrogen).

Example 9

Tobacco Seedling Growth Test Demonstrated Early Vigor of AtCKX Transgenics

Seeds of AtCKX1-50 and AtCKX2-38 overexpressing transgenics and WT tobacco were sown in vitro on MS medium, brought to culture room 4 days after cold treatment and germinated after 6 days. Observations on seedling growth were made 10 days after germination (see also FIG. 8C) and are summarized below. At least 20 individuals were scored per clone. Similar data have been obtained in two other experiments.

A. Total Length of the Root System

| Line | Wild-type | AtCKX1-50 | AtCKX2-38 |
| --- | --- | --- | --- |
| Length (mm) | 61.1 | 122.0 | 106.5 |

B. Primary Root Length

| Line | Wild-type | AtCKX1-50 | AtCKX2-38 |
| --- | --- | --- | --- |
| Length (mm) | 32.3 ± 2.6 | 50.8 ± 4.5 | 52.4 ± 4.8 |

C. Lateral Roots Length

| Line | Wild-type | AtCKX1-50 | AtCKX2-38 |
| --- | --- | --- | --- |
| Length (mm) | 9.8 ± 5.5 | 18.0 ± 8.1 | 13.0 ± 6.0 |

D. Adventitious Roots Length

| Line | Wild-type | AtCKX1-50 | AtCKX2-38 |
| --- | --- | --- | --- |
| Length (mm) | 19.0 ± 5.0 | 53.0 ± 12.0 | 42.0 ± 9.8 |

E. Number of Lateral Roots (LR)

| Line | Wild-type | AtCKX1-50 | AtCKX2-38 |
| --- | --- | --- | --- |
| Number of LR | 1.9 ± 0.9 | 6.5 ± 2.2 | 5.6 ± 2.0 |

F. Number of Adventitious Roots (AR)

| Line | Wild-type | AtCKX1-50 | AtCKX2-38 |
| --- | --- | --- | --- |
| Number of AR | 2.2 ± 0.6 | 3.5 ± 0.9 | 3.6 ± 1.3 |

AtCKX1 and AtCKX2 Plants, General Observations:

Seedlings of AtCKX1 and AtCKX2 overexpressing tobacco plants had 60% more adventitious roots and three times more lateral roots than untransformed control plants 10 days after germination. The length of the primary root was increased by about 70%. This—together with more and longer side roots and secondary roots—resulted in a 70-100% increase in total root length. These results showed that overexpression of cytokinin oxidase enhances the growth and development of both the main root and the adventitious roots, resulting in early vigor.

Example 10

Histological Analysis of Altered Plant Morphology in AtCKX1 Overexpressing Tobacco Plants Microscopic analysis of different tissues revealed that the morphological changes in AtCKX transgenics are reflected by distinct changes in cell number and rate of cell formation (see FIG. 10). The shoot apical meristem (SAM) of AtCKX1 transgenics was smaller than in wild type and fewer cells occupy the space between the central zone and the peripheral zone of lateral organ formation, but the cells were of the same size (FIG. 10A). The reduced cell number and size of the SAM as a consequence of a reduced cytokinin content indicates that cytokinins have a role in the control of SAM proliferation. No obvious changes in the differentiation pattern occurred, suggesting that the spatial organization of the differentiation zones in the SAM is largely independent from cell number and from the local cytokinin concentration. The overall tissue pattern of leaves in cytokinin oxidase overexpressors was unchanged. However, the size of the phloem and xylem was significantly reduced (FIG. 10B). By contrast, the average cell size of leaf parenchyma and epidermal cells was increased four- to fivefold (FIG. 10C, D). New cells of AtCKX1 transgenics are formed at 3-4% of the rate of wild type leaves and final leaf cell number was estimated to be in the range of 5-6% of wild type. This indicates an absolute requirement for cytokinins in leaves to maintain the cell division cycle. Neither cell size nor cell form of floral organs was altered and seed yield per capsule was similar in wild type and AtCKX transgenic plants. The cell population of root meristems of AtCKX1 transgenic plants was enlarged approximately 4-fold and the cell numbers in both the central and lateral columnella were enhanced (FIGS. 10E, F). The final root diameter was increased by 60% due to an increased diameter of all types of root cells. The radial root patterns was identical in wild type and transgenics, with the exception that frequently a fourth layer of cortex cells was noted in transgenic roots (FIGS. 10 G). The increased cell number and the slightly reduced cell length indicates that the enhanced root growth is due to an increased number of cycling cells rather than increased cell growth. In the presence of lowered cytokinin content, root meristem cells must undergo additional rounds of mitosis before they leave the meristem and start to elongate. The exit from the meristem is therefore regulated by a mechanism that is sensitive to cytokinins. Apparently, cytokinins have a negative regulatory role in the root meristem and wild type cytokinin concentrations are inhibitory to the development of a maximal root system. Therefore, reducing the level of active cytokinins by overexpressing cytokinin oxidases stimulates root development, which results in an increase in the size of the root with more lateral and adventitious roots as compared to WT plants.

Example 11

AtCKX1 and AtCKX2-Overexpressing Tobacco Plants had a Reduced Cytokinin Content Among the 16 different cytokinin metabolites that were measured, the greatest change occurred in the iP-type cytokinins in AtCKX2 overexpressers (Table 11): the overall decrease in the content of iP-type cytokinins is more pronounced in AtCKX2 expressing plants than in AtCKX1 transgenics. AtCKX1 transgenics showed a stronger phenotype in the shoot. It is not known which cytokinin metabolite is relevant for the different traits that were analysed. It may be that different cytokinin forms play different roles in the various development processes. Smaller alterations were noted for Z-type cytokinins, which could be due to a different accessibility of the substrate or a lower substrate specificity of the protein. The total content of iP and Z metabolites in individual transgenic clones was between 31% and 63% of wild type. The cytokinin reserve pool of O-glucosides was also lowered in the transgenics (Table 14). The concentration of N-glucosides and DHZ-type cytokinins was very low and was not or only marginally, altered in transgenic seedlings (data not shown).

Table 14: Cytokinin content of AtCKX transgenic plants. Cytokinin extraction, immunopurification, HPLC separation and quantification by ELISA methods was carried out as described by Faiss et al., 1997. Three independently pooled samples of approximately 100 two week old seedlings (2.5 g per sample) were analysed for each clone. Concentrations are in pmol×g fresh weight$^{-1}$. Abbreviations: iP, $N^6$-($\Delta^2$isopentenyl)adenine; iPR, $N^6$-($\Delta^2$ isopentenyl)adenine riboside; iPRP, $N^6$-($\Delta^2$isopentenyl)adenine riboside 5'-monophosphate; Z, trans-zeatin; ZR, zeatin riboside; ZRP, zeatin riboside 5'-monophosphate; ZOG, zeatin O-glucoside; ZROG, zeatin riboside O-glucoside.

AtCKX2 transgenic tobacco plant and a WT tobacco. The transgenic plant used in this experiment was AtCKX2-38, which displayed a strong phenotype characterized by enhanced root growth and reduced development of the aerial plant parts. As described in Example 3 through 6, these were two important phenotypes that resulted from cytokinin oxidase overexpression in tobacco and *arabidopsis*.

Plants were about 15 cm tall when grafted and the graft junction was about 10 cm above the soil. FIG. 12 shows plants 15 weeks after grafting. The main results were that: (i) the aerial phenotype of a WT scion grafted on a transgenic rootstock was similar to the WT control graft (=WT scion on WT rootstock). Importantly, this showed that overexpression of the AtCKX2 transgene in the rootstock did not induce dwarfing of the non-transgenic aerial parts of the plant (see FIG. 12A). Improved root growth of the transgenic rootstock was maintained, indicating that improved root growth of AtCKX transgenics is autonomous and does not depend on an AtCKX transgenic shoot (FIG. 12C). Interestingly, the WT scions grafted on the transgenic rootstocks looked healthier and were better developed. Notably, senescence of the basal leaves was retarded in these plants (see FIG. 12A); (ii) the transgenic scion grafted on the WT rootstock looked similar to the aerial part of the transgenic plant from which it was derived, i.e. the shoot dwarfing phenotype is also autonomous and not dependent on the improved root growth (see FIG. 12B).

In addition to the above-mentioned better appearance of WT shoots grafted on a transgenic rootstock, the formation of adventitious roots on the basal part of WT shoots was noted (FIG. 12D, right plant). Formation of adventitious roots also occurred on the stem of AtCKX transgenics but not on stems of WT control grafts (FIG. 12D, left plant) and therefore seems to be a non-autonomous trait.

In summary, it is disclosed in this invention that enhanced root formation and dwarfing of the shoot in AtCKX overex-

| Line | | AtCKX1-2 | | AtCKX1-28 | | AtCKX2-38 | | AtCKX2-40 | |
|---|---|---|---|---|---|---|---|---|---|
| Cytokinin meta-bolite | WT Concentration | Concentration | % of WT | Concentration | % of WT | Concentration | % of WT | Concentration | % of WT |
| iP | 5.90 ± 1.80 | 4.76 ± 0.82 | 81 | 4.94 ± 2.62 | 84 | 1.82 ± 0.44 | 31 | 2.85 ± 0.62 | 48 |
| iPR | 2.36 ± 0.74 | 1.53 ± 0.14 | 65 | 0.75 ± 0.27 | 32 | 0.55 ± 0.39 | 23 | 0.89 ± 0.07 | 38 |
| iPRP | 3.32 ± 0.73 | 0.87 ± 0.26 | 26 | 1.12 ± 0.13 | 34 | 0.80 ± 0.48 | 24 | 1.68 ± 0.45 | 51 |
| Z | 0.24 ± 0.06 | 0.17 ± 0.02 | 71 | 0.22 ± 0.03 | 92 | 0.21 ± 0.06 | 88 | 0.22 ± 0.02 | 92 |
| ZR | 0.60 ± 0.13 | 0.32 ± 0.12 | 53 | 0.34 ± 0.03 | 57 | 0.34 ± 0.15 | 57 | 0.32 ± 0.05 | 53 |
| ZRP | 0.39 ± 0.17 | 0.42 ± 0.11 | 107 | 0.28 ± 0.15 | 72 | 0.06 ± 0.01 | 15 | 0.17 ± 0.06 | 44 |
| ZOG | 0.46 ± 0.20 | 0.32 ± 0.09 | 70 | 0.26 ± 0.13 | 57 | 0.20 ± 0.07 | 43 | 0.12 ± 0.02 | 26 |
| ZROG | 0.48 ± 0.17 | 0.30 ± 0.06 | 63 | 0.47 ± 0.02 | 98 | 0.23 ± 0.05 | 48 | 0.30 ± 0.13 | 63 |
| Total | 13.75 | 8.69 | 63 | 8.38 | 61 | 4.21 | 31 | 6.55 | 48 |

Example 12

Grafting Experiments Showed that Dwarfing and Enhanced Root Development Due to AtCKX Overexpression is Confined to Transgenic Tissues To investigate which phenotypic effects of cytokinin oxidase overexpression are restricted to expressing tissues, i.e. are cell- or organ-autonomous traits, grafting experiments were performed. Reciprocal grafts were made between an pressing tobacco are autonomous traits and can be uncoupled by grafting procedures. Surprisingly, grafting of a WT scion on an AtCKX transgenic rootstock resulted in more vigorously growing plants and retardation of leaf senescence.

As an alternative to grafting, tissue-specific promoters could be used for uncoupling the autonomous phenotypic effects of cytokinin overexpression. Therefore, it is disclosed in this invention that cytokinin oxidase overexpression in a tissue specific manner can be used to alter the morphology of a plant such as the shoot or root system.

Example 13

Expression of an AtCKX Gene Under a Root-Specific Promoter in Transgenic Plants Leads to Increased Root Production An AtCKX gene (see example 4) is cloned under control of the root clavata homolog promoter of *Arabidopsis* (SEQ ID NO: 36), which is a promoter that drives root-specific expression. Other root-specific promoters may also be used for the purpose of this invention. See Table 7 for exemplary root-specific promoters.

Transgenic plants expressing the AtCKX gene specifically in the roots show increased root production without negatively affecting growth and development of the aerial parts of the plant. Positive effects on leaf senescence and growth of aerial plant parts are observed.

Example 14

Suppression of an AtCKX Gene Under a Senescence-Induced Promoter in Transgenic Plants Leads to Delayed Leaf Senescence and Enhanced Seed Yield A chimeric gene construct derived from an AtCKX gene and designed to suppress expression of endogenous cytokinin oxidase gene(s) is cloned under control of a senescence-induced promoter. For example, promoters derived from senescence-associated genes (SAG) such as the SAG12 promoter can be used (Quirino et al., 2000). Transgenic plants suppressing endogenous cytokinin oxidase gene(s) specifically in senescing leaves show delayed leaf senescence and higher seed yield without negatively affecting the morphology and growth and development of the plant.

promoter as described supra. Transgenic plants, in particular those expressing the AtCKX1 and AtCKX3 genes, developed seeds with increased size which was almost entirely due to an enlarged embryo. Details of the seed, embryo and early postembryonic phenotypes are shown in FIGS. 13A through 13E. Table 16 shows seed weight of wild type and two independent clones for each of the four investigated AtCKX genes. Average weight was obtained by analysing five different batches of 200 seeds for each clone. A quantitative evaluation showed that the seed weight of AtCKX1 and AtCKX3 expressing clones was app. 1.8-2.3-fold higher than in wild type. Gain of weight for seeds of AtCKX2 and AtCKX4 expressing lines was in the range of 10-25% (Table 16 and FIG. 14).

The increases in size and weight for seeds, embryos, and cotyledons are unexpected as a reduced cytokinin content would have been expected to be associated with a reduced organ growth. One possible reason for the increases in seed, embryo, and cotyledon size is a previously unknown negative regulatory function of cytokinins in these storage organs. A negative regulatory functions of cytokinins in the control of organ growth is so far only known from roots (Werner et al. 2001). We propose, therefore, that localized expression of cytokinin oxidase genes in tissues where growth is negatively regulated by cytokinins leads to enhanced growth of this tissue. For example, localized expression of CKX genes during cotyledon development likely leads to enhanced growth of cotyledons and in species with cotyledons as storage organs, to enhanced yield and to an enhanced growth performance of seedlings. Total number of seeds is lowered in AtCKX1 and AtCKX3 expressers. There have been no previous reports however, of lower seed number in *Arabidopsis* being linked to an increase in size.

TABLE 16

|  | WT | CKX1-11-7 | CKX1-15-1 | CKX2-2-4 | CKX2-9-3 | CKX3-9-4 | CKX3-12-13 | CKX4-37-2 | CKX4-41-7 |
|---|---|---|---|---|---|---|---|---|---|
| Seed Weight | 0.0158 ± 0.0009 | 0.0372 ± 0.0015 | 0.0352 ± 0.0023 | 0.0201 ± 0.0017 | 0.0180 ± 0.0001 | 0.0340 ± 0.0027 | 0.0280 ± 0.0027 | 0.0185 ± 0.0004 | 0.0179 ± 0.0007 |
| % of WT | 100 | 235.5 | 222.6 | 126.7 | 113.7 | 215.0 | 176.7 | 116.8 | 112.7 |

Example 15

Overexpression of an AtCKX Gene in the Female Reproductive Organs Leads to Parthenocarpic Fruit Development The open reading frame of an AtCKX gene is cloned under control of a promoter that confers overexpression in the female reproductive organs such as for example the DefH9 promoter from *Antirrhinum majus* or one of its homologues, which have high expression specificity in the placenta and ovules. Transgenic plants with enhanced cytokinin oxidase activity in these tissues show parthenocarpic fruit development.

Example 16

Overexpression of AtCKX Genes Result in Increased Seed and Cotyledon Size

Transgenic *Arabidopsis thaliana* plants that overexpress cytokinin oxidase (AtCKX) genes under control of the 35S

Example 17

Seed-Preferred or Seedling-Preferred Expression of a CKX2 Gene Results in Increased Seed Yield A) DNA Manipulation and Cloning of AtCKX2

Unless otherwise stated, recombinant DNA techniques are performed according to standard protocols described in (Sambrook (2001) Molecular Cloning: a laboratory manual, 3rd Edition Cold Spring Harbor Laboratory Press, CSH, New York) or in Volumes 1 and 2 of Ausubel et al. (1994), Current Protocols in Molecular Biology, Current Protocols. Standard materials and methods for plant molecular work are described in Plant Molecular Biology Labfax (1993) by R. D. D. Croy, published by BIOS Scientific Publications Ltd (UK) and Blackwell Scientific Publications (UK).

The *Arabidopsis* CKX2 (corresponding to SEQ ID NO:44) was amplified by PCR using as template an *Arabidopsis thaliana* seedling cDNA library (Invitrogen, Paisley, UK). After reverse transcription of RNA extracted from seedlings, the cDNAs were cloned into pCMV Sport 6.0. Average insert size of the bank was 1.5 kb, and original number of clones was 1.59×10$^7$ cfu. The original titer was determined to be 9.6×10$^5$ cfu/ml, and became after a first amplification 6×10$^{11}$ cfu/ml. After plasmid extraction, 200 ng of template was used in a 50 µl PCR mix. Primers prm3769 (SEQ ID NO: 40) and prm1526 (SEQ ID NO: 41), which include the AttB sites for Gateway recombination, were used for PCR amplification.

PCR was performed using Hifi Taq DNA polymerase in standard conditions. A PCR fragment of 1506 bp was amplified and purified also using standard methods. The first step of the Gateway procedure, the BP reaction, was then performed, during which the PCR fragment recombines in vivo with the pDONR plasmid to produce, according to the Gateway terminology, an "entry clone", p41 (FIG. 15). pDONR was purchased from Invitrogen, as part of the Gateway technology.

B) Vector Construction

The entry clone p41 was subsequently used in an LR reaction with p831 or p830, both destination vectors according to the Gateway™ terminology, used for rice transformation.

p831 contains as functional elements within the T-DNA borders a plant selectable marker, a screenable marker and a Gateway cassette intended for LR in vivo recombination with the sequence of interest already cloned in the donor vector.

The PRO0218 promoter for embryo and aleurone preferred expression is located upstream of this Gateway cassette.

Similarly, p830 contains as functional elements within the T-DNA borders: a plant selectable marker; a screenable marker; and a Gateway cassette intended for LR in vivo recombination with the sequence of interest already cloned in the donor vector. The PRO0090 promoter for endosperm-preferred expression is located upstream of this Gateway cassette.

After the recombination step, the resulting expression vectors p37 (originating from p831, FIG. 16) and p35 (originating from p830, FIG. 17) were transformed into *Agrobacterium* strain LBA4404 and subsequently into *Oryza sativa* plants.

C) Transformation of Rice

Mature dry seeds of the rice japonica cultivar Nipponbare were dehusked. Sterilization was done by incubating the seeds for one minute in 70% ethanol, followed by 30 minutes in 0.2% $HgCl_2$ and by 6 washes of 15 minutes with sterile distilled water. The sterile seeds were then germinated on a medium containing 2,4-D (callus induction medium). After a 4-week incubation in the dark, embryogenic, scutellum-derived calli were excised and propagated on the same medium. Two weeks later, the calli were multiplied or propagated by subculture on the same medium for another 2 weeks. 3 days before co-cultivation, embryogenic callus pieces were subcultured on fresh medium to boost cell division activity. The *Agrobacterium* strain LBA4404, harbouring T-DNA vectors comprising a suitable selection marker, was used for co-cultivation. *Agrobacterium* was cultured for 3 days at 28° C. on AB medium with the appropriate antibiotics. The bacteria were then collected and suspended in liquid co-cultivation medium at an $OD_{600}$ of about 1. The suspension was transferred to a petri dish and the calli were immersed in the suspension during 15 minutes. Next, the callus tissues were blotted dry on a filter paper, transferred to solidified co-cultivation medium and incubated for 3 days in the dark at 25° C.

Hereafter, co-cultivated callus was grown on 2,4-D-containing medium for 4 weeks in the dark at 28° C. in the presence of a selective agent at a suitable concentration. During this period, rapidly growing resistant callus islands developed. Upon transfer of this material to a regeneration medium and incubation in the light, the embryogenic potential was released and shoots developed in the next four to five weeks. Shoots were excised from the callus and incubated for 2 to 3 weeks on an auxin-containing medium from which they were transferred to soil. Hardened shoots were grown under high humidity and short days in a greenhouse. Finally seeds were harvested three to five months after transplanting. The method yielded single locus transformants at a rate of over 50% (Aldemita and Hodges, 1996, Chan et al., 1993, Hiei et al., 1994).

D) Evaluation of Transformants: Vegetative Growth Measurements

Approximately 15 to 20 independent T0 transformants were generated. The primary transformants were transferred from tissue culture chambers to a greenhouse for growing and harvest of T1 seed. Four events (for p37 transformants, PRO0218 promoter) or five events (for p35 transformants, PRO0090 promoter) of which the T1 progeny segregated 3:1 for presence/absence of the transgene were retained. For each of these events, 10 T1 seedlings containing the transgene (hetero- and homo-zygotes), and 10 T1 seedlings lacking the transgene (nullizygotes), were selected by monitoring visual marker expression. The selected T1 plants were transferred to a greenhouse.

Each plant received a unique barcode label to link unambiguously the phenotyping data to the corresponding plant. The selected T1 plants were grown on soil in 10 cm diameter pots under the following environmental settings: photoperiod=11.5 h, daylight intensity=30,000 lux or more, daytime temperature=28° C. or higher, night time temperature=22° C., relative humidity=60-70%. Transgenic plants and the corresponding nullizygotes were grown side-by-side at random positions. From the stage of sowing until the stage of maturity the plants were passed several times through a digital imaging cabinet. At each time point digital images (2048×1536 pixels, 16 million colours) were taken of each plant from at least 6 different angles.

In a next step, the mature primary panicles were harvested, bagged, barcode-labelled and then dried for three days in the oven at 37° C. The panicles were then threshed and all the seeds were collected and counted. The filled husks were separated from the empty ones using an air-blowing device. The empty husks were discarded and the remaining fraction was counted again. The filled husks were weighed on an analytical balance and the cross-sectional area of the seeds was measured using digital imaging. This procedure allows deriving a set of seed-related parameters.

The parameters described below were derived in an automated way from the digital images using image analysis software and were analysed statistically. A two factor ANOVA (analysis of variance) corrected for the unbalanced design was used as statistical model for the overall evaluation of plant phenotypic characteristics. An F-test was carried out on all the parameters measured in all the plants and of all the events transformed with that gene. The F-test was carried out to check for an effect of the gene over all the transformation events and to verify for an overall effect of the gene, also named herein "global gene effect". If the value of the F test showed that the data are significant, than it was concluded that there is a "gene" effect, meaning that not only presence or the position of the gene is causing the effect. The threshold for significance for a true global gene effect was set at 5% probability level for the F test.

To check for an effect of the genes within an event, i.e., for a line-specific effect, a t-test was performed within each event using data sets from the transgenic plants and the corresponding null plants. "Null plants" or "Null segregants" or "Nullizygotes" are the plants treated in the same way as the transgenic plant, but from which the transgene has segregated. Null plants can also be described as the homozygous negative transformed plants. The threshold for significance for the t-test was set at a 10% probability level. The results for some events can be under or below this threshold. This is based on the hypothesis that a gene might only have an effect in certain positions in the genome, and that the occurrence of this position-dependent effect is not uncommon. This kind of gene effect is also named herein a "line effect of the gene". The p value was obtained by comparing the t value to the t distribution or alternatively, by comparing the F value to the F distribution. The p value gives the probability of the null hypothesis (i.e., that there is no effect of the transgene) is correct. The threshold for significance was set at a 5% p-value for the F test and a 10% p-value for the t-test.

Vegetative growth and seed yield was measured according to the methods as described above. The inventors surprisingly found that the seed yield (expressed as total weight of seeds, number of (filled) seeds, harvest index, and/or Thousand Kernel Weight) was increased in the rice plants transformed with the AtCKX2 gene when compared with control plants without the AtCKX2 gene, as shown in paragraphs E and F.

The data obtained in the experiment with T1 plants were then confirmed in a further experiment with T2 plants. Seed batches from the positive plants (both hetero- and homozygotes) in T1, were screened by monitoring marker expression. For each chosen event, the heterozygote seed batches were then retained for T2 evaluation. Within each seed batch an equal number of positive and negative plants were grown in the greenhouse for evaluation. In particular, four events of p37 T2 transformants and three events of p35 T2 transformants were selected for further analysis. For both p37 T2 transformants and p35 T2 transformants, a total of 120 plants were tested, evenly distributed over each event.

E) Evaluation of p37 Transformants: Measurement of Seed-Related Parameters

Upon analysis of the seeds as described above, the inventors found that plants transformed with the AtCKX2 gene under control of the PRO0218 promoter had a higher total weight of seeds, a higher number of filled seeds, a higher harvest index and a higher Thousand Kernel Weight than plants lacking the CKX2 transgene. These findings were consistent over 2 independent experiments with T1 plants as well as in an experiment with T2 plants, as shown in Table 17. In addition to these yield parameters, 3 lines in T1 scored also positive for the total number of seeds. This increase in total seed number was confirmed in T2, where the effect was shown to be a significant global gene effect (mean increase +24%, p-value from the F-test 0.0032).

TABLE 17

Analysis of seed related parameters for p37 transformants

| parameter | T1 generation, 1st experiment Difference over null plants | T1 generation, 2nd experiment Difference over null plants | T2 generation Difference over null plants | p-value |
|---|---|---|---|---|
| Total weight of seeds | +22% | +22% | +51% | 0.0000 |
| Number of filled seeds | +22% | +17% | +46 | 0.0000 |
| Harvest Index | +25% | +20% | +37% | 0.0025 |
| Thousand Kernel Weight | +1% | +5% | +3% | 0.0000 |

The total seed weight was measured by weighing all filled seeds harvested from a transformed rice plant. The number of filled seeds was determined by counting the number of filled seeds harvested from a transformed rice plant. The total seed number was determined by counting the number of seeds harvested from a plant. The harvest index is defined as the ratio between the total seed weight and the above ground area (mm$^2$), multiplied by a factor $10^6$. Thousand Kernel Weight (TKW) was derived from the number of filled seeds that were counted, and their total weight. The figures gave the mean increase (in %) of each parameter calculated from transgenes versus corresponding nullizygotes of 4 independent events in T1 generation, each event comprising 10 plants carrying the transgene and 10 nullizygotes, and of 4 independent events in the T2 generation, each event comprising 20 plants carrying the transgene and 20 nullizygotes. The p-values of the F-test listed for the data of the T2 generation demonstrate that the obtained increases for the various seed yield parameters are all significant and that there is clearly an overall gene effect.

F) Evaluation of p35 Transformants: Measurement of Seed-Related Parameters

Plants transformed with the AtCKX2 gene under control of the PRO0090 promoter also had a better yield compared to the control nullizygous plants, in particular for total seed weight, number of filled seeds and harvest index. The total seed weight was measured by weighing all filled seeds harvested from a plant. The number of filled seeds was determined by counting the number of filled seeds harvested from a plant. The harvest index in the present invention is defined as the ratio between the total seed weight and the above ground area (mm$^2$), multiplied by a factor $10^6$.

In a first experiment, plants of the T1 generation of five independent events were compared, for each event 10 T1 plants carrying the transgene versus 10 corresponding control T1 plants. For the parameter "total seed weight", two out of the five events had a significant increase (58% and 67%, with a p-value of the t-test of 0.0551 and 0.0211 respectively). Similar results were obtained for the number of filled seeds, for which these two lines showed in increase of 47% and 68% with a p-value of respectively 0.0846 and 0.0166. The two lines also scored positive for Harvest Index (increases of 41% (p-value of 0.0223) and 31% respectively). Besides these two lines, a third line also scored significantly higher than the corresponding nullizygous control plants (+41%, p-value of 0.035).

The positive data for seed yield observed in the T1 generation were confirmed in the T2 generation. Data are given in Table 18.

TABLE 18

| Parameter | T2 generation | |
|---|---|---|
| | Difference over null plants | p-value |
| Total seed weight | +24% | 0.0484 |
| Number of filled seeds | +26% | 0.0254 |
| Harvest index | +19% | 0.0277 |

The figures give the mean increase (in %) of each parameter calculated from transgenes versus corresponding nullizygotes of 3 independent events in the T2 generation, each event comprising 20 plants carrying the transgene and 20 nullizygotes. The p-values of the F-test listed for the data of the T2 generation demonstrate that the obtained increases for the various seed yield parameters are all significant and that there is clearly an overall gene effect.

TABLE 19

Alternative promoters suitable for seed specific or seedling preferred expression

| Gene name | Expression |
|---|---|
| Metallothionein Mte | embryo/scutellum + calli |
| putative beta-amylase | embryo/scutellum |
| Unknown | Scutellum |
| proteinase inhibitor Rgpi9 | Seed |
| structural protein | young tissues, calli, embryo/scutellum |
| prolamine 10 Kda | strong in endosperm |
| allergen RA2 | Seed |
| prolamine RP7 | Endosperm |
| Metallothioneine-like ML2 | embryo/scutellum + calli |
| prolamine RM9 | strong in endosperm |
| prolamine RP5 | strong in endosperm |
| putative methionine aminopeptidase | Embryo |
| putative 40S ribosomal protein | weak in endosperm |
| alpha-globulin | strong in endosperm |
| alanine aminotransferase | aleurone, endosperm |
| cyclophyllin 2 | shoot, embryo/endosperm |
| sucrose synthase SS1 (barley) | medium constitutive, shoot endosperm/aleurone |
| trypsin inhibitor ITR1 (barley) | weak in endosperm |
| WSI18 | embryo/aleurone |
| Aquaporine | seedlings |
| RAB21 | embryo/aleurone |
| OSH1 | seedling |
| Arceline 5A | seed |
| Cruciferine | seed |
| Albumine 2S3 | seed |
| Albumine 2S2 | seed |
| FAE1 | embryo |
| Phaseolin Beta subunit | seed |
| Lec1 | embryo |
| Gamma zein | seed |
| lipid Transfer Protein | seed |

Example 18

Seed-Preferred Expression the CKX1 Gene Results in Increased Seed Yield

DNA Manipulation

Unless otherwise stated, recombinant DNA techniques are performed according to standard protocols described in (Sambrook (2001) Molecular Cloning: a laboratory manual, 3rd Edition Cold Spring Harbor Laboratory Press, CSH, New York) or in Volumes 1 and 2 of Ausubel et al. (1994), Current Protocols in Molecular Biology, Current Protocols. Standard materials and methods for plant molecular work are described in Plant Molecular Biology Labfax (1993) by R. D. D. Croy, published by BIOS Scientific Publications Ltd (UK) and Blackwell Scientific Publications (UK).

Cloning of CKX1

The *Arabidopsis* CKX1 gene (internal reference CDS1499_2, corresponding to SEQ ID NO:48) was re-amplified by PCR using as template p0432, the pUC19 plasmid containing the *Arabidopsis thaliana* CKX1 2235-bp PCR fragment. The primers used here contained attB sites to be Gateway-compatible. Sequences of the primers used for PCR amplification were SEQ ID NO:45 (PRM02958) and SEQ ID NO:46 (PRM02959), which included the attB sites for Gateway recombination (sequence upstream of the ATG or TTA in PRM02958 respectively PRM02959). PCR was performed using Hifi Taq DNA polymerase in standard conditions. A PCR fragment of 2299 bp was amplified (including the attB sites) and purified also using standard methods. The first step of the Gateway procedure, the BP reaction, was then performed, during which the PCR fragment recombines in vivo with the pDONR plasmid to produce, according to the Gateway terminology, an "entry clone", EC p049 (FIG. 18). pDONR was purchased from Invitrogen, as part of the Gateway technology.

Vector Construction

The entry clone p049 was subsequently used in an LR reaction with p831, a destination vector according to the Gateway™ terminology, used for rice transformation. p831 contains as functional elements within the T-DNA borders a plant selectable marker, a screenable marker and a Gateway cassette intended for LR in vivo recombination with the sequence of interest already cloned in the donor vector. The PRO0218 promoter for embryo and aleurone preferred expression is located upstream of this Gateway cassette.

After the recombination step, the resulting expression vector p051 (originating from p831, FIG. 19) was transformed into *Agrobacterium* strain LBA4404 and subsequently into *Oryza sativa* plants.

Evaluation of p051 Transformants: Measurement of Seed-Related Parameters

Upon analysis of the seeds as described in example 17, the inventors found that plants transformed with the AtCKX1 gene under control of the PRO0218 promoter had a higher number of seeds, and a higher harvest index than plants lacking the CKX1 transgene. These findings were consistent over 2 independent experiments with T1 plants as well as in an experiment with T2 plants, as shown in Table 20.

TABLE 20

Analysis of seed related parameters for p051_transformants

| Parameter | T1 generation Difference over null plants | T2 generation Difference over null plants | Combined p-value |
|---|---|---|---|
| Number of seeds | 11% | 5% | 0.0475 |
| Harvest Index | 3% | 10% | 0.0206 |

The total seed number was determined by counting the number of seeds harvested from a plant. The harvest index is defined as the ratio between the total seed weight and the above ground area ($mm^2$), multiplied by a factor $10^6$. The figures gave the mean increase (in %) of each parameter calculated from transgenes versus corresponding nullizygotes of 5 independent events in T1 generation, each event comprising 10 plants carrying the transgene and 10 nullizygotes, and of 4 independent events in the T2 generation, each event comprising 20 plants carrying the transgene and 20 nullizygotes.

When two experiments (T1 and T2, for example) with overlapping events have been carried out, a combined analysis can be considered. This is useful to check consistency of the effects over the two experiments, and if this is the case, to accumulate evidence from both experiments in order to increase confidence in the conclusion. The method used is a mixed-model approach that takes into account the multilevel structure of the data (i.e. experiment—event—segregants). P-values are obtained by comparing likelihood ratio test to chi square distributions (for the overall gene effects).

Example 19

Gene Cloning

DNA Manipulation

Unless otherwise stated, recombinant DNA techniques are performed according to standard protocols described in (Sambrook (2001) Molecular Cloning: a laboratory manual, 3rd Edition Cold Spring Harbor Laboratory Press, CSH, New York) or in Volumes 1 and 2 of Ausubel et al. (1994), Current Protocols in Molecular Biology, Current Protocols. Standard materials and methods for plant molecular work are described in Plant Molecular Biology Labfase (1993) by R. D. D. Croy, published by BIOS Scientific Publications Ltd (UK) and Blackwell Scientific Publications (UK).

The *Arabidopsis* CKX encoding sequence corresponding to SEQ ID NO 50 was amplified by PCR using as template an *Arabidopsis thaliana* seedling cDNA library (Invitrogen, Paisley, UK). After reverse transcription of RNA extracted from seedlings, the cDNAs were cloned into pCMV Sport 6.0. Average insert size of the bank was 1.5 kb, and original number of clones was of $1.59 \times 10^7$ cfu. The original titer was determined to be $9.6 \times 10^5$ cfu/ml, after first amplification of $6 \times 10^{11}$ cfu/ml. After plasmid extraction, 200 ng of template was used in a 50 µl PCR mix. Primers PRM3769 (SEQ ID NO:40) and PRM1526 (SEQ ID NO:41), which include the AttB sites for Gateway recombination, were used for PCR amplification.

PCR was performed using Hifi Taq DNA polymerase in standard conditions. A PCR fragment of 1506 bp was amplified and purified also using standard methods. The first step of the Gateway procedure, the BP reaction, was then performed, during which the PCR fragment recombines in vivo with the pDONR plasmid to produce, according to the Gateway terminology, an "entry clone", p41. pDONR was purchased from Invitrogen, as part of the Gateway technology.

Example 20

Vector Construction

The entry clone p41 from Example 1 was subsequently used in an LR reaction with p3391, a destination vector according to the Gateway™ terminology and used for rice transformation. This vector contains as functional elements within the T-DNA borders a plant selectable marker and a Gateway cassette intended for LR in vivo recombination with the sequence of interest already cloned in the donor vector. Upstream of this Gateway cassette is located the rice promoter PRO0109 for weak shoot-preferred expression of the AtCKX gene.

After the recombination step, the resulting expression vector p39 (FIG. 20) was transformed into *Agrobacterium* strain LBA4404 and subsequently into plants.

Example 21

Transformation of Rice

Mature dry seeds of the rice japonica cultivar Nipponbare were dehusked. Sterilization was done by incubating the seeds for one minute in 70% ethanol, followed by 30 minutes in 0.2% $HgCl_2$ and by 6 washes of 15 minutes with sterile distilled water. The sterile seeds were then germinated on a medium containing 2,4-D (callus induction medium). After a 4-week incubation in the dark, embryogenic, scutellum-derived calli were excised and propagated on the same medium. Two weeks later, the calli were multiplied or propagated by subculture on the same medium for another 2 weeks. 3 days before co-cultivation, embryogenic callus pieces were subcultured on fresh medium to boost cell division activity. The *Agrobacterium* strain LBA4404, harbouring T-DNA vectors comprising a suitable selection marker, was used for co-cultivation. The *Agrobacterium* strain was cultured for 3 days at 28° C. on AB medium with the appropriate antibiotics. The bacteria were then collected and suspended in liquid co-cultivation medium at an $OD_{600}$ of about 1. The suspension was transferred to a petri dish and the calli were immersed in the suspension during 15 minutes. Next, the callus tissues were blotted dry on a filter paper, transferred to solidified co-cultivation medium and incubated for 3 days in the dark at 25° C. Hereafter, co-cultivated callus was grown on 2,4-D-containing medium for 4 weeks in the dark at 28° C. in the presence of a selective agent at a suitable concentration. During this period, rapidly growing resistant callus islands developed. Upon transfer of this material to a regeneration medium and incubation in the light, the embryogenic potential was released and shoots developed in the next four to five weeks. Shoots were excised from the callus and incubated for 2 to 3 weeks on an auxin-containing medium from which they were transferred to soil. Hardened shoots were grown under high humidity and short days in a greenhouse. Finally seeds were harvested three to five months after transplanting. The method yielded single locus transformants at a rate of over 50% (Aldemita and Hodges, 1996, Chan et al., 1993, Hiei et al., 1994).

Example 22

Evaluation of Transformants: Vegetative Growth Measurements

Approximately 15 to 20 independent T0 transformants were generated. The primary transformants were transferred from tissue culture chambers to a greenhouse for growing and harvest of T1 seed. Six events of which the T1 progeny segregated 3:1 for presence/absence of the transgene were retained. For each of these events, 10 T1 seedlings containing the transgene (hetero- and homo-zygotes), and 10 T1 seedlings lacking the transgene (nullizygotes), were selected by visual marker screening. The selected T1 plants were transferred to a greenhouse. Each plant received a unique barcode label to link unambiguously the phenotyping data to the corresponding plant. The selected T1 plants were grown on soil in 10 cm diameter pots under the following environmental settings: photoperiod=11.5 h, daylight intensity=30,000 lux or more, daytime temperature=28° C. or higher, night time temperature=22° C., relative humidity=60-70%. Transgenic plants and the corresponding nullizygotes were grown side-by-side at random positions. From the stage of sowing until the stage of maturity the plants were passed several times through a digital imaging cabinet. At each time point digital images (2048×1536 pixels, 16 million colours) were taken of each plant from at least 6 different angles.

The mature primary panicles were harvested, bagged, bar-code-labelled and then dried for three days in the oven at 37° C. The panicles were then threshed and all the seeds collected. The filled husks were separated from the empty ones using an air-blowing device. After separation, both seed lots were then counted using a commercially available counting machine. The empty husks were discarded. The filled husks were weighed on an analytical balance and the cross-sectional area of the seeds was measured using digital imaging. This procedure resulted in the set of seed-related parameters described below.

These parameters were derived in an automated way from the digital images using image analysis software and were analysed statistically. A two factor ANOVA (analyses of variance) corrected for the unbalanced design was used as statistical model for the overall evaluation of plant phenotypic characteristics. An F-test was carried out on all the parameters measured of all the plants of all the events transformed with that gene. The F-test was carried out to check for an effect of the gene over all the transformation events and to verify for an overall effect of the gene, also named herein "global gene effect". If the value of the F test shows that the data are significant, than it is concluded that there is a "gene" effect, meaning that not only presence or the position of the gene is causing the effect. The threshold for significance for a true global gene effect is set at 5% probability level for the F test.

To check for an effect of the genes within an event, i.e., for a line-specific effect, a t-test was performed within each event using data sets from the transgenic plants and the corresponding null plants. "Null plants" or "Null segregants" or "Nullizygotes" are the plants treated in the same way as the transgenic plant, but from which the transgene has segregated. Null plants can also be described as the homozygous negative transformed plants. The threshold for significance for the t-test is set at 10% probability level. The results for some events can be above or below this threshold. This is based on the hypothesis that a gene might only have an effect in certain positions in the genome, and that the occurrence of this position-dependent effect is not uncommon. This kind of gene effect is also named herein a "line effect of the gene". The p-value is obtained by comparing the t-value to the t-distribution or alternatively, by comparing the F-value to the F-distribution. The p-value then gives the probability that the null hypothesis (i.e., that there is no effect of the transgene) is correct.

Vegetative growth and seed yield were measured according to the methods as described above. The inventors surprisingly found that the total weight of seeds, the number of filled seeds and the harvest index were increased in the rice plants transformed with the At CKX gene when compared the control plants without the At CKX gene.

The data obtained in the first experiment were confirmed in a second experiment with T2 plants. Seed batches from the positive plants (both hetero- and homozygotes) in T1, were screened by monitoring marker expression. For each chosen event, the heterozygote seed batches were then retained for T2 evaluation. Within each seed batch an equal number of positive and negative plants were grown in the greenhouse for evaluation. Three lines that had the correct expression pattern were selected for further analysis.

A total number of 120 CKX transformed plants were evaluated in the T2 generation, that is 40 plants per event of which 20 positives for the transgene, and 20 negatives.

Example 23

Evaluation of Transformants: Measurement of Seed-Related Parameters

Upon analysis of the seeds as described above, the inventors found that plants transformed with the CKX gene construct had a higher number of filled seeds, a higher total weight of seeds and an increased harvest index compared to plants lacking the CKX transgene. Positive results obtained for plants in the T1 generation were again obtained in the T2 generation. Not only individual transgenic lines scored significantly better than the corresponding nullizygous control lines, but there was also a significant positive overall effect when all plants of all tested T2 events were evaluated, strongly indicating a global gene effect.

(i) Total Number of Filled Seeds per Plant

The total seed number was measured by counting the number of filled husks harvested from a plant. When all tested lines are considered, there is an overall increase of 9% in the number of filled seeds of the transgenics compared to the nullizygotes in the T1 generation.

Evaluation of transgenic T2 plants confirmed the observations made for T1 plants. The number of filled seeds is significantly increased in the transgenic plants with respect to the nullizygote control plants. There was a particularly high overall increase in the number of filled seeds of +26%, which increase was also significant as shown by the F-test (p-value of 0.0077).

(ii) Total Seed Yield per Plant

The total seed yield was measured by weighing all filled husks harvested from a plant. Overall, the increase in total weight of seeds for the T1 transgenic plants was 11%, when compared to control plants.

Evaluation of transgenic T2 plants of these lines confirmed the observations from T1 plants. The total weight of seeds was increased in the individual transgenic plant lines, with respect to the nullizygote control plants. There was also a significant overall increase of total seed weight of +30% with a p-value of 0.0044, as calculated by an F-test.

(iii) Harvest Index of Plants

The harvest index in the present invention is defined as the ratio between the total seed yield and the above ground area (mm$^2$), multiplied by a factor $10^6$. Overall, the increase in harvest index was 9% for plants of the T1 generation.

Again, these results were confirmed in the T2 generation. Tested lines had a significantly higher harvest index than the control plants; in addition also the overall effect was significant, with an increase of 33% and a p-value calculated by the F-test of 0.0001.

The data are combined in Table 21:

TABLE 21

Overall effects of the CKX2 transgene on seed yield parameters

| Parameter | T1 generation | T2 generation | |
|---|---|---|---|
| | Mean overall effect | Mean overall effect | p-value |
| Number of filled seeds | +9% | +26% | 0.0077 |
| Total weight of seeds | +11% | +30% | 0.0044 |
| Harvest Index | +9% | +33% | 0.0001 |

From the combined results of the plant evaluation, and from the statistical analysis performed on these, it can be concluded that the presence of the transgene has an overall effect mainly on harvest index. Since the plants with an increased harvest index had the same above ground biomass as the nullizygote plants (see FIG. 21), the increased harvest index can be attributed to an increase in number of filled seeds.

These specific phenotypic effects are the result of the introducing into a plant a gene encoding CKX, under the control of a weak shoot preferred promoter. In particular, the promoter as presented in SEQ ID NO:49 was used.

It is envisaged by the present invention that any cytokinin oxidase or dehydrogenase whose expression is under control of a weak shoot preferred promoter can be used to increase seed yield in a plant of interest. It is to be understood that still other cytokinin oxidase/dehydrogenase genes and/or weak shoot preferred promoters can also be used.

Example 24

Isolation and Characterisation of a Beta-Expansin Promoter i) Identification and Isolation of the Promoter Using the Tentative Contig TC89913 (TIGR database accession number), a corresponding genomic sequence (BAC clone AC020666) was identified. From this BAC clone, the sequence identity of the promoter region could be determined. Starting from the sequence information of the gene and its location in the rice genome, the promoter region was isolated as the DNA region spanning about 1.2 kb upstream of the translation initiation codon (i.e. first ATG), which codon was excluded. The promoter region was isolated from genomic DNA of *Oryza sativa* Japonica via PCR using specific primers prm2426 (SEQ ID NO: 58) and prm2427 (SEQ ID NO: 59). These specific primers comprise AttB recombination sites, suitable for recombination cloning of the isolated promoter region. Conditions for PCR were as follows: 1 cycle of 2 min at 94° C., 35 cycles of 1 min at 94° C., 1 min at 58° C. and 2 min at 68° C., and 1 cycle of 5 min at 68° C. The length of the expected PCR fragment is 1243 bp (SEQ ID NO: 60). The corresponding PCR fragment was purified from the PCR reaction mix via gel electrophoresis and subsequent purification using Zymoclean Gel DNA Recovery Kit (Zymo Research, Orange, Calif.).

ii) Cloning of Promoter-GUS Reporter Vectors for Plant Transformation

The purified PCR fragment was cloned into the pDONR201 entry plasmid of the Gateway™ system (Life Technologies) using the "BP recombination reaction". The identity and base pair composition of the cloned insert was confirmed by sequencing and additionally, the resulting plasmid was tested via restriction digests. The entry clone was subsequently used in an "LR recombination reaction" (Gateway™) with the destination vector p4581. This destination vector was designed to operably link the promoter to the *Escherichia coli* beta-glucuronidase (GUS) gene via the substitution of the Gateway recombination cassette in front of the GUS gene. This destination vector is furthermore suitable for transformation of plants and comprises within the T-DNA left and right borders the resulting promoter-GUS cassette, a selectable marker and a screenable marker cassette. The resulting reporter vector, comprising the beta expansin promoter operably linked to GUS, is subsequently transformed into *Agrobacterium* strain LBA4044 and subsequently into rice plants using standard transformation techniques.

iii) Expression Patterns of the Promoter-GUS Reporter Cassette in Plants

3 T0 transgenic rice plants were generated from transformed cells. Plant growth was performed under normal conditions. The first transgenic plant was harvested for GUS staining when it had reached a size of about 5 cm, which plant is named herein "C plant". The second transgenic plant was used for GUS staining when it had reached a size of about 10 cm, which plant is named herein "B plant". The third transgenic plant was kept for seed production and is named herein "A plant". GUS staining was performed on complete C and B plants. On A plants, GUS staining was performed on leaf pieces, flowers and section of seeds at various developmental stages. A plants were allowed to set seed, which seeds were used after harvest for confirmation of the expression pattern in T1 plants.

The harvested plants or plant parts were covered with 90% ice-cold acetone and incubated for 30 min at 4° C. After 3 washes of 5 min with Tris buffer [15.76 g Trizma HCl (Sigma T3253)+2,922 g NaCl in 1 l bidistilled water, adjusted to pH 7.0 with NaOH], the material was covered by a Tris/ferricyanate/X-Gluc solution [9.8 ml Tris buffer+0.2 ml ferricyanate stock (0.33 g Potassium ferricyanate (Sigma P3667) in 10 ml Tris buffer)+0.2 ml X-Gluc stock (26.1 mg X-Gluc (Europa Bioproducts ML 113A) in 500 µl DMSO)]. Vacuum infiltration was applied for 15 to 30 minutes. The plants or plant parts were incubated for up to 16 hours at 37° C. until development of blue colour was visible. The samples were washed 3 times for 5 minutes with Tris buffer. Chlorophyll was extracted in ethanol series of 50%, 70% and 90% (each for 30 minutes).

iv) Results for the 5-Beta Expansin EXPB9 Promoter 2 constructs (OS1441 and OS1460) were investigated. 20 calli, 32 C, 32 B plants and 32 A plants were analysed. Weak expression was observed in the leaves of C and B plants. In A plants expression in the flowers was observed (44%), more particularly in lemma of young spikelets, but no expression was observed in seeds. An overview is given in FIG. 22. It was concluded that the promoter EXPB9 (SEQ ID NO: 53) is suitable for expression in young tissue, more preferably in young, developing or expanding tissue, more preferably in green tissue.

REFERENCES

WO0105985. Method to modulate the expression of genes inducing the parthenocarpic trait in plants.

Alberts, B., Bray, D., Lewis, J., Raff, M., Roberts, K., and Watson, J. D. (1994). "Molecular Biology of the Cell." Garland Publishing Inc.

Aldemita, R. R. and Hodges, T. K. (1996) *Agrobacterium tumefaciens*-mediated transformation of japonica and indica rice varieties. *Planta* 199, 612-617.

Altschul, S. F., Madden, T. L., Schäffer, A. A., Zhang, J., Zhang, Z., Miller, W. & Lipman, D. J. (1997) "Gapped BLAST and PSI-BLAST: a new generation of protein database search programs." *Nucl. Acids Res.* 25, 3389-3402.

Armstrong, D. J. (1994) in *Cytokinins: Chemistry, Activity and Functions*, eds. Mok. D. W. S & Mok, M. C. (CRC Boca Raton, Fla.), pp. 139-154.

An, G., Watson, B. D., Stachel, S., Gordon, M. P., and Nester, E. W. (1985). New cloning vehicles for transformation of higher plants. *EMBO J.* 4, 277-284.

Armstrong, C. L., Petersen, W. P., Buchholz, W. G., Bowen, B. A., and Sulc, S. L. (1990). Factors affecting PEG-mediated stable transformation of maize protoplasts. *Plant Cell Reports* 9, 335-339.

Banerjee, A., Pramanik, A., Bhattachaijya, S., and Balaram, P. (1996). Omega amino acids in peptide design: incorporation into helices. *Biopolymers* 39, 769-777.

Baron, M. H. and Baltimore, D. (1982). Antibodies against the chemically synthesized genome-linked protein of poliovirus react with native virus-specific proteins. *Cell* 28, 395-404.

Bartel, P. L. and Fields, S. (1997). "The Yeast Two-Hybrid System." Oxford University Press.

Benkirane, N., Guichard, G., Briand, J. P., and Muller, S. (1996). Exploration of requirements for peptidomimetic immune recognition. Antigenic and immunogenic properties of reduced peptide bond pseudopeptide analogues of a histone hexapeptide. *J. Biol Chem.* 271, 33218-33224.

Berry, A. and Brenner, S. E. (1994). A prototype computer system for de novo protein design. *Biochem. Soc. Trans.* 22, 1033-1036.

Chan, M. T., Chang, H. H., Ho, S. L., Tong, W. F., and Yu, S. M. (1993) *Agrobacterium* mediated production of transgenic rice plants expressing a chimeric alpha-amylase promoter/beta-glucuronidase gene. *Plant Mol. Biol.* 22, 491-506.

Christou, P., McCabe, D. E., and Swain, W. F. (1988). Stable transformation of soybean callus by DNA-coated gold particles. *Plant Physiol.* 87, 671-674.

Crossway, A., Oakes, J. V., Irvine, J. M., Ward, B., Knauf, V. C., and Shewmaker, C. K. (1986). Integration of foreign DNA following microinjection of tobacco mesophyll protoplasts. *Mol. Gen. Genet.* 202, 179-185.

Dale, E. C. and Ow, D. W. (1990). Intra- and intermolecular site-specific recombination in plant cells mediated by bacteriophage P1 recombinase. *Gene* 91, 79-85.

Dodds, J. H. (1985). "Plant genetic engineering." Cambridge University Press.

Doerner, P., Jorgensen, J. E., You, R., Steppuhn, J., and Lamb, C. (1996). Control of root growth and development by cyclin expression. *Nature* 380, 520-523.

Dorner, B., Husar, G. M., Ostresh, J. M., and Houghten, R. A. (1996). The synthesis of peptidomimetic combinatorial libraries through successive amide alkylations. *Bioorg. Med. Chem.* 4, 709-715.

Ellis, J. G., Llewellyn, D. J., Dennis, E. S., and Peacock, W. J. (1987). Maize Adh-1 promoter sequences control anaerobic regulation: addition of upstream promoter elements from constitutive genes is necessary for expression in tobacco. *EMBO J.* 6, 11-16.

Faiss, M., Zalubilová, J., Strnad, M., Schmülling, T. (1997). Conditional transgenic expression of the ipt gene indicates a function for cytokinins in paracrine signaling in whole tobacco plants. *Plant J.* 12, 401-415.

Fassina, G. and Melli, M. (1994). Identification of interactive sites of proteins and protein receptors by computer-assisted searches for complementary peptide sequences. *Immunomethods.* 5, 114-120.

Fedoroff, N. V. and Smith, D. L. (1993). A versatile system for detecting transposition in *Arabidopsis*. *Plant J.* 3, 273-289.

Hanahan, D. (1983). Studies on transformation of *Escherichia coli* with plasmids. *J. Mol. Biol.* 166, 557-580.

Hansen, G. and Chilton, M. D. (1996). "Agrolistic" transformation of plant cells: integration of T-strands generated in planta. *Proc. Natl. Acad. Sci. U.S.A* 93, 14978-14983.

Hansen, G., Shillito, R. D., and Chilton, M. D. (1997). T-strand integration in maize protoplasts after codelivery of a T-DNA substrate and virulence genes. *Proc. Natl. Acad. Sci. U.S.A* 94, 11726-11730.

Hanson, B., Engler, D., Moy, Y., Newman, B., Ralston, E., and Gutterson, N. (1999). A simple method to enrich an *Agrobacterium*-transformed population for plants containing only T-DNA sequences. *Plant J.* 19, 727-734.

Harlow, E. and Lane, D. (1988). "Antibodies: A Laboratory Manual." Cold Spring Harbor Laboratory Press.

Herrera-Estrella, L., De Block, M., Messens, E. H. J. P., Van Montagu, M., and Schell, J. (1983). Chimeric genes as dominant selectable markers in plant cells. *EMBO J.* 2, 987-995.

Hiei, Y.; Ohta, S.; Komari, T.; and Kumashiro, T. (1994) Efficient transformation of rice (*Oryza sativa* L.) mediated by *Agrobacterium* and sequence analysis of the boundaries of the T-DNA. *Plant J.* 6, 271-282.

Hoffman, D. L., Laiter, S., Singh, R. K., Vaisman, I. I., and Tropsha, A. (1995). Rapid protein structure classification using one-dimensional structure profiles on the bioSCAN parallel computer. *Comput. Appl. Biosci.* 11, 675-679.

Hooykens, P. J. J., Hall, M. A. & Libbeuga, K. R., eds. (1999) *Biochemistry and Molecular Biology of Plant Hormones* (Elsevier, Amsterdam).

Houba-Heria, N., Pethe, C. d'Alayer, J & Lelouc, M. (1999) *Plant J.* 17:615-626.

Klee, H. J. & Lanehon, M. B. (1995) in *Plant H'ormones: Physiology, Biochemisry and Molecular Biology*, ed. Davies, P. J. (Kluwer, Dordrdrocht, the Netherlands), pp. 340-353.

Krens, F. A., Molendijk, L., Wullems, G. J., and Schilperoort, R. A. (1982). In vitro transformation of plant protoplasts with Ti-plasmid DNA. *Nature* 296, 72-74.

Lerner, R. A. (1982). Tapping the immunological repertoire to produce antibodies of predetermined specificity. *Nature* 299, 593-596.

Lerner, R. A., Green, N., Alexander, H., Liu, F. T., Sutcliffe, J. G., and Shinnick, T. M. (1981). Chemically synthesized peptides predicted from the nucleotide sequence of the hepatitis B virus genome elicit antibodies reactive with the native envelope protein of Dane particles. *Proc. Natl. Acad. Sci. U.S.A* 78, 3403-3407.

Liddle, J. E. and Cryer, A. (1991). "A Practical Guide to Monoclonal Antibodies." Wiley New York.

Loffler, J., Langui, D., Probst, A., and Huber, G. (1994). Accumulation of a 50 kDa N-terminal fragment of beta-APP695 in Alzheimer's disease hippocampus and neocortex. *Neurochem. Int.* 24, 281-288.

Mok M. C. (1994) in *Cytokines: Chemistry, Activity and Function*, eds., Mok, D. W. S. & Mok, M. C. (CRC Boca Raton, Fla.), pp. 155-166.

Monge, A., Lathrop, E. J., Gunn, J. R., Shenkin, P. S., and Friesner, R. A. (1995). Computer modeling of protein folding: conformational and energetic analysis of reduced and detailed protein models. *J. Mol. Biol.* 247, 995-1012.

Morris, R. O. et al. (1999). Isolation of a gene encoding a glycosylated cytokinin oxidase from maize. Biochem. Biophys. Res. Commun. 255, 328-333

Motyka, V., Faiss, M., Strnad, M., Kaminek, M. and Schmuelling, T. (1996). Changes in cytokinin content and cytokinin oxidase activity in response to derepression of ipt gene transcription in transgenic tobacco calli and plants. Plant Physiol. 112, 1035-1043.

Murakami, T., Simonds, W. F., and Spiegel, A. M. (1992). Site-specific antibodies directed against G protein beta and gamma subunits: effects on alpha and beta gamma subunit interaction. Biochemistry 31, 2905-2911.

Olszewski, K. A., Kolinski, A., and Skolnick, J. (1996). Folding simulations and computer redesign of protein A three-helix bundle motifs. Proteins 25, 286-299.

Osborne, B. I., Wirtz, U., and Baker, B. (1995). A system for insertional mutagenesis and chromosomal rearrangement using the Ds transposon and Cre-lox. Plant J. 7, 687-701.

Ostresh, J. M., Blondelle, S. E., Dorner, B., and Houghten, R. A. (1996). Generation and use of nonsupport-bound peptide and peptidomimetic combinatorial libraries. Methods Enzymol. 267, 220-234.

Pabo, C. O. and Suchanek, E. G. (1986). Computer-aided model-building strategies for protein design. Biochemistry 25, 5987-5991.

Paszkowski, J., Shillito, R. D., Saul, M., Mandak, V., and Hohn, T. H. B. P. I. (1984). Direct gene transfer to plants. EMBO J. 3, 2717-2722.

Peralta, E. G., Hellmiss, R., and Ream, W. (1986). Overdrive, a T-DNA transmission enhancer on the A. tumefaciens tumour-inducing plasmid. EMBO J. 5, 1137-1142.

Quirino, B. F., Noh, Y.-S., Himelbau, E., and Amasino, R. M. (2000). Molecular aspects of leaf senescence. Trends in Plant Science 5, 278-282.

Renouf, D. V. and Hounsell, E. F. (1995). Molecular modelling of glycoproteins by homology with non-glycosylated protein domains, computer simulated glycosylation and molecular dynamics. Adv. Exp. Med. Biol 376, 37-45.

Rinaldi, A. C. and Comandini, O. (1999). Cytokinin oxidase strikes again. Trends in Plant Sc. 4, 300.

Rose, R. B., Craik, C. S., Douglas, N. L., and Stroud, R. M. (1996). Three-dimensional structures of HIV-1 and SIV protease product complexes. Biochemistry 35, 12933-12944.

Rutenber, E. E., McPhee, F., Kaplan, A. P., Gallion, S. L., Hogan, J. C., Jr., Craik, C. S., and Stroud, R. M. (1996). A new class of HIV-1 protease inhibitor: the crystallographic structure, inhibition and chemical synthesis of an aminimide peptide isostere. Bioorg. Med. Chem. 4, 1545-1558.

Sambrook, J., Fritsch, E. F., and Maniatis, T. (1989). "Molecular Cloning: A Laboratory Manual." Cold Spring Harbor Laboratory Press.

Schlappi, M., Smith, D., and Fedoroff, N. (1993). TnpA trans-activates methylated maize Suppressor-mutator transposable elements in transgenic tobacco. Genetics 133, 1009-1021.

Shioda, T., Andriole, S., Yahata, T., and Isselbacher, K. J. (2000). A green fluorescent protein-reporter mammalian two-hybrid system with extrachromosomal maintenance of a prey expression plasmid: Application to interaction screening. Proc. Natl. Acad. Sci. U.S.A 97, 5220-5224.

Smulling, T., Rupp, H. M. Frank, M& Schafer, S. (1999) in Advances in Regulation of Plant Growth and Development, eds. Surnad, M. Pac P. & Beck, E. (Peres, Prague), pp. 85-96.

Tamura, R. N., Cooper, H. M., Collo, G., and Quaranta, V. (1991). Cell type-specific integrin variants with alternative alpha chain cytoplasmic domains. Proc. Natl. Acad. Sci. U.S.A 88, 10183-10187.

Werner, T., Vadau Motyka, Miroslav Strnad, and Thomas Schmülling (2001) Regulation of plant growth by cytokinin. Proc. Nat. Acad. Sci., 58 (18) 10487-10492.

Van Haaren, M. J., Sedee, N. J., Schilperoort, R. A., and Hooykaas, P. J. (1987). Overdrive is a T-region transfer enhancer which stimulates T-strand production in Agrobacterium tumefaciens. Nucleic Acids Res. 15, 8983-8997.

Van Sluys, M. A., Tempe, J., and Fedoroff, N. (1987). Studies on the introduction and mobility of the maize Activator element in Arabidopsis thaliana and Daucus carota. EMBO J. 6, 3881-3889.

Wang, K., Genetello, C., Van Montagu, M., and Zambryski, P. C. (1987). Sequence context of the T-DNA border repeat element determines its relative activity during T-DNA transfer to plant cells. Mol. Gen. Genet. 210, 338-346.

Woulfe, J., Lafortune, L., de Nadai, F., Kitabgi, P., and Beaudet, A. (1994). Post-translational processing of the neurotensin/neuromedin N precursor in the central nervous system of the rat-II. Immunohistochemical localization of maturation products. Neuroscience 60, 167-181.

Zhang, Y. L., Dawe, A. L., Jiang, Y., Becker, J. M., and Naider, F. (1996). A superactive peptidomimetic analog of a farnesylated dodecapeptide yeast pheromone. Biochem. Biophys. Res. Commun. 224, 327-331.

What is claimed is:

1. A method for increasing seed yield of a plant, said method comprising the introduction and expression in said plant of an isolated nucleic acid molecule encoding a cytokinin oxidase/dehydrogenase having the amino acid sequence set forth in SEQ ID NO:4 or having at least 99% sequence identity to SEQ ID NO:4, wherein said isolated nucleic acid molecule is under the control of a shoot-preferred promoter in said plant and wherein said increased seed yield comprises at least one of an increased total weight of seeds, an increased number of filled seeds or an increased harvest index, relative to a corresponding wild type plant.

2. The method according to claim 1, wherein said shoot-preferred promoter is a weak shoot preferred promoter.

3. The method according to claim 2, wherein said weak shoot-preferred promoter comprises the sequence set forth in SEQ ID NO:49.

4. The method according to any one of claims 1, 2 and 3, wherein said plant is a monocotyledonous plant.

5. The method according to claim 4 wherein the monocotyledonous plant is a member of the family Poaceae.

6. The method according to claim 5 wherein the member of the family Poaceae is sugarcane.

7. The method according to claim 4 wherein the monocotyledonous plant is a cereal.

8. The method according to claim 7 wherein the cereal is at least any one of rice, maize, wheat, millet, barley, oats, rye and sorghum.

9. The method according to any one of claims 1, 2 and 3, wherein said isolated nucleic acid molecule is derived from a plant.

10. A method for the production of a transgenic plant having increased seed yield, said method comprising:

(a) introducing into a plant or into a plant cell, a genetic construct comprising an isolated nucleic acid molecule encoding a cytokinin oxidase/dehydrogenase having the amino acid sequence set forth in SEQ ID NO:4 or having at least 99% sequence identity to SEQ ID NO:4, said nucleic acid molecule operably linked to one or more control sequences wherein the one or more control sequences are capable of directing shoot-preferred expression of the nucleic acid molecule; and (b) cultivating the plant or plant cell under conditions promoting regeneration and mature plant growth.

11. A transgenic plant comprising a genetic construct comprising an isolated nucleic acid molecule encoding a cytokinin oxidase/dehydrogenase having the amino acid sequence set forth in SEQ ID NO:4 or having at least 99% sequence identity to SEQ ID NO:4, said nucleic acid molecule operably linked to one or more control sequences wherein the one or more control sequences are capable of directing shoot-preferred expression of the nucleic acid molecule and wherein the transgenic plant has increased seed yield relative to a corresponding wild type plant.

12. The transgenic plant according to claim 11, wherein increased seed yield comprises increased total weight of seeds relative to a corresponding wild type plant.

13. The transgenic plant according to claim 11, wherein increased seed yield comprises increased number of filled seeds relative to a corresponding wild type plant.

14. The transgenic plant according to claim 11, wherein increased seed yield comprises increased harvest index relative to corresponding wild type plants.

15. The transgenic plant according to claim 11 wherein said transgenic plant is a monocotyledonous plant.

16. The transgenic plant according to claim 15 wherein said monocotyledonous plant is a member of the family Poaceae.

17. The transgenic plant according to claim 16 wherein the member of the family Poaceae is sugarcane.

18. The transgenic plant according to claim 15 wherein said monocotyledonous plant is a cereal.

19. The transgenic plant according to claim 18 wherein the cereal is at least any one of rice, maize, wheat, millet, barley, oats, rye, and sorghum.

20. Transgenic plant cells, transgenic plant parts, including harvestable parts, propagules, seeds or progeny, and products directly derived therefrom, of the plant according to claim 11 wherein said plant cells, plant parts, harvestable parts, propagules, seeds, progeny and products directly derived therefrom comprise the construct that was introduced into the parent plant.

21. Transgenic plant cells, transgenic plant parts, including harvestable parts, propagules, seeds or progeny, and products directly derived therefrom, of the plant according to claim 15 wherein said plant cells, plant parts, harvestable parts, propagules, seeds, progeny and products directly derived therefrom comprise the construct that was introduced into the parent plant.

22. Transgenic plant cells, transgenic plant parts, including harvestable parts, propagules, seeds or progeny, and products directly derived therefrom, of the plant according to claim 16 wherein said plant cells, plant parts, harvestable parts, propagules, seeds, progeny and products directly derived therefrom comprise the construct that was introduced into the parent plant.

23. Transgenic plant cells, transgenic plant parts, including harvestable parts, propagules, seeds or progeny, and products directly derived therefrom, of the plant according to claim 17 wherein said plant cells, plant parts, harvestable parts, propagules, seeds, progeny and products directly derived therefrom comprise the construct that was introduced into the parent plant.

24. Transgenic plant cells, transgenic plant parts, including harvestable parts, propagules, seeds or progeny, and products directly derived therefrom, of the plant according to claim 18 wherein said plant cells, plant parts, harvestable parts, propagules, seeds, progeny and products directly derived therefrom comprise the construct that was introduced into the parent plant.

25. Transgenic plant cells, transgenic plant parts, including harvestable parts, propagules, seeds or progeny, and products directly derived therefrom, of the plant according to claim 19 wherein said plant cells, plant parts, harvestable parts, propagules, seeds, progeny and products directly derived therefrom comprise the construct that was introduced into the parent plant.

* * * * *

```
                            SEQUENCE LISTING

<160> NUMBER OF SEQ ID NOS: 53

<210> SEQ ID NO 1
<211> LENGTH: 2236
<212> TYPE: DNA
<213> ORGANISM: Arabidopsis thaliana

<400> SEQUENCE: 1
atgggattga cctcatcctt acggttccat agacaaaaca acaagacttt cctcggaatc      60
ttcatgatct tagttctaag ctgtatacca ggtagaacca atctttgttc caatcattct     120
gttagtaccc caaaagaatt accttcttca aatccttcag atattcgttc ctcattagtt     180
tcactagatt tggagggtta tataagcttc gacgatgtcc acaatgtggc caaggacttt     240
```

```
ggcaacagat accagttacc acctttggca attctacatc caaggtcagt ttttgatatt     300
tcatcgatga tgaagcatat agtacatctg gctccacct caaatcttac agtagcagct      360
agaggccatg gtcactcgct tcaaggacaa gctctagctc atcaaggtgt tgtcatcaaa     420
atggagtcac ttcgaagtcc tgatatcagg atttataagg ggaagcaacc atatgttgat    480
gtctcaggtg gtgaaatatg gataaacatt ctacgcgaga ctctaaaata cggtctttca    540
ccaaagtcct ggacagacta ccttcatttg accgttggag gtacactatc taatgctgga    600
atcagcggtc aagcattcaa gcatggaccc caaatcaaca acgtctacca gctagagatt    660
gttacaggta tttcattcat gctttatctc tgcggtagtc tcaaaaaaat atgcacctgt    720
aaagaatatc catctcttca tgagcaaaaa cactgacgac tttaaataat ttttgactat    780
aaaacaagag tgcataggca caaatgtgaa atatgcaaca cacaattgta acttgcacca    840
agaaaaaagt tataaaaaca aacaactgat aagcaatata tttccaatat ttaatcaggg    900
aaaggagaag tcgtaacctg ttctgagaag cggaattctg aacttttctt cagtgttctt    960
ggcgggcttg gacagtttgg cataatcacc cgggcacgga tctctcttga ccagcaccg    1020 catatggtaa agttctatct tgaacaaagt tcaaacaata tacgctatga ttctaagaac    1080
cactttcctg acacagtcaa ataactttta ataggttaaa tggatcaggg tactctactc    1140
tgacttttct gcattttcaa gggaccaaga atatctgatt tcgaaggaga aaactttga    1200 ttacgttgaa ggatttgtga taatcaatag aacagacctt ctcaataatt ggcgatcgtc    1260
attcagtccc aacgattcca cacaggcaag cagattcaag tcagtgggga aaactcttta    1320
ttgcctagaa gtggtcaaat atttcaaccc agaagaagct agctctatgg atcaggtaag    1380
atgtgaaagc aatatataac tagacttagt ttccacagag agctccaaat caaccgttgg    1440
ctactagcct actaacataa tgaatggttg ccgtgcagga aactggcaag ttactttcag    1500
agttaaatta tattccatcc actttgtttt catctgaagt gccatatatc gagtttctgg    1560
atcgcgtgca tatcgcagag agaaaactaa gagcaaaggg tttatgggag gttccacatc    1620
cctggctgaa tctcctgatt cctaagagca gcatatacca atttgctaca gaagttttca    1680
acaacattct cacaagcaac aacaacggtc ctatccttat ttatccagtc aatcaatcca    1740
agtaagtgag caaaatgcca aaagcaaatg cgtccagtga ttctgaaaca taaattacta    1800
accatatcca acattttgtg gtttcaggtg gaagaaacat acatctttga taactccaaa    1860
tgaagatata ttctatctcg tagcctttct cccctctgca gtgccaaatt cctcagggaa    1920
aaacgatcta gagtaccttt tgaaacaaaa ccaaagagtt atgaacttct gcgcagcagc    1980
aaacctcaac gtgaagcagt atttgcccca ttatgaaact caaaaagagt ggaaatcaca    2040
ctttggcaaa agatgggaaa catttgcaca gaggaaacaa gcctacgacc tctagcgat    2100 tctagcaccc tggccaagaa tattccaaaa gacaacagga aaattatctc ccatccaact    2160
cgcaaagtca aaggcaacag gaagtcctca aaggtaccat tacgcatcaa tactgccgaa    2220
acctagaact gtataa                                                    2236
```

<210> SEQ ID NO 2
<211> LENGTH: 575
<212> TYPE: PRT
<213> ORGANISM: Arabidopsis thaliana

<400> SEQUENCE: 2

Met Gly Leu Thr Ser Ser Leu Arg Phe His Arg Gln Asn Asn Lys Thr
 1               5                  10                  15

```
Phe Leu Gly Ile Phe Met Ile Leu Val Leu Ser Cys Ile Pro Gly Arg
                20                  25                  30

Thr Asn Leu Cys Ser Asn His Ser Val Ser Thr Pro Lys Glu Leu Pro
            35                  40                  45

Ser Ser Asn Pro Ser Asp Ile Arg Ser Ser Leu Val Ser Leu Asp Leu
        50                  55                  60

Glu Gly Tyr Ile Ser Phe Asp Asp Val His Asn Val Ala Lys Asp Phe
 65                  70                  75                  80

Gly Asn Arg Tyr Gln Leu Pro Pro Leu Ala Ile Leu His Pro Arg Ser
                85                  90                  95

Val Phe Asp Ile Ser Ser Met Met Lys His Ile Val His Leu Gly Ser
            100                 105                 110

Thr Ser Asn Leu Thr Val Ala Ala Arg Gly His Gly His Ser Leu Gln
        115                 120                 125

Gly Gln Ala Leu Ala His Gln Gly Val Val Ile Lys Met Glu Ser Leu
    130                 135                 140

Arg Ser Pro Asp Ile Arg Ile Tyr Lys Gly Lys Gln Pro Tyr Val Asp
145                 150                 155                 160

Val Ser Gly Gly Glu Ile Trp Ile Asn Ile Leu Arg Glu Thr Leu Lys
                165                 170                 175

Tyr Gly Leu Ser Pro Lys Ser Trp Thr Asp Tyr Leu His Leu Thr Val
            180                 185                 190

Gly Gly Thr Leu Ser Asn Ala Gly Ile Ser Gly Gln Ala Phe Lys His
        195                 200                 205

Gly Pro Gln Ile Asn Asn Val Tyr Gln Leu Glu Ile Val Thr Gly Lys
    210                 215                 220

Gly Glu Val Val Thr Cys Ser Glu Lys Arg Asn Ser Glu Leu Phe Phe
225                 230                 235                 240

Ser Val Leu Gly Gly Leu Gly Gln Phe Gly Ile Ile Thr Arg Ala Arg
                245                 250                 255

Ile Ser Leu Glu Pro Ala Pro His Met Val Lys Trp Ile Arg Val Leu
            260                 265                 270

Tyr Ser Asp Phe Ser Ala Phe Ser Arg Asp Gln Glu Tyr Leu Ile Ser
        275                 280                 285

Lys Glu Lys Thr Phe Asp Tyr Val Glu Gly Phe Val Ile Ile Asn Arg
    290                 295                 300

Thr Asp Leu Leu Asn Asn Trp Arg Ser Ser Phe Ser Pro Asn Asp Ser
305                 310                 315                 320

Thr Gln Ala Ser Arg Phe Lys Ser Asp Gly Lys Thr Leu Tyr Cys Leu
                325                 330                 335

Glu Val Val Lys Tyr Phe Asn Pro Glu Glu Ala Ser Ser Met Asp Gln
            340                 345                 350

Glu Thr Gly Lys Leu Leu Ser Glu Leu Asn Tyr Ile Pro Ser Thr Leu
        355                 360                 365

Phe Ser Ser Glu Val Pro Tyr Ile Glu Phe Leu Asp Arg Val His Ile
    370                 375                 380

Ala Glu Arg Lys Leu Arg Ala Lys Gly Leu Trp Glu Val Pro His Pro
385                 390                 395                 400

Trp Leu Asn Leu Leu Ile Pro Lys Ser Ser Ile Tyr Gln Phe Ala Thr
                405                 410                 415

Glu Val Phe Asn Asn Ile Leu Thr Ser Asn Asn Gly Pro Ile Leu
            420                 425                 430
```

-continued

```
Ile Tyr Pro Val Asn Gln Ser Lys Trp Lys His Thr Ser Leu Ile
    435                 440                 445

Thr Pro Asn Glu Asp Ile Phe Tyr Leu Val Ala Phe Leu Pro Ser Ala
450                 455                 460

Val Pro Asn Ser Ser Gly Lys Asn Asp Leu Glu Tyr Leu Leu Lys Gln
465                 470                 475                 480

Asn Gln Arg Val Met Asn Phe Cys Ala Ala Asn Leu Asn Val Lys
                485                 490                 495

Gln Tyr Leu Pro His Tyr Glu Thr Gln Lys Glu Trp Lys Ser His Phe
            500                 505                 510

Gly Lys Arg Trp Glu Thr Phe Ala Gln Arg Lys Gln Ala Tyr Asp Pro
        515                 520                 525

Leu Ala Ile Leu Ala Pro Gly Gln Arg Ile Phe Gln Lys Thr Thr Gly
    530                 535                 540

Lys Leu Ser Pro Ile Gln Leu Ala Lys Ser Lys Ala Thr Gly Ser Pro
545                 550                 555                 560

Gln Arg Tyr His Tyr Ala Ser Ile Leu Pro Lys Pro Arg Thr Val
                565                 570                 575
```

<210> SEQ ID NO 3
<211> LENGTH: 2991
<212> TYPE: DNA
<213> ORGANISM: Arabidopsis thaliana

<400> SEQUENCE: 3

| | | |
|---|---|---|
| atggctaatc ttcgtttaat gatcactta atcacggttt taatgatcac caaatcatca | 60 |
| aacggtatta aaattgattt acctaaatcc cttaacctca ccctctctac cgatccttcc | 120 |
| atcatctccg cagcctctca tgacttcgga acataacca ccgtgacccc cggcggcgta | 180 |
| atctgcccct cctccaccgc tgatatctct cgtctcctcc aatacgccgc aaacggaaaa | 240 |
| agtacattcc aagtagcggc tcgtggccaa ggcactcct taaacggcca agcctcggtc | 300 |
| tccggcggag taatcgtcaa catgacgtgt atcactgacg tggtggtttc aaaagacaag | 360 |
| aagtacgctg acgtggcggc cgggacgtta tgggtggatg tgcttaagaa gacggcggag | 420 |
| aaaggggtgt cgccggtttc ttggacggat tatttgcata taccgtcgg aggaacgttg | 480 |
| tcgaatggtg gaattggtgg tcaagtgttt cgaaacggtc tcttgttag taacgtcctt | 540 |
| gaattggacg ttattactgg tacgcatctt ctaaactttg atgtacatac aacaacaaaa | 600 |
| actgtttttg ttttatagta ttttttcattt tttgtaccat aggttttatg tttttatagtt | 660 |
| gtgctaaact tcttgcacca cacgtaagtc ttcgaaacac aaaatgcgta acgcatctat | 720 |
| atgttttttg tacatattga atgttgttca tgagaaataa agtaattaca tatacacaca | 780 |
| tttattgtcg tacatatata aataattaaa gacaaatttt cacaattggt agcgtgttaa | 840 |
| tttgggattt tgtaatgta catgcatgac gcatgcatat ggagcttttc ggttttctta | 900 |
| gatttgtgta gtatttcaaa tatatcattt attttctttc gaataaagag gtggtatatt | 960 |
| tttaaaatag caacatttca gaattttct ttgaatttac acttttaaa ttgttattgt | 1020 |
| taatatggat tttgaataaa taatttcagg gaaaggtgaa atgttgacat gctcgcgaca | 1080 |
| gctaaaccca gaattgttct atggagtgtt aggaggtttg ggtcaattg aattataac | 1140 |
| gagagccaga attgttttgg accatgcacc taaacgggta cgtatcatca tattttacca | 1200 |
| tttgttttag tcagcattca ttttttcatta gtaattccgt ttcaattct aaatttttt | 1260 |
| agtcaataga aaatgattct tatgtcagag cttgattatt tagtgatttt tattgagata | 1320 |

```
aaataaaata taacctaacg gaaataatta tttactaat cggataatgt ctgattaaaa    1380 catttatga tattacacta agagagttag agacgtatgg atcacaaaac atgaagcttt    1440
cttagatggt atcctaaaac taaagttagg tacaagtttg gaattaggt caaatgctta    1500 agttgcatta atttgaacaa aatctatgca ttgaataaaa aaaagatatg gattatttta   1560
taaagtatag tccttgtaat cctaggactt gttgtctaat cttgtcttat gcgtgcaaat   1620
ctttttgatg tcaatatata atccttgttt attagagtca agctctttca ttagtcaact   1680
actcaaatat actccaaagt ttagaatata gtcttctgac taattagaat cttacaaccg   1740
ataaacgtta caatttggtt atcattttaa aaaacagatt tggtcataat atacgatgac   1800
gttctgtttt agtttcatct attcacaaat tttatataat tattttcaag aaaatattga   1860
aatactatac tgtaatatgg tttctttata tatgtgtgta taaattaaat gggattgttt   1920
tctctaaatg aaattgtgta ggccaaatgg tttcggatgc tctacagtga tttcacaact   1980
tttacaaagg accaagaacg tttgatatca atggcaaacg atattggagt cgactattta   2040
gaaggtcaaa tatttctatc aaacggtgtc gttgacacct cttttttccc accttcagat   2100
caatctaaag tcgctgatct agtcaagcaa cacggtatca tctatgttct tgaagtagcc   2160
aagtattatg atgatcccaa tctccccatc atcagcaagg tactacacat ttacattttc   2220
atcatcgttt ttatcatacc ataagatatt taaatgattc atcattgcac acattaaga   2280 tattcatcat catcatcgtt acattttttt ttgcatctta tgcttctcat aatctactat   2340
tgtgtaggtt attgacacat taacgaaaac attaagttac ttgcccgggt tcatatcaat   2400
gcacgacgtg gcctacttcg atttcttgaa ccgtgtacat gtcgaagaaa ataaactcag   2460
atctttggga ttatgggaac ttcctcatcc ttggcttaac ctctacgttc ctaaatctcg   2520
gattctcgat tttcataacg gtgttgtcaa agacattctt cttaagcaaa aatcagcttc   2580
gggactcgct cttctctatc caacaaaccg gaataagtac atacttctct tcattcatat   2640
ttatcttcaa gaaccaaagt aaataaattt ctatgaactg attatgctgt tattgttaga   2700
tgggacaatc gtatgtcggc gatgatacca gagatcgatg aagatgttat atatattatc   2760
ggactactac aatccgctac cccaaaggat cttccagaag tggagagcgt taacgagaag   2820
ataattaggt tttgcaagga ttcaggtatt aagattaagc aatatctaat gcattatact   2880
agtaaagaag attggattga gcattttgga tcaaaatggg atgattttc gaagaggaaa    2940 gatctatttg atcccaagaa actgttatct ccagggcaag acatctttg a              2991
```

<210> SEQ ID NO 4
<211> LENGTH: 501
<212> TYPE: PRT
<213> ORGANISM: Arabidopsis thaliana

<400> SEQUENCE: 4

```
Met Ala Asn Leu Arg Leu Met Ile Thr Leu Ile Thr Val Leu Met Ile
  1               5                  10                  15

Thr Lys Ser Ser Asn Gly Ile Lys Ile Asp Leu Pro Lys Ser Leu Asn
             20                  25                  30

Leu Thr Leu Ser Thr Asp Pro Ser Ile Ile Ser Ala Ala Ser His Asp
         35                  40                  45

Phe Gly Asn Ile Thr Thr Val Thr Pro Gly Gly Val Ile Cys Pro Ser
     50                  55                  60

Ser Thr Ala Asp Ile Ser Arg Leu Leu Gln Tyr Ala Ala Asn Gly Lys
 65                  70                  75                  80
```

-continued

```
Ser Thr Phe Gln Val Ala Ala Arg Gly Gln Gly His Ser Leu Asn Gly
                85                  90                  95
Gln Ala Ser Val Ser Gly Gly Val Ile Val Asn Met Thr Cys Ile Thr
            100                 105                 110
Asp Val Val Ser Lys Asp Lys Lys Tyr Ala Asp Val Ala Ala Gly
        115                 120                 125
Thr Leu Trp Val Asp Val Leu Lys Lys Thr Ala Glu Lys Gly Val Ser
    130                 135                 140
Pro Val Ser Trp Thr Asp Tyr Leu His Ile Thr Val Gly Gly Thr Leu
145                 150                 155                 160
Ser Asn Gly Gly Ile Gly Gly Gln Val Phe Arg Asn Gly Pro Leu Val
                165                 170                 175
Ser Asn Val Leu Glu Leu Asp Val Ile Thr Gly Lys Gly Glu Met Leu
            180                 185                 190
Thr Cys Ser Arg Gln Leu Asn Pro Glu Leu Phe Tyr Gly Val Leu Gly
        195                 200                 205
Gly Leu Gly Gln Phe Gly Ile Ile Thr Arg Ala Arg Ile Val Leu Asp
    210                 215                 220
His Ala Pro Lys Arg Ala Lys Trp Phe Arg Met Leu Tyr Ser Asp Phe
225                 230                 235                 240
Thr Thr Phe Thr Lys Asp Gln Glu Arg Leu Ile Ser Met Ala Asn Asp
                245                 250                 255
Ile Gly Val Asp Tyr Leu Glu Gly Gln Ile Phe Leu Ser Asn Gly Val
            260                 265                 270
Val Asp Thr Ser Phe Phe Pro Ser Asp Gln Ser Lys Val Ala Asp
        275                 280                 285
Leu Val Lys Gln His Gly Ile Ile Tyr Val Leu Glu Val Ala Lys Tyr
    290                 295                 300
Tyr Asp Asp Pro Asn Leu Pro Ile Ile Ser Lys Val Ile Asp Thr Leu
305                 310                 315                 320
Thr Lys Thr Leu Ser Tyr Leu Pro Gly Phe Ile Ser Met His Asp Val
                325                 330                 335
Ala Tyr Phe Asp Phe Leu Asn Arg Val His Val Glu Glu Asn Lys Leu
            340                 345                 350
Arg Ser Leu Gly Leu Trp Glu Leu Pro His Pro Trp Leu Asn Leu Tyr
        355                 360                 365
Val Pro Lys Ser Arg Ile Leu Asp Phe His Asn Gly Val Val Lys Asp
    370                 375                 380
Ile Leu Leu Lys Gln Lys Ser Ala Ser Gly Leu Ala Leu Leu Tyr Pro
385                 390                 395                 400
Thr Asn Arg Asn Lys Trp Asp Asn Arg Met Ser Ala Met Ile Pro Glu
                405                 410                 415
Ile Asp Glu Asp Val Ile Tyr Ile Ile Gly Leu Leu Gln Ser Ala Thr
            420                 425                 430
Pro Lys Asp Leu Pro Glu Val Glu Ser Val Asn Glu Lys Ile Ile Arg
        435                 440                 445
Phe Cys Lys Asp Ser Gly Ile Lys Ile Lys Gln Tyr Leu Met His Tyr
    450                 455                 460
Thr Ser Lys Glu Asp Trp Ile Glu His Phe Gly Ser Lys Trp Asp Asp
465                 470                 475                 480
Phe Ser Lys Arg Lys Asp Leu Phe Asp Pro Lys Lys Leu Leu Ser Pro
                485                 490                 495
Gly Gln Asp Ile Phe
```

<210> SEQ ID NO 5
<211> LENGTH: 3302
<212> TYPE: DNA
<213> ORGANISM: Arabidopsis thaliana

<400> SEQUENCE: 5

| | | | | | |
|---|---|---|---|---|---|
| atggcgagtt | ataatcttcg | ttcacaagtt | cgtcttatag | caataacaat | agtaatcatc | 60 |
| attactctct | caactccgat | cacaaccaac | acatcaccac | aaccatggaa | tatcctttca | 120 |
| cacaacgaat | tcgccggaaa | actcacctcc | tcctcctcct | ccgtcgaatc | agccgccaca | 180 |
| gatttcggcc | acgtcaccaa | aatcttccct | tccgccgtct | taatcccttc | ctccgttgaa | 240 |
| gacatcacag | atctcataaa | actctctttt | gactctcaac | tgtctttcc | tttagccgct | 300 |
| cgtggtcacg | gacacagcca | ccgtggccaa | gcctcggcta | agacggagt | tgtggtcaac | 360 |
| atgcggtcca | tggtaaaccg | ggatcgaggt | atcaaggtgt | ctaggacctg | tttatatgtt | 420 |
| gacgtggacg | ctgcgtggct | atggattgag | gtgttgaata | aaactttgga | gttagggtta | 480 |
| acgccggttt | cttggacgga | ttatttgtat | ttaacagtcg | gtgggacgtt | atcaaacggc | 540 |
| ggaattagtg | acaaacgtt | tcggtacggt | ccacagatca | ctaatgttct | agagatggat | 600 |
| gttattactg | gtacgtacca | cgatcttttt | cacacagaga | ttaaaaaaaa | cagtaatagt | 660 |
| gattttaact | tcgtacgttt | ctgatagaca | acaagaact | tcgtacgttt | ttcgaagttt | 720 |
| tttcgtcttt | ttcattttag | atctgcgcgg | ccatttttgg | ttatgctatt | gtttgttttgt | 780 |
| attgtttgtc | tctgtttatt | tatttctcga | acttgttgat | agcttttctt | cttttcacac | 840 |
| atcaatctaa | tcaccttttt | tggtcttaag | attagaaaga | agatacggac | taggtaaaaa | 900 |
| taggtggttg | taaacgtaga | cgcattaaaa | aaatattggt | ttttttattt | tttgataagc | 960 |
| aaaattggtg | gttggtctaa | gattataaac | ttgatattaa | tgcaaaggtc | gatctagcaa | 1020 |
| tagaagatta | atcaatattc | ttggtgtttt | aacaacagat | tatttcatca | ttaaaatcgt | 1080 |
| gaaacaaaga | aatttggta | gtatacatta | cgtgtagttt | tgttagttta | ttaaaaaaaa | 1140 |
| tagtatatag | ttttgttaaa | acgcgattta | tttagtaaca | cattagtata | ttacacgttt | 1200 |
| aaccaactaa | acttttttttt | ttgaataatt | atgttctata | tttcttactc | aaattatgca | 1260 |
| aatttcgtgg | attcgaagtc | aaatttctgc | gaaatttaca | tggtcatata | ttataaaact | 1320 |
| gttcatataa | cccggtgaac | aaacagacaa | ttaagggttt | gaatggttac | ggcggttggg | 1380 |
| gcggacacaa | ccgtcaatag | atcagaccgt | tttttattta | ccattcatca | attatattcc | 1440 |
| gcagtggttt | ggggtaaaaa | aaatagaaga | aaaccgcagc | ggaccaattc | cataccgttt | 1500 |
| ttacatacaa | ataaacatgg | tgcgcaacgg | tttattgtcc | gcctcaaaaa | tgaaatggac | 1560 |
| taaaccgcag | ataaattaga | ccgctttgtc | cgctgcctcc | attcatagac | taaaaaaaaa | 1620 |
| caaccaaaaa | aaaaatggtc | ccacgcccat | gattttacac | gaggtttctt | gtggcgtaag | 1680 |
| gacaaaactc | aaaagttcat | aacgtttggt | cctaaccagg | tgtaatggat | taagtaacag | 1740 |
| tcaattttct | tattatagct | gtatccatta | tgtccacata | tgcatccata | tacattacac | 1800 |
| tgttggtctc | aagtgtagtt | agattacgaa | gactttcaag | ttccattttt | tggttaggag | 1860 |
| ataaacataa | tttaatgata | ccgactttag | cactctaggc | tcaaacaag | tacagaagag | 1920 |
| aatagtttta | tttcaaactc | gttgcattgt | tgtatcaatt | aattgtgtta | gtctttgtat | 1980 |
| attcttacat | aacggtccaa | gtttgttgaa | atagtttact | tactaaactt | ttcctaatgg | 2040 |
| ggtcaaattt | tattttatag | gaaaaggaga | gattgcaact | tgttccaagg | acatgaactc | 2100 |

-continued

```
ggatcttttc ttcgcggtgt taggaggttt gggtcaattc ggcattataa caagagccag    2160
aattaaactt gaagtagctc cgaaaagggt atgttaaatt tgtaaattat gcaactacag    2220
aaaattctat gaaatttatg aatgaacata tatgcatttt tggatttttg taggccaagt    2280
ggttaaggtt tctatacata gatttctccg aattcacaag agatcaagaa cgagtgatat    2340
cgaaaacgga cggtgtagat ttcttagaag gttccattat ggtggaccat ggcccaccgg    2400
ataactggag atccacgtat tatccaccgt ccgatcactt gaggatcgcc tcaatggtca    2460
aacgacatcg tgtcatctac tgccttgaag tcgtcaagta ttacgacgaa acttctcaat    2520
acacagtcaa cgaggtccgt acatacatac aatcataaat catacatgta taattgggag    2580
atctttatgc attattcaat tatattaatt tactttagtt atttaactta tgcaggaaat    2640
ggaggagtta agcgatagtt taaccatgt aagagggttt atgtacgaga agatgtgac     2700 gtatatggat ttcctaaacc gagttcgaac cggagagcta aacctgaaat ccaaaggcca    2760
atgggatgtt ccacatccat ggcttaatct cttcgtacca aaaactcaaa tctccaaatt    2820
tgatgatggt gttttaagg gtattatcct aagaaataac atcactagcg gtcctgttct     2880
tgtttatcct atgaatcgca acaagtaagt ttaactcgat attgcaaaat ttactatcta    2940
cattttcgtt ttggaatccg aaatattctt acaagctaat tttatgcggc gtttttaggt    3000
ggaatgatcg gatgtctgcc gctatacccg aggaagatgt attttatgcg gtagggtttt    3060
taagatccgc gggttttgac aattgggagg cttttgatca agaaaacatg gaaatactga    3120
agttttgtga ggatgctaat atgggggtta tacaatatct tccttatcat tcatcacaag    3180
aaggatgggt tagacatttt ggtccgaggt ggaatatttt cgtagagaga aaatataaat    3240
atgatcccaa aatgatatta tcaccgggac aaaatatatt tcaaaaaata aactcgagtt    3300
ag                                                                   3302
```

<210> SEQ ID NO 6
<211> LENGTH: 523
<212> TYPE: PRT
<213> ORGANISM: Arabidopsis thaliana

<400> SEQUENCE: 6

```
Met Ala Ser Tyr Asn Leu Arg Ser Gln Val Arg Leu Ile Ala Ile Thr
  1               5                  10                  15

Ile Val Ile Ile Ile Thr Leu Ser Thr Pro Ile Thr Thr Asn Thr Ser
                 20                  25                  30

Pro Gln Pro Trp Asn Ile Leu Ser His Asn Glu Phe Ala Gly Lys Leu
             35                  40                  45

Thr Ser Ser Ser Ser Val Glu Ser Ala Ala Thr Asp Phe Gly His
         50                  55                  60

Val Thr Lys Ile Phe Pro Ser Ala Val Leu Ile Pro Ser Ser Val Glu
 65                  70                  75                  80

Asp Ile Thr Asp Leu Ile Lys Leu Ser Phe Asp Ser Gln Leu Ser Phe
                 85                  90                  95

Pro Leu Ala Ala Arg Gly His Gly His Ser His Arg Gly Gln Ala Ser
            100                 105                 110

Ala Lys Asp Gly Val Val Val Asn Met Arg Ser Met Val Asn Arg Asp
        115                 120                 125

Arg Gly Ile Lys Val Ser Arg Thr Cys Leu Tyr Val Asp Val Asp Ala
    130                 135                 140

Ala Trp Leu Trp Ile Glu Val Leu Asn Lys Thr Leu Glu Leu Gly Leu
```

```
                    145                 150                 155                 160
Thr Pro Val Ser Trp Thr Asp Tyr Leu Tyr Leu Thr Val Gly Gly Thr
                165                 170                 175

Leu Ser Asn Gly Gly Ile Ser Gly Gln Thr Phe Arg Tyr Gly Pro Gln
            180                 185                 190

Ile Thr Asn Val Leu Glu Met Asp Val Ile Thr Gly Lys Gly Glu Ile
            195                 200                 205

Ala Thr Cys Ser Lys Asp Met Asn Ser Asp Leu Phe Phe Ala Val Leu
        210                 215                 220

Gly Gly Leu Gly Gln Phe Gly Ile Ile Thr Arg Ala Arg Ile Lys Leu
225                 230                 235                 240

Glu Val Ala Pro Lys Arg Ala Lys Trp Leu Arg Phe Leu Tyr Ile Asp
                245                 250                 255

Phe Ser Glu Phe Thr Arg Asp Gln Glu Arg Val Ile Ser Lys Thr Asp
                260                 265                 270

Gly Val Asp Phe Leu Glu Gly Ser Ile Met Val Asp His Gly Pro Pro
            275                 280                 285

Asp Asn Trp Arg Ser Thr Tyr Tyr Pro Pro Ser Asp His Leu Arg Ile
        290                 295                 300

Ala Ser Met Val Lys Arg His Arg Val Ile Tyr Cys Leu Glu Val Val
305                 310                 315                 320

Lys Tyr Tyr Asp Glu Thr Ser Gln Tyr Thr Val Asn Glu Glu Met Glu
                325                 330                 335

Glu Leu Ser Asp Ser Leu Asn His Val Arg Gly Phe Met Tyr Glu Lys
            340                 345                 350

Asp Val Thr Tyr Met Asp Phe Leu Asn Arg Val Arg Thr Gly Glu Leu
            355                 360                 365

Asn Leu Lys Ser Lys Gly Gln Trp Asp Val Pro His Pro Trp Leu Asn
        370                 375                 380

Leu Phe Val Pro Lys Thr Gln Ile Ser Lys Phe Asp Asp Gly Val Phe
385                 390                 395                 400

Lys Gly Ile Ile Leu Arg Asn Asn Ile Thr Ser Gly Pro Val Leu Val
                405                 410                 415

Tyr Pro Met Asn Arg Asn Lys Trp Asn Asp Arg Met Ser Ala Ala Ile
            420                 425                 430

Pro Glu Glu Asp Val Phe Tyr Ala Val Gly Phe Leu Arg Ser Ala Gly
        435                 440                 445

Phe Asp Asn Trp Glu Ala Phe Asp Gln Glu Asn Met Glu Ile Leu Lys
        450                 455                 460

Phe Cys Glu Asp Ala Asn Met Gly Val Ile Gln Tyr Leu Pro Tyr His
465                 470                 475                 480

Ser Ser Gln Glu Gly Trp Val Arg His Phe Gly Pro Arg Trp Asn Ile
                485                 490                 495

Phe Val Glu Arg Lys Tyr Lys Tyr Asp Pro Lys Met Ile Leu Ser Pro
            500                 505                 510

Gly Gln Asn Ile Phe Gln Lys Ile Asn Ser Ser
        515                 520

<210> SEQ ID NO 7
<211> LENGTH: 2782
<212> TYPE: DNA
<213> ORGANISM: Arabidopsis thaliana

<400> SEQUENCE: 7
```

```
atgactaata ctctctgttt aagcctcatc accctaataa cgcttttat aagtttaacc      60
ccaaccttaa tcaaatcaga tgagggcatt gatgttttct tacccatatc actcaacctt     120
acggtcctaa ccgatccctt ctccatctct gccgcttctc acgacttcgg taacataacc     180
gacgaaaatc ccggcgccgt cctctgccct tcctccacca cggaggtggc tcgtctcctc     240
cgtttcgcta acggaggatt ctcttacaat aaaggctcaa ccagcccgc gtctactttc      300
aaagtggctg ctcgaggcca aggccactcc ctccgtggcc aagcctctgc acccggaggt     360
gtcgtcgtga acatgacgtg tctcgccatg gcggctaaac cagcggcggt tgttatctcg     420
gcagacggga cttacgctga cgtggctgcc gggacgatgt gggtggatgt tctgaaggcg     480
gcggtggata gaggcgtctc gccggttaca tggacggatt atttgtatct cagcgtcggc     540
gggacgttgt cgaacgctgg aatcggtggt cagacgttta gacacggccc tcagattagt     600
aacgttcatg agcttgacgt tattaccggt acgtaaatac caaaacttca ctaatctcgt     660
tacaattttt taatttttttg gtaatataaa ttttgtacgg ctcaactctt aattaagaat    720
gaaacagtat ctatgatctt ctagatgctc tttttttgtc tgcaagcttt aattgtagta    780
acatcagcga tatatatatc acatgcatgt gtattattga tgataatata taatgttta     840
gttacaaatt tgattctcaa ggtaaaactc acacgccata accagtataa aactccaaaa    900
atcacgtttt ggtcagaaat acatatcctt cattaacagt agttatgcta aatttgtga    960
ttataaataa ctccggagtt tgttcacaat actaaatttc aggaaaaggt gaaatgatga   1020
cttgctctcc aaagttaaac cctgaattgt tctatggagt tttaggaggt ttgggtcaat   1080
tcggtattat aacgagggcc aggattgcgt tggatcatgc acccacaagg gtatgtatca   1140
tgcatctata gtgtaatcaa tttataattt taatgtagtg gtcctaaatc caaaatttga   1200
tttgatttgg ttggaacgta cgtatatata ataagtcaaa aggctgattt tgaagacgaa   1260
tttatatact tttgttgaat taaatctgat tttgcttacg ttttattaga ttctgcgtaa   1320
taaatcctag gacttgctcg agtgtaatct tgtcttatgc ttgcaaatct tgttgatgtc   1380
aatatctaat cttttttatt atatttccct acgtaagttt tagatatagt tattttaaac   1440
tgctataaat tgtgtacgta tagactttag ataaaaagtt gtggtcgctt gcacctattt   1500
gtttatcgct atagtgattc aaaggtctat atatgattct tggttttct tttttgaaaaa   1560
aatagaccat acaatccaag gaagatgatc ttaaatggac taatttatgg atataaattg   1620
atatacaaat ctgcaggtga atggtctcg catactctac agtgacttct cggcttttaa    1680
aagagaccaa gagcgtttaa tatcaatgac caatgatctc ggagttgact ttttggaagg   1740
tcaacttatg atgtcaaatg gcttcgtaga cacctctttc ttcccactct ccgatcaaac   1800
aagagtcgca tctcttgtga atgaccaccg gatcatctat gttctcgaag tagccaagta   1860
ttatgacaga accacccttc ccattattga ccaggtacta aaatccatta ttcatgatga   1920
ttatcttcac acaatcagta tcatccacaa ttaccatcat cacttgtcat atatgatcca   1980
aagtaaatat atcacatgat ataaataaat cgttcaaatc tttttttta aagaataaaa    2040
gaatcatttt caagcattac tcatacacat ctacgaatca ccgtgaccat atataaccat   2100
acgcttatta aataatcatt tttgtttgta ggtgattgac acgttaagta gaactctagg   2160
tttcgctcca gggtttatgt tcgtacaaga tgttccgtat ttcgatttct tgaaccgtgt   2220
ccgaaacgaa gaagataaac tcagatcttt aggactatgg gaagttcctc atccatggct   2280
taacatcttt gtcccggggt ctcgaatcca agattttcat gatggtgtta ttaatggcct   2340
tcttctaaac caaacctcaa cttctggtgt tactctcttc tatcccacaa accgaaacaa   2400
```

```
gtaaatattt acttttttgat tttgttttat ttgaaagtat atcccaataa tgtatgttaa    2460
attgttaaca agaatttatt ttattaatag atggaacaac cgcatgtcaa cgatgacacc    2520
ggacgaagat gtttttatg tgatcggatt actgcaatca gctggtggat ctcaaaattg    2580
gcaagaactt gaaatctca acgacaaggt tattcagttt tgtgaaaact cgggaattaa    2640
gattaaggaa tatttgatgc actatacaag aaaagaagat tgggttaaac attttggacc    2700
aaaatgggat gatttttaa gaaagaaaat tatgtttgat cccaaaagac tattgtctcc    2760
aggacaagac atatttaatt aa                                              2782
```

<210> SEQ ID NO 8
<211> LENGTH: 524
<212> TYPE: PRT
<213> ORGANISM: Arabidopsis thaliana

<400> SEQUENCE: 8

```
Met Thr Asn Thr Leu Cys Leu Ser Leu Ile Thr Leu Ile Thr Leu Phe
 1               5                  10                  15

Ile Ser Leu Thr Pro Thr Leu Ile Lys Ser Asp Glu Gly Ile Asp Val
                20                  25                  30

Phe Leu Pro Ile Ser Leu Asn Leu Thr Val Leu Thr Asp Pro Phe Ser
            35                  40                  45

Ile Ser Ala Ala Ser His Asp Phe Gly Asn Ile Thr Asp Glu Asn Pro
        50                  55                  60

Gly Ala Val Leu Cys Pro Ser Ser Thr Thr Glu Val Ala Arg Leu Leu
 65                  70                  75                  80

Arg Phe Ala Asn Gly Gly Phe Ser Tyr Asn Lys Gly Ser Thr Ser Pro
                 85                  90                  95

Ala Ser Thr Phe Lys Val Ala Ala Arg Gly Gln Gly His Ser Leu Arg
            100                 105                 110

Gly Gln Ala Ser Ala Pro Gly Gly Val Val Val Asn Met Thr Cys Leu
        115                 120                 125

Ala Met Ala Ala Lys Pro Ala Ala Val Val Ile Ser Ala Asp Gly Thr
    130                 135                 140

Tyr Ala Asp Val Ala Ala Gly Thr Met Trp Val Asp Val Leu Lys Ala
145                 150                 155                 160

Ala Val Asp Arg Gly Val Ser Pro Val Thr Trp Thr Asp Tyr Leu Tyr
                165                 170                 175

Leu Ser Val Gly Gly Thr Leu Ser Asn Ala Gly Ile Gly Gly Gln Thr
            180                 185                 190

Phe Arg His Gly Pro Gln Ile Ser Asn Val His Glu Leu Asp Val Ile
        195                 200                 205

Thr Gly Lys Gly Glu Met Met Thr Cys Ser Pro Lys Leu Asn Pro Glu
    210                 215                 220

Leu Phe Tyr Gly Val Leu Gly Gly Leu Gly Gln Phe Gly Ile Ile Thr
225                 230                 235                 240

Arg Ala Arg Ile Ala Leu Asp His Ala Pro Thr Arg Val Lys Trp Ser
                245                 250                 255

Arg Ile Leu Tyr Ser Asp Phe Ser Ala Phe Lys Arg Asp Gln Glu Arg
            260                 265                 270

Leu Ile Ser Met Thr Asn Asp Leu Gly Val Asp Phe Leu Glu Gly Gln
        275                 280                 285

Leu Met Met Ser Asn Gly Phe Val Asp Thr Ser Phe Phe Pro Leu Ser
    290                 295                 300
```

```
Asp Gln Thr Arg Val Ala Ser Leu Val Asn Asp His Arg Ile Ile Tyr
305                 310                 315                 320

Val Leu Glu Val Ala Lys Tyr Tyr Asp Arg Thr Thr Leu Pro Ile Ile
                325                 330                 335

Asp Gln Val Ile Asp Thr Leu Ser Arg Thr Leu Gly Phe Ala Pro Gly
                340                 345                 350

Phe Met Phe Val Gln Asp Val Pro Tyr Phe Asp Phe Leu Asn Arg Val
            355                 360                 365

Arg Asn Glu Glu Asp Lys Leu Arg Ser Leu Gly Leu Trp Glu Val Pro
        370                 375                 380

His Pro Trp Leu Asn Ile Phe Val Pro Gly Ser Arg Ile Gln Asp Phe
385                 390                 395                 400

His Asp Gly Val Ile Asn Gly Leu Leu Leu Asn Gln Thr Ser Thr Ser
                405                 410                 415

Gly Val Thr Leu Phe Tyr Pro Thr Asn Arg Asn Lys Trp Asn Asn Arg
            420                 425                 430

Met Ser Thr Met Thr Pro Asp Glu Asp Val Phe Tyr Val Ile Gly Leu
        435                 440                 445

Leu Gln Ser Ala Gly Gly Ser Gln Asn Trp Gln Glu Leu Glu Asn Leu
450                 455                 460

Asn Asp Lys Val Ile Gln Phe Cys Glu Asn Ser Gly Ile Lys Ile Lys
465                 470                 475                 480

Glu Tyr Leu Met His Tyr Thr Arg Lys Glu Asp Trp Val Lys His Phe
                485                 490                 495

Gly Pro Lys Trp Asp Asp Phe Leu Arg Lys Lys Ile Met Phe Asp Pro
            500                 505                 510

Lys Arg Leu Leu Ser Pro Gly Gln Asp Ile Phe Asn
            515                 520
```

<210> SEQ ID NO 9
<211> LENGTH: 2805
<212> TYPE: DNA
<213> ORGANISM: Arabidopsis thaliana

<400> SEQUENCE: 9

```
atgacgtcaa gctttcttct cctgacgttc gccatatgta aactgatcat agccgtgggt    60
ctaaacgtgg gccccagtga gctcctccgc atcggagcca tagatgtcga cggccacttc   120
accgtccacc cttccgactt agcctccgtc tcctcagact tcggtatgct gaagtcacct   180
gaagagccat ggccgtgctc tcatccatca tcggccgaag acgtggcacg actcgtcaga   240
acagcttacg gttcagccac ggcgtttccg gtctcagccc gaggccacgg ccattccata   300
aacggacaag ccgcggcggg gaggaacggt gtggtggttg aaatgaacca cggcgtaacc   360
gggacgccca gccactcgt ccgaccggat gaaatgtatg tggatgtatg gggtggagag   420
ttatgggtcg atgtgttgaa gaaaacgttg gagcatggct agcaccaaa atcatggacg   480
gattacttgt atctaaccgt tggaggtaca ctctccaatg caggaatcag tggtcaagct   540
tttcaccatg gtcctcaaat tagtaacgtc cttgagctcg acgttgtaac tggttagtat   600
taaaacattc aagttcatat attttaaatg cttttgtctg aagttttact aataacaaga   660
aattgatacc aaaaagtagg gaaggagag gtgatgagat gctcagaaga agagaacaca   720
aggctattcc atggagttct tggtggatta ggtcaatttg ggatcatcac tcgagcacga   780
atctctctcg aaccagctcc ccaaagggta atattttttt aatgactagc tatcaaaaat   840
```

```
ccctggcggg tccatacgtt gtaatctttt tagtttttac tgttgatggt attttttata    900
tattttggat aataaaaccc taaaatggta tattgtgatg acaggtgaga tggatacggg    960
tattgtattc gagcttcaaa gtgtttacgg aggaccaaga gtacttaatc tcaatgcatg   1020
gtcaattaaa gtttgattac gtggaaggtt ttgtgattgt ggacgaagga ctcgtcaaca   1080
attggagatc ttctttcttc tctccacgta accccgtcaa gatctcctct gttagttcca   1140
acggctctgt tttgtattgc cttgagatca ccaagaacta ccacgactcc gactccgaaa   1200
tcgttgatca ggtcactttc attattcact tagaaaaaag cgatattttc attttttata   1260
ttgatgaata tctggaagga tttaacgcta tgcgactatt gggaaatcat tatgaaaaaa   1320
tatttagttt atatgattga aagtggtctc catagtattt tgttgtgtc gactttatta   1380
taacttaaat ttggaagagg acatgaagaa gaagccagag aggatctaca gagatctagc   1440
ttttccacct gaacttaata atgcacattt ataaattat ttttcttctt ctaaagttta   1500
gtttatcact agcgaattaa tcatggttac taattaagta gtggacaggg tcatggacca   1560
ctcactcacc aaataatgat tcctctttac tcttaagttt aattttaata aaaccaactc   1620
tactggaatc ttaacttatc cttggttttg gtaggctttt atagcaacac ggtttttta   1680
attttcctat tccagatttt gtatattaaa tgtcgatttt ttttcttttt gtttcaggaa   1740
gttgagattc tgatgaagaa attgaatttc ataccgacat cggtctttac aacggattta   1800
caatatgtgg actttctcga ccgggtacac aaggccgaat gaagctccg gtccaagaat   1860
ttatgggagg ttccacaccc atggctcaac ctcttcgtgc caaaatcaag aatctctgac   1920
ttcgataaag gcgttttcaa gggcattttg ggaaataaaa caagtggccc tattcttatc   1980
taccccatga acaaagacaa gtaagtcttg acattaccat tgattactac ttctaaattt   2040
cttctctaga aaaagaata aaacgagttt tgcattgcat gcatgcaaag ttacacttgt   2100
ggggattaat tagtggtcca agaaaaaaag tttgtcaaaa ttgaaaaaaa ctagacacgt   2160
ggtacatggg attgtccgaa aaacgttgtc cacatgtgca tcgaaccagc taagattgac   2220
aacaacactt cgtcggctcg tatttctctt tttgttttgt gaccaaatcc gatggtccag   2280
attgggttta tttgttttta agttcctaga actcatggtg ggtgggtccc aatcagattc   2340
tcctagacca aaccgatctc aacgaaccct ccgcacatca ttgattatta cattaatata   2400
gatattgtcg ttgctgacgt gtcgtaattt gatgttattg tcagatggga cgagaggagc   2460
tcagccgtga cgccggatga ggaagttttc tatctggtgg ctctattgag atcagcttta   2520
acggacggtg aagagacaca gaagctagag tatctgaaag atcagaaccg tcggatcttg   2580
gagttctgtg aacaagccaa gatcaatgtg aagcagtatc ttcctcacca cgcaacacag   2640
gaagagtggg tggctcattt tggggacaag tgggatcggt tcagaagctt aaaggctgag   2700
tttgatccgc gacacatact cgctactggt cagagaatct ttcaaaaccc atctttgtct   2760
ttgtttcctc cgtcgtcgtc ttcttcgtca gcggcttcat ggtga             2805
```

<210> SEQ ID NO 10
<211> LENGTH: 536
<212> TYPE: PRT
<213> ORGANISM: Arabidopsis thaliana

<400> SEQUENCE: 10

```
Met Thr Ser Ser Phe Leu Leu Leu Thr Phe Ala Ile Cys Lys Leu Ile
 1               5                  10                  15

Ile Ala Val Gly Leu Asn Val Gly Pro Ser Glu Leu Leu Arg Ile Gly
            20                  25                  30
```

```
Ala Ile Asp Val Asp Gly His Phe Thr Val His Pro Ser Asp Leu Ala
         35                  40                  45

Ser Val Ser Ser Asp Phe Gly Met Leu Lys Ser Pro Glu Glu Pro Leu
     50                  55                  60

Ala Val Leu His Pro Ser Ser Ala Glu Asp Val Ala Arg Leu Val Arg
 65                  70                  75                  80

Thr Ala Tyr Gly Ser Ala Thr Ala Phe Pro Val Ser Ala Arg Gly His
             85                  90                  95

Gly His Ser Ile Asn Gly Gln Ala Ala Ala Gly Arg Asn Gly Val Val
            100                 105                 110

Val Glu Met Asn His Gly Val Thr Gly Thr Pro Lys Pro Leu Val Arg
        115                 120                 125

Pro Asp Glu Met Tyr Val Asp Val Trp Gly Gly Leu Trp Val Asp
        130                 135                 140

Val Leu Lys Lys Thr Leu Glu His Gly Leu Ala Pro Lys Ser Trp Thr
145                 150                 155                 160

Asp Tyr Leu Tyr Leu Thr Val Gly Gly Thr Leu Ser Asn Ala Gly Ile
                165                 170                 175

Ser Gly Gln Ala Phe His His Gly Pro Gln Ile Ser Asn Val Leu Glu
            180                 185                 190

Leu Asp Val Val Thr Gly Lys Gly Glu Val Met Arg Cys Ser Glu Glu
        195                 200                 205

Glu Asn Thr Arg Leu Phe His Gly Val Leu Gly Gly Leu Gly Gln Phe
        210                 215                 220

Gly Ile Ile Thr Arg Ala Arg Ile Ser Leu Glu Pro Ala Pro Gln Arg
225                 230                 235                 240

Val Arg Trp Ile Arg Val Leu Tyr Ser Ser Phe Lys Val Phe Thr Glu
                245                 250                 255

Asp Gln Glu Tyr Leu Ile Ser Met His Gly Gln Leu Lys Phe Asp Tyr
            260                 265                 270

Val Glu Gly Phe Val Ile Val Asp Glu Gly Leu Val Asn Asn Trp Arg
        275                 280                 285

Ser Ser Phe Phe Ser Pro Arg Asn Pro Val Lys Ile Ser Ser Val Ser
        290                 295                 300

Ser Asn Gly Ser Val Leu Tyr Cys Leu Glu Ile Thr Lys Asn Tyr His
305                 310                 315                 320

Asp Ser Asp Ser Glu Ile Val Asp Gln Glu Val Glu Ile Leu Met Lys
                325                 330                 335

Lys Leu Asn Phe Ile Pro Thr Ser Val Phe Thr Thr Asp Leu Gln Tyr
            340                 345                 350

Val Asp Phe Leu Asp Arg Val His Lys Ala Glu Leu Lys Leu Arg Ser
        355                 360                 365

Lys Asn Leu Trp Glu Val Pro His Pro Trp Leu Asn Leu Phe Val Pro
        370                 375                 380

Lys Ser Arg Ile Ser Asp Phe Asp Lys Gly Val Phe Lys Gly Ile Leu
385                 390                 395                 400

Gly Asn Lys Thr Ser Gly Pro Ile Leu Ile Tyr Pro Met Asn Lys Asp
                405                 410                 415

Lys Trp Asp Glu Arg Ser Ser Ala Val Thr Pro Asp Glu Glu Val Phe
            420                 425                 430

Tyr Leu Val Ala Leu Leu Arg Ser Ala Leu Thr Asp Gly Glu Glu Thr
        435                 440                 445
```

```
Gln Lys Leu Glu Tyr Leu Lys Asp Gln Asn Arg Arg Ile Leu Glu Phe
    450                 455                 460

Cys Glu Gln Ala Lys Ile Asn Val Lys Gln Tyr Leu Pro His His Ala
465                 470                 475                 480

Thr Gln Glu Glu Trp Val Ala His Phe Gly Asp Lys Trp Asp Arg Phe
                485                 490                 495

Arg Ser Leu Lys Ala Glu Phe Asp Pro Arg His Ile Leu Ala Thr Gly
            500                 505                 510

Gln Arg Ile Phe Gln Asn Pro Ser Leu Ser Leu Phe Pro Pro Ser Ser
        515                 520                 525

Ser Ser Ser Ala Ala Ser Trp
    530             535

<210> SEQ ID NO 11
<211> LENGTH: 1936
<212> TYPE: DNA
<213> ORGANISM: Arabidopsis thaliana

<400> SEQUENCE: 11
```

| | | | | | |
|---|---|---|---|---|---|
| atgcttatag | taagaagttt | caccatcttg | cttctcagct | gcatagcctt | taagttggct | 60 |
| tgctgcttct | ctagcagcat | ttcttctttg | aaggcgcttc | ccctagtagg | ccatttggag | 120 |
| tttgaacatg | tccatcacgc | ctccaaagat | tttggaaatc | gataccagtt | gatcccttg | 180 |
| gcggtcttac | atcccaaatc | ggtaagcgac | atcgcctcaa | cgatacgaca | catctggatg | 240 |
| atgggcactc | attcacagct | tacagtggca | gcgagaggtc | gtggacattc | actccaaggc | 300 |
| caagctcaaa | caagacatgg | aattgttata | cacatggaat | cactccatcc | ccagaagctg | 360 |
| caggtctaca | gtgtggattc | ccctgctcca | tatgttgatg | tgtctggtgg | tgagctgtgg | 420 |
| ataaacattt | tgcatgagac | cctcaagtac | gggcttgcac | caaaatcatg | gacggattac | 480 |
| ctgcatttaa | ctgtaggtgg | tactctgtcc | aatgctggaa | taagcggcca | ggcattccga | 540 |
| catggaccac | agatcagcaa | tgttcatcaa | ctggagattg | tcacaggtta | gttcagagtt | 600 |
| gcagtattcg | tgttttgaaa | gcatagactc | tatatggttg | gtgactatta | caacatgaa | 660 |
| gagattcccg | agaatagcta | cccactaatg | tcatgcctat | ttattgactg | caggaaaagg | 720 |
| cgagatccta | aactgtacaa | agaggcagaa | cagcgactta | tttaatggtg | ttcttggtgg | 780 |
| tttaggtcag | tttggcatca | taacgcgggc | aagaatagca | ttggaaccag | caccaaccat | 840 |
| ggtaaacaat | aaataaataa | aaacttaaa | aactgaacac | gcgtgtgtcc | tcctaactct | 900 |
| gtataatgga | caggtaaaat | ggataagagt | gttataccctg | gattttgcag | cttttgccaa | 960 |
| ggaccaagag | caactaatat | ctgcccaggg | ccacaaattc | gattacatag | aagggtttgt | 1020 |
| gataataaac | aggacaggcc | tcctgaacag | ctggaggttg | tctttcaccg | cagaagagcc | 1080 |
| tttagaagca | agccaattca | gtttgatgg | aaggactctg | tattgtctgg | agctagccaa | 1140 |
| gtatttgaag | caagataaca | aagacgtaat | caaccaggtg | agaaaacaga | gtagaagcaa | 1200 |
| tcggtagaat | cttctttggt | agatgacatt | cattggaact | gaaaatatat | atatatttgt | 1260 |
| ccaatccagg | aagtgaaaga | acattatca | gagctaagct | acgtgacgtc | gacactgttt | 1320 |
| acaacggagg | tagcatatga | agcattcttg | gacagggtac | atgtgtctga | ggtaaaactc | 1380 |
| cgatcgaaag | ggcagtggga | ggtgccacat | ccatggctga | acctcctggt | accaagaagc | 1440 |
| aaaatcaatg | aatttgcaag | aggtgtattt | ggaaacatac | taacggatac | aagcaacggc | 1500 |
| ccagtcatcg | tctacccagt | gaacaaatca | agtaagaaa | gaaagaaaga | aagagctagt | 1560 |
| catgattttg | tttcttttca | cttgttgaca | aaacaaaagc | atgttggtga | gcaggtggga | 1620 |

-continued

```
caatcaaaca tcagcagtaa caccggagga agaggtattc tacctggtgg cgatcctaac   1680
atcggcatct ccagggtcgg caggaaagga tggagtagaa gagatcttga ggcggaacag   1740
aagaatactg gaattcagtg aagaagcagg gatagggttg aagcagtatc tgccacatta   1800
cacgacaaga gaagagtgga gatcccattt cggggacaag tggggagaat tgtgaggag    1860 gaaatccaga tatgatccat tggcaattct tgcgcctggc caccgaattt ttcaaaaggc   1920
agtctcatac tcatga                                                  1936
```

<210> SEQ ID NO 12
<211> LENGTH: 504
<212> TYPE: PRT
<213> ORGANISM: Arabidopsis thaliana

<400> SEQUENCE: 12

```
Met Leu Ile Val Arg Ser Phe Thr Ile Leu Leu Ser Cys Ile Ala
  1               5                  10                  15

Phe Lys Leu Ala Cys Cys Phe Ser Ser Ile Ser Ser Leu Lys Ala
                 20                  25                  30

Leu Pro Leu Val Gly His Leu Glu Phe Glu His Val His Ala Ser
                 35                  40                  45

Lys Asp Phe Gly Asn Arg Tyr Gln Leu Ile Pro Leu Ala Val Leu His
     50                  55                  60

Pro Lys Ser Val Ser Asp Ile Ala Ser Thr Ile Arg His Ile Trp Met
 65                  70                  75                  80

Met Gly Thr His Ser Gln Leu Thr Val Ala Ala Arg Gly Arg Gly His
                 85                  90                  95

Ser Leu Gln Gly Gln Ala Gln Thr Arg His Gly Ile Val Ile His Met
                100                 105                 110

Glu Ser Leu His Pro Gln Lys Leu Gln Val Tyr Ser Val Asp Ser Pro
                115                 120                 125

Ala Pro Tyr Val Asp Val Ser Gly Gly Glu Leu Trp Ile Asn Ile Leu
            130                 135                 140

His Glu Thr Leu Lys Tyr Gly Leu Ala Pro Lys Ser Trp Thr Asp Tyr
145                 150                 155                 160

Leu His Leu Thr Val Gly Gly Thr Leu Ser Asn Ala Gly Ile Ser Gly
                165                 170                 175

Gln Ala Phe Arg His Gly Pro Gln Ile Ser Asn Val His Gln Leu Glu
            180                 185                 190

Ile Val Thr Gly Lys Gly Glu Ile Leu Asn Cys Thr Lys Arg Gln Asn
            195                 200                 205

Ser Asp Leu Phe Asn Gly Val Leu Gly Gly Leu Gly Gln Phe Gly Ile
        210                 215                 220

Ile Thr Arg Ala Arg Ile Ala Leu Glu Pro Ala Pro Thr Met Asp Gln
225                 230                 235                 240

Glu Gln Leu Ile Ser Ala Gln Gly His Lys Phe Asp Tyr Ile Glu Gly
                245                 250                 255

Phe Val Ile Ile Asn Arg Thr Gly Leu Leu Asn Ser Trp Arg Leu Ser
            260                 265                 270

Phe Thr Ala Glu Glu Pro Leu Glu Ala Ser Gln Phe Lys Phe Asp Gly
        275                 280                 285

Arg Thr Leu Tyr Cys Leu Glu Leu Ala Lys Tyr Leu Lys Gln Asp Asn
    290                 295                 300

Lys Asp Val Ile Asn Gln Glu Val Lys Glu Thr Leu Ser Glu Leu Ser
```

```
                305                 310                 315                 320
Tyr Val Thr Ser Thr Leu Phe Thr Thr Glu Val Ala Tyr Glu Ala Phe
                325                 330                 335
Leu Asp Arg Val His Val Ser Glu Val Lys Leu Arg Ser Lys Gly Gln
                340                 345                 350
Trp Glu Val Pro His Pro Trp Leu Asn Leu Leu Val Pro Arg Ser Lys
                355                 360                 365
Ile Asn Glu Phe Ala Arg Gly Val Phe Gly Asn Ile Leu Thr Asp Thr
                370                 375                 380
Ser Asn Gly Pro Val Ile Val Tyr Pro Val Asn Lys Ser Lys Trp Asp
385                 390                 395                 400
Asn Gln Thr Ser Ala Val Thr Pro Glu Glu Val Phe Tyr Leu Val
                405                 410                 415
Ala Ile Leu Thr Ser Ala Ser Pro Gly Ser Ala Gly Lys Asp Gly Val
                420                 425                 430
Glu Glu Ile Leu Arg Arg Asn Arg Arg Ile Leu Glu Phe Ser Glu Glu
                435                 440                 445
Ala Gly Ile Gly Leu Lys Gln Tyr Leu Pro His Tyr Thr Thr Arg Glu
                450                 455                 460
Glu Trp Arg Ser His Phe Gly Asp Lys Trp Gly Glu Phe Val Arg Arg
465                 470                 475                 480
Lys Ser Arg Tyr Asp Pro Leu Ala Ile Leu Ala Pro Gly His Arg Ile
                485                 490                 495
Phe Gln Lys Ala Val Ser Tyr Ser
                500

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence:
      oligonucleotide: primer or probe

<400> SEQUENCE: 13
cggtcgacat gggattgacc tcatccttac g                                 31

<210> SEQ ID NO 14
<211> LENGTH: 35
<212> TYPE: DNA
<213> ORGANISM: Artificial Sequence
<220> FEATURE:
<223> OTHER INFORMATION: Description of Artificial Sequence:
      oligonucleotide: primer or probe

<400> SEQUENCE: 14
gcgtcgactt atacagttct aggtttcggc agtat                             35

<210> SEQ ID NO 15
<211> LENGTH: 33
<212> TYPE: DNA
<213> ORGANISM: Artificial Sequence
<220> FEATURE:
<223> OTHER INFORMATION: Description of Artificial Sequence:
      oligonucleotide: primer or probe

<400> SEQUENCE: 15
gcggtaccag agagagaaac ataaacaaat ggc                               33

<210> SEQ ID NO 16
```

-continued

```
<211> LENGTH: 31
<212> TYPE: DNA
<213> ORGANISM: Artificial Sequence
<220> FEATURE:
<223> OTHER INFORMATION: Description of Artificial Sequence:
      oligonucleotide: primer or probe

<400> SEQUENCE: 16
gcggtaccca attttacttc caccaaaatg c                                  31

<210> SEQ ID NO 17
<211> LENGTH: 34
<212> TYPE: DNA
<213> ORGANISM: Artificial Sequence
<220> FEATURE:
<223> OTHER INFORMATION: Description of Artificial Sequence:
      oligonucleotide: primer or probe

<400> SEQUENCE: 17
gcggtacctt cattgataag aatcaagcta ttca                               34

<210> SEQ ID NO 18
<211> LENGTH: 31
<212> TYPE: DNA
<213> ORGANISM: Artificial Sequence
<220> FEATURE:
<223> OTHER INFORMATION: Description of Artificial Sequence:
      oligonucleotide: primer or probe

<400> SEQUENCE: 18
gcggtaccca aagtggtgag aacgactaac a                                  31

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence:
      oligonucleotide: primer or probe

<400> SEQUENCE: 19
gcggtacccc cattaaccta cccgtttg                                      28

<210> SEQ ID NO 20
<211> LENGTH: 32
<212> TYPE: DNA
<213> ORGANISM: Artificial Sequence
<220> FEATURE:
<223> OTHER INFORMATION: Description of Artificial Sequence:
      oligonucleotide: primer or probe

<400> SEQUENCE: 20
gcggtaccag acgatgaacg tacttgtctg ta                                 32

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence:
      oligonucleotide: primer or probe

<400> SEQUENCE: 21
ggggtacctt gatgaatcgt gaaatgac                                      28

<210> SEQ ID NO 22
<211> LENGTH: 31
```

```
<212> TYPE: DNA
<213> ORGANISM: Artificial Sequence
<220> FEATURE:
<223> OTHER INFORMATION: Description of Artificial Sequence:
      oligonucleotide: primer or probe

<400> SEQUENCE: 22 ggggtacccct ttcctcttgg ttttgtcctg t                                   31

<210> SEQ ID NO 23
<211> LENGTH: 32
<212> TYPE: DNA
<213> ORGANISM: Artificial Sequence
<220> FEATURE:
<223> OTHER INFORMATION: Description of Artificial Sequence:
      oligonucleotide: primer or probe

<400> SEQUENCE: 23
gctctagatc aggaaaagaa ccatgcttat ag                                   32

<210> SEQ ID NO 24
<211> LENGTH: 32
<212> TYPE: DNA
<213> ORGANISM: Artificial Sequence
<220> FEATURE:
<223> OTHER INFORMATION: Description of Artificial Sequence:
      oligonucleotide: primer or probe

<400> SEQUENCE: 24
gctctagatc atgagtatga gactgccttt tg                                   32

<210> SEQ ID NO 25
<211> LENGTH: 1728
<212> TYPE: DNA
<213> ORGANISM: Arabidopsis thaliana

<400> SEQUENCE: 25
atgggattga cctcatcctt acggttccat agacaaaaca acaagacttt cctcggaatc     60
ttcatgatct tagttctaag ctgtatacca ggtagaacca atctttgttc caatcattct    120
gttagtaccc caaaagaatt accttcttca aatccttcag atattcgttc ctcattagtt    180
tcactagatt tggagggtta tataagcttc gacgatgtcc acaatgtggc caaggacttt    240
ggcaacagat accagttacc acctttggca attctacatc caaggtcagt ttttgatatt    300
tcatcgatga tgaagcatat agtacatctg ggctccacct caaatcttac agtagcagct    360
agaggccatg gtcactcgct tcaaggacaa gctctagctc atcaaggtgt tgtcatcaaa    420
atggagtcac ttcgaagtcc tgatatcagg atttataagg ggaagcaacc atatgttgat    480
gtctcaggtg gtgaaatatg gataaacatt ctacgcgaga ctctaaaata cggtctttca    540
ccaaagtcct ggacagacta cctcattttg accgttggag gtacactatc taatgctgga    600
atcagcggtc aagcattcaa gcatggaccc caaatcaaca cgtctacca gctagagatt    660 gttacaggga aaggagaagt cgtaacctgt tctgagaagc ggaattctga actttcttc    720 agtgttcttg gcgggcttgg acagtttggc ataatcaccc gggcacggat ctctcttgaa    780
ccagcaccgc atatggttaa atggatcagg gtactctact ctgactttc tgcatttca    840 agggaccaag aatatctgat ttcgaaggag aaaactttg attacgttga aggatttgtg    900
ataatcaata gaacagacct tctcaataat tggcgatcgt cattcagtcc caacgattcc    960
acacaggcaa gcagattcaa gtcagatggg aaaactcttt attgcctaga agtggtcaaa   1020
tatttcaacc cagaagaagc tagctctatg gatcaggaaa ctggcaagtt acttcagag   1080
```

| | |
|---|---|
| ttaaattata ttccatccac tttgttttca tctgaagtgc catatatcga gtttctggat | 1140 |
| cgcgtgcata tcgcagagag aaaactaaga gcaaagggtt tatgggaggt tccacatccc | 1200 |
| tggctgaatc tcctgattcc taagagcagc atataccaat ttgctacaga agttttcaac | 1260 |
| aacattctca caagcaacaa caacggtcct atccttattt atccagtcaa tcaatccaag | 1320 |
| tggaagaaac atacatcttt gataactcca aatgaagata tattctatct cgtagccttt | 1380 |
| ctcccctctg cagtgccaaa ttcctcaggg aaaaacgatc tagagtacct tttgaaacaa | 1440 |
| aaccaaagag ttatgaactt ctgcgcagca gcaaacctca acgtgaagca gtatttgccc | 1500 |
| cattatgaaa ctcaaaaaga gtggaaatca cactttggca aaagatggga aacatttgca | 1560 |
| cagaggaaac aagcctacga ccctctagcg attctagcac ctggccaaag aatattccaa | 1620 |
| aagacaacag gaaaattatc tcccatccaa ctcgcaaagt caaaggcaac aggaagtcct | 1680 |
| caaaggtacc attacgcatc aatactgccg aaacctagaa ctgtataa | 1728 |

<210> SEQ ID NO 26
<211> LENGTH: 1506
<212> TYPE: DNA
<213> ORGANISM: Arabidopsis thaliana

<400> SEQUENCE: 26

| | |
|---|---|
| atggctaatc ttcgtttaat gatcacttta atcacggttt taatgatcac caaatcatca | 60 |
| aacggtatta aaattgattt acctaaatcc cttaacctca ccctctctac cgatccttcc | 120 |
| atcatctccg cagcctctca tgacttcgga aacataacca ccgtgacccc cggcggcgta | 180 |
| atctgcccct cctccaccgc tgatatctct cgtctcctcc aatacgccgc aaacggaaaa | 240 |
| agtacattcc aagtagcggc tcgtggccaa ggccactcct taaacggcca agcctcggtc | 300 |
| tccggcggag taatcgtcaa catgacgtgt atcactgacg tggtggtttc aaaagacaag | 360 |
| aagtacgctg acgtggcggc cgggacgtta tgggtggatg tgcttaagaa gacggcggag | 420 |
| aaaggggtgt cgccggtttc ttggacggat tatttgcata taccgtcgg aggaacgttg | 480 |
| tcgaatggtg gaattggtgg tcaagtgttt cgaaacggtc ctcttgttag taacgtcctt | 540 |
| gaattggacg ttattactgg gaaaggtgaa atgttgacat gctcgcgaca gctaaaccca | 600 |
| gaattgttct atggagtgtt aggaggtttg ggtcaatttg gaattataac gagagccaga | 660 |
| attgttttgg accatgcacc taaacgggcc aaatggtttc ggatgctcta cagtgatttc | 720 |
| acaacttta caaggaccaa gaacgtttg atatcaatgg caaacgatat tggagtcgac | 780 |
| tatttagaag gtcaaatatt tctatcaaac ggtgtcgttg acacctcttt tttcccacct | 840 |
| tcagatcaat ctaaagtcgc tgatctagtc aagcaacacg gtatcatcta tgttcttgaa | 900 |
| gtagccaagt attatgatga tcccaatctc cccatcatca gcaaggttat tgacacatta | 960 |
| acgaaaacat taagttactt gcccgggttc atatcaatgc acgacgtggc ctacttcgat | 1020 |
| ttcttgaacc gtgtacatgt cgaagaaaat aaactcagat ctttgggatt atgggaactt | 1080 |
| cctcatcctt ggcttaacct ctacgttcct aaatctcgga ttctcgattt tcataacggt | 1140 |
| gttgtcaaag acattcttct taagcaaaaa tcagcttcgg gactcgctct tctctatcca | 1200 |
| acaaaccgga ataatggga caatcgtatg tcggcgatga taccagagat cgatgaagat | 1260 |
| gttatatata ttatcggact actacaatcc gctaccccaa aggatcttcc agaagtggag | 1320 |
| agcgttaacg agaagataat taggttttgc aaggattcag gtattaagat taagcaatat | 1380 |
| ctaatgcatt atactagtaa agaagattgg attgagcatt ttggatcaaa atgggatgat | 1440 |

```
ttttcgaaga ggaaagatct atttgatccc aagaaactgt tatctccagg gcaagacatc   1500
ttttga                                                              1506

<210> SEQ ID NO 27
<211> LENGTH: 1572
<212> TYPE: DNA
<213> ORGANISM: Arabidopsis thaliana

<400> SEQUENCE: 27
atggcgagtt ataatcttcg ttcacaagtt cgtcttatag caataacaat agtaatcatc     60
attactctct caactccgat cacaaccaac acatcaccac aaccatggaa tatcctttca    120
cacaacgaat tcgccggaaa actcacctcc tcctcctcct ccgtcgaatc agccgccaca    180
gatttcggcc acgtcaccaa aatcttccct tccgccgtct taatcccttc ctccgttgaa    240
gacatcacag atctcataaa actctctttt gactctcaac tgtcttttcc tttagccgct    300
cgtggtcacg acacagcca  ccgtggccaa gcctcggcta aagacggagt tgtggtcaac    360
atgcggtcca tggtaaaccg ggatcgaggt atcaaggtgt ctaggacctg tttatatgtt    420
gacgtggacg ctgcgtggct atggattgag gtgttgaata aaactttgga gttagggtta    480
acgccggttt cttggacgga ttatttgtat ttaacagtcg gtgggacgtt atcaaacggc    540
ggaattagtg gacaaacgtt tcggtacggt ccacagatca ctaatgttct agagatggat    600
gttattactg gaaaaggaga gattgcaact tgttccaagg acatgaactc ggatcttttc    660
ttcgcggtgt taggaggttt gggtcaattc ggcattataa caagagccag aattaaactt    720
gaagtagctc cgaaaagggc caagtggtta aggtttctat acatagattt ctccgaattc    780
acaagagatc aagaacgagt gatatcgaaa acggacggtg tagatttctt agaaggttcc    840
attatggtgg accatggccc accggataac tggagatcca cgtattatcc accgtccgat    900
cacttgagga tcgcctcaat ggtcaaacga catcgtgtca tctactgcct tgaagtcgtc    960
aagtattacg acgaaacttc tcaatacaca gtcaacgagg aaatggagga gttaagcgat   1020
agtttaaacc atgtaagagg gtttatgtac gagaaagatg tgacgtatat ggatttccta   1080
aaccgagttc gaaccggaga gctaaacctg aaatccaaag gccaatggga tgttccacat   1140
ccatggctta atctcttcgt accaaaaact caaatctcca aatttgatga tggtgttttt   1200
aagggtatta tcctaagaaa taacatcact agcggtcctg ttcttgttta tcctatgaat   1260
cgcaacaagt ggaatgatcg gatgtctgcc gctataccg  aggaagatgt attttatgcg   1320
gtagggtttt taagatccgc gggttttgac aattgggagg ctttgatca agaaaacatg    1380 gaaatactga gttttgtga  ggatgctaat atggggtta  acaatatct tccttatcat    1440 tcatcacaag aaggatgggt tagacatttt ggtccgaggt ggaatatttt cgtagagaga   1500
aaatataaat atgatcccaa aatgatatta tcaccgggac aaaatatatt tcaaaaaata   1560
aactcgagtt ag                                                      1572

<210> SEQ ID NO 28
<211> LENGTH: 1575
<212> TYPE: DNA
<213> ORGANISM: Arabidopsis thaliana

<400> SEQUENCE: 28
atgactaata ctctctgttt aagcctcatc accctaataa cgcttttat  aagtttaacc     60 ccaaccttaa tcaaatcaga tgagggcatt gatgttttct acccatatc  actcaacctt    120 acggtcctaa ccgatcccct ctccatctct gccgcttctc acgacttcgg taacataacc    180
```

```
gacgaaaatc ccggcgccgt cctctgccct tcctccacca cggaggtggc tcgtctcctc    240
cgtttcgcta acggaggatt ctcttacaat aaaggctcaa ccagcccgc gtctactttc     300 aaagtggctg ctcgaggcca aggccactcc ctccgtggcc aagcctctgc acccggaggt    360
gtcgtcgtga acatgacgtg tctcgccatg gcggctaaac cagcggcggt tgttatctcg    420
gcagacggga cttacgctga cgtggctgcc gggacgatgt gggtggatgt tctgaaggcg    480
gcggtggata gaggcgtctc gccggttaca tggacggatt atttgtatct cagcgtcggc    540
gggacgttgt cgaacgctgg aatcggtggt cagacgttta cacggccc tcagattagt      600 aacgttcatg agcttgacgt tattaccgga aaaggtgaaa tgatgacttg ctctccaaag    660
ttaaaccctg aattgttcta tggagttta ggaggtttgg gtcaattcgg tattataacg     720
agggccagga ttgcgttgga tcatgcaccc acaagggtga atggtctcg catactctac     780 agtgacttct cggctttaa aagagaccaa gagcgtttaa tatcaatgac caatgatctc     840
ggagttgact ttttggaagg tcaacttatg atgtcaaatg cttcgtaga cacctctttc     900 ttcccactct ccgatcaaac aagagtcgca ctcttgtga atgaccaccg gatcatctat     960
gttctcgaag tagccaagta ttatgacaga accaccct tccattattga ccaggtgatt    1020 gacacgttaa gtagaactct aggtttcgct ccagggttta tgttcgtaca agatgttccg   1080
tatttcgatt tcttgaaccg tgtccgaaac gaagaagata aactcagatc tttaggacta   1140
tgggaagttc ctcatccatg gcttaacatc tttgtcccgg ggtctcgaat ccaagatttt   1200
catgatggtg ttattaatgg ccttcttcta aaccaaacct caacttctgg tgttactctc   1260
ttctatccca caaaccgaaa caatggaac aaccgcatgt caacgatgac accggacgaa   1320 gatgttttt atgtgatcgg attactgcaa tcagctggtg gatctcaaaa ttggcaagaa    1380
cttgaaaatc tcaacgacaa ggttattcag ttttgtgaaa actcgggaat taagattaag   1440
gaatatttga tgcactatac aagaaaagaa gattgggtta acatttttgg accaaaatgg   1500
gatgattttt taagaaagaa aattatgttt gatcccaaaa gactattgtc tccaggacaa   1560
gacatattta attaa                                                    1575

<210> SEQ ID NO 29
<211> LENGTH: 1611
<212> TYPE: DNA
<213> ORGANISM: Arabidopsis thaliana

<400> SEQUENCE: 29
atgacgtcaa gctttcttct cctgacgttc gccatatgta aactgatcat agccgtgggt     60
ctaaacgtgg gccccagtga gctcctccgc atcggagcca tagatgtcga cggccacttc    120
accgtccacc cttccgactt agcctccgtc tcctcagact tcggtatgct gaagtcacct    180
gaagagccat tggccgtgct tcatccatca tcggccgaag acgtggcacg actcgtcaga    240
acagcttacg gttcagccac ggcgtttccg gtctcagccc gaggccacgg ccattccata    300
aacggacaag ccgcggcggg gaggaacggt gtggtggttg aaatgaacca cggcgtaacc    360
gggacgccca agccactcgt ccgaccggat gaaatgtatg tggatgtatg gggtggagag    420
ttatgggtcg atgtgttgaa gaaaacgttg gagcatggct tagcaccaaa atcatggacg    480
gattacttgt atctaaccgt tggaggtaca ctctccaatg caggaatcag tggtcaagct    540
tttcaccatg gtcctcaaat tagtaacgtc cttgagctcg acgttgtaac tgggaaagga    600
gaggtgatga gatgctcaga agaagagaac acaaggctat ccatggagt tcttggtgga    660
```

```
ttaggtcaat tgggatcat cactcgagca cgaatctctc tcgaaccagc tccccaaagg    720
gtgagatgga tacgggtatt gtattcgagc ttcaaagtgt ttacggagga ccaagagtac    780
ttaatctcaa tgcatggtca attaaagttt gattacgtgg aaggttttgt gattgtggac    840
gaaggactcg tcaacaattg gagatcttct ttcttctctc cacgtaaccc cgtcaagatc    900
tcctctgtta gttccaacgg ctctgttttg tattgccttg agatcaccaa gaactaccac    960
gactccgact ccgaaatcgt tgatcaggaa gttgagattc tgatgaagaa attgaatttc   1020
ataccgacat cggtctttac aacggattta caatatgtgg actttctcga ccgggtacac   1080
aaggccgaat tgaagctccg gtccaagaat ttatgggagg ttccacaccc atggctcaac   1140
ctcttcgtgc aaaatcaag aatctctgac ttcgataaag gcgttttcaa gggcattttg   1200
ggaaataaaa caagtgggcc tattcttatc taccccatga caaagacaa atgggacgag   1260 aggagctcag ccgtgacgcc ggatgaggaa gttttctatc tggtggctct attgagatca   1320
gctttaacgg acggtgaaga gacacagaag ctagagtatc tgaaagatca gaaccgtcgg   1380
atcttggagt tctgtgaaca agccaagatc aatgtgaagc agtatcttcc tcaccacgca   1440
acacaggaag agtgggtggc tcattttggg gacaagtggg atcggttcag aagcttaaag   1500
gctgagtttg atccgcgaca catactcgct actggtcaga gaatctttca aaacccatct   1560
ttgtctttgt ttcctccgtc gtcgtcttct tcgtcagcgg cttcatggtg a            1611

<210> SEQ ID NO 30
<211> LENGTH: 1515
<212> TYPE: DNA
<213> ORGANISM: Arabidopsis thaliana

<400> SEQUENCE: 30
atgcttatag taagaagttt caccatcttg cttctcagct gcatagcctt taagttggct     60
tgctgcttct ctagcagcat ttcttctttg aaggcgcttc ccctagtagg ccatttggag    120
tttgaacatg tccatcacgc ctccaaagat tttggaaatc gataccagtt gatcccttttg   180 gcggtcttac atcccaaatc ggtaagcgac atcgcctcaa cgatacgaca catctggatg    240
atgggcactc attcacagct tacagtggca gcgagaggtc gtggacattc actccaaggc    300
caagctcaaa caagacatgg aattgttata cacatggaat cactccatcc ccagaagctg    360
caggtctaca gtgtggattc ccctgctcca tatgttgatg tgtctggtgg tgagctgtgg    420
ataaacattt tgcatgagac cctcaagtac gggcttgcac caaaatcatg gacggattac    480
ctgcatttaa ctgtaggtgg tactctgtcc aatgctgaa taagcggcca ggcattccga    540
catggaccac agatcagcaa tgttcatcaa ctggagattg tcacaggaaa aggcgagatc    600
ctaaactgta caaagaggca gaacagcgac ttatttaatg gtgttcttgg tggtttaggt    660
cagtttggca tcataacgcg gcaagaata gcattggaac cagcaccaac catggaccaa    720
gagcaactaa tatctgccca gggccacaaa ttcgattaca tagaagggtt tgtgataata    780
aacaggacag gcctcctgaa cagctggagg ttgtctttca ccgcagaaga gcctttagaa    840
gcaagccaat tcaagtttga tggaaggact ctgtattgtc tggagctagc caagtatttg    900
aagcaagata caaagacgt aatcaaccag gaagtgaaag aaacattatc agagctaagc    960
tacgtgacgt cgacactgtt tacaacgag gtagcatatg aagcattctt ggacagggta   1020
catgtgtctg aggtaaaact ccgatcgaaa gggcagtggg aggtgccaca tccatggctg   1080
aacctcctgg taccaagaag caaaatcaat gaatttgcaa gaggtgtatt tggaaacata   1140
ctaacggata caagcaacgg cccagtcatc gtctacccag tgaacaaatc aaagtgggac   1200
```

```
aatcaaacat cagcagtaac accggaggaa gaggtattct acctggtggc gatcctaaca    1260
tcggcatctc cagggtcggc aggaaaggat ggagtagaag agatcttgag gcggaacaga    1320
agaatactgg aattcagtga agaagcaggg ataggggtta agcagtatct gccacattac    1380
acgacaagag aagagtggag atcccatttc ggggacaagt ggggagaatt tgtgaggagg    1440
aaatccagat atgatccatt ggcaattctt gcgcctggcc accgaatttt tcaaaaggca    1500
gtctcatact catga                                                    1515

<210> SEQ ID NO 31
<211> LENGTH: 84
<212> TYPE: DNA
<213> ORGANISM: Arabidopsis thaliana

<400> SEQUENCE: 31
tcagcttcgg gactcgctct tctctatcca acaaaccgga ataaatggga caatcgtatg     60
tcggcgatga taccagagat cgat                                            84

<210> SEQ ID NO 32
<211> LENGTH: 28
<212> TYPE: PRT
<213> ORGANISM: Arabidopsis thaliana

<400> SEQUENCE: 32

Ser Ala Ser Gly Leu Ala Leu Leu Tyr Pro Thr Asn Arg Asn Lys Trp
  1               5                  10                  15

Asp Asn Arg Met Ser Ala Met Ile Pro Glu Ile Asp
             20                  25

<210> SEQ ID NO 33
<211> LENGTH: 2814
<212> TYPE: DNA
<213> ORGANISM: Arabidopsis thaliana

<400> SEQUENCE: 33
atgaatcgta tgacgtcaag ctttcttctc ctgacgttcg ccatatgtaa actgatcata     60
gccgtgggtc taaacgtggg ccccagtgag ctcctccgca tcggagccat agatgtcgac    120
ggccacttca ccgtccaccc ttccgactta gcctccgtct cctcagactt cggtatgctg    180
aagtcacctg aagagccatt ggccgtgctt catccatcat cggccgaaga cgtggcacga    240
ctcgtcagaa cagcttacgg ttcagccacg gcgtttccgg tctcagcccg aggccacggc    300
cattccataa acggacaagc cgcggcgggg aggaacggtg tggtggttga atgaaccac     360 ggcgtaaccg ggacgcccaa gccactcgtc cgaccggatg aaatgtatgt ggatgtatgg    420
ggtggagagt tatgggtcga tgtgttgaag aaaacgttgg agcatggctt agcaccaaaa    480
tcatggacgg attacttgta tctaaccgtt ggaggtacac tctccaatgc aggaatcagt    540
ggtcaagctt tcaccatggt cctcaaatt agtaacgtcc ttgagctcga cgttgtaact    600
ggttagtatt aaaacattca agttcatata ttttaaatgc ttttgtctga agttttacta    660
ataacaagaa attgatacca aaaagtaggg aaggagagg tgatgagatg ctcagaagaa    720
gagaacacaa ggctattcca tggagttctt ggtggattag gtcaatttgg gatcatcact    780
cgagcacgaa tctctctcga accagctccc caaagggtaa tatttttta atgactagct    840 atcaaaaatc cctggcgggt ccatacgttg taatcttttt agttttact gttgatggta    900 ttttttatat attttggata ataaaaccct aaaatggtat attgtgatga caggtgagat    960
```

```
ggatacgggt attgtattcg agcttcaaag tgtttacgga ggaccaagag tacttaatct    1020
caatgcatgg tcaattaaag tttgattacg tggaaggttt tgtgattgtg gacgaaggac    1080
tcgtcaacaa ttggagatct tctttcttct ctccacgtaa ccccgtcaag atctcctctg    1140
ttagttccaa cggctctgtt ttgtattgcc ttgagatcac caagaactac cacgactccg    1200
actccgaaat cgttgatcag gtcactttca ttattcactt agaaaaaagc gatattttca    1260
ttttttatat tgatgaatat ctggaaggat ttaacgctat gcgactattg ggaaatcatt    1320
atgaaaaaat atttagttta tatgattgaa agtggtctcc atagtatttt tgttgtgtcg    1380
actttattat aacttaaatt tggaagagga catgaagaag aagccagaga ggatctacag    1440
agatctagct tttccacctg aacttaataa tgcacattta tataattatt tttcttcttc    1500
taaagtttag tttatcacta gcgaattaat catggttact aattaagtag tggacagggt    1560
catggaccac tcactcacca ataatgatt cctctttact cttaagttta attttaataa    1620
aaccaactct actggaatct taacttatcc ttggttttgg taggctttta tagcaacacg    1680
gtttttttaa ttttcctatt ccagattttg tatattaaat gtcgattttt tttctttttg    1740
tttcaggaag ttgagattct gatgaagaaa ttgaatttca taccgacatc ggtctttaca    1800
acggatttac aatatgtgga ctttctcgac cgggtacaca aggccgaatt gaagctccgg    1860
tccaagaatt tatgggaggt tccacaccca tggctcaacc tcttcgtgcc aaaatcaaga    1920
atctctgact tcgataaagg cgttttcaag ggcattttgg gaaataaaac aagtggccct    1980
attcttatct accccatgaa caaagacaag taagtcttga cattaccatt gattactact    2040
tctaaatttc ttctctagaa aaaagaataa aacgagtttt gcattgcatg catgcaaagt    2100
tacacttgtg gggattaatt agtggtccaa gaaaaaaagt ttgtcaaaat tgaaaaaaac    2160
tagacacgtg gtacatggga ttgtccgaaa acgttgtcc acatgtgcat cgaaccagct    2220
aagattgaca caacacttc gtcggctcgt atttctcttt ttgttttgtg accaaatccg    2280
atggtccaga ttgggtttat tgttttttaa gttcctagaa ctcatggtgg gtgggtccca    2340
atcagattct cctagaccaa accgatctca acgaaccctc cgcacatcat tgattattac    2400
attaatatag atattgtcgt tgctgacgtg tcgtaatttg atgttattgt cagatgggac    2460
gagaggagct cagccgtgac gccggatgag gaagttttct atctggtggc tctattgaga    2520
tcagctttaa cggacggtga agagacacag aagctagagt atctgaaaga tcagaaccgt    2580
cggatcttgg agttctgtga acaagccaag atcaatgtga agcagtatct tcctcaccac    2640
gcaacacagg aagagtgggt ggctcatttt ggggacaagt gggatcggtt cagaagctta    2700
aaggctgagt ttgatccgcg acacatactc gctactggtc agagaatctt tcaaacccca    2760
tctttgtctt tgtttcctcc gtcgtcgtct tcttcgtcag cggcttcatg gtga          2814
```

<210> SEQ ID NO 34
<211> LENGTH: 1620
<212> TYPE: DNA
<213> ORGANISM: Arabidopsis thaliana

<400> SEQUENCE: 34

```
atgaatcgta tgacgtcaag ctttcttctc ctgacgttcg ccatatgtaa actgatcata      60
gccgtgggtc taaacgtggg ccccagtgag ctcctccgca tcgagccat agatgtcgac     120 ggccacttca ccgtccaccc ttccgactta gcctccgtct cctcagactt cggtatgctg     180
aagtcacctg aagagccatt ggccgtgctt catccatcat cggccgaaga cgtggcacga     240
ctcgtcagaa cagcttacgg ttcagccacg gcgtttccgg tctcagcccg aggccacggc     300
```

```
cattccataa acggacaagc cgcggcgggg aggaacggtg tggtggttga aatgaaccac    360
ggcgtaaccg ggacgcccaa gccactcgtc cgaccggatg aaatgtatgt ggatgtatgg    420
ggtggagagt tatgggtcga tgtgttgaag aaaacgttgg agcatggctt agcaccaaaa    480
tcatggacgg attacttgta tctaaccgtt ggaggtacac tctccaatgc aggaatcagt    540
ggtcaagctt ttcaccatgg tcctcaaatt agtaacgtcc ttgagctcga cgttgtaact    600
gggaaaggag aggtgatgag atgctcagaa gaagagaaca caaggctatt ccatggagtt    660
cttggtggat taggtcaatt tgggatcatc actcgagcac gaatctctct cgaaccagct    720
ccccaaaggg tgagatggat acgggtattg tattcgagct tcaaagtgtt tacggaggac    780
caagagtact aatctcaat gcatggtcaa ttaaagtttg attacgtgga aggttttgtg    840
attgtggacg aaggactcgt caacaattgg agatcttctt tcttctctcc acgtaaccc    900 gtcaagatct cctctgttag ttccaacggc tctgttttgt attgccttga gatcaccaag    960
aactaccacg actccgactc cgaaatcgtt gatcaggaag ttgagattct gatgaagaaa    1020
ttgaatttca taccgacatc ggtctttaca acggatttac aatatgtgga ctttctcgac    1080
cgggtacaca aggccgaatt gaagctccgg tccaagaatt tatgggaggt tccacaccca    1140
tggctcaacc tcttcgtgcc aaaatcaaga atctctgact tcgataaagg cgttttcaag    1200
ggcattttgg gaaataaaac aagtggccct attcttatct accccatgaa caaagacaaa    1260
tgggacgaga ggagctcagc cgtgacgccg gatgaggaag ttttctatct ggtggctcta    1320
ttgagatcag ctttaacgga cggtgaagag acacagaagc tagagtatct gaaagatcag    1380
aaccgtcgga tcttggagtt ctgtgaacaa gccaagatca atgtgaagca gtatcttcct    1440
caccacgcaa cacaggaaga gtgggtggct catttggggg acaagtggga tcggttcaga    1500
agcttaaagg ctgagtttga tccgcgacac atactcgcta ctggtcagag aatctttcaa    1560
aacccatctt tgtctttgtt tcctccgtcg tcgtcttctt cgtcagcggc ttcatggtga    1620
```

<210> SEQ ID NO 35
<211> LENGTH: 539
<212> TYPE: PRT
<213> ORGANISM: Arabidopsis thaliana

<400> SEQUENCE: 35

```
Met Asn Arg Met Thr Ser Ser Phe Leu Leu Leu Thr Phe Ala Ile Cys
  1               5                  10                  15

Lys Leu Ile Ile Ala Val Gly Leu Asn Val Gly Pro Ser Glu Leu Leu
             20                  25                  30

Arg Ile Gly Ala Ile Asp Val Asp Gly His Phe Thr Val His Pro Ser
         35                  40                  45

Asp Leu Ala Ser Val Ser Ser Asp Phe Gly Met Leu Lys Ser Pro Glu
     50                  55                  60

Glu Pro Leu Ala Val Leu His Pro Ser Ser Ala Glu Asp Val Ala Arg
 65                  70                  75                  80

Leu Val Arg Thr Ala Tyr Gly Ser Ala Thr Ala Phe Pro Val Ser Ala
                 85                  90                  95

Arg Gly His Gly His Ser Ile Asn Gly Gln Ala Ala Gly Arg Asn
            100                 105                 110

Gly Val Val Val Glu Met Asn His Gly Val Thr Gly Thr Pro Lys Pro
        115                 120                 125

Leu Val Arg Pro Asp Glu Met Tyr Val Asp Val Trp Gly Gly Glu Leu
    130                 135                 140
```

```
Trp Val Asp Val Leu Lys Lys Thr Leu Glu His Gly Leu Ala Pro Lys
145                 150                 155                 160

Ser Trp Thr Asp Tyr Leu Tyr Leu Thr Val Gly Gly Thr Leu Ser Asn
            165                 170                 175

Ala Gly Ile Ser Gly Gln Ala Phe His His Gly Pro Gln Ile Ser Asn
        180                 185                 190

Val Leu Glu Leu Asp Val Val Thr Gly Lys Gly Glu Val Met Arg Cys
    195                 200                 205

Ser Glu Glu Glu Asn Thr Arg Leu Phe His Gly Val Leu Gly Gly Leu
210                 215                 220

Gly Gln Phe Gly Ile Ile Thr Arg Ala Arg Ile Ser Leu Glu Pro Ala
225                 230                 235                 240

Pro Gln Arg Val Arg Trp Ile Arg Val Leu Tyr Ser Ser Phe Lys Val
            245                 250                 255

Phe Thr Glu Asp Gln Glu Tyr Leu Ile Ser Met His Gly Gln Leu Lys
        260                 265                 270

Phe Asp Tyr Val Glu Gly Phe Val Ile Val Asp Glu Gly Leu Val Asn
    275                 280                 285

Asn Trp Arg Ser Ser Phe Phe Ser Pro Arg Asn Pro Val Lys Ile Ser
290                 295                 300

Ser Val Ser Ser Asn Gly Ser Val Leu Tyr Cys Leu Glu Ile Thr Lys
305                 310                 315                 320

Asn Tyr His Asp Ser Asp Ser Glu Ile Val Asp Gln Glu Val Glu Ile
            325                 330                 335

Leu Met Lys Lys Leu Asn Phe Ile Pro Thr Ser Val Phe Thr Thr Asp
        340                 345                 350

Leu Gln Tyr Val Asp Phe Leu Asp Arg Val His Lys Ala Glu Leu Lys
    355                 360                 365

Leu Arg Ser Lys Asn Leu Trp Glu Val Pro His Pro Trp Leu Asn Leu
370                 375                 380

Phe Val Pro Lys Ser Arg Ile Ser Asp Phe Asp Lys Gly Val Phe Lys
385                 390                 395                 400

Gly Ile Leu Gly Asn Lys Thr Ser Gly Pro Ile Leu Ile Tyr Pro Met
            405                 410                 415

Asn Lys Asp Lys Trp Asp Glu Arg Ser Ser Ala Val Thr Pro Asp Glu
        420                 425                 430

Glu Val Phe Tyr Leu Val Ala Leu Leu Arg Ser Ala Leu Thr Asp Gly
    435                 440                 445

Glu Glu Thr Gln Lys Leu Glu Tyr Leu Lys Asp Gln Asn Arg Arg Ile
450                 455                 460

Leu Glu Phe Cys Glu Gln Ala Lys Ile Asn Val Lys Gln Tyr Leu Pro
465                 470                 475                 480

His His Ala Thr Gln Glu Glu Trp Val Ala His Phe Gly Asp Lys Trp
            485                 490                 495

Asp Arg Phe Arg Ser Leu Lys Ala Glu Phe Asp Pro Arg His Ile Leu
        500                 505                 510

Ala Thr Gly Gln Arg Ile Phe Gln Asn Pro Ser Leu Ser Leu Phe Pro
    515                 520                 525

Pro Ser Ser Ser Ser Ser Ala Ala Ser Trp
530                 535

<210> SEQ ID NO 36
<211> LENGTH: 842
```

```
<212> TYPE: DNA
<213> ORGANISM: Arabidopsis thaliana

<400> SEQUENCE: 36
aagcttaaat gacaatttag taccttgggt tggtcatgat ttagagcgga acaaatatac      60
catacatcaa acgaggatat acagagaaaa ttcatggaag tatggaattt agaggacaat     120
ttctcttctg ggctacaacg gaccggccca ttcgctcatt tacccagagg tatcgagttt     180
gtggactttt gatgccgcta gagactattg gcatcggatt gaaaaaaatg tttacttcgt     240
tgttaacaat tttctgaatg caatattttc cttgtcatga atatttaaac ttgttattac     300
tttcttttag cttaggtgtg gacaattatg gagtttactt caaacgagga agaatcttaa     360
acgctcggtt caggtctcga aaacaaacca actcacaatc ctgacttaat tgaggaaaac     420
aatgcaaaac cacatgcatg cttccatatt tctatcataa tcttataaga aaaaacacta     480
ctaagtgaaa tgattctgta tatatataac caatgccttt tgttttgtga tattttatgt     540
atatataact attgactttt gtcatctatg gatagtgtct cgggctcttg gcaaacatat     600
ttcaaagaaa agttaatgac tgtaattaat taatctgaag ctagaaacag aaccccgagg     660
taaaagaaaa agacagagca catgaagttt agtacttta tatatttaat atatcattct      720
ttcttattgc ttatctctaa agcaaaaact tccctaaacc ctaagccaaa ggactcagat     780
cgatgcagaa ccaagaaggc ttgttttgga tttgagagcc aaatgcaaag aaaaaaactc     840
tt                                                                    842

<210> SEQ ID NO 37
<211> LENGTH: 501
<212> TYPE: PRT
<213> ORGANISM: Arabidopsis thaliana

<400> SEQUENCE: 37
```

Met Ala Asn Leu Arg Leu Met Ile Thr Leu Ile Thr Val Leu Met Ile
1               5                   10                  15

Thr Lys Ser Ser Asn Gly Ile Lys Ile Asp Leu Pro Lys Ser Leu Asn
            20                  25                  30

Leu Thr Leu Ser Thr Asp Pro Ser Ile Ile Ser Ala Ala Ser His Asp
        35                  40                  45

Phe Gly Asn Ile Thr Thr Val Thr Pro Gly Gly Val Ile Cys Pro Ser
    50                  55                  60

Ser Thr Ala Asp Ile Ser Arg Leu Leu Gln Tyr Ala Ala Asn Gly Lys
65                  70                  75                  80

Ser Thr Phe Gln Val Ala Ala Arg Gly Gln Gly His Ser Leu Asn Gly
                85                  90                  95

Gln Ala Ser Val Ser Gly Gly Val Ile Val Asn Met Thr Cys Ile Thr
            100                 105                 110

Asp Val Val Ser Lys Asp Lys Lys Tyr Ala Asp Val Ala Ala Gly
        115                 120                 125

Thr Leu Trp Val Asp Val Leu Lys Lys Thr Ala Glu Lys Gly Val Ser
    130                 135                 140

Pro Val Ser Trp Thr Asp Tyr Leu His Ile Thr Val Arg Gly Thr Leu
145                 150                 155                 160

Ser Asn Gly Gly Ile Gly Gly Gln Val Phe Arg Asn Gly Pro Leu Val
                165                 170                 175

Ser Asn Val Leu Glu Leu Asp Val Ile Thr Gly Lys Gly Glu Met Leu
            180                 185                 190

```
Thr Cys Ser Arg Gln Leu Asn Pro Glu Leu Phe Tyr Gly Val Leu Gly
        195                 200                 205

Gly Leu Gly Gln Phe Gly Ile Ile Thr Arg Ala Arg Ile Val Leu Asp
    210                 215                 220

His Ala Pro Lys Arg Ala Lys Trp Phe Arg Met Leu Tyr Ser Asp Phe
225                 230                 235                 240

Thr Thr Phe Thr Lys Asp Gln Glu Arg Leu Ile Ser Met Ala Asn Asp
                245                 250                 255

Ile Gly Val Asp Tyr Leu Glu Gly Gln Ile Phe Leu Ser Asn Gly Val
            260                 265                 270

Val Asp Thr Ser Phe Phe Pro Ser Asp Gln Ser Lys Val Ala Asp
        275                 280                 285

Leu Val Lys Gln His Gly Ile Ile Tyr Val Leu Glu Val Ala Lys Tyr
    290                 295                 300

Tyr Asp Asp Pro Asn Leu Pro Ile Ile Ser Lys Val Ile Asp Thr Leu
305                 310                 315                 320

Thr Lys Thr Leu Ser Tyr Leu Pro Gly Phe Ile Ser Met His Asp Val
                325                 330                 335

Ala Tyr Phe Asp Phe Leu Asn Arg Val His Val Glu Glu Asn Lys Leu
            340                 345                 350

Arg Ser Leu Gly Leu Trp Glu Leu Pro His Pro Trp Leu Asn Leu Tyr
        355                 360                 365

Val Pro Lys Ser Arg Ile Leu Asp Phe His Asn Gly Val Val Lys Asp
    370                 375                 380

Ile Leu Leu Lys Gln Lys Ser Ala Ser Gly Leu Ala Leu Leu Tyr Pro
385                 390                 395                 400

Thr Asn Arg Asn Lys Trp Asp Asn Arg Met Ser Ala Met Ile Pro Glu
                405                 410                 415

Ile Asp Glu Asp Val Ile Tyr Ile Ile Gly Leu Leu Gln Ser Ala Thr
            420                 425                 430

Pro Lys Asp Leu Pro Glu Val Glu Ser Val Asn Glu Lys Ile Ile Arg
        435                 440                 445

Phe Cys Lys Asp Ser Gly Ile Lys Ile Lys Gln Tyr Leu Met His Tyr
    450                 455                 460

Thr Ser Lys Glu Asp Trp Ile Glu His Phe Gly Ser Lys Trp Asp Asp
465                 470                 475                 480

Phe Ser Lys Arg Lys Asp Leu Phe Asp Pro Lys Lys Leu Leu Ser Pro
                485                 490                 495

Gly Gln Asp Ile Phe
            500

<210> SEQ ID NO 38
<211> LENGTH: 1455
<212> TYPE: DNA
<213> ORGANISM: Arabidopsis thaliana

<400> SEQUENCE: 38
atggctaatc ttcgtttaat gatcacttta atcacggttt taatgatcac caaatcatca      60
aacggtatta aaattgattt acctaaatcc cttaacctca ccctctctac cgatccttcc     120
atcatctccg cagcctctca tgacttcgga aacataacca ccgtgacccc cggcggcgta     180
atctgcccct cctccaccgc tgatatctct cgtctcctcc aatacgccgc aaacggaaaa     240
agtacattcc aagtagcggc tcgtggccaa ggccactcct taaacggcca agcctcggtc     300
tccggcggag taatcgtcaa catgacgtgt atcactgacg tggtggtttc aaaagacaag     360
```

-continued

```
aagtacgctg acgtggcggc cgggacgtta tgggtggatg tgcttaagaa gacggcggag      420
aaagggtgt cgccggtttc ttggacggat tatttgcata taaccgtccg aggaacgttg       480
tcgaatggtg gaattggtgg tcaagtgttt cgaaacggtc ctcttgttag taacgtcctt      540
gaattggacg ttattactgg gaaaggtgaa atgttgacat gctcgcgaca gctaaaccca      600
gaattgttct atggagtgtt aggaggtttg ggtcaatttg gaattataac gagagccaga      660
attgttttgg accatgcacc taaacggcaa gaacgtttga tatcaatggc aaacgatatt      720
ggagtcgact atttagaagg tcaaatattt ctatcaaacg gtgtcgttga caccctctttt     780
ttcccacctt cagatcaatc taaagtcgct gatctagtca agcaacacgg tatcatctat      840
gttcttgaag tagccaagta ttatgatgat cccaatctcc ccatcatcag caaggttatt      900
gacacattaa cgaaaacatt aagttacttg cccgggttca tatcaatgca cgacgtggcc     960
tacttcgatt tcttgaaccg tgtacatgtc gaagaaaata aactcagatc tttgggatta      1020
tgggaacttc ctcatccttg gcttaacctc tacgttccta aatctcggat tctcgatttt      1080
cataacggtg ttgtcaaaga cattcttctt aagcaaaaat cagcttcggg actcgctctt      1140
ctctatccaa caaaccggaa taaatgggac aatcgtatgt cggcgatgat accagagatc      1200
gatgaagatg ttatatatat tatcggacta ctacaatccg ctaccccaaa ggatcttcca      1260
gaagtggaga gcgttaacga aagataatt aggttttgca aggattcagg tattaagatt       1320
aagcaatatc taatgcatta tactagtaaa gaagattgga ttgagcattt tggatcaaaa      1380
tgggatgatt tttcgaagag gaaagatcta tttgatccca agaaactgtt atctccaggg      1440
caagacatct tttga                                                       1455
```

<210> SEQ ID NO 39
<211> LENGTH: 484
<212> TYPE: PRT
<213> ORGANISM: Arabidopsis thaliana

<400> SEQUENCE: 39

Met Ala Asn Leu Arg Leu Met Ile Thr Leu Ile Thr Val Leu Met Ile
1               5                   10                  15

Thr Lys Ser Ser Asn Gly Ile Lys Ile Asp Leu Pro Lys Ser Leu Asn
                20                  25                  30

Leu Thr Leu Ser Thr Asp Pro Ser Ile Ile Ser Ala Ala Ser His Asp
            35                  40                  45

Phe Gly Asn Ile Thr Thr Val Thr Pro Gly Gly Val Ile Cys Pro Ser
        50                  55                  60

Ser Thr Ala Asp Ile Ser Arg Leu Leu Gln Tyr Ala Ala Asn Gly Lys
65                  70                  75                  80

Ser Thr Phe Gln Val Ala Ala Arg Gly Gln Gly His Ser Leu Asn Gly
                85                  90                  95

Gln Ala Ser Val Ser Gly Gly Val Ile Val Asn Met Thr Cys Ile Thr
            100                 105                 110

Asp Val Val Ser Lys Asp Lys Lys Tyr Ala Asp Val Ala Ala Gly
        115                 120                 125

Thr Leu Trp Val Asp Val Leu Lys Lys Thr Ala Glu Lys Gly Val Ser
    130                 135                 140

Pro Val Ser Trp Thr Asp Tyr Leu His Ile Thr Val Arg Gly Thr Leu
145                 150                 155                 160

Ser Asn Gly Gly Ile Gly Gly Gln Val Phe Arg Asn Gly Pro Leu Val
                165                 170                 175

Ser Asn Val Leu Glu Leu Asp Val Ile Thr Gly Lys Gly Glu Met Leu
        180                 185                 190

Thr Cys Ser Arg Gln Leu Asn Pro Glu Leu Phe Tyr Gly Val Leu Gly
        195                 200                 205

Gly Leu Gly Gln Phe Gly Ile Ile Thr Arg Ala Arg Ile Val Leu Asp
        210                 215                 220

His Ala Pro Lys Arg Gln Glu Arg Leu Ile Ser Met Ala Asn Asp Ile
225                 230                 235                 240

Gly Val Asp Tyr Leu Glu Gly Gln Ile Phe Leu Ser Asn Gly Val Val
                245                 250                 255

Asp Thr Ser Phe Phe Pro Ser Asp Gln Ser Lys Val Ala Asp Leu
                260                 265                 270

Val Lys Gln His Gly Ile Ile Tyr Val Leu Glu Val Ala Lys Tyr Tyr
                275                 280                 285

Asp Asp Pro Asn Leu Pro Ile Ile Ser Lys Val Ile Asp Thr Leu Thr
290                 295                 300

Lys Thr Leu Ser Tyr Leu Pro Gly Phe Ile Ser Met His Asp Val Ala
305                 310                 315                 320

Tyr Phe Asp Phe Leu Asn Arg Val His Val Glu Asn Lys Leu Arg
                325                 330                 335

Ser Leu Gly Leu Trp Glu Leu Pro His Pro Trp Leu Asn Leu Tyr Val
                340                 345                 350

Pro Lys Ser Arg Ile Leu Asp Phe His Asn Gly Val Val Lys Asp Ile
                355                 360                 365

Leu Leu Lys Gln Lys Ser Ala Ser Gly Leu Ala Leu Leu Tyr Pro Thr
        370                 375                 380

Asn Arg Asn Lys Trp Asp Asn Arg Met Ser Ala Met Ile Pro Glu Ile
385                 390                 395                 400

Asp Glu Asp Val Ile Tyr Ile Ile Gly Leu Leu Gln Ser Ala Thr Pro
                405                 410                 415

Lys Asp Leu Pro Glu Val Glu Ser Val Asn Glu Lys Ile Ile Arg Phe
                420                 425                 430

Cys Lys Asp Ser Gly Ile Lys Ile Lys Gln Tyr Leu Met His Tyr Thr
        435                 440                 445

Ser Lys Glu Asp Trp Ile Glu His Phe Gly Ser Lys Trp Asp Phe
        450                 455                 460

Ser Lys Arg Lys Asp Leu Phe Asp Pro Lys Lys Leu Leu Ser Pro Gly
465                 470                 475                 480

Gln Asp Ile Phe

<210> SEQ ID NO 40
<211> LENGTH: 60
<212> TYPE: DNA
<213> ORGANISM: Artificial Sequence
<220> FEATURE:
<223> OTHER INFORMATION: oligonucleotide

<400> SEQUENCE: 40
ggggacaagt ttgtacaaaa aagcaggctt cacaatggct aatcttcgtt taatgatcac    60

<210> SEQ ID NO 41
<211> LENGTH: 49
<212> TYPE: DNA
<213> ORGANISM: Artificial Sequence
<220> FEATURE:
<223> OTHER INFORMATION: oligonucleotide

```
<400> SEQUENCE: 41
ggggaccact tgtacaaga aagctgggtt caaaagatgt cttgccctg                49

<210> SEQ ID NO 42
<211> LENGTH: 3328
<212> TYPE: DNA
<213> ORGANISM: Artificial Sequence
<220> FEATURE:
<223> OTHER INFORMATION: expression cassette
<220> FEATURE:
<221> NAME/KEY: misc_feature
<222> LOCATION: (2495)..(2496)
<223> OTHER INFORMATION: n is a, c, g, or t

<400> SEQUENCE: 42
ggtcagccaa tacattgatc cgttgccaat catgcaaagt attttggctg tggccgagtg     60
ccggaattga taattgtgtt ctgactaaat taaatgacca gaagtcgcta tcttccaatg    120
tatccgaaac ctggattaaa caatcctgtt ctgttctcta gcccctcctg catggccgga    180 ttgtttttt  gacatgtttt cttgactgag gcctgtttgt tctaaacttt ttcttcaaac    240
ttttaacttt ttcatcacat cagaactttt ctacacatat aaactttaa cttttccgtc     300 acatcgttcc aatttcaatc aaactttcaa ttttggcgtg aactaaacac ccctgagtc     360 ttttattgct cctccgtacg ggttggctgg ttgagaataa gtattttcag agagaaaatc    420
tagatattgg gaggaacttg gcatgaatgg ccactatatt tagagcaatt ctacggtcct    480
tgaggaggta ccatgaggta ccaaaatttt agtgtaaatt ttagtatctc attataacta    540
ggtattatga ggtaccaaat ttacaataga aaaatagta cttcatggta ctttcttaag    600
taccgtaaaa ttgctcctat atttaagggg atgtttatat ctatccatat ccataatttg    660
attttgataa gaaaaaatgt gagcacacca agcatgtcca tgaccttgca ctcttggctc    720
actcgtcaac tgtgaagaac ctcaaaaatg ctcaatatag ctacaggtgc ctgaaaaaat    780
aactttaaag ttttgaacat cgatttcact aaacaacaat tattatctcc ctctgaaaga    840
tgatagttta gaactctaga atcattgtcg gcggagaaaa taattatttt tccccaaatt    900
tccagctatg aaaaaaccct caccaaacac catcaaacaa gagttcacca aaccgcccat    960
gcggccatgc tgtcacgcaa cgcaccgcat tgcctgatgg ccgctcgatg catgcatgct   1020
tccccgtgca catatccgac agacgcgccg tgtcagcgag ctcctcgacc gacctgtgta   1080
gcccatgcaa gcatccaccc ccgccacgta caccccctcc tcctccctac gtgtcaccgc   1140
tctctccacc tatatatgcc cacctggccc ctctcctccc atctccactt cacccgatcg   1200
cttcttcttc ttcttcgttg cattcatctt gctagcattt aaatcaacta gggatatcac   1260
aagtttgtac aaaaagcag gcttcacaat ggctaatctt cgtttaatga tcactttaat    1320
cacggtttta atgatcacca aatcatcaaa cggtattaaa attgatttac ctaaatccct   1380
taacctcacc ctctctaccg atccttccat catctccgca gcctctcatg acttcggaaa   1440
cataaccacc gtgacccccg gcggcgtaat ctgcccctcc tccaccgctg atatctctcg   1500
tctcctccaa tacgccgcaa acggaaaaag tacattccaa gtagcggctc gtggccaagg   1560
ccactcctta aacggccaag cctcggtctc cggcggagta atcgtcaaca tgacgtgtat   1620
cactgacgtg gtggtttcaa aagacaagaa gtacgctgac gtggcggccg ggacgttatg   1680
ggtggatgtg cttaagaaga cggcggagaa aggggtgtcg ccggtttctt ggacggatta   1740
tttgcatata accgtcggag gaacgttgtc gaatggtgga attggtggtc aagtgtttcg   1800
```

-continued

```
aaacggtcct cttgttagta acgtccttga attggacgtt attactggga aaggtgaaat      1860
gttgacatgc tcgcgacagc taaacccaga attgttctat ggagtgttag gaggtttggg      1920
tcaatttgga attataacga gagccagaat tgttttggac catgcaccta aacggcaaga     1980
acgtttgata tcaatggcaa acgatattgg agtcgactat ttagaaggtc aaatatttct      2040
atcaaacggt gtcgttgaca cctcttttt cccaccttca gatcaatcta aagtcgctga      2100
tctagtcaag caacacggta tcatctatgt tcttgaagta gccaagtatt atgatgatcc      2160
caatctcccc atcatcagca aggttattga cacattaacg aaaacattaa gttacttgcc      2220
cgggttcata tcaatgcacg acgtggccta cttcgatttc ttgaaccgtg tacatgtcga      2280
agaaaataaa ctcagatctt tgggattatg ggaacttcct catccttggc ttaacctcta      2340
cgttcctaaa tctcggattc tcgattttca taacggtgtt gtcaaagaca ttcttcttaa      2400
gcaaaaatca gcttcgggac tcgctcttct ctatccaaca aaccggaata agtacatact      2460
tctcttcatt catatttatc ttcaagaacc aaagnnatgg gacaatcgta tgtcggcgat      2520
gataccagag atcgatgaag atgttatata tattatcgga ctactacaat ccgctacccc      2580
aaaggatctt ccagaagtgg agagcgttaa cgagaagata attaggtttt gcaaggattc      2640
aggtattaag attaagcaat atctaatgca ttatactagt aaagaagatt ggattgagca      2700
ttttggatca aaatgggatg atttttcgaa gaggaaagat ctatttgatc caagaaaact      2760
gttatctcca gggcaagaca tcttttgaac ccagctttct tgtacaaagt ggtgatatca      2820
caagcccggg cggtcttcta gggataacag ggtaattata tccctctaga tcacaagccc      2880
gggcggtctt ctacgatgat tgagtaataa tgtgtcacgc atcaccatgg gtggcagtgt      2940
cagtgtgagc aatgacctga atgaacaatt gaaatgaaaa gaaaaaaagt actccatctg      3000
ttccaaatta aaattcattt taaccttta ataggtttat acaataattg atatatgttt      3060
tctgtatatg tctaatttgt tatcatccgg gcggtcttct agggataaca gggtaattat      3120
atccctctag acaacacaca acaaataaga gaaaaaacaa ataatattaa tttgagaatg      3180
aacaaaagga ccatatcatt cattaactct tctccatcca tttccatttc acagttcgat      3240
agcgaaaacc gaataaaaaa cacagtaaat tacaagcaca acaaatggta caagaaaaac      3300
agttttccca atgccataat actcgaac                                         3328
```

<210> SEQ ID NO 43
<211> LENGTH: 2746
<212> TYPE: DNA
<213> ORGANISM: Artificial Sequence
<220> FEATURE:
<223> OTHER INFORMATION: expression cassette
<220> FEATURE:
<221> NAME/KEY: misc_feature
<222> LOCATION: (1913)..(1914)
<223> OTHER INFORMATION: n is a, c, g, or t

<400> SEQUENCE: 43

```
cttctacatc ggcttaggtg tagcaacacg actttattat tattattatt attattatta        60
ttattttaca aaaatataaa atagatcagt ccctcaccac aagtagagca agttggtgag       120
ttattgtaaa gttctacaaa gctaatttaa aagttattgc attaacttat ttcatattac       180
aaacaagagt gtcaatggaa caatgaaaac catatgacat actataattt tgtttttatt       240
attgaaatta taattcaa agagaataaa tccacatagc cgtaaagttc tacatgtggt        300
gcattaccaa aatatatata gcttacaaaa catgacaagc ttagtttgaa aaattgcaat       360
ccttatcaca ttgacacata aagtgagtga tgagtcataa tattatttc tttgctaccc       420
```

```
atcatgtata tatgatagcc acaaagttac tttgatgatg atatcaaaga acattttag    480
gtgcacctaa cagaatatcc aaataatatg actcacttag atcataatag agcatcaagt   540
aaaactaaca ctctaaagca accgatggga agcatctat aaatagacaa gcacaatgaa   600
aatcctcatc atccttcacc acaattcaaa tattatagtt gaagcatagt agtaatttaa   660
atcaactagg gatatcacaa gtttgtacaa aaaagcaggc ttcacaatgg ctaatcttcg   720
tttaatgatc actttaatca cggttttaat gatcaccaaa tcatcaaacg gtattaaaat   780
tgatttacct aaatccctta acctcaccct ctctaccgat ccttccatca tctccgcagc   840
ctctcatgac ttcggaaaca taaccaccgt gaccccggc ggcgtaatct gcccctcctc    900
caccgctgat atctctcgtc tcctccaata cgccgcaaac ggaaaaagta cattccaagt   960
agcggctcgt ggccaaggcc actccttaaa cggccaagcc tcggtctccg gcggagtaat  1020
cgtcaacatg acgtgtatca ctgacgtggt ggtttcaaaa gacaagaagt acgctgacgt  1080
ggcggccggg acgttatggg tggatgtgct taagaagacg gcggagaaag gggtgtcgcc  1140
ggtttcttgg acggattatt tgcatataac cgtcggagga acgttgtcga atggtggaat  1200
tggtggtcaa gtgtttcgaa acggtcctct tgttagtaac gtccttgaat tggacgttat  1260
tactgggaaa ggtgaaatgt tgacatgctc gcgacagcta aacccagaat tgttctatgg  1320
agtgttagga ggtttgggtc aatttggaat tataacgaga gccagaattg ttttggacca  1380
tgcacctaaa cggcaagaac gtttgatatc aatggcaaac gatattggag tcgactattt  1440
agaaggtcaa atatttctat caaacggtgt cgttgacacc tcttttttcc caccttcaga  1500
tcaatctaaa gtcgctgatc tagtcaagca acacggtatc atctatgttc ttgaagtagc  1560
caagtattat gatgatccca atctccccat catcagcaag gttattgaca cattaacgaa  1620
aacattaagt tacttgcccg ggttcatatc aatgcacgac gtggcctact tcgatttctt  1680
gaaccgtgta catgtcgaag aaaataaact cagatctttg ggattatggg aacttcctca  1740
tccttggctt aacctctacg ttcctaaatc tcggattctc gattttcata acggtgttgt  1800
caaagacatt cttcttaagc aaaaatcagc ttcgggactc gctcttctct atccaacaaa  1860
ccggaataag tacatacttc tcttcattca tatttatctt caagaaccaa agnnatggga  1920
caatcgtatg tcggcgatga taccagagat cgatgaagat gttatatata ttatcggact  1980
actacaatcc gctaccccaa aggatcttcc agaagtggag agcgttaacg agaagataat  2040
taggttttgc aaggattcag gtattaagat taagcaatat ctaatgcatt atactagtaa  2100
agaagattgg attgagcatt ttggatcaaa atgggatgat ttttcgaaga ggaaagatct  2160
atttgatccc aagaaactgt tatctccagg gcaagacatc ttttgaaccc agctttcttg  2220
tacaaagtgg tgatatcaca agcccgggcg gtcttctagg gataacaggg taattatatc  2280
cctctagatc acaagcccgg gcggtcttct acgatgattg agtaataatg tgtcacgcat  2340
caccatgggt ggcagtgtca gtgtgagcaa tgacctgaat gaacaattga aatgaaaaga  2400
aaaaaagtac tccatctgtt ccaaattaaa attcatttta accttttaat aggtttatac  2460
aataattgat atatgttttc tgtatatgtc taatttgtta tcatccgggc ggtcttctag  2520
ggataacagg gtaattatat ccctctagac aacacacaac aaataagaga aaaaacaaat  2580
aatattaatt tgagaatgaa caaaaggacc atatcattca ttaactcttc tccatccatt  2640
tccatttcac agttcgatag cgaaaaccga ataaaaaaca cagtaaatta caagcacaac  2700
aaatggtaca agaaaaacag ttttcccaat gccataatac tcgaac                 2746
```

<210> SEQ ID NO 44
<211> LENGTH: 1506
<212> TYPE: DNA
<213> ORGANISM: Arabidopsis thaliana

<400> SEQUENCE: 44

| | | | | | |
|---|---|---|---|---|---|
| atggctaatc | ttcgtttaat | gatcactta | atcacggttt | taatgatcac | caaatcatca | 60 |
| aacggtatta | aaattgattt | acctaaatcc | cttaacctca | ccctctctac | cgatccttcc | 120 |
| atcatctccg | cagcctctca | tgacttcgga | aacataacca | ccgtgacccc | cggcggcgta | 180 |
| atctgcccct | cctccaccgc | tgatatctct | cgtctcctcc | aatacgccgc | aaacggaaaa | 240 |
| agtacattcc | aagtagcggc | tcgtggccaa | ggccactcct | taaacggcca | agcctcggtc | 300 |
| tccggcggag | taatcgtcaa | catgacgtgt | atcactgacg | tggtggtttc | aaaagacaag | 360 |
| aagtacgctg | acgtggcggc | cgggacgtta | tgggtggatg | tgcttaagaa | gacggcggag | 420 |
| aaagggggtgt | cgccggtttc | ttggacggat | tatttgcata | taccgtccg | aggaacgttg | 480 |
| tcgaatggtg | gaattggtgg | tcaagtgttt | cgaaacggtc | ctcttgttag | taacgtcctt | 540 |
| gaattggacg | ttattactgg | gaaggtgaa | atgttgacat | gctcgcgaca | gctaaaccca | 600 |
| gaattgttct | atggagtgtt | aggaggtttg | ggtcaatttg | gaattataac | gagagccaga | 660 |
| attgttttgg | accatgcacc | taaacgggcc | aaatggtttc | ggatgctcta | cagtgatttc | 720 |
| acaactttta | caaggaccaa | gaacgtttg | atatcaatgg | caaacgatat | tggagtcgac | 780 |
| tatttagaag | gtcaaatatt | tctatcaaac | ggtgtcgttg | acacctcttt | tttcccacct | 840 |
| tcagatcaat | ctaaagtcgc | tgatctagtc | aagcaacacg | gtatcatcta | tgttcttgaa | 900 |
| gtagccaagt | attatgatga | tcccaatctc | cccatcatca | gcaaggttat | tgacacatta | 960 |
| acgaaaacat | taagttactt | gcccgggttc | atatcaatgc | acgacgtggc | ctacttcgat | 1020 |
| ttcttgaacc | gtgtacatgt | cgaagaaaat | aaactcagat | ctttgggatt | atgggaactt | 1080 |
| cctcatcctt | ggcttaacct | ctacgttcct | aaatctcgga | ttctcgattt | tcataacggt | 1140 |
| gttgtcaaag | acattcttct | taagcaaaaa | tcagcttcgg | gactcgctct | tctctatcca | 1200 |
| acaaaccgga | ataaatggga | caatcgtatg | tcggcgatga | taccagagat | cgatgaagat | 1260 |
| gttatatata | ttatcggact | actacaatcc | gctaccccaa | aggatcttcc | agaagtggag | 1320 |
| agcgttaacg | agaagataat | taggttttgc | aaggattcag | gtattaagat | taagcaatat | 1380 |
| ctaatgcatt | atactagtaa | agaagattgg | attgagcatt | ttggatcaaa | atgggatgat | 1440 |
| ttttcgaaga | ggaaagatct | atttgatccc | aagaaactgt | tatctccagg | gcaagacatc | 1500 |
| ttttga | | | | | | 1506 |

<210> SEQ ID NO 45
<211> LENGTH: 56
<212> TYPE: DNA
<213> ORGANISM: Artificial Sequence
<220> FEATURE:
<223> OTHER INFORMATION: oligonucleotide

<400> SEQUENCE: 45
ggggacaagt ttgtacaaaa aagcaggctt cacaatggga ttgacctcat ccttac      56

<210> SEQ ID NO 46
<211> LENGTH: 53
<212> TYPE: DNA
<213> ORGANISM: Artificial Sequence
<220> FEATURE:
<223> OTHER INFORMATION: oligonucleotide

<400> SEQUENCE: 46
ggggaccact tgtacaaga aagctgggtt tatacagttc taggtttcgg cag         53

<210> SEQ ID NO 47
<211> LENGTH: 2746
<212> TYPE: DNA
<213> ORGANISM: Artificial Sequence
<220> FEATURE:
<223> OTHER INFORMATION: expression cassette
<220> FEATURE:
<221> NAME/KEY: misc_feature
<222> LOCATION: (1913)..(1914)
<223> OTHER INFORMATION: n is a, c, g, or t

<400> SEQUENCE: 47

```
cttctacatc ggcttaggtg tagcaacacg actttattat tattattatt attattatta    60
ttattttaca aaaatataaa atagatcagt ccctcaccac aagtagagca agttggtgag   120
ttattgtaaa gttctacaaa gctaatttaa aagttattgc attaacttat ttcatattac   180
aaacaagagt gtcaatggaa caatgaaaac catatgacat actataattt tgttttttatt  240
attgaaatta taaattcaa agagaataaa tccacatagc cgtaaagttc tacatgtggt   300
gcattaccaa aatatatata gcttacaaaa catgacaagc ttagtttgaa aaattgcaat   360
ccttatcaca ttgacacata aagtgagtga tgagtcataa tattattttc tttgctaccc   420
atcatgtata tatgatagcc acaaagttac tttgatgatg atatcaaaga acattttttag  480
gtgcacctaa cagaatatcc aaataatatg actcacttag atcataatag agcatcaagt   540
aaaactaaca ctctaaagca accgatggga aagcatctat aaatagacaa gcacaatgaa   600
aatcctcatc atccttcacc acaattcaaa tattatagtt gaagcatagt agtaatttaa   660
atcaactagg gatatcacaa gtttgtacaa aaaagcaggc ttcacaatgg ctaatcttcg   720
tttaatgatc actttaatca cggttttaat gatcaccaaa tcatcaaacg gtattaaaat   780
tgatttacct aaatccctta acctcaccct ctctaccgat ccttccatca tctccgcagc   840
ctctcatgac ttcggaaaca taaccaccgt gaccccggc ggcgtaatct gcccctcctc    900
caccgctgat atctctcgtc tcctccaata cgccgcaaac ggaaaaagta cattccaagt   960
agcggctcgt ggccaaggcc actccttaaa cggccaagcc tcggtctccg gcggagtaat  1020
cgtcaacatg acgtgtatca ctgacgtggt ggtttcaaaa gacaagaagt acgctgacgt  1080
ggcggccggg acgttatggg tggatgtgct taagaagacg gcggagaaag gggtgtcgcc  1140
ggtttcttgg acggattatt tgcatataac cgtcggagga acgttgtcga atggtggaat  1200
tggtggtcaa gtgtttcgaa acggtcctct tgttagtaac gtccttgaat tggacgttat  1260
tactgggaaa ggtgaaatgt tgacatgctc gcgacagcta aacccagaat tgttctatgg  1320
agtgttagga ggtttgggtc aatttggaat tataacgaga gccagaattg ttttggacca  1380
tgcacctaaa cggcaagaac gtttgatatc aatggcaaac gatattggag tcgactattt  1440
agaaggtcaa atatttctat caacggtgt cgttgcacac tcttttttcc caccttcaga  1500
tcaatctaaa gtcgctgatc tagtcaagca acacggtatc atctatgttc ttgaagtagc  1560
caagtattat gatgatccca atctccccat catcagcaag gttattgaca cattaacgaa  1620
aacattaagt tacttgcccg ggttcatatc aatgcacgac gtggcctact tcgatttctt  1680
gaaccgtgta catgtcgaag aaaataaact cagatctttg ggattatggg aacttcctca  1740
tccttggctt aacctctacg ttcctaaatc tcggattctc gattttcata acggtgttgt  1800
```

-continued

```
caaagacatt cttcttaagc aaaaatcagc ttcgggactc gctcttctct atccaacaaa    1860
ccggaataag tacatacttc tcttcattca tatttatctt caagaaccaa agnnatggga    1920
caatcgtatg tcggcgatga taccagagat cgatgaagat gttatatata ttatcggact    1980
actacaatcc gctaccccaa aggatcttcc agaagtggag agcgttaacg agaagataat    2040
taggttttgc aaggattcag gtattaagat taagcaatat ctaatgcatt atactagtaa    2100
agaagattgg attgagcatt ttggatcaaa atgggatgat ttttcgaaga ggaaagatct    2160
atttgatccc aagaaactgt tatctccagg gcaagacatc tttttgaaccc agctttcttg    2220 tacaaagtgg tgatatcaca agcccgggcg gtcttctagg gataacaggg taattatatc    2280
cctctagatc acaagcccgg gcggtcttct acgatgattg agtaataatg tgtcacgcat    2340
caccatgggt ggcagtgtca gtgtgagcaa tgacctgaat gaacaattga atgaaaaga    2400 aaaaaagtac tccatctgtt ccaaattaaa attcatttta accttttaat aggtttatac    2460
aataattgat atatgttttc tgtatatgtc taatttgtta tcatccgggc ggtcttctag    2520
ggataacagg gtaattatat ccctctagac aacacacaac aaataagaga aaaaacaaat    2580
aatattaatt tgagaatgaa caaaaggacc atatcattca ttaactcttc tccatccatt    2640
tccatttcac agttcgatag cgaaaaccga ataaaaaaca cagtaaatta caagcacaac    2700
aaatggtaca agaaaaacag tttttcccaat gccataatac tcgaac               2746
```

<210> SEQ ID NO 48
<211> LENGTH: 2291
<212> TYPE: DNA
<213> ORGANISM: Arabidopsis thaliana

<400> SEQUENCE: 48

```
caaagtagaa atgggattga cctcatcctt acggttccat agacaaaaca acaagacttt     60
cctcggaatc ttcatgatct tagttctaag ctgtatacca ggtagaacca atctttgttc    120
caatcattct gttagtaccc caaaagaatt accttcttca aatccttcag atattcgttc    180
ctcattagtt tcactagatt tggagggtta tataagcttc gacgatgtcc acaatgtggc    240
caaggacttt ggcaacagat accagttacc acctttggca attctacatc caaggtcagt    300
ttttgatatt tcatcgatga tgaagcatat agtacatctg gctccacct caaatcttac    360 agtagcagct agaggccatg gtcactcgct tcaaggacaa gctctagctc atcaaggtgt    420
tgtcatcaaa atgagtcac ttcgaagtcc tgatatcagg atttataagg ggaagcaacc    480
atatgttgat gtctcaggtg gtgaaatatg gataaacatt ctacgcgaga ctctaaaata    540
cggtctttca ccaaagtcct ggacagacta ccttcatttg accgttggag gtacactatc    600
taatgctgga atcagcggtc aagcattcaa gcatggaccc caaatcaaca acgtctacca    660
gctagagatt gttacaggta tttcattcat gctttatctc tgcggtagtc tcaaaaaaat    720
atgcacctgt aaagaatatc catctcttca tgagcaaaaa cactgacgac tttaaataat    780
ttttgactat aaaacaagag tgcataggca caaatgtgaa atatgcaaca cacaattgta    840
acttgcacca agaaaaagt tataaaaaca aacaactgat aagcaatata tttccaatat    900
ttaatcaggg aaaggagaag tcgtaacctg ttctgagaag cggaattctg aacttttctt    960
cagtgttctt ggcgggcttg gacagttggg cataatcacc cggcacggga tctctcttga   1020
accagcaccg catatggtaa agttctatct tgaacaaagt tcaaacaata tacgctatga   1080
ttctaagaac cactttcctg acacagtcaa ataacttttta ataggttaaa tggatcaggg   1140
tactctactc tgacttttct gcattttcaa gggaccaaga atatctgatt tcgaaggaga   1200
```

-continued

```
aaacttttga ttacgttgaa ggatttgtga taatcaatag aacagacctt ctcaataatt      1260
ggcgatcgtc attcagtccc aacgattcca cacaggcaag cagattcaag tcagatggga      1320
aaactcttta ttgcctagaa gtggtcaaat atttcaaccc agaagaagct agctctatgg      1380
atcaggtaag atgtgaaagc aatatataac tagacttagt ttccacagag agctccaaat      1440
caaccgttgg ctactagcct actaacataa tgaatggttg ccgtgcagga aactggcaag      1500
ttactttcag agttaaatta tattccatcc actttgtttt catctgaagt gccatatatc      1560
gagtttctgg atcgcgtgca tatcgcagag agaaaactaa gagcaaaggg tttatgggag      1620
gttccacatc cctggctgaa tctcctgatt cctaagagca gcatatacca atttgctaca      1680
gaagttttca acaacattct cacaagcaac aacaacggtc ctatccttat ttatccagtc      1740
aatcaatcca agtaagtgag caaaatgcca aaagcaaatg cgtccagtga ttctgaaaca      1800
taaattacta accatatcca acattttgtg gtttcaggtg gaagaaacat acatctttga      1860
taactccaaa tgaagatata ttctatctcg tagcctttct cccctctgca gtgccaaatt      1920
cctcagggaa aaacgatcta gagtaccttt tgaaacaaaa ccaaagagtt atgaacttct      1980
gcgcagcagc aaacctcaac gtgaagcagt atttgcccca ttatgaaact caaaagagt      2040 ggaaatcaca ctttggcaaa agatgggaaa catttgcaca gaggaaacaa gcctacgacc      2100
ctctagcgat tctagcacct ggccaaagaa tattccaaaa gacaacagga aaattatctc      2160
ccatccaact cgcaaagtca aaggcaacag gaagtcctca aaggtaccat tacgcatcaa      2220
tactgccgaa acctagaact gtataaaagt ttcctgtgtc cgtccttgta accgctcagg      2280
ctaggcagca a                                                          2291
```

<210> SEQ ID NO 49
<211> LENGTH: 1208
<212> TYPE: DNA
<213> ORGANISM: Oryza sativa

<400> SEQUENCE: 49

```
cgtagtggct ggctgggcga cgtgggttta aggaagagt gacctgctca agtgctcagt       60
agattaatta agggatttga attctggtcg tacgataaat taacttgagt tcaaaaatac      120
aagaaacatc agtttatatt tcatttcgtg taggacctat caatccaatt cgtacaagag      180
gaattgcata tttcaactca tagtcttaac taccattcaa attgatattt gcacgatgat      240
gattgtctgg tatagatttg acttttggg aactgaatca aatccagcat gattcatgca      300
agaaacttga attcaactca tacaagaaac atattcaatt tcaagctgtg caataatgca      360
cgtatcttaa gcaaagagta gtacgtctgc atcatatagt actcatgcaa gattgaaaca      420
gctaagaact tgatcaaatt caaagttttt ttgtgatcga agtttaaatc cagttcatac      480
aagaaacgca ttaaaaataa tcgatttaaa tatgagcaat aatgcatcta ctttaagcat      540
agggtttgac atcacggtat ggaagcaaat ttgaattaga cgcaaacttg gatctcattt      600
ttccagaaac tttgttcgat tggtaattaa aacagtgcaa cctttgcacg caaccaaata      660
tataaaaatc cctggttgct aggactgttg taatcctgac aaatttcctc taatcttaaa      720
acacttgggt cggctttctt tgccaacccg gcgaaaaaa actatataaa aatcataatt      780
attactacct tcatttcagg ttataagact ttctaacatt gtccatattt atatatatgt      840
taatgaatct agacatatat ttgtgtctgg attcattaac atctatatga atgtggacaa      900
tgctagaaag tttataacc tgaaacggag aagtatattt ttttgggtac ttgtgtcata      960
```

```
ttgtcatgtc atcaatgtgt atagtactaa ggttcaatga gaaatgatac aattgcaagc    1020
caaacaaatt gccgttacag aaatctgacg tcaacgacat tctggcaaga taatgcttga    1080
tacaatttgt gcagctatgc tactataaat agggggggggg gggcgttat atctgcactg    1140 agttcatatc aagctttcaa tctctcattg catacaagtc cctgaagagt ttacaagaga    1200
cccagaag                                                             1208

<210> SEQ ID NO 50
<211> LENGTH: 3090
<212> TYPE: DNA
<213> ORGANISM: Artificial sequence
<220> FEATURE:
<223> OTHER INFORMATION: sequence expression cassette

<400> SEQUENCE: 50
cgtagtggct ggctgggcga cgtgggttta aggaagagt gacctgctca agtgctcagt      60
agattaatta agggatttga attctggtcg tacgataaat taacttgagt tcaaaaatac    120
aagaaacatc agtttatatt tcatttcgtg taggacctat caatccaatt cgtacaagag    180
gaattgcata tttcaactca tagtcttaac taccattcaa attgatattt gcacgatgat    240
gattgtctgg tatagatttg actttttggg aactgaatca aatccagcat gattcatgca    300
agaaacttga attcaactca tacaagaaac atattcaatt tcaagctgtg caataatgca    360
cgtatcttaa gcaaagagta gtacgtctgc atcatatagt actcatgcaa gattgaaaca    420
gctaagaact tgatcaaatt caagtttttt ttgtgatcga agtttaaatc cagttcatac    480
aagaaacgca ttaaaaataa tcgatttaaa tatgagcaat aatgcatcta ctttaagcat    540
agggtttgac atcacggtat ggaagcaaat ttgaattaga cgcaaacttg gatctcattt    600
ttccagaaac tttgttcgat tggtaattaa acagtgcaa cctttgcacg caaccaaata    660
tataaaaatc cctggttgct aggactgttg taatcctgac aaatttcctc taatcttaaa    720
acacttgggt cggctttctt tgccaacccg gcgaaaaaaa actatataaa aatcataatt    780
attactacct tcatttcagg ttataagact ttctaacatt gtccatattt atatatatgt    840
taatgaatct agacatatat ttgtgtctgg attcattaac atctatatga atgtggacaa    900
tgctagaaag ttttataacc tgaaacggag aagtatattt ttttgggtac ttgtgtcata    960
ttgtcatgtc atcaatgtgt atagtactaa ggttcaatga gaaatgatac aattgcaagc   1020
caaacaaatt gccgttacag aaatctgacg tcaacgacat tctggcaaga taatgcttga   1080
tacaatttgt gcagctatgc tactataaat agggggggggg gggcgttat atctgcactg   1140 agttcatatc aagctttcaa tctctcattg catacaagtc cctgaagagt ttacaagaga   1200
cccagaagat cattttttca ccagcaaagt tcatttaaat caactaggga tatcacaagt   1260
ttgtacaaaa aagcaggctt cacaatggct aatcttcgtt taatgatcac tttaatcacg   1320
gttttaatga tcaccaaatc atcaaacggt attaaaattg atttacctaa atcccttaac   1380
ctcaccctct ctaccgatcc ttccatcatc tccgcagcct tcatgacttt cggaaacata   1440
accaccgtga ccccccggcgg cgtaatctgc ccctcctcca ccgctgatat ctctcgtctc   1500
ctccaatacg ccgcaaacgg aaaaagtaca ttccaagtag cggctcgtgg ccaaggccac   1560
tccttaaacg gccaagcctc ggtctccggc ggagtaatcg tcaacatgac gtgtatcact   1620
gacgtggtgg tttcaaaaga caagaagtac gctgacgtgg cggccgggac gttatgggtg   1680
gatgtgctta agaagacggc ggagaaaggg gtgtcgccgg tttcttggac ggattatttg   1740
catataaccg tccgaggaac gttgtcgaat ggtggaattg gtggtcaagt gtttcgaaac   1800
```

-continued

```
ggtcctcttg ttagtaacgt ccttgaattg gacgttatta ctgggaaagg tgaaatgttg        1860
acatgctcgc gacagctaaa cccagaattg ttctatggag tgttaggagg tttgggtcaa        1920
tttggaatta taacgagagc cagaattgtt ttggaccatg cacctaaacg ggccaaatgg        1980
tttcggatgc tctacagtga tttcacaact tttacaaagg accaagaacg tttgatatca        2040
atggcaaacg atattggagt cgactattta gaaggtcaaa tatttctatc aaacggtgtc        2100
gttgacacct cttttttccc accttcagat caatctaaag tcgctgatct agtcaagcaa        2160
cacggtatca tctatgttct tgaagtagcc aagtattatg atgatcccaa tctccccatc        2220
atcagcaagg ttattgacac attaacgaaa acattaagtt acttgcccgg ttcatatca         2280 atgcacgacg tggcctactt cgatttcttg aaccgtgtac atgtcgaaga aaataaactc        2340
agatctttgg gattatggga acttcctcat ccttggctta acctctacgt tcctaaatct        2400
cggattctcg attttcataa cggtgttgtc aaagacattc ttcttaagca aaaatcagct        2460
tcgggactcg ctcttctcta ccaacaaac cggaataaat gggacaatcg tatgtcggcg         2520
atgataccag agatcgatga agatgttata tatattatcg gactactaca atccgctacc        2580
ccaaaggatc ttccagaagt ggagagcgtt aacgagaaga taattaggtt ttgcaaggat        2640
tcaggtatta agattaagca atatctaatg cattatacta gtaaagaaga ttggattgag        2700
cattttggat caaaatggga tgattttttcg aagaggaaag atctatttga tcccaagaaa       2760
ctgttatctc cagggcaaga catcttttga acccagcttt cttgtacaaa gtggtgatat        2820
cacaagcccg ggcggtcttc tagggataac agggtaatta tatccctcta gatcacaagc        2880
ccgggcggtc ttctacgatg attgagtaat aatgtgtcac gcatcaccat gggtggcagt        2940
gtcagtgtga gcaatgacct gaatgaacaa ttgaaatgaa agaaaaaaa gtactccatc         3000 tgttccaaat taaaattcat tttaacccttt taataggttt atacaataat tgatatatgt       3060
tttctgtata tgtctaattt gttatcatcc                                         3090
```

<210> SEQ ID NO 51
<211> LENGTH: 53
<212> TYPE: DNA
<213> ORGANISM: Artificial sequence
<220> FEATURE:
<223> OTHER INFORMATION: primer

<400> SEQUENCE: 51

```
ggggacaagt ttgtacaaaa aagcaggcta aaaccaccga gggacctgat ctg               53
```

<210> SEQ ID NO 52
<211> LENGTH: 54
<212> TYPE: DNA
<213> ORGANISM: Artificial sequence
<220> FEATURE:
<223> OTHER INFORMATION: primer

<400> SEQUENCE: 52

```
ggggaccact ttgtacaaga aagctgggtt gtcgcttta tttggcttgg tgtg               54
```

<210> SEQ ID NO 53
<211> LENGTH: 1243
<212> TYPE: DNA
<213> ORGANISM: beta-expansion EXPB9 promoter sequence

<400> SEQUENCE: 53

```
aaaaccaccg agggacctga tctgcaccgg ttttgatagt tgagggaccc gttgtgtctg        60
```

-continued

```
gttttccgat cgagggacga aaatcggatt cggtgtaaag ttaagggacc tcagatgaac    120
ttattccgga gcatgattgg gaagggagga cataaggccc atgtcgcatg tgtttggacg    180
gtccagatct ccagatcact cagcaggatc ggccgcgttc gcgtagcacc cgcggtttga    240
ttcggcttcc cgcaaggcgg cggccggtgg ccgtgccgcc gtagcttccg ccggaagcga    300
gcacgccgcc gccgccgacc cggctctgcg tttgcaccgc cttgcacgcg atacatcggg    360
atagatagct actactctct ccgtttcaca atgtaaatca ttctactatt ttccacattc    420
atattgatgt taatgaatat agacatatat atctatttag attcattaac atcaatatga    480
atgtaggaaa tgctagaatg acttacattg tgaattgtga aatggacgaa gtacctacga    540
tggatggatg caggatcatg aaagaattaa tgcaagatcg tatctgccgc atgcaaaatc    600
ttactaattg cgctgcatat atgcatgaca gcctgcatgc gggcgtgtaa gcgtgttcat    660
ccattaggaa gtaaccttgt cattacttat accagtacta catactatat agtattgatt    720
tcatgagcaa atctacaaaa ctggaaagca ataaggaata cgggactgga aaagactcaa    780
cattaatcac caaatatttc gccttctcca gcagaatata tatctctcca tcttgatcac    840
tgtacacact gacagtgtac gcataaacgc agcagccagc ttaactgtcg tctcaccgtc    900
gcacactggc cttccatctc aggctagctt tctcagccac ccatcgtaca tgtcaactcg    960
gcgcgcgcac aggcacaaat tacgtacaaa acgcatgacc aaatcaaaac caccggagaa   1020
gaatcgctcc cgcgcgcggc ggcggcgcgc acgtacgaat gcacgcacgc acgcccaacc   1080
ccacgacacg atcgcgcgcg acgccggcga caccggccat ccaccgcgc cctcacctcg    1140 ccgactataa atacgtaggc atctgcttga tcttgtcatc catctcacca ccaaaaaaaa   1200
aggaaaaaaa aacaaaacac accaagccaa ataaaagcga caa                    1243
```